US012622899B2

(12) United States Patent
Chen et al.

(10) Patent No.: US 12,622,899 B2

(45) Date of Patent: May 12, 2026

---

(54) METHODS OF TREATING IDIOPATHIC PULMONARY FIBROSIS WITH DEUPIRFENIDONE

(71) Applicant: PureTech LYT 100, Inc., Boston, MA (US)

(72) Inventors: Michael C. Chen, Norwood, MA (US); Eric Elenko, Boston, MA (US); Heather A. Paden, Woodbury, CT (US); Christopher C. Korth, Rye, NH (US); Paul Andrew Ford, Hassocks (GB); Julie S. Krop, West Haven, CT (US); Camilla S. Graham, Framingham, MA (US); Liza C. Micioni, Wall Township, NJ (US); Simon John Hatch, Wayne, PA (US); Varun Garg, Framingham, MA (US); Yanqiong Zhang, Westborough, MA (US); Carol Ann Satler, Boston, MA (US); David Andrew Golod, Newton, MA (US)

(73) Assignee: PureTech LYT 100, Inc., Boston, MA (US)

( * ) Notice: Subject to any disclaimer, the term of this patent is extended or adjusted under 35 U.S.C. 154(b) by 0 days.

(21) Appl. No.: 19/299,954

(22) Filed: Aug. 14, 2025

(65) Prior Publication Data

US 2025/0375431 A1 Dec. 11, 2025

Related U.S. Application Data

(63) Continuation of application No. 19/286,158, filed on Jul. 30, 2025, which is a continuation of application No. 18/982,798, filed on Dec. 16, 2024, now abandoned, which is a continuation-in-part of application No. 18/806,289, filed on Aug. 15, 2024, now abandoned, and a continuation-in-part of application No. 18/758,783, filed on Jun. 28, 2024, and a continuation of application No. 18/437,614, filed on Feb. 9, 2024, now abandoned, which is a continuation of application No. 18/330,154, filed on Jun. 6, 2023, now abandoned, said application No. 18/758,783 is a continuation of application No. PCT/US2023/060185, filed on Jan. 5, 2023, said application No. 18/982,798 is a continuation-in-part of application No. 18/150,055, filed on Jan. 4, 2023, which is a continuation of application No. PCT/US2021/040551, filed on Jul. 6, 2021, said application No. 18/330,154 is a continuation of application No. 17/144,018, filed on Jan. 7, 2021, now abandoned, which is a continuation of application No. 16/572,595, filed on Sep. 16, 2019, now abandoned.

(60) Provisional application No. 63/432,208, filed on Dec. 13, 2022, provisional application No. 63/431,530, filed on Dec. 9, 2022, provisional application No. 63/403,481, filed on Sep. 2, 2022, provisional application No. 63/374,362, filed on Sep. 1, 2022, provisional application No. 63/356,653, filed on Jun. 29, 2022, provisional application No. 63/352,107, filed on Jun. 14, 2022, provisional application No. 63/341,828, filed on May 13, 2022, provisional application No. 63/341,279, filed on May 12, 2022, provisional application No. 63/341,281, filed on May 12, 2022, provisional application No. 63/341,269, filed on May 12, 2022, provisional application No. 63/326,129, filed on Mar. 31, 2022, provisional application No. 63/326,132, filed on Mar. 31, 2022, provisional application No. 63/296,826, filed on Jan.

(Continued)

(51) Int. Cl.
| | |
|---|---|
| *A61K 31/4412* | (2006.01) |
| *A61P 11/00* | (2006.01) |
| *A61P 29/00* | (2006.01) |

(52) U.S. Cl.
CPC .......... *A61K 31/4412* (2013.01); *A61P 11/00* (2018.01); *A61P 29/00* (2018.01)

(58) Field of Classification Search
CPC ............................ A61K 31/4418; A61P 19/04
See application file for complete search history.

(56) References Cited

U.S. PATENT DOCUMENTS

| | | |
|---|---|---|
| 7,566,729 B1 | 7/2009 | Bradford et al. |
| 7,635,707 B1 | 12/2009 | Bradford et al. |
| | (Continued) | |

FOREIGN PATENT DOCUMENTS

| | | |
|---|---|---|
| WO | 2008/157786 A1 | 12/2008 |
| WO | 2009/035598 A1 | 3/2009 |
| | (Continued) | |

OTHER PUBLICATIONS

Chen et al. "A Randomized Phase 1 Evaluation of Deupirfenidone, a Novel Deuterium-Containing Drug Candidate for Interstitial Lung Disease and Other Inflammatory and Fibrotic Diseases" Clinical Pharmacology in Drug Development; vol. 11, p. 220-234 (2021).

(Continued)

*Primary Examiner* — Timothy R Rozof
(74) *Attorney, Agent, or Firm* — WOMBLE BOND DICKINSON (US) LLP; Danielle L. Herritt

(57) ABSTRACT

Disclosed herein is a method of treating Idiopathic Pulmonary Fibrosis (IPF). The method includes administering to a subject in need thereof the deuterium-enriched pirfenidone LYT-100 at a total daily dose from about 1650 mg to about 2500 mg.

6 Claims, 55 Drawing Sheets

Related U.S. Application Data 5, 2022, provisional application No. 63/296,843, filed on Jan. 5, 2022, provisional application No. 63/296,818, filed on Jan. 5, 2022, provisional application No. 63/175,063, filed on Apr. 15, 2021, provisional application No. 63/135,374, filed on Jan. 8, 2021, provisional application No. 63/123,989, filed on Dec. 10, 2020, provisional application No. 63/121,168, filed on Dec. 3, 2020, provisional application No. 63/116,520, filed on Nov. 20, 2020, provisional application No. 63/087,116, filed on Oct. 2, 2020, provisional application No. 63/048,564, filed on Jul. 6, 2020, provisional application No. 62/884,984, filed on Aug. 9, 2019, provisional application No. 62/839,256, filed on Apr. 26, 2019, provisional application No. 62/750,377, filed on Oct. 25, 2018, provisional application No. 62/731,570, filed on Sep. 14, 2018.

(56) References Cited

U.S. PATENT DOCUMENTS

| | | | |
|---|---|---|---|
| 7,696,236 B2 | 4/2010 | Bradford | |
| 7,767,700 B2 | 8/2010 | Bradford | |
| 7,816,383 B1 | 10/2010 | Bradford et al. | |
| 8,383,823 B2 | 2/2013 | Gant et al. | |
| 8,609,701 B2 | 12/2013 | Bradford et al. | |
| 8,680,123 B1 * | 3/2014 | Gant | A61P 37/06 |
| | | | 514/345 |
| 8,754,109 B2 | 6/2014 | Bradford et al. | |
| 8,969,575 B2 | 3/2015 | Gant et al. | |
| 8,969,576 B2 | 3/2015 | Gant et al. | |
| 9,062,001 B2 | 6/2015 | Gant et al. | |
| 9,504,677 B2 | 11/2016 | Gant et al. | |
| 2008/0287508 A1 | 11/2008 | Robinson et al. | |
| 2011/0313004 A1 | 12/2011 | Harbeson | |
| 2013/0018193 A1 | 1/2013 | Liu et al. | |
| 2014/0066484 A1 | 3/2014 | Bradford | |

FOREIGN PATENT DOCUMENTS

| | | |
|---|---|---|
| WO | 2012122165 A2 | 9/2012 |
| WO | 2015/112701 A1 | 7/2015 |
| WO | 2016127013 A1 | 8/2016 |
| WO | 2020056430 A1 | 3/2020 |
| WO | 2021181368 A1 | 9/2021 |
| WO | 2021186401 A1 | 9/2021 |
| WO | 2022010925 A1 | 1/2022 |

OTHER PUBLICATIONS

International Search Report issued by the United States Patent Office as International Searching Authority for International Application No. PCT/US2023/017213; mailed Jun. 16, 2023, 3 pages.

Harbeson et al., "Deuterium in Drug Discovery and Development," Annual Reports in Medicinal Chemistry, vol. 46:403-417 (Dec. 2011).

King et al., "A Phase 3 Trial of Pirfenidone in Patients with Idiopathic Pulmonary Fibrosis," New England Journal of Medicine, vol. 370, No. 22, May 2014 (pp. 2083-2092).

Lancaster et al., "Pirfenidone safety and adverse event management in idiopathic pulmonary fibrosis," European Respiratory Review, vol. 26, No. 146, Dec. 2017 (pp. 1-10).

Mei et al., "Protection of Pirfenidone against an Early Phase of Oleic Acid-Induced Acute Lung Injury in Rats," Journal of Pharmacology and Experimental Therapeutics, vol. 313, No. 1, Apr. 2004 (pp. 379-388).

Concert Pharmaceuticals "Precision Deuterium Chemistry Backgrounder", Internet Citation, 2007, pp. 1-6, XP002636701, Retrieved from the Internet: URL:http://www.webcitation.org/5e81SGCnl [retrieved on Oct. 1, 2025].

No Author Listed, European Medicines Agency CHMP Assessment Report on Esbriet (Pirfenidone), Procedure No. EMEA/H/C/002154/2011, Dec. 16, 2010 (84 pages).

Noble et al., "Pirfenidone in patients with idiopathic pulmonary fibrosis (CAPACITY): two randomised trials," Lancet, vol. 377(9779):1760-1769 (May 2011).

Rubino et al., "Effect of Food and antacids on the pharmacokinetics of pirfenidone in older healthy adults," Pulmonary Pharmacology & Therapeutics; vol. 22(4):279-285 (Aug. 2009).

Saito et al., "Pirfenidone alleviates lung ischemia-reperfusion injury in a rat model," Journal of Thoracic and Cardiovascular Surgery, vol. 158(1):289-296 (Jul. 2018).

Taniguchi et al., "Pirfenidone in idiopathic pulmonary fibrosis," European Respiratory Journal, vol. 35(4):821-829 (Apr. 2010).

International Search Report issued by the European Patent Office as International Searching Authority for International Application No. PCT/US2019/051369, mailed Jan. 28, 2020; 6 pages.

Grada et al., J. Ameri. Acad. Dermatol., Amer. Acad. Derm., vol. 77, pp. 1009-1020 (2017).

U.S. Appl. No. 12/143,484, Declaration of Margaret Bradbury, Ph.D. Under 37 C.F.R. § 1.132, Jun. 27, 2011 (23 paqes).

International Search Report issued by the United States Patent Office as International Searching Authority for International Application No. PCT/US2021/040551 mailed Oct. 13, 2021, 3 pages.

Raghu, Ganesh, et al., "Pirfenidone for IPF: pro/con debate; the 'con' viewpoint", Thorax, vol. 68, No. 7, pp. 605-608 (Jul. 2013).

Cottin et al., "Long-term safety of pirfenidone: results of the prospective, observational PASSPORT study" ERJ Open Res.; vol. 4(4):00084-2018 (Oct. 19, 2018).

Dempsey et al., "Adoption of the Antifibrotic Medications Pirfenidone and Nintedanib for Patients with Idiopathic Pulmonary Fibrosis" Ann Am Thorac Soc.; vol. 18(7):1121-1128 (2021).

Dhooria et al., "A real-world study of the dosing and tolerability of pirfenidone and its effect on survival in idiopathic pulmonary fibrosis"; Sarcoidosis Vasculitis and Diffuse Lung Diseases; vol. 37 (1); 148-157 (2020).

FDA (2022) Esbriet Prescribing Information, Feb. 2022; retrieved from https://www.accessdata.fda.gov/drugsatfda_docs/label/2014/022535s000lbl.pdf; 23 pages.

FDA (2009) Esbriet New Drug Application, Clinical Pharmacology and Biopharmaceutics review; Application No. 022535Orig1s000; Dec. 31, 2009; Retrieved from https://www.accessdata.fda.gov/drugsatfda_docs/nda/2014/022535Orig1s000ClinPharmR.pdf; 204 pages.

Galli et al., "Pirfenidone and nintedanib for pulmonary fibrosis in clinical practice: Tolerability and adverse drug reactions"; Respirology; vol. 22, 1171-1178 (2017).

Graham et al., "Perspectives of people living with idiopathic pulmonary fibrosis: a qualitative and quantitative study"; BMC Pulmonary Medicine; vol. 25:221, 18 pages (2025).

Huang et al., "Pharmacokinetics, Safety and Tolerability of Pirfenidone and its Major Metabolite after Single and Multiple Oral Doses in Healthy Chinese Subjects under Fed Conditions."; Drug Res (Stuttg); vol. 63, 388-395 (2013).

International Search Report issued by the European Patent Office as International Searching Authority for International Application No. PCT/IB/2021052145, mailed May 21, 2021, 3 pages.

Nathan et al., "Dose modification and dose intensity during treatment with pirfenidone: analysis of pooled data from three multinational phase III trials"; BMJ Open Respir. Res.; vol. 5(1):e000323 (2018).

Noble et al., "Pirfenidone for idiopathic pulmonary fibrosis: analysis of pooled data from three multinational phase 3 trials"; Eur Respir J. vol. 47(1):243-253 (2016).

Raghu et al., "Treatment of Idiopathic Pulmonary Fibrosis with a New Antifibrotic Agent, Pirfenidone—Results of a Prospective, Open-label Phase II Study"; American Journal Of Respiratory And Critical Care Medicine; vol. 159:1061-1069 (1999).

Song et al., "Efficacy of low dose pirfenidone in idiopathic pulmonary fibrosis: real world experience from a tertiary university hospital"; Nature Reports (2020) 10:21218.

(56) References Cited

OTHER PUBLICATIONS

Study Details NCT04243837 LYT-100 in Patients with BCRL.

Study Details NCT04652518 LYT-100 in Post-Acute COVID19.

Study Details NCT05321420 LYT-100 in Patients with Idiopathic Pulmonary Fibrosis.

Study Details NCT06717100 Study to Determine Potential Drug-drug Interactions.

PureTech Initiates Phase 2a trial of LYT-100 (Deupirfenidone) in Lymphedema. Dec. 10, 2020.

PureTech Presents Phase 1 Data for LYT-100 at the European Respiratory Society International Congress 2021. Aug. 23, 2021.

PureTech Announces Publication of Phase 1 Results for LYT-100 in the Journal Clinical Pharmacology in Drug Development and Provides Timing Updates. Nov. 16, 2021.

PureTech's LYT-100 (Deupirfenidone) Achieves 50% Reduction in Healthy Older Adults Experiencing GI-Related Adverse Events Compared to Pirfenidone. Jan. 6, 2022.

PureTech Reports Results from Phase 2 Study of LYT-100-COV in Post-Acute Long COVID with Respiratory Complications. Jun. 14, 2022.

PureTech Initiates Late-Stage Clinical Study of Wholly-Owned Candidate LYT-100 (Deupirfenidone) in IPF and Advances LYT-200 (Anti-Galectin-9 mAb). Jun. 30, 2022.

PureTech Presents Additional Phase 1 Data for LYT-100 at American Thoracic Society 2022. May 16, 2022.

PureTech Presents Data for LYT-100 (Deupirfenidone) Supporting Design of Dose-Ranging Trial in Idiopathic Pulmonary Fibrosis (IPF) at European Respiratory Society International Congress 2022. Sep. 5, 2022.

PureTech Provides End of Year Report on Key Progress. Dec. 22, 2022.

PureTech Presents Data from LYT-100 (Deupirfenidone) Trial in Healthy Older Adults at CHEST Annual Meeting. Oct. 11, 2023.

PureTech Announces Completion of Enrollment in Phase 2b ELEVATE IPF Trial of LYT-100 (Deupirfenidone) in Idiopathic Pulmonary Fibrosis. Apr. 16, 2024.

PureTech to Present at CHEST 2024 Annual Meeting. Oct. 1, 2024.

PureTech Presents Research Highlighting Burden of Idiopathic Pulmonary Fibrosis and Use of a Bayesian Statistical Analysis for LYT-100 (Deupirfenidone). Oct. 9, 2024.

Extended European Search Report for corresponding EP23737759.3 mailed Dec. 1, 2025, 11 pages.

* cited by examiner

Low treatment Rates and Poor Tolerability with Current Antifibrotics for IPF

| LYT-100 Dose (mg TID) | Daily Dose (mg) | Parameter | Cohort | Lower Limit | Point Estimate | Upper Limit |
|---|---|---|---|---|---|---|
| 450 | 1350 | AUC24ss | 12A | 0.746308317 | 0.795353433 | 0.847621644 |
| 450 | 1350 | AUC24ss | 12B | 0.781796432 | 0.818575161 | 0.857084103 |
| 450 | 1350 | AUC24ss | Pooled | 0.776443094 | 0.805953306 | 0.83658511 |
| 450 | 1350 | CMAXss | 12A | 0.490375293 | 0.531749175 | 0.576613848 |
| 450 | 1350 | CMAXss | 12B | 0.515157044 | 0.565387983 | 0.620516745 |
| 450 | 1350 | CMAXss | Pooled | 0.516491704 | 0.551235434 | 0.588316331 |
| 500 | 1500 | AUC24ss | 12A | 0.829231464 | 0.883726036 | 0.941801827 |
| 500 | 1500 | AUC24ss | 12B | 0.868662703 | 0.909527956 | 0.95231567 |
| 500 | 1500 | AUC24ss | Pooled | 0.862714549 | 0.895503674 | 0.929539011 |
| 500 | 1500 | CMAXss | 12A | 0.544861437 | 0.590832416 | 0.640682053 |
| 500 | 1500 | CMAXss | 12B | 0.572396715 | 0.62820887 | 0.68946305 |
| 500 | 1500 | CMAXss | Pooled | 0.573879671 | 0.612483816 | 0.653684812 |
| 550 | 1650 | AUC24ss | 12A | 0.91215461 | 0.97209864 | 1.035982009 |
| 550 | 1650 | AUC24ss | 12B | 0.955528973 | 1.000480752 | 1.047547237 |
| 550 | 1650 | AUC24ss | Pooled | 0.948986004 | 0.985054041 | 1.022492913 |
| 550 | 1650 | CMAXss | 12A | 0.59934758 | 0.649915658 | 0.704750259 |
| 550 | 1650 | CMAXss | 12B | 0.629636387 | 0.691029758 | 0.758409354 |
| 550 | 1650 | CMAXss | Pooled | 0.631267638 | 0.673732198 | 0.719053294 |
| 600 | 1800 | AUC24ss | 12A | 0.995077757 | 1.060471244 | 1.130162192 |
| 600 | 1800 | AUC24ss | 12B | 1.042395243 | 1.091433546 | 1.142778804 |
| 600 | 1800 | AUC24ss | Pooled | 1.035257459 | 1.074604408 | 1.115446814 |
| 600 | 1800 | CMAXss | 12A | 0.653833724 | 0.7089989 | 0.768818464 |
| 600 | 1800 | CMAXss | 12B | 0.686876058 | 0.753850645 | 0.827355659 |
| 600 | 1800 | CMAXss | Pooled | 0.638655605 | 0.734980579 | 0.784421775 |
| 650 | 1950 | AUC24ss | 12A | 1.078000903 | 1.148843847 | 1.224342375 |
| 650 | 1950 | AUC24ss | 12B | 1.129261513 | 1.182386343 | 1.238010371 |
| 650 | 1950 | AUC24ss | Pooled | 1.121528914 | 1.164154776 | 1.208400715 |
| 650 | 1950 | CMAXss | 12A | 0.708319868 | 0.768082141 | 0.83288667 |
| 650 | 1950 | CMAXss | 12B | 0.74411573 | 0.816671532 | 0.896301964 |
| 650 | 1950 | CMAXss | Pooled | 0.746043572 | 0.796228961 | 0.849790256 |

FIG. 5

Extrapolated AUC and Cmax Comparisons for LYT-100 BID and TID dosing; % of pirfenidone at 801 mg TID

| Dose | AUC24ss | CMAXss |
|---|---|---|
| 450 mg TID | 80.6% | 55.1% |
| 500 mg TID | 89.6% | 61.2% |
| 550 mg TID | 98.5% | 67.4% |
| 600 mg TID | 107.5% | 73.5% |
| 650 mg TID | 116.4% | 79.6% |
| 700 mg TID | 125.4% | 85.7% |
| 850 mg TID | 152.6% | 104.1% |
| Dose | AUC24ss | CMAXss |
| 700 mg BID | 83.6% | 85.7% |
| 750 mg BID | 89.6% | 91.9% |
| 800 mg BID | 95.5% | 98.0% |
| 825 mg BID | 98.5% | 101.1% |
| 850 mg BID | 101.5% | 104.1% |
| 900 mg BID | 107.5% | 110.2% |
| 950 mg BID | 113.4% | 116.4% |
| 1000 mg BID | 119.4% | 122.5% |

FIG. 6A 850 mg BID LYT-100 provides same AUC and Cmax of parent drug as 801 mg TID pirfenidone

| LYT-100 Dose | AUC | Cmax |
|---|---|---|
| 850 mg BID | 102% of pirfenidone @ 801 mg TID | 104% of pirfenidone @ 801 mg TID |

FIG. 6B

Adverse Events for LYT-100 (850 mg BID) vs. pirfenidone (801 mg TID)

| System | LYT-100 (850 mg BID; n=35) | | Pirfenidone (801 mg TID; n=37) | |
|---|---|---|---|---|
| Gastrointestinal | 37.1% (13 events; 13 participants) | | 29.7% (13 events; 11 participants) | |
| Nervous | 45.7% (19 events; 16 participants) | | 35.1% (17 events; 13 participants) | |
| Disorder | Fed | Fasted | Fed | Fasted |
| Nausea | 11.4% | 20.6% | 8.1% | 20% |

FIG. 9

| | $C_{max}$ (µg/mL) | $T_{max}$ (hr) | $AUC_{0-24}$ (µg*hr/mL) |
|---|---|---|---|
| Parent | | | |
| LYT-100 550 mg TID (n = 21) | 8.35 (45.8) | 2.00 (1.00-4.00) | 97.7 (63.0) |
| LYT-100 824 mg TID (n = 19) | 12.2 (48.8) | 1.00 (1.00-3.00) | 146 (75.3) |
| Ratio (824/550)[a] | 1.45 (39.5) | — | 1.44 (60.8) |
| 5-Carboxy Metabolite | $C_{max}$ (µg/mL) | $T_{max}$ (hr) | $AUC_{0-24}$ (µg*hr/mL) |
| LYT-100 550 mg TID (n = 21) | 4.20 (40.3) | 2.00 (1.00-4.00) | 49.8 (59.1) |
| LYT-100 824 mg TID (n = 19) | 5.48 (60.5) | 2.00 (1.00-3.00) | 71.7 (87.4) |
| Ratio (824/550)[a] | 1.32 (36.5) | — | 1.42 (63.4) |

Stats shown as geometric mean (CV%) or Median (Min – Max) for Tmax

[a] Ratio statistics are derived from subjects who received both treatments and had 24 hours of data for each treatment (n = 18)

Mean Plasma Concentrations of 5-Carboxypirfenidone

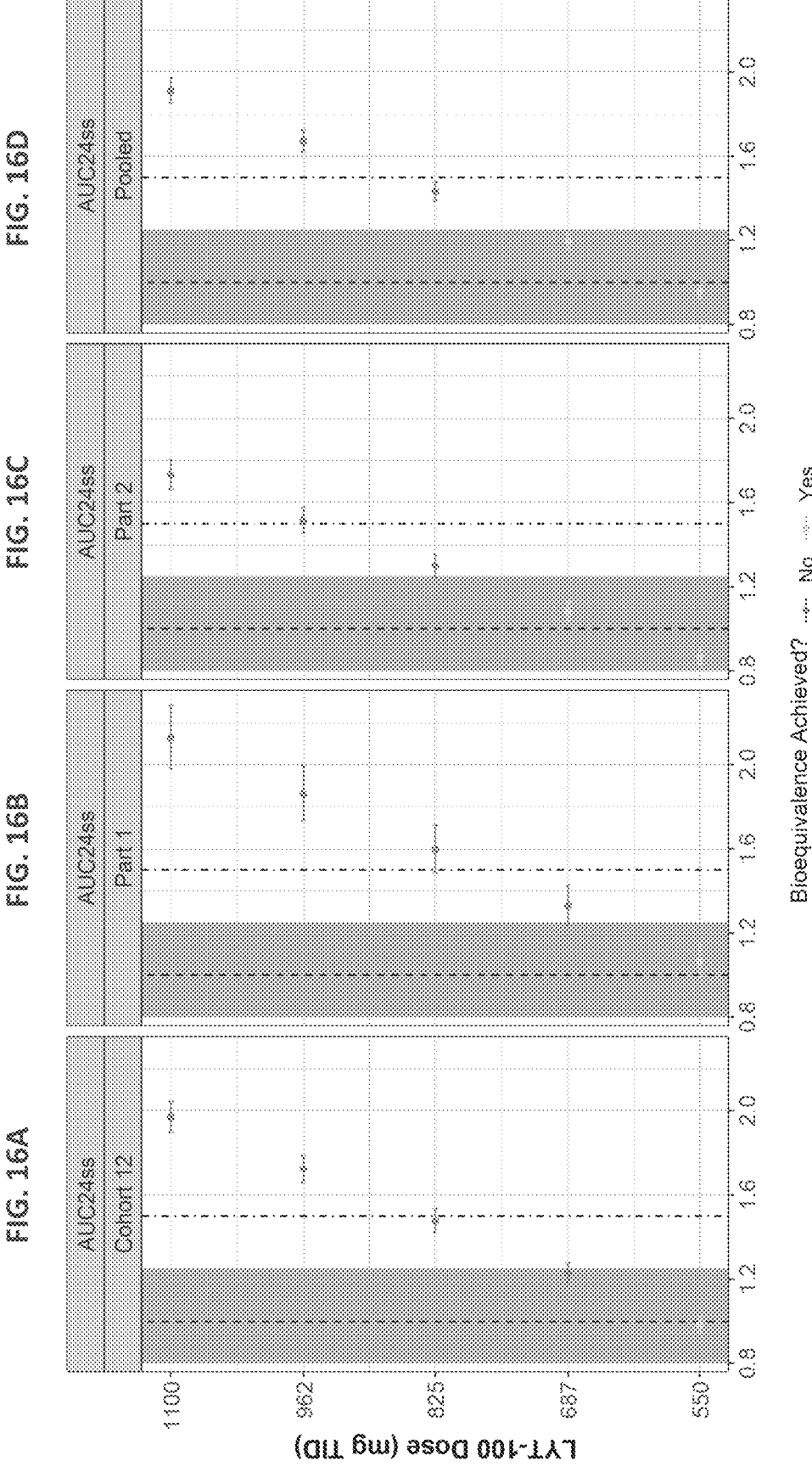

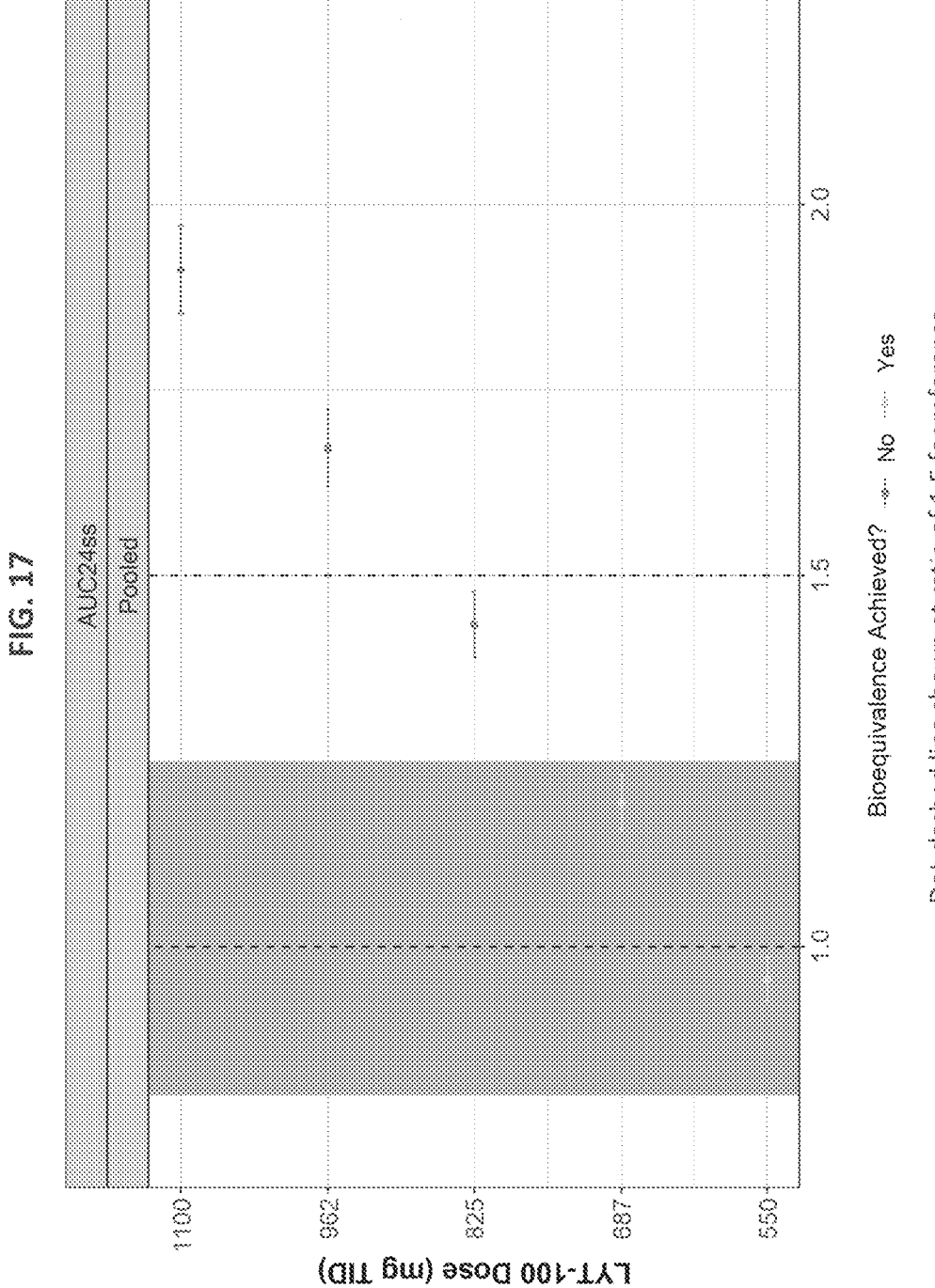

FIG. 18

| LYT-100 Dose (mg TID) | Cohort_Group | Point Estimate | Lower Limit | Upper Limit | BE achieved? |
|---|---|---|---|---|---|
| 550 | Cohort 12 | 0.985 | 0.949 | 1.022 | Yes |
| | Part 1 | 1.064 | 0.991 | 1.141 | Yes |
| | Part 2 | 0.866 | 0.831 | 0.901 | Yes |
| | Pooled | 0.956 | 0.926 | 0.986 | Yes |
| 687 | Cohort 12 | 1.230 | 1.185 | 1.277 | No |
| | Part 1 | 1.329 | 1.238 | 1.426 | No |
| | Part 2 | 1.081 | 1.038 | 1.126 | Yes |
| | Pooled | 1.194 | 1.157 | 1.231 | Yes |
| 825 | Cohort 12 | 1.478 | 1.423 | 1.534 | No |
| | Part 1 | 1.595 | 1.487 | 1.712 | No |
| | Part 2 | 1.298 | 1.247 | 1.352 | No |
| | Pooled | 1.434 | 1.390 | 1.479 | No |
| 962 | Cohort 12 | 1.723 | 1.660 | 1.788 | No |
| | Part 1 | 1.860 | 1.733 | 1.997 | No |
| | Part 2 | 1.514 | 1.454 | 1.576 | No |
| | Pooled | 1.672 | 1.620 | 1.724 | No |
| 1100 | Cohort 12 | 1.970 | 1.898 | 2.045 | No |
| | Part 1 | 2.127 | 1.982 | 2.283 | No |
| | Part 2 | 1.731 | 1.662 | 1.802 | No |
| | Pooled | 1.911 | 1.853 | 1.972 | No |

*All predictions assume a pirfenidone reference dose of 801 mg TID*

| LYT-100 Dose | AUC$_{0-24}$ | C$_{max}$ |
|---|---|---|
| 550 mg | 0.966 | 0.764 |
| 825 mg | 1.43 | 1.15 |

*vs pirfenidone 801 mg TID

Pirfenidone 801 mg

LYT-100 825 mg

LYT-100 550 mg

Plasma concentrations

Time

PK parameter predictions are illustrative only

FIG. 20

| Parameters | Placebo (N=85) | LYT-100 (N=92) | All Subjects (N=177) |
|---|---|---|---|
| Age (years) at Screening | | | |
| Mean | 52.7 | 56.6 | 54.7 |
| Age group n (%) | | | |
| < 65 years | 67 (78.8) | 69 (75.0) | 136 (76.8) |
| >= 65 year | 18 (21.2) | 23 (25.0) | 41 (23.2) |
| Sex n (%) | | | |
| Female | 35 (41.2) | 32 (34.8) | 67 (37.9) |
| Male | 50 (58.8) | 60 (65.2) | 110 (62.1) |

FIG. 21

| Parameters | Placebo (N=85) | LYT-100 (N=92) | All Subjects (N=177) |
|---|---|---|---|
| Ethnicity n (%) | | | |
| Hispanic or Latino | 8 (9.4) | 10 (10.9) | 18 (10.2) |
| Not Hispanic or Latino | 76 (89.4) | 82 (89.1) | 158 (89.3) |
| Not Reported | 1 (1.2) | 0 (0.0) | 1 (0.6) |
| Race n (%) | | | |
| White | 61 (71.8) | 79 (85.9) | 140 (79.1) |
| Asian | 20 (23.5) | 10 (10.9) | 30 (16.9) |
| Black or African American | 2 (2.4) | 1 (1.1) | 3 (1.7) |
| Other | 2 (2.4) | 2 (2.2) | 4 (2.4) |
| Time from COVID diagnosis to first dose of study drug (days) | | | |
| Mean | 58.1 | 56.3 | 57.1 |
| SD | 27.56 | 28.16 | 27.81 |
| Median | 57 | 51.5 | 54 |
| Minimum | 15 | 14 | 14 |
| Maximum | 127 | 125 | 127 |

|  | Placebo N (%) | LYT-100 N (%) | All Subjects N (%) |
|---|---|---|---|
| Received At Least One Dose Of Study Drug | 85 (100.0) | 92 (100.0) | 177 (100.0) |
| Completed Treatment Period Part A | 74 (87.1) | 73 (79.3) | 147 (83.1) |
| Discontinued Treatment Period Part A | 11 (12.9) | 19 (20.7) | 30 (16.9) |
| Reason For Premature Treatment Discontinuation |  |  |  |
| Lost To Follow-Up | 1 (1.2) | 1 (1.1) | 2 (1.1) |
| Physician Decision | 0 (0.0) | 1 (1.1) | 1 (0.6) |
| Withdrawal of Consent | 6 (7.1) | 3 (3.3) | 9 (5.1) |
| Adverse Event | 3 (3.5) | 11 (12.0) | 14 (7.9) |
| Other | 1 (1.2) | 3 (3.3) | 4 (2.4) |
| Completed Study Part A Enrolled in OLE | 57 (67.1) | 48 (52.2) | 105 (59.3) |

FIG. 22

|  | Placebo N (%) | LYT-100 N (%) | All Subjects N (%) |
|---|---|---|---|
| Number of subjects with at least one at least possibly related TEAE | 2 (2.4) | 8 (8.6) | 10 (5.6) |
| Photosensitivity Reaction | 0 (0.0) | 2 (2.2) | 2 (2.2) |
| Pruritus | 0 (0.0) | 1 (1.1) | 1 (1.1) |
| Dyspepsia | 1 (1.1) | 1 (1.1) | 2 (2.2) |
| Diarrhea | 0 (0.0) | 1 (1.1) | 1 (1.1) |
| Liver Function Test Increased | 0 (0.0) | 1 (1.1) | 1 (1.1) |
| Alanine Aminotransferase Increased | 0 (0.0) | 1 (1.1) | 1 (1.1) |
| Hepatic Steatosis | 0 (0.0) | 1 (1.1) | 1 (1.1) |
| Drug Hypersensitivity | 0 (0.0) | 1 (1.1) | 1 (1.1) |

Figure 24D:
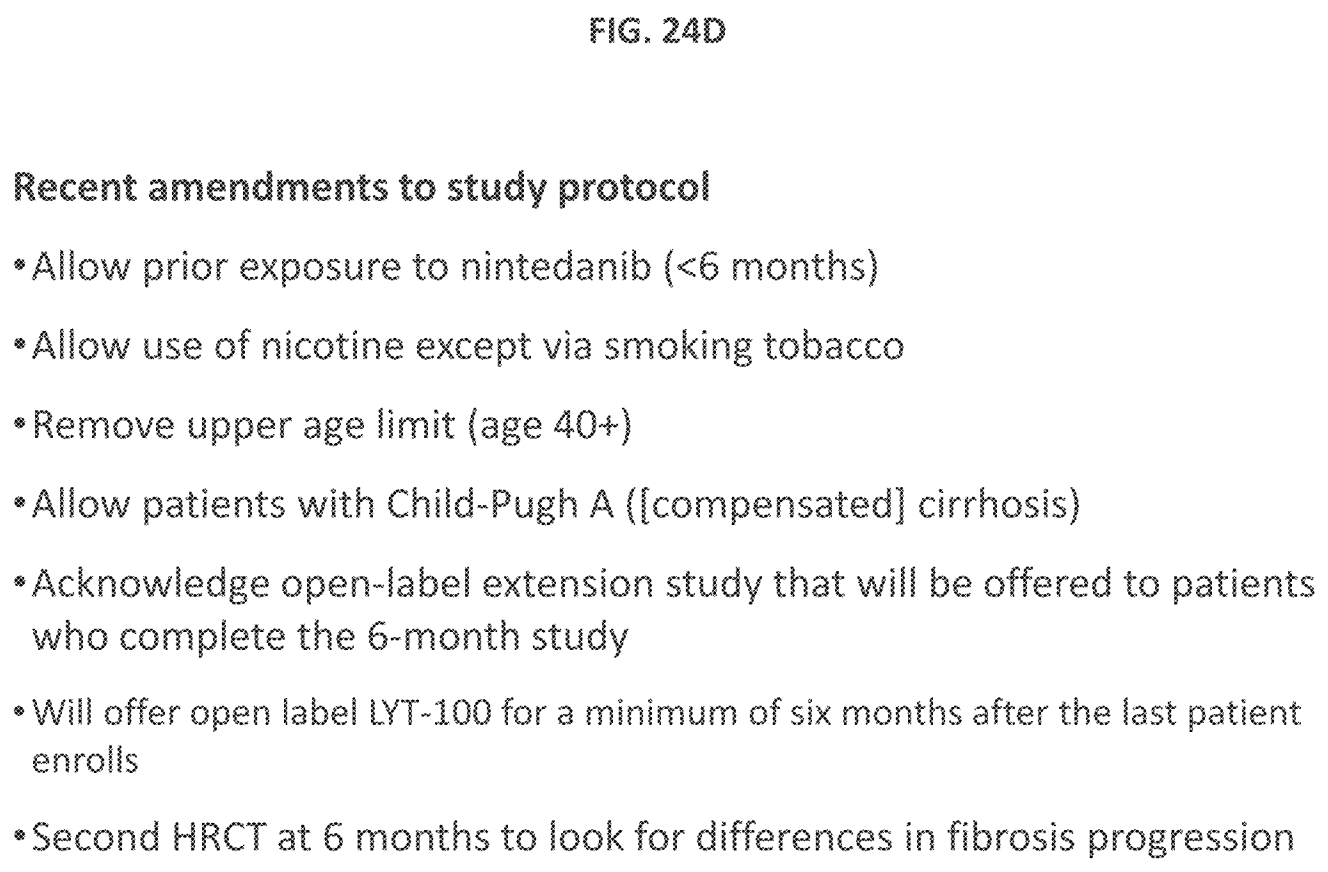

Recent amendments to study protocol

• Allow prior exposure to nintedanib (<6 months)

• Allow use of nicotine except via smoking tobacco

• Remove upper age limit (age 40+)

• Allow patients with Child-Pugh A ([compensated] cirrhosis)

• Acknowledge open-label extension study that will be offered to patients who complete the 6-month study

• Will offer open label LYT-100 for a minimum of six months after the last patient enrolls

• Second HRCT at 6 months to look for differences in fibrosis progression

FIG. 25A

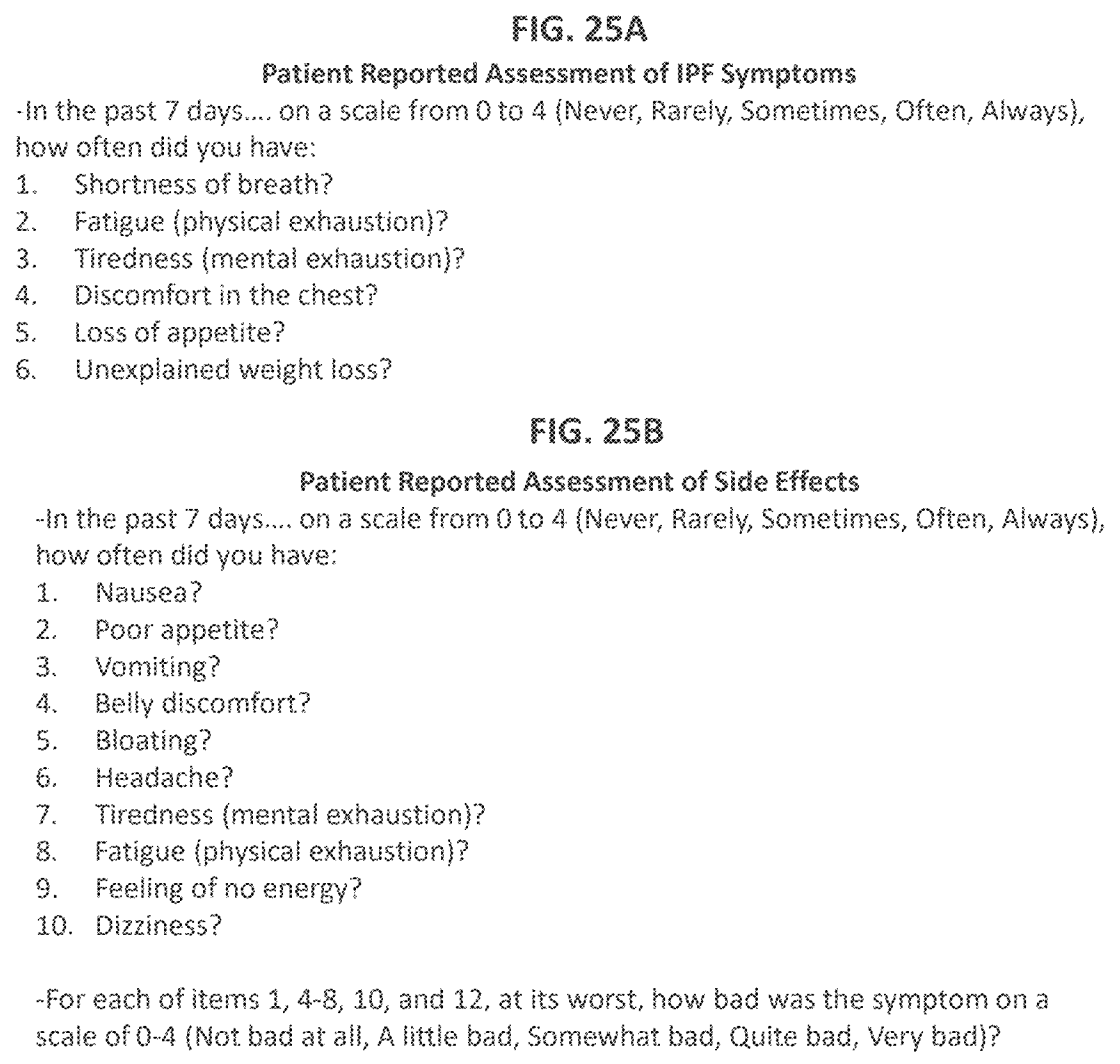

Patient Reported Assessment of IPF Symptoms

-In the past 7 days.... on a scale from 0 to 4 (Never, Rarely, Sometimes, Often, Always), how often did you have:

1. Shortness of breath?
2. Fatigue (physical exhaustion)?
3. Tiredness (mental exhaustion)?
4. Discomfort in the chest?
5. Loss of appetite?
6. Unexplained weight loss?

FIG. 25B

Patient Reported Assessment of Side Effects

-In the past 7 days.... on a scale from 0 to 4 (Never, Rarely, Sometimes, Often, Always), how often did you have:

1. Nausea?
2. Poor appetite?
3. Vomiting?
4. Belly discomfort?
5. Bloating?
6. Headache?
7. Tiredness (mental exhaustion)?
8. Fatigue (physical exhaustion)?
9. Feeling of no energy?
10. Dizziness?

-For each of items 1, 4-8, 10, and 12, at its worst, how bad was the symptom on a scale of 0-4 (Not bad at all, A little bad, Somewhat bad, Quite bad, Very bad)?

FIG. 26

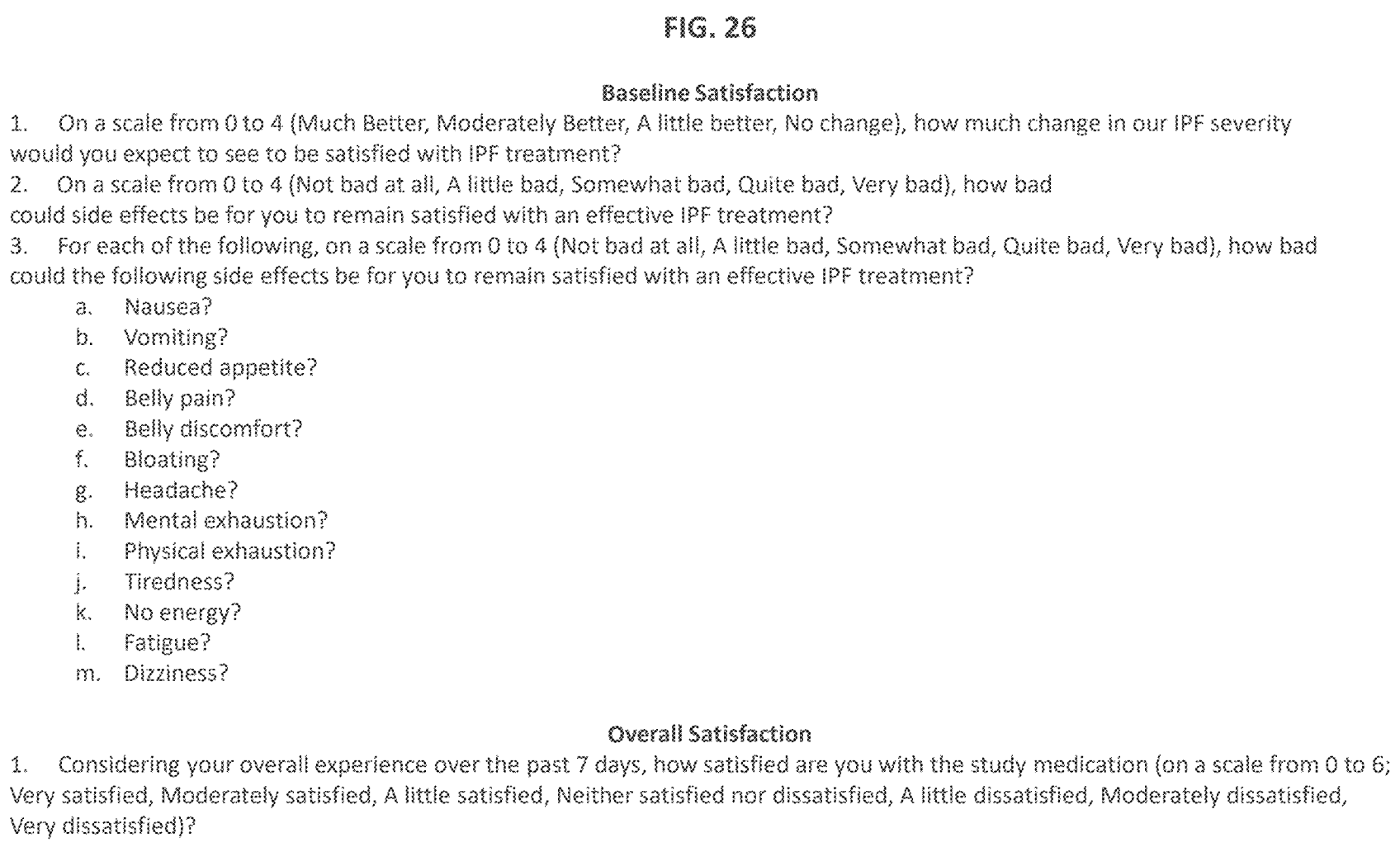

Baseline Satisfaction

1. On a scale from 0 to 4 (Much Better, Moderately Better, A little better, No change), how much change in our IPF severity would you expect to see to be satisfied with IPF treatment?

2. On a scale from 0 to 4 (Not bad at all, A little bad, Somewhat bad, Quite bad, Very bad), how bad could side effects be for you to remain satisfied with an effective IPF treatment?

3. For each of the following, on a scale from 0 to 4 (Not bad at all, A little bad, Somewhat bad, Quite bad, Very bad), how bad could the following side effects be for you to remain satisfied with an effective IPF treatment?

a. Nausea?
   b. Vomiting?
   c. Reduced appetite?
   d. Belly pain?
   e. Belly discomfort?
   f. Bloating?
   g. Headache?
   h. Mental exhaustion?
   i. Physical exhaustion?
   j. Tiredness?
   k. No energy?
   l. Fatigue?
   m. Dizziness?

Overall Satisfaction

1. Considering your overall experience over the past 7 days, how satisfied are you with the study medication (on a scale from 0 to 6; Very satisfied, Moderately satisfied, A little satisfied, Neither satisfied nor dissatisfied, A little dissatisfied, Moderately dissatisfied, Very dissatisfied)?

FIG. 27

Metabolism of Pirfenidone and LYT-100 in the Presence of Individual CYP Isozymes

| Compound | Metabolism Half-Life (t1/2) by CYP Isozyme (hr) | | |
|---|---|---|---|
| | CYP1A2* | CYP2D6** | CYCP2C19** |
| Pirfenidone | 3.18 ± 0.11 | 2.13 | 2.30 |
| LYT-100 | 9/08 ± 0.67 | 3.67 | 2.72 |

*Data represent Mean ± standard deviation for CYP1A2 (one lot of isozymes, tested in duplicate in two experiments
**Data represent Mean for CYP2D6 and 2C1: one lot of isozymes, tested in duplicate in one experiment Day 28

Lung weight (g)

Group 4 (Saline/Vehicle, (1% CMC in MilliQ water), Oral, QD) Treatment
Group 5 (Bleo/Vehicle, (1% CMC in MilliQ water), Oral, QD) Treatment
Group 6 (Bleo/LYT-100, 400 mg/kg, Oral, QD) Treatment
Group 7 (Bleo/Nintedanib, 60 mg/kg, Oral, BID) Treatment $p < 0.0001 = ****$

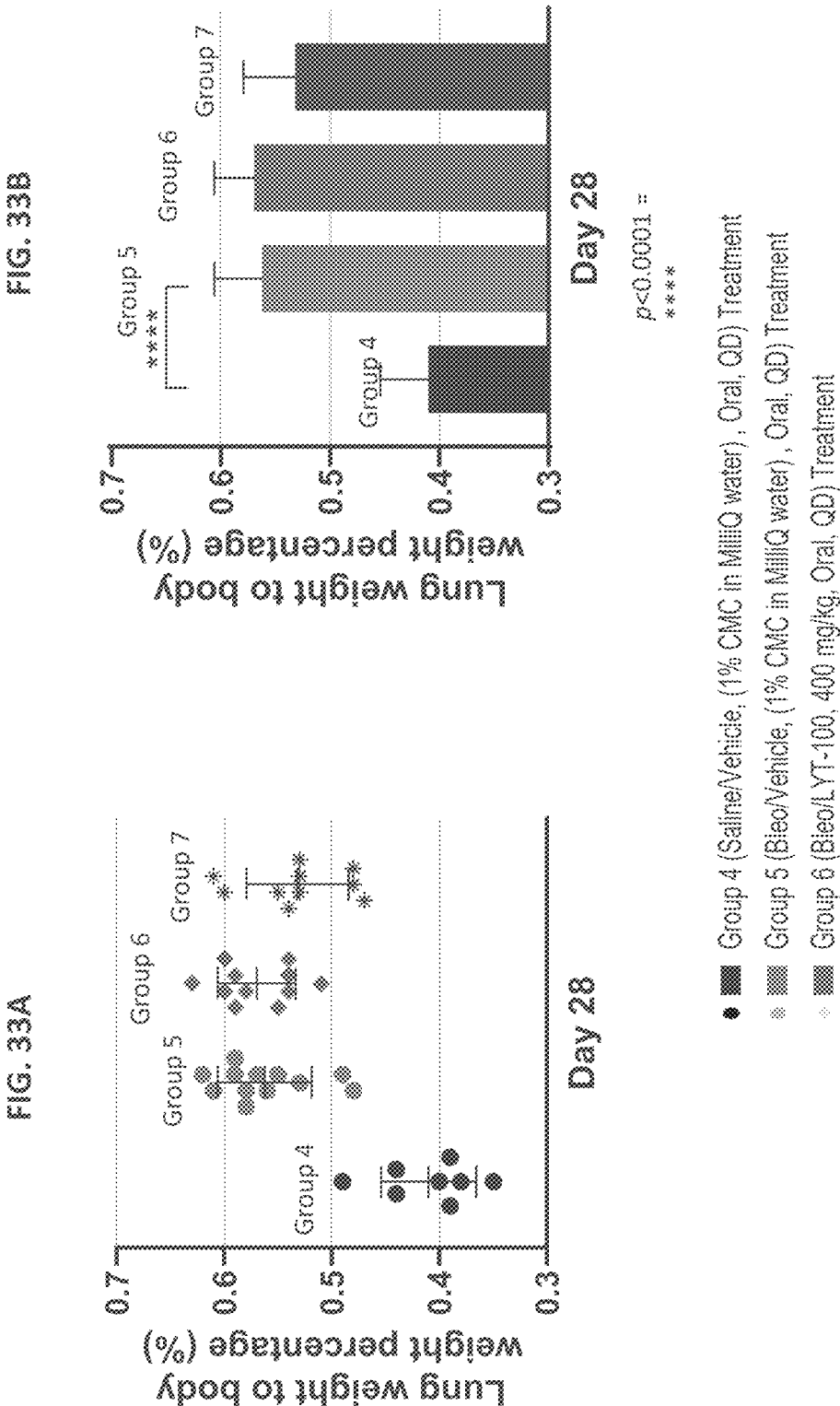

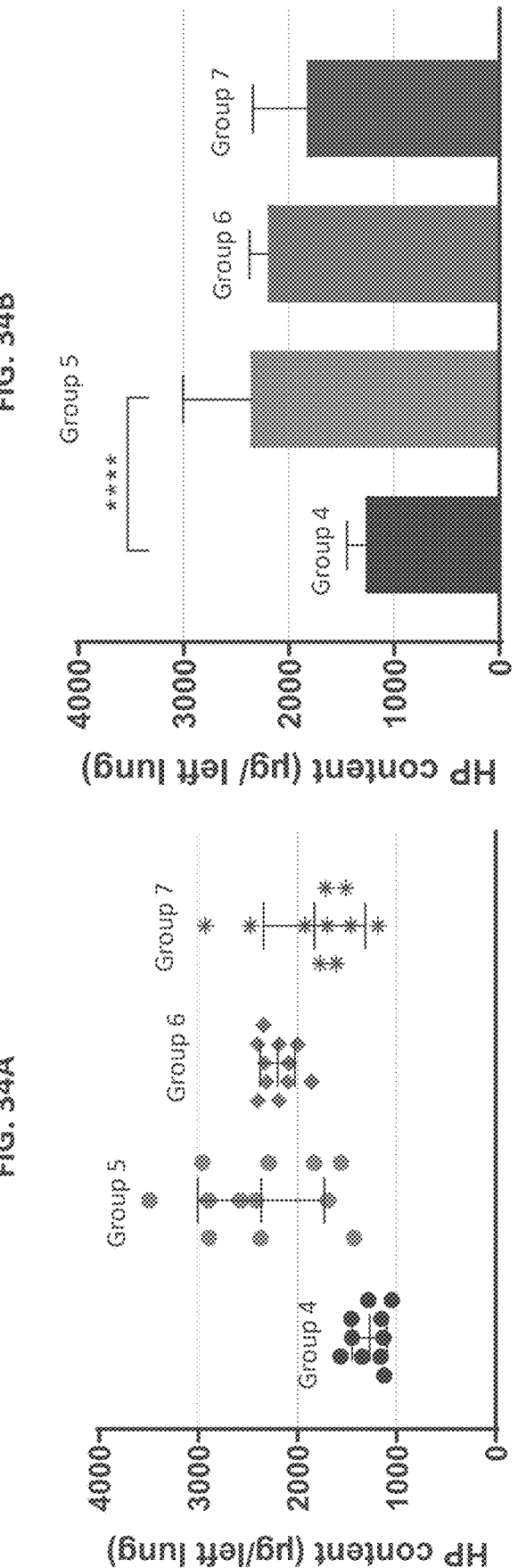

FIG. 35

Total Lung HP content (μg per left lung)

|  | Group 4 (Saline/Vehicle, (Saline), Oral, QD) Treatment | Group 5 (Bleo/Vehicle, (Saline), Oral, QD) Treatment | Group 6 (Bleo/LYT-100, 400 mg/kg, Oral, QD) Treatment | Group 7 (Bleo/Nintedanib, 60 mg/kg, Oral, BID) Treatment |
|---|---|---|---|---|
| Number of Values | 10 | 12 | 11 | 10 |
| Mean | 1276 | 2369 | 2203 | 1831 |
| Std. Deviation | 174.4 | 639.3 | 176.2 | 512.8 |
| Std. Error of Mean | 55.14 | 184.6 | 53.12 | 162.2 |
| Coefficient of variation | 13.67% | 26.98% | 7.997% | 28.00% |
| T-test p Value Group 4 vs 5 | -- | <0.0001 | -- | -- |
| T-test p Value Group 5 vs 6 | -- | -- | 0.4024 | -- |

FIG. 37

| | Group 4 (Saline/Vehicle, (Saline), Oral, QD) Treatment | Group 5 (Bleo/Vehicle, (Saline), Oral, QD) Treatment | Group 6 (Bleo/LYT-100, 400 mg/kg, Oral, QD) Treatment | Group 7 (Bleo/Nintedanib, 60 mg/kg, Oral, BID) Treatment |
|---|---|---|---|---|
| Number of Values | 10 | 12 | 11 | 10 |
| Mean | 2.838 | 4.453 | 3.724 | 3.872 |
| Std. Deviation | 0.3149 | 0.9325 | 0.4649 | 0.6235 |
| Std. Error of Mean | 0.09959 | 0.2692 | 0.1402 | 0.1972 |
| Coefficient of variation | 11.10% | 20.94% | 12.48% | 16.10% |
| T-test p Value Group 4 vs 5 | -- | <0.0001 | -- | -- |
| T-test p Value Group 5 vs 6 | -- | -- | 0.0202 | -- |

- Group 4 (Saline/Vehicle, (1% CMC in MilliQ water) , Oral, QD) Treatment
- Group 5 (Bleo/Vehicle, (1% CMC in MilliQ water) , Oral, QD) Treatment
- Group 6 (Bleo/LYT-100, 400 mg/kg, Oral, QD) Treatment
- Group 7 (Bleo/Nintedanib, 60 mg/kg,Oral, BID) Treatment

* Group 5 (Bleo/Vehicle, (1% CMC in MilliQ water), Oral, QD) Treatment
* Group 6 (Bleo/LYT-100, 400 mg/kg, Oral, QD) Treatment
* Group 7 (Bleo/Nintedanib, 60 mg/kg,Oral, BID) Treatment

FIG. 40

Adjusted Mean (SE) Change from Baseline in Forced Vital Capacity % Predicted (FVCpp) over Time by Frequentist Analysis - Part A Full Analysis Set Adjusted Mean (SE) Change from Baseline in Forced Vital Capacity (FVC) over Time by Frequentist Analysis - Part A Full Analysis Set

FIG. 45

| Population | Placebo | LYT-100 | Healthy Adults |
|---|---|---|---|
| | ELEVATE Placebo in IPF Patients¹ | ELEVATE DPF 825 mg in IPF Patients¹ | Healthy Adults Aged ≥60 Years² |
| FVC Decline Over 26 Weeks | ~112.5 mL | ~21.5 mL | ~15 – 25 mL |

Mean (SE) Change from Part A Baseline in Forced Vital Capacity (FVC) over Time - Full Analysis Set

FIG. 49

METHODS OF TREATING IDIOPATHIC PULMONARY FIBROSIS WITH DEUPIRFENIDONE

CROSS-REFERENCE TO RELATED APPLICATIONS

This application is a continuation of U.S. application Ser. No. 19/286,158, filed Jul. 30, 2025, which is a continuation of U.S. application Ser. No. 18/982,798, filed Dec. 16, 2024, which is a continuation-in-part of U.S. application Ser. No. 18/806,289, filed Aug. 15, 2024, which is a continuation of U.S. application Ser. No. 18/437,614, filed Feb. 9, 2024, which is a continuation of U.S. application Ser. No. 18/330, 154, filed Jun. 6, 2023, which is a continuation of U.S. application Ser. No. 17/144,018, filed Jan. 7, 2021, which is a continuation of U.S. application Ser. No. 16/572,595, filed Sep. 16, 2019, which claims the benefit of U.S. Provisional Application No. 62/884,984, filed Aug. 9, 2019, and claims the benefit of U.S. Provisional Application No. 62/839,256, filed Apr. 26, 2019, and claims the benefit of U.S. Provisional Application No. 62/750,377, filed Oct. 25, 2018, and claims the benefit of U.S. Provisional Application No. 62/731,570, filed Sep. 14, 2018; and said Ser. No. 18/982, 798 is also a continuation-in-part of U.S. application Ser. No. 18/758,783, filed Jun. 28, 2024, which is a continuation of International Application No. PCT/US2023/060185, filed Jan. 5, 2023, which claims the benefit of U.S. Provisional Application No. 63/432,208, filed Dec. 13, 2022, and claims the benefit of U.S. Provisional Application No. 63/431,530, filed Dec. 9, 2022, and claims the benefit of U.S. Provisional Application No. 63/403,481, filed Sep. 2, 2022, and claims the benefit of U.S. Provisional Application No. 63/374,362, filed Sep. 1, 2022, and claims the benefit of U.S. Provisional Application No. 63/356,653, filed Jun. 29, 2022, and claims the benefit of U.S. Provisional Application No. 63/352,107, filed Jun. 14, 2022, and claims the benefit of U.S. Provisional Application No. 63/341,828, filed May 13, 2022, and claims the benefit of U.S. Provisional Application No. 63/341,269, filed May 12, 2022, and claims the benefit of U.S. Provisional Application No. 63/341,279, filed May 12, 2022, and claims the benefit of U.S. Provisional Application No. 63/341,281, filed May 12, 2022, and claims the benefit of U.S. Provisional Application No. 63/326,132, filed Mar. 31, 2022, and claims the benefit of U.S. Provisional Application No. 63/326,129, filed Mar. 31, 2022, and claims the benefit of U.S. Provisional Application No. 63/296,818, filed Jan. 5, 2022, and claims the benefit of U.S. Provisional Application No. 63/296,843, filed Jan. 5, 2022, and claims the benefit of U.S. Provisional Application No. 63/296,826, filed Jan. 5, 2022; and said Ser. No. 18/982,798 is also a continuation-in-part of U.S. application Ser. No. 18/150, 055, filed Jan. 4, 2023, which is a continuation of International Application No. PCT/US2021/040551, filed Jul. 6, 2021, which claims the benefit of U.S. Provisional Application No. 63/175,063, filed Apr. 15, 2021, and claims the benefit of U.S. Provisional Application No. 63/135,374, filed Jan. 8, 2021, and claims the benefit of U.S. Provisional Application No. 63/123,989, filed Dec. 10, 2020, and claims the benefit of 63/121,168, filed Dec. 3, 2020, and claims the benefit of U.S. Provisional Application No. 63/116,520, filed Nov. 20, 2020, and claims the benefit of U.S. Provisional Application No. 63/087,116, filed Oct. 2, 2020, and claims the benefit of U.S. Provisional Application No. 63/048,564, filed Jul. 6, 2020.

BACKGROUND

There exists a need for a therapy that can slow disease progression in patients with idiopathic pulmonary fibrosis (IPF) while having a superior tolerability profile compared to pirfenidone and other antifibrotics approved for treatment of IPF. High doses of pirfenidone are required to achieve efficacy in the treatment of IPF. However, tolerability issues, including dose-limiting side effects and toxicity associated with gastrointestinal intolerability (e.g., nausea, diarrhea, vomiting, dyspepsia, and other GI events), headache, dizziness, and photosensitivity, as well as other adverse side-effects, limits current treatment for IPF. Such dose-limiting side effects and/or toxicity typically require, and are therefore managed by, one or more of the following treatment options: administration of lower, less efficacious doses, periodic reduction(s) of efficacious dose, periodic or permanent cessation of drug (treatment interruption or discontinuation), and/or inability to maintain patients on a sustained treatment program or long-term maintenance dose (e.g., without treatment interruption).

These tolerability issues significantly limit the usage of pirfenidone, resulting in dose reduction, switch of drug, and/or interruption or discontinuation of antifibrotic therapy. It is estimated that about 75% of IPF patients are not on standard of care therapy as a consequence of poor drug tolerability, and that over 40% of patients eventually discontinue antifibrotic therapy, in large part due to tolerability issues (FIG. 1A). In particular, studies have indicated that only 21% of patients who initiated therapy with pirfenidone remained on pirfenidone at the recommended dose after 2 years (FIG. 1B). (Dempsey, 2021). Such poor tolerability, and the current treatment management thereof, including a significant incidence of permanent dose reduction and treatment discontinuation, is associated with reduced clinical efficacy and a lost opportunity for full clinical benefit.

Such poor tolerability is associated with reduced clinical efficacy and is a major unmet need in the treatment of IPF. Accordingly, there exists a need for a therapy having a superior tolerability profile compared to current antifibrotics for the treatment of IPF.

SUMMARY

In one aspect is provided a method of treating Idiopathic Pulmonary Fibrosis (IPF) in a subject in need thereof, the method comprising administering to the subject a total daily dose from about 1650 mg to about 2500 mg of a deuterium-enriched pirfenidone having the structure:

(LYT-100)

wherein the IPF is treated in the subject.

In one aspect is provided a method of treating Idiopathic Pulmonary Fibrosis (IPF) in a subject in need thereof, the method comprising administering to the subject a total daily dose of 1650 mg to 2475 mg of a deuterium-enriched pirfenidone having the structure:

(LYT-100)

wherein the IPF is treated in the subject.

In one aspect is provided a method of treating Idiopathic Pulmonary Fibrosis (IPF) in a subject in need thereof, the method comprising administering to the subject a total daily dose of 1650 mg of a deuterium-enriched pirfenidone having the structure:

(LYT-100)

wherein the IPF is treated in the subject.

In one aspect is provided a method of treating Idiopathic Pulmonary Fibrosis (IPF) in a subject in need thereof, the method comprising administering to the subject a total daily dose of 2475 mg of a deuterium-enriched pirfenidone having the structure:

(LYT-100)

wherein the IPF is treated in the subject.

In one aspect, is provided a method of treating Idiopathic Pulmonary Fibrosis (IPF) in a subject in need thereof, the method comprising administering to a subject a total daily dose from about 825 mg to about 2500 mg of a deuterium-enriched pirfenidone having the structure:

(LYT-100)

wherein the IPF is treated in the subject.

In one aspect, is provided a method of treating Idiopathic Pulmonary Fibrosis (IPF) in a subject in need thereof, the method comprising administering to a subject a total daily dose of 825 mg of a deuterium-enriched pirfenidone having the structure:

(LYT-100)

wherein the IPF is treated in the subject.

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is the same or about the same as the systemic exposure of pirfenidone achieved when pirfenidone is administered at a total daily dose of 2403 mg.

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is greater than the systemic exposure of pirfenidone achieved when pirfenidone is administered at a total daily dose of 2403 mg. In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is greater than the systemic exposure of pirfenidone achieved when pirfenidone is administered at a total daily dose of 2403 mg, wherein the total daily dose of pirfenidone is administered in three doses of 801 mg each (801 mg TID).

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is about 1.1× to about 1.9× the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is about 1.25× to about 1.75× the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the dose of LYT-100 administered achieves a systemic exposure that is 1.25×-1.75× the systemic exposure of pirfenidone achieved when pirfenidone is administered at a total daily dose of 2403 mg. In some embodiments, the administering is at a dose that achieves a systemic exposure of LYT-100 in the subject which is about 1.4× to 1.6× the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is 1.4× to 1.5× the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is about 1.5× the systemic exposure of pirfenidone achieved when pirfenidone is administered at a total daily dose of 2403 mg, optionally wherein the total daily dose of pirfenidone is administered in three doses of 801 mg each (801 mg TID).

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is about 85% to about 125% the systemic exposure of pirfenidone achieved when pirfenidone is administered at a total daily dose of 2403 mg, optionally wherein the total daily dose of pirfenidone is administered in three doses of 801 mg each (801 mg TID).

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is 125% to 175% the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is 140% to 160% greater than the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is 140% to 150% greater than the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is about 150% of the systemic exposure of pirfenidone achieved when pirfenidone is administered at a total daily dose of 2403 mg, optionally wherein the total daily dose of pirfenidone is administered in three doses of 801 mg each (801 mg TID).

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is about 10% to about 90% greater than the systemic exposure of pirfenidone achieved when pirfenidone is administered at a total daily dose of 2403 mg, optionally wherein the total daily dose of pirfenidone is administered in three doses of 801 mg each (801 mg TID).

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a systemic exposure of LYT-100 in the subject which is about 25% to about 75% greater than the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is 25% to 75% greater than the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is 40% to 60% greater than the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is 40% to 50% greater than the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a systemic exposure of LYT-100 in the subject which is about 50% greater than the systemic exposure of pirfenidone achieved when pirfenidone is administered at a total daily dose of 2403 mg, optionally wherein the total daily dose of pirfenidone is administered in three doses of 801 mg each (801 mg TID).

In some embodiments of these methods, the dose of LYT-100 is 550 mg TID.

In one aspect is provided a method of treating Idiopathic Pulmonary Fibrosis (IPF), the method comprising administering to a subject in need thereof a deuterium-enriched pirfenidone having the structure:

(LYT-100)

8 wherein the administering is at a dose that achieves a $C_{max}$ of LYT-100 in the subject which is the same or about the same as the $C_{max}$ of pirfenidone achieved when pirfenidone is administered at a total daily dose of 2403 mg, optionally wherein the total daily dose of pirfenidone is administered in three doses of 801 mg each (801 mg TID).

In one aspect is provided a method of treating Idiopathic Pulmonary Fibrosis (IPF), the method comprising administering to a subject in need thereof a deuterium-enriched pirfenidone having the structure:

(LYT-100)

wherein the administering is at a dose that achieves a $C_{max}$ of LYT-100 in the subject which is equivalent to the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a $C_{max}$ of LYT-100 in the subject which is about 105% to about 125% of the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a $C_{max}$ of LYT-100 in the subject which is about 110% to about 120% of the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the administering is at a dose that achieves a $C_{max}$ of LYT-100 in the subject which is about 115% of the $C_{max}$ of pirfenidone achieved when pirfenidone is administered at a total daily dose of 2403 mg, optionally wherein the total daily dose of pirfenidone is administered in three doses of 801 mg each (801 mg TID).

In some embodiments of these methods, the dose of LYT-100 is 825 mg TID.

In any of the methods provided herein, the administration of LYT-100 is three times daily.

In some embodiments, the method comprises administering a total daily dose of 825 mg LYT-100 administered in three equal administrations of 275 mg each. In some embodiments, the method comprises administering a total daily dose of 1650 mg LYT-100 administered in three equal administrations of 550 mg each. In some embodiments, the method comprises administering a total daily dose of 2475 mg LYT-100 administered in three equal administrations of 825 mg each. In some embodiments, each dose is administered with approximately 6 hours between each dose.

In one aspect is provided a method of treating Idiopathic Pulmonary Fibrosis (IPF), the method comprising administering to a subject in need thereof a total daily dose of 825 mg of a deuterium-enriched pirfenidone having the structure:

(LYT-100)

wherein the LYT-100 is administered in in three equal administrations of 275 mg each and wherein IPF is treated in the subject.

In one aspect is provided a method of treating Idiopathic Pulmonary Fibrosis (IPF), the method comprising administering to a subject in need thereof a total daily dose of 1650 mg of a deuterium-enriched pirfenidone having the structure:

(LYT-100)

wherein the LYT-100 is administered in in three equal administrations of 550 mg each and wherein IPF is treated in the subject.

In one aspect is provided a method of treating Idiopathic Pulmonary Fibrosis (IPF), the method comprising administering to a subject in need thereof a total daily dose of 2475 mg of a deuterium-enriched pirfenidone having the structure:

(LYT-100)

wherein the LYT-100 is administered in in three equal administrations of 825 mg each and wherein IPF is treated in the subject.

In some embodiments, the LYT-100 is administered without regard to food. In some embodiments, the LYT-100 is administered without food. In some embodiments, the LYT-100 is administered with food.

In some embodiments, the LYT-100 is administered orally without food in three daily doses of 275 mg each. In some embodiments, the LYT-100 is administered orally with food in three daily doses of 275 mg each. In some embodiments, the LYT-100 is administered orally without food in three daily doses of 550 mg each. In some embodiments, the LYT-100 is administered orally with food in three daily doses of 550 mg each.

In some embodiments, the LYT-100 is administered orally without food in three daily doses of 825 mg each. In some embodiments, the LYT-100 is administered orally with food in three daily doses of 825 mg each.

In some embodiments, the method comprises administering LYT-100 at a first total daily dose of 825 mg for a first period and a second total daily maintenance dose of 1650 mg. In some embodiments, the method comprises administering LYT-100 at a first total daily dose of 1650 mg for a first period and a second total daily maintenance dose of 2475 mg. In some embodiments, the method comprises administering LYT-100 at a first total daily dose of 825 mg for a first period, a second total daily dose of 1650 mg for a second period, and then a total maintenance dose of 2475 mg. In some embodiments, the method comprises administering LYT-100 at a first total daily dose of 825 mg for a first period of about 7 days and a second total daily maintenance dose of 1650 mg. In some embodiments, the method comprises administering LYT-100 at a first total daily dose of 1650 mg for a first period of about 7 days and a second total daily maintenance dose of 2475 mg. In some embodiments, the method comprises administering LYT-100 at a first total daily dose of 825 mg for a first period of about 7 days, a second total daily dose of 1650 mg for a second period of about 7 days, and then a total maintenance dose of 2475 mg. In some embodiments, the method comprises administering LYT-100 at a first total daily dose of 825 mg for a first period of about 14 days and a second total daily maintenance dose of 1650 mg. In some embodiments, the method comprises administering LYT-100 at a first total daily dose of 1650 mg for a first period of about 14 days and a second total daily maintenance dose of 2475 mg. In some embodiments, the method comprises administering LYT-100 at a first total daily dose of 825 mg for a first period of about 14 days, a second total daily dose of 1650 mg for a second period of about 14 days, and then a total maintenance dose of 2475 mg. In some embodiments, the method comprises administering LYT-100 at a first total daily dose of 825 mg for a first period of 7-14 days and a second total daily maintenance dose of 1650 mg. In some embodiments, the method comprises administering LYT-100 at a first total daily dose of 1650 mg for a first period of 7-14 days and a second total daily maintenance dose of 2475 mg. In some embodiments, the method comprises administering LYT-100 at a first total daily dose of 825 mg for a first period of 7-14 days, a second total daily dose of 1650 mg for a second period of 7-14 days, and then a total maintenance dose of 2475 mg.

In some embodiments, the method comprises administering LYT-100 in three daily doses of 275 mg each for a first period and in three daily doses of 550 mg each for a second maintenance dose. In some embodiments, the method comprises administering LYT-100 in three daily doses of 550 mg each for a first period and in three daily doses of 825 mg each for a second maintenance dose. In some embodiments, the method comprises administering LYT-100 in three daily doses of 275 mg each for a first period, in three daily doses of 550 mg each for a second period, and then in three daily doses of 825 mg each for a maintenance dose. In some embodiments, the method comprises administering LYT-100 in three daily doses of 275 mg each for a first period of about 7 days and in three daily doses of 550 mg each for a second maintenance dose. In some embodiments, the method comprises administering LYT-100 in three daily doses of 550 mg each for a first period of about 7 days and in three daily doses of 825 mg each for a second maintenance dose. In some embodiments, the method comprises administering LYT-100 in three daily doses of 275 mg each for a first period of about 7 days, in three daily doses of 550 mg each for a second period of about 7 days, and then in three daily doses of 825 mg each for a maintenance dose. In some embodiments, the method comprises administering LYT-100 in three daily doses of 275 mg each for a first period of about 14 days and in three daily doses of 550 mg each for a second maintenance dose. In some embodiments, the method comprises administering LYT-100 in three daily doses of 550 mg each for a first period of about 14 days and in three daily doses of 825 mg each for a second maintenance dose. In some embodiments, the method comprises administering LYT-100 in three daily doses of 275 mg each for a first period of about 14 days, in three daily doses of 550 mg each for a second period of about 14 days, and then in three daily doses of 825 mg each for a maintenance dose. In some embodiments, the method comprises administering LYT-100 in three daily doses of 275 mg each for a first period of 7-14 days and in three daily doses of 550 mg each for a second maintenance dose. In some embodiments, the method comprises administering LYT-100 in three daily doses of 550 mg each for a first period of 7-14 days and in three daily doses of 825 mg each for a second maintenance dose. In some embodiments, the method comprises administering LYT-100 in three daily doses of 275 mg each for a first period of 7-14 days, in three daily doses of 550 mg each for a second period of 7-14 days, and then in three daily doses of 825 mg each for a maintenance dose.

In any of the above embodiments, the LYT-100 is administered orally without food. In any of the above embodiments, the LYT-100 is administered orally with food. In any of the above embodiments, the LYT-100 is administered orally without regard to food. In any of the above embodiments, the total daily dose, e.g., 825 mg, 1650 mg or 2475 mg may be adjusted to lower daily dose, for example, as described elsewhere in the specification.

In some embodiments, the method comprises administering the LYT-100 at a dose that achieves a systemic exposure of LYT-100 in the subject which is about 140% to about 160% of the systemic exposure of pirfenidone achieved when pirfenidone is administered at a total daily dose of 2403 mg, optionally wherein the total daily dose of pirfenidone is administered in three doses of 801 mg each (801 mg TID). In some embodiments, the method comprises administering the LYT-100 at a dose that achieves a systemic exposure of LYT-100 in the subject which is about 150% of the systemic exposure of pirfenidone achieved when pirfenidone is administered at a total daily dose of 2403 mg, optionally wherein the total daily dose of pirfenidone is administered in three doses of 801 mg each (801 mg TID). In some of these embodiments, the dose of LYT-100 is 825 mg TID. In any of these embodiments, the adverse events (AEs) are similar to or about the same as the AEs observed when pirfenidone is administered at a total daily dose of 2403 mg, optionally wherein the total daily dose of pirfenidone is administered in three doses of 801 mg each (801 mg TID). In any of these embodiments, the incidence, occurrence, or frequency of adverse events (AEs) is similar to or about the same as the incidence, occurrence, or frequency of AEs observed when pirfenidone is administered at a total daily dose of 2403 mg, optionally wherein the total daily dose of pirfenidone is administered in three doses of 801 mg each (801 mg TID). In any of these embodiments, the safety and tolerability profile is similar to or about the same as the safety and tolerability profile observed when pirfenidone is administered at a total daily dose of 2403 mg, optionally wherein the total daily dose of pirfenidone is administered in three doses of 801 mg each (801 mg TID).

In some embodiments, the dose of LYT-100 that achieves the systemic exposure of LYT-100 in the subject which is about 150% of the systemic exposure of pirfenidone (administered at a total daily dose of 2403 mg) achieves a $C_{max}$ of LYT-100 in the subject which is about the same as the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the dose of LYT-100 that achieves the systemic exposure of LYT-100 in the subject which is about 150% of the systemic exposure of pirfenidone (administered at a total daily dose of 2403 mg) achieves a $C_{max}$ of LYT-100 in the subject which is equivalent to the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the dose of LYT-100 that achieves the systemic exposure of LYT-100 in the subject which is about 150% of the systemic exposure of pirfenidone (administered at a total daily dose of 2403 mg) achieves a $C_{max}$ of LYT-100 in the subject which is about 105% to about 125% of the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the dose of LYT-100 that achieves the systemic exposure of LYT-100 in the subject which is about 150% of the systemic exposure of pirfenidone (administered at a total daily dose of 2403 mg) achieves a $C_{max}$ of LYT-100 in the subject which is about 110% to about 120% of the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the dose of LYT-100 that achieves the systemic exposure of LYT-100 in the subject which is about 150% of the systemic exposure of pirfenidone (administered at a total daily dose of 2403 mg) achieves a $C_{max}$ of LYT-100 in the subject which is about 115% of the $C_{max}$ of pirfenidone achieved when pirfenidone is administered at a total daily dose of 2403 mg, optionally wherein the total daily dose of pirfenidone is administered in three doses of 801 mg each (801 mg TID). In some embodiments, the dose of LYT-100 is 825 mg TID. In any of these embodiments, the adverse events (AEs) are similar to or about the same as the AEs observed when pirfenidone is administered at a total daily dose of 2403 mg, optionally wherein the total daily dose of pirfenidone is administered in three doses of 801 mg each (801 mg TID). In any of these embodiments, the incidence, occurrence, or frequency of adverse events (AEs) is similar to or about the same as the incidence, occurrence, or frequency of AEs observed when pirfenidone is administered at a total daily dose of 2403 mg, optionally wherein the total daily dose of pirfenidone is administered in three doses of 801 mg each (801 mg TID). In any of these embodiments, gastrointestinal-related adverse events associated with the administration LYT-100 are similar to gastrointestinal-related adverse events associated with the administration pirfenidone, optionally wherein the total daily dose of pirfenidone is administered at a total daily dose of 2403 mg, and optionally wherein the total daily dose of pirfenidone is administered in three doses of 801 mg each (801 mg TID).

In any of these embodiments, the safety and tolerability profile is similar to or about the same as the safety and tolerability profile observed when pirfenidone is administered at a total daily dose of 2403 mg, optionally wherein the total daily dose of pirfenidone is administered in three doses of 801 mg each (801 mg TID).

In any of the embodiments herein, the method of treating prevents, delays, or slows the progression of impaired respiratory function or IPF in the subject.

In one aspect is provided a method of treating Idiopathic Pulmonary Fibrosis (IPF), the method comprising administering to a subject in need thereof a total daily dose of 825 mg administered in three equal doses of 275 mg each of a deuterium-enriched pirfenidone having the structure:

(LYT-100)

wherein the LYT-100 administration prevents, delays, or slows the progression of impaired respiratory function in the subject.

In one aspect is provided a method of treating Idiopathic Pulmonary Fibrosis (IPF), the method comprising administering to a subject in need thereof a total daily dose of 1650 mg administered in three equal doses of 550 mg each of a deuterium-enriched pirfenidone having the structure:

(LYT-100)

wherein the LYT-100 administration prevents, delays, or slows the progression of impaired respiratory function in the subject.

In one aspect is provided a method of treating Idiopathic Pulmonary Fibrosis (IPF), the method comprising administering to a subject in need thereof a total daily dose of 2475 mg administered in three equal doses of 825 mg each of a deuterium-enriched pirfenidone having the structure:

(LYT-100)

wherein the LYT-100 administration prevents, delays, or slows the progression of impaired respiratory function in the subject.

In any of the methods described herein, the method of treating prevents, delays, or slows the progression of impaired respiratory function or IPF in the subject. In some embodiments, progression of IPF is delayed, slowed or arrested.

Respiratory function, e.g., impaired respiratory function, can be measured using various methods. In some embodiments, the respiratory function is determined by measuring Forced Vital Capacity (FVC) in the subject. In some embodiments, the progression of impaired respiratory function in the subject is determined by measuring a change in FVC over a period of treatment. In some embodiments, the period of treatment for measuring change in FVC is from baseline to a treatment period selected from: at least 26 weeks, at least 52 weeks, at least 78 weeks, or at least 104 weeks. In some embodiments, the period of treatment for measuring change in FVC is at least 26 weeks. In some embodiments, the change in FVC is measured from baseline to at least 26 weeks of treatment. In some embodiments, the period of treatment for measuring change in FVC is at least 52 weeks. In some embodiments, the change in FVC is measured from baseline to at least 52 weeks of treatment.

In some embodiments, the change in FVC is measured as a rate of decline in FVC (mL). In one aspect is provided a method of treating Idiopathic Pulmonary Fibrosis (IPF), the method comprising administering to a subject in need thereof a total daily dose of 825 mg administered in three equal doses of 275 mg each of LYT-100, wherein the rate of decline in FVC (mL) is lower relative to a subject who has not received LYT-100. In one aspect is provided a method of treating Idiopathic Pulmonary Fibrosis (IPF), the method comprising administering to a subject in need thereof a total daily dose of 1650 mg administered in three equal doses of 550 mg each of LYT-100, wherein the rate of decline in FVC (mL) is lower relative to a subject who has not received LYT-100. In one aspect is provided a method of treating Idiopathic Pulmonary Fibrosis (IPF), the method comprising administering to a subject in need thereof a total daily dose of 2475 mg administered in three equal doses of 825 mg each of LYT-100, wherein the rate of decline in FVC (mL) is lower relative to a subject who has not received LYT-100. In some embodiments, the period of treatment for measuring the rate of decline in FVC (mL) is at least 26 weeks. In some embodiments, the rate of decline in FVC (mL) is measured from baseline to at least 26 weeks of treatment. In some embodiments, the period of treatment for measuring the rate of decline in FVC (mL) is at least 52 weeks. In some embodiments, the rate of decline in FVC (mL) is measured from baseline to at least 52 weeks of treatment. In some embodiments, the rate of decline in FVC (mL) over at least a 26-week treatment period is a value less than the rate of decline exhibited by a subject who has not received LYT-100. In some embodiments, the rate of decline in FVC (mL) over at least a 52-week treatment period is a value less than the rate of decline exhibited by a subject who has received LYT-100.

In some embodiments, the change in FVC is measured as a change in FVC % predicted (FVCpp). In some embodiments, the change in FVC is measured as a decline in FVC % predicted (FVCpp). In one aspect is provided a method of treating IPF, the method comprising administering to a subject in need thereof a total daily dose of 825 mg administered in three equal doses of 275 mg each of LYT-100, wherein the rate of decline in FVCpp is lower relative to a subject who has not received LYT-100. In one aspect is provided a method of treating IPF, the method comprising administering to a subject in need thereof a total daily dose of 1650 mg administered in three equal doses of 550 mg each of LYT-100, wherein the rate of decline in FVCpp is lower relative to a subject who has not received LYT-100. In one aspect is provided a method of treating IPF, the method comprising administering to a subject in need thereof a total daily dose of 2475 mg administered in three equal doses of 825 mg each of LYT-100, wherein the rate of decline in FVCpp is lower relative to a subject who has not received LYT-100. In some embodiments, the period of treatment for measuring the rate of decline in FVCpp is at least 26 weeks. In some embodiments, the rate of decline in FVCpp is measured from baseline to at least 26 weeks of treatment. In some embodiments, the rate of decline in FVCpp over at least a 26-week treatment period is a value less than the rate of decline exhibited by a subject who has not received LYT-100. In some embodiments, the decline in FVCpp in the treated subject is less than 5% when measured over 26 weeks of treatment. In any of the treatment methods described herein, a delayed progression of IPF or slower rate of progression of IPF is demonstrated in a subject exhibiting a decline in FVCpp of less than 5% when measured over 26 weeks of treatment, e.g., measured from baseline to week 26 of treatment. In some embodiments, the period of treatment for measuring the rate of decline in FVCpp is at least 52 weeks. In some embodiments, the rate of decline in FVCpp is measured from baseline to at least 52 weeks of treatment. In some embodiments, the rate of decline in FVCpp over at least a 52-week treatment period is a value less than the rate of decline exhibited by a subject who has not received LYT-100. In some embodiments, the decline in FVCpp in the treated subject is less than 10% when measured over 52 weeks of treatment. In any of the methods described herein, a delayed progression of IPF or slower rate of progression of IPF is demonstrated in a subject exhibiting a decline in FVCpp of less than 10% when measured over 52 weeks of treatment, e.g., measured from baseline to week 52 of treatment.

In some embodiments, the treatment of IPF is demonstrated or exhibited by a delay in the time to progression of IPF in the subject. In some embodiments, the treatment of IPF is demonstrated or exhibited by a slower rate of progression of IPF in the subject. In any of the methods disclosed herein, the length of time to IPF progression is longer (increased, greater) in the subject treated with LYT-100 relative to a subject who has not received LYT-100. IPF progression can be determined using various methods, including by measuring the change in FVC, e.g., a decline in FVC mL or FVCpp. In some embodiments, IPF progression is determined by a decline in FVCpp of 5% or greater. In some embodiments, IPF progression is determined by a decline in FVCpp of 10% or greater. In any of the methods disclosed herein, the length of time to IPF progression, as determined by a decline in FVCpp of 5% or greater, is longer (increased, greater) in the subject treated with LYT-100 relative to a subject who has not received LYT-100. In any of the methods disclosed herein, the length of time to IPF progression, as determined by a decline in FVCpp of 10% or greater, is longer (increased, greater) in the subject treated with LYT-100 relative to a subject who has not received LYT-100.

In any of the methods disclosed herein, the subject exhibits a longer period of time to hospitalization due to impaired respiratory function relative to a subject who has not received LYT-100. In some instances, the longer length of time to hospitalization is a longer length of time for an initial hospitalization due to impaired respiratory function. In some instances, the longer length of time to hospitalization is not an initial hospitalization, e.g., it is a longer length of time for subsequent hospitalization(s) due to impaired respiratory function.

In any of the methods disclosed herein, the subject has less frequent hospitalizations due to impaired respiratory function relative to a subject who has not received LYT-100. Thus, in some embodiments, the subject has a lower number of hospitalizations due to impaired respiratory function relative to a subject who has not received LYT-100. In any of the methods disclosed herein, the subject has a shorter duration of hospitalization time(s) due to impaired respiratory function relative to a subject who has not received LYT-100.

In some embodiments, the number of hospitalizations and/or the duration of hospitalization time(s) due to impaired respiratory function is measured over at least a 26-week treatment period, e.g., baseline to week 26 of treatment. In some embodiments, the number of hospitalizations and/or the duration of hospitalization time(s) due to impaired respiratory function is measured over at least a 52-week treatment period, e.g., baseline to week 52 of treatment.

In any of the methods disclosed herein, the subject exhibits a longer period of time to mortality due to impaired respiratory function relative to a subject who has not received LYT-100. In any of the methods disclosed herein, the subject exhibits a longer period of time to mortality due to IPF relative to a subject who has not received LYT-100. In some embodiments, the time to mortality due to impaired respiratory function or IPF is measured over at least a 26-week treatment period. In some embodiments, the time to mortality due to impaired respiratory function or IPF is measured over at least a 52-week treatment period.

In any of the methods disclosed herein, the subject has a change in one or more serum biomarker(s) related to impaired respiratory function relative to a subject who has not received LYT-100. In some embodiments, the serum biomarker is collagen type 4. In some embodiments, the change in serum biomarker(s) related to impaired respiratory function is measured over at least a 26-week treatment period. In some embodiments, the change in serum biomarker(s) related to impaired respiratory function is measured over at least a 52-week treatment period.

In any of the methods disclosed herein, the subject is treated as determined by one or more of: King's Brief Interstitial Lung Disease Questionnaire (K-BILD) total score; Saint George Respiratory Questionnaire (SGRQ-I) domain score; EuroQol 5-Dimensional (EQ5D) Questionnaire score; and Cough visual analog scale (VAS), relative to a subject who has not received LYT-100. In some embodiments, the treatment is measured over at least a 26-week treatment period. In some embodiments, the treatment is measured over at least a 52-week treatment period.

In any of the methods disclosed herein, the subject is treated without any dose reduction in the administered daily dose over the course of treatment. In any of the methods disclosed herein, the subject is treated without any interruption in treatment or temporary stoppage in treatment over the course of treatment. In any of the methods disclosed herein, the subject is treated without any discontinuation in treatment over the course of treatment. In some embodiments, the course of treatment is at least 26 weeks. In some embodiments, the course of treatment is at least 52 weeks.

In one aspect is provided a method of treating IPF, the method comprising administering to a subject in need thereof a total daily dose of 825 mg administered in three equal doses of 275 mg each of LYT-100, wherein the subject exhibits a reduced number of one or more adverse event(s) (AE) relative to a subject who has been treated with 801 mg TID pirfenidone over the same treatment period. In one aspect is provided a method of treating IPF, the method comprising administering to a subject in need thereof a total daily dose of 1650 mg administered in three equal doses of 550 mg each of LYT-100, wherein the subject exhibits a reduced number of one or more adverse event(s) (AE)

relative to a subject who has been treated with 801 mg TID pirfenidone over the same treatment period. In one aspect is provided a method of treating IPF, the method comprising administering to a subject in need thereof a total daily dose of 2475 mg administered in three equal doses of 825 mg each of LYT-100, wherein the subject exhibits a reduced number of one or more adverse event(s) (AE) relative to a subject who has been treated with 801 mg TID pirfenidone over the same treatment period.

In one aspect is provided a method for reducing the number of one or more adverse event(s) (AE) in the treatment of IPF, the method comprising administering to a subject in need thereof a total daily dose of 825 mg administered in three equal doses of 275 mg each of LYT-100, wherein the subject exhibits a reduced number of one or more adverse event(s) (AE) relative to a subject who has been treated with 801 mg TID pirfenidone over the same treatment period. In one aspect is provided a method for reducing the number of one or more adverse event(s) (AE) in the treatment of IPF, the method comprising administering to a subject in need thereof a total daily dose of 1650 mg administered in three equal doses of 550 mg each of LYT-100, wherein the subject exhibits a reduced number of one or more adverse event(s) (AE) relative to a subject who has been treated with 801 mg TID pirfenidone over the same treatment period. In one aspect is provided a method for reducing the number of one or more adverse event(s) (AE) in the treatment of IPF, the method comprising administering to a subject in need thereof a total daily dose of 2475 mg administered in three equal doses of 825 mg each of LYT-100, wherein the subject exhibits a reduced number of one or more adverse event(s) (AE) relative to a subject who has been treated with 801 mg TID pirfenidone over the same treatment period.

In one aspect is provided a method of treating IPF, the method comprising administering to a subject in need thereof a total daily dose of 825 mg administered in three equal doses of 275 mg each of LYT-100, wherein the subject exhibits a shorter duration of one or more adverse event(s) (AE) relative to a subject who has been treated with 801 mg TID pirfenidone over the same treatment period. In one aspect is provided a method of treating IPF, the method comprising administering to a subject in need thereof a total daily dose of 1650 mg administered in three equal doses of 550 mg each of LYT-100, wherein the subject exhibits a shorter duration of one or more adverse event(s) (AE) relative to a subject who has been treated with 801 mg TID pirfenidone over the same treatment period. In one aspect is provided a method of treating IPF, the method comprising administering to a subject in need thereof a total daily dose of 2475 mg administered in three equal doses of 825 mg each of LYT-100, wherein the subject exhibits a shorter duration of one or more adverse event(s) (AE) relative to a subject who has been treated with 801 mg TID pirfenidone over the same treatment period.

In one aspect is provided a method for reducing the duration of one or more adverse event(s) (AE) in the treatment of IPF, the method comprising administering to a subject in need thereof a total daily dose of 825 mg administered in three equal doses of 275 mg each of LYT-100, wherein the subject exhibits a shorter duration of one or more adverse event(s) (AE) relative to a subject who has been treated with 801 mg TID pirfenidone over the same treatment period. In one aspect is provided a method for reducing the duration of one or more adverse event(s) (AE) in the treatment of IPF, the method comprising administering to a subject in need thereof a total daily dose of 1650 mg administered in three equal doses of 550 mg each of LYT-100, wherein the subject exhibits a shorter duration of one or more adverse event(s) (AE) relative to a subject who has been treated with 801 mg TID pirfenidone over the same treatment period. In one aspect is provided a method for reducing the duration of one or more adverse event(s) (AE) in the treatment of IPF, the method comprising administering to a subject in need thereof a total daily dose of 2475 mg administered in three equal doses of 825 mg each of LYT-100, wherein the subject exhibits a shorter duration of one or more adverse event(s) (AE) relative to a subject who has been treated with 801 mg TID pirfenidone over the same treatment period.

In any of the above-described methods, the one or more adverse event(s) is a gastrointestinal-related adverse event selected from nausea, vomiting, abdominal pain or distension, dyspepsia, diarrhea, decreased appetite, and constipation. In any of the above-described methods, the one or more adverse event(s) is a nervous system-related adverse event selected from headache, dizziness, and somnolence. In any of the above-described methods, the one or more adverse event(s) is selected from fatigue, drug intolerance, and photosensitivity. In any of the above-described methods, the one or more adverse event(s) is selected from increased AST, ALT, GGT, and liver toxicity.

In one aspect is provided a method of treating IPF, the method comprising administering to a subject in need thereof a total daily dose of 825 mg administered in three equal doses of 275 mg each of LYT-100, wherein the subject exhibits a longer (e.g., lengthened) period of time to first dose reduction in the administered daily dose relative to a subject who has been treated with 801 mg TID pirfenidone over the same treatment period. In one aspect is provided a method of treating IPF, the method comprising administering to a subject in need thereof a total daily dose of 1650 mg administered in three equal doses of 550 mg each of LYT-100, wherein the subject exhibits a longer (e.g., lengthened) period of time to first dose reduction in the administered daily dose relative to a subject who has been treated with 801 mg TID pirfenidone over the same treatment period. In one aspect is provided a method of treating IPF, the method comprising administering to a subject in need thereof a total daily dose of 2475 mg administered in three equal doses of 825 mg each of LYT-100, wherein the subject exhibits a longer (e.g., lengthened) period of time to first dose reduction in the administered daily dose relative to a subject who has been treated with 801 mg TID pirfenidone over the same treatment period.

In one aspect is provided a method for delaying (e.g., increasing, extending) the time to first dose reduction in the administered daily dose in the treatment of IPF, the method comprising administering to a subject in need thereof a total daily dose of 825 mg administered in three equal doses of 275 mg each of LYT-100, wherein the subject exhibits a longer (lengthened) time to first dose reduction relative to a subject who has been treated with 801 mg TID pirfenidone over the same treatment period. In one aspect is provided a method for delaying (e.g., increasing, extending) the time to first dose reduction in the administered daily dose in the treatment of IPF, the method comprising administering to a subject in need thereof a total daily dose of 1650 mg administered in three equal doses of 550 mg each of LYT-100, wherein the subject exhibits a longer (lengthened) time to first dose reduction relative to a subject who has been treated with 801 mg TID pirfenidone over the same treatment period. In one aspect is provided a method for delaying (e.g., increasing, extending) the time to first dose reduction in the administered daily dose in the treatment of IPF, the method comprising administering to a subject in need thereof a total daily dose of 2475 mg administered in three equal doses of 825 mg each of LYT-100, wherein the subject exhibits a longer (lengthened) time to first dose reduction relative to a subject who has been treated with 801 mg TID pirfenidone over the same treatment period.

In one aspect is provided a method of treating IPF, the method comprising administering to a subject in need thereof a total daily dose of 825 mg administered in three equal doses of 275 mg each of LYT-100, wherein the subject exhibits less frequent (e.g., a lower number of) dose reduction(s) in the administered daily dose relative to a subject who has been treated with 801 mg TID pirfenidone over the same treatment period. In one aspect is provided a method of treating IPF, the method comprising administering to a subject in need thereof a total daily dose of 1650 mg administered in three equal doses of 550 mg each of LYT-100, wherein the subject exhibits less frequent (e.g., a lower number of) dose reduction(s) in the administered daily dose relative to a subject who has been treated with 801 mg TID pirfenidone over the same treatment period. In one aspect is provided a method of treating IPF, the method comprising administering to a subject in need thereof a total daily dose of 2475 mg administered in three equal doses of 825 mg each of LYT-100, wherein the subject exhibits less frequent (e.g., a lower number of) dose reduction(s) in the administered daily dose relative to a subject who has been treated with 801 mg TID pirfenidone over the same treatment period.

In one aspect is provided a method for reducing (e.g., decreasing) the number of dose reductions in the administered daily dose in the treatment of IPF, the method comprising administering to a subject in need thereof a total daily dose of 825 mg administered in three equal doses of 275 mg each of LYT-100, wherein the subject exhibits less frequent (e.g., a lower number of) dose reduction(s) in the administered daily dose relative to a subject who has been treated with 801 mg TID pirfenidone over the same treatment period. In one aspect is provided a method for reducing (e.g., decreasing) the number of dose reductions in the administered daily dose in the treatment of IPF, the method comprising administering to a subject in need thereof a total daily dose of 1650 mg administered in three equal doses of 550 mg each of LYT-100, wherein the subject exhibits less frequent (e.g., a lower number of) dose reduction(s) in the administered daily dose relative to a subject who has been treated with 801 mg TID pirfenidone over the same treatment period. In one aspect is provided a method for reducing (e.g., decreasing) the number of dose reductions in the administered daily dose in the treatment of IPF, the method comprising administering to a subject in need thereof a total daily dose of 2475 mg administered in three equal doses of 825 mg each of LYT-100, wherein the subject exhibits less frequent (e.g., a lower number of) dose reduction(s) in the administered daily dose relative to a subject who has been treated with 801 mg TID pirfenidone over the same treatment period.

In one aspect is provided a method of treating IPF, the method comprising administering to a subject in need thereof a total daily dose of 825 mg administered in three equal doses of 275 mg each of LYT-100, wherein the subject exhibits a longer (e.g., lengthened) period of time to first treatment interruption or temporary stoppage in treatment relative to a subject who has been treated with 801 mg TID pirfenidone over the same treatment period. In one aspect is provided a method of treating IPF, the method comprising administering to a subject in need thereof a total daily dose of 1650 mg administered in three equal doses of 550 mg each of LYT-100, wherein the subject exhibits a longer (e.g., lengthened) period of time to first treatment interruption or temporary stoppage in treatment relative to a subject who has been treated with 801 mg TID pirfenidone over the same treatment period. In one aspect is provided a method of treating IPF, the method comprising administering to a subject in need thereof a total daily dose of 2475 mg administered in three equal doses of 825 mg each of LYT-100, wherein the subject exhibits a longer (e.g., lengthened) period of time to first treatment interruption or temporary stoppage in treatment relative to a subject who has been treated with 801 mg TID pirfenidone over the same treatment period.

In one aspect is provided a method for delaying (e.g., increasing, extending) the period of time to first treatment interruption or temporary stoppage in the treatment of IPF, the method comprising administering to a subject in need thereof a total daily dose of 825 mg administered in three equal doses of 275 mg each of LYT-100, wherein the subject exhibits a longer (e.g., lengthened) period of time to first treatment interruption or temporary stoppage in treatment relative to a subject who has been treated with 801 mg TID pirfenidone over the same treatment period. In one aspect is provided a method for delaying (e.g., increasing, extending) the time to first treatment interruption or temporary stoppage in the treatment of IPF, the method comprising administering to a subject in need thereof a total daily dose of 1650 mg administered in three equal doses of 550 mg each of LYT-100, wherein the subject exhibits a longer (e.g., lengthened) period of time to first treatment interruption or temporary stoppage in treatment relative to a subject who has been treated with 801 mg TID pirfenidone over the same treatment period. In one aspect is provided a method for delaying (e.g., increasing, extending) the time to first treatment interruption or temporary stoppage in the treatment of IPF, the method comprising administering to a subject in need thereof a total daily dose of 2475 mg administered in three equal doses of 825 mg each of LYT-100, wherein the subject exhibits a longer (e.g., lengthened) period of time to first treatment interruption or temporary stoppage in treatment relative to a subject who has been treated with 801 mg TID pirfenidone over the same treatment period.

In one aspect is provided a method of treating IPF, the method comprising administering to a subject in need thereof a total daily dose of 825 mg administered in three equal doses of 275 mg each of LYT-100, wherein the subject exhibits less frequent (e.g., a lower number of) treatment interruptions or temporary stoppages in treatment relative to a subject who has been treated with 801 mg TID pirfenidone over the same treatment period. In one aspect is provided a method of treating IPF, the method comprising administering to a subject in need thereof a total daily dose of 1650 mg administered in three equal doses of 550 mg each of LYT-100, wherein the subject exhibits less frequent (e.g., a lower number of) treatment interruptions or temporary stoppages in treatment relative to a subject who has been treated with 801 mg TID pirfenidone over the same treatment period. In one aspect is provided a method of treating IPF, the method comprising administering to a subject in need thereof a total daily dose of 2475 mg administered in three equal doses of 825 mg each of LYT-100, wherein the subject exhibits less frequent (e.g., a lower number of) treatment interruptions or temporary stoppages in treatment relative to a subject who has been treated with 801 mg TID pirfenidone over the same treatment period.

In one aspect is provided a method for reducing the frequency (e.g., decreasing the number) of treatment interruptions or temporary stoppages in the treatment of IPF, the method comprising administering to a subject in need thereof a total daily dose of 825 mg administered in three equal doses of 275 mg each of LYT-100, wherein the subject exhibits less frequent (e.g., a lower number of) treatment interruptions or temporary stoppages in treatment relative to a subject who has been treated with 801 mg TID pirfenidone over the same treatment period. In one aspect is provided a method for reducing the frequency (e.g., decreasing the number) of treatment interruption or temporary stoppage in treatment in the treatment of IPF, the method comprising administering to a subject in need thereof a total daily dose of 1650 mg administered in three equal doses of 550 mg each of LYT-100, wherein the subject exhibits less frequent (e.g., a lower number of) treatment interruptions or temporary stoppages in treatment relative to a subject who has been treated with 801 mg TID pirfenidone over the same treatment period. In one aspect is provided a method for reducing the frequency (decreasing the number) of treatment interruptions or temporary stoppages in treatment of IPF, the method comprising administering to a subject in need thereof a total daily dose of 2475 mg administered in three equal doses of 825 mg each of LYT-100, wherein the subject exhibits less frequent (e.g., a lower number of) treatment interruptions or temporary stoppages in treatment relative to a subject who has been treated with 801 mg TID pirfenidone over the same treatment period.

In one aspect is provided a method of treating IPF, the method comprising administering to a subject in need thereof a total daily dose of 825 mg administered in three equal doses of 275 mg each of LYT-100, wherein the subject exhibits a longer (e.g., lengthened) period of time to treatment discontinuation relative to a subject who has been treated with 801 mg TID pirfenidone over the same treatment period. In one aspect is provided a method of treating IPF, the method comprising administering to a subject in need thereof a total daily dose of 1650 mg administered in three equal doses of 550 mg each of LYT-100, wherein the subject exhibits a longer (e.g., lengthened) period of time to treatment discontinuation relative to a subject who has been treated with 801 mg TID pirfenidone over the same treatment period. In one aspect is provided a method of treating IPF, the method comprising administering to a subject in need thereof a total daily dose of 2475 mg administered in three equal doses of 825 mg each of LYT-100, wherein the subject exhibits a longer (e.g., lengthened) period of time to treatment discontinuation relative to a subject who has been treated with 801 mg TID pirfenidone over the same treatment period.

In one aspect is provided a method for delaying (e.g., increasing, extending) the period of time to treatment discontinuation of IPF treatment, the method comprising administering to a subject in need thereof a total daily dose of 825 mg administered in three equal doses of 275 mg each of LYT-100, wherein the subject exhibits a longer (e.g., lengthened) period of time to treatment discontinuation relative to a subject who has been treated with 801 mg TID pirfenidone over the same treatment period. In one aspect is provided a method for delaying (e.g., increasing, extending) the time to treatment discontinuation of IPF treatment, the method comprising administering to a subject in need thereof a total daily dose of 1650 mg administered in three equal doses of 550 mg each of LYT-100, wherein the subject exhibits a longer (e.g., lengthened) period of time to treatment discontinuation relative to a subject who has been treated with 801 mg TID pirfenidone over the same treatment period. In one aspect is provided a method for delaying (e.g., increasing, extending) the time to treatment discontinuation of IPF treatment, the method comprising administering to a subject in need thereof a total daily dose of 2475 mg administered in three equal doses of 825 mg each of LYT-100, wherein the subject exhibits a longer (e.g., lengthened) period of time to treatment discontinuation relative to a subject who has been treated with 801 mg TID pirfenidone over the same treatment period.

In one aspect is provided a method for improving the treatment for IPF, relative to treatment with pirfenidone. In some embodiments, the improvement in treatment is an improved tolerability. In some embodiments, the improved tolerability is due to a decrease in the frequency, incidence, or number of adverse events and/or the duration of adverse events. In one aspect is provided a method for improving the treatment for IPF, the method comprising administering to a subject in need thereof a total daily dose of 825 mg administered in three equal doses of 275 mg each of LYT-100, wherein the subject exhibits an improvement in treatment, relative to a subject which has been treated with 801 mg TID pirfenidone. In one aspect is provided a method for improving the treatment for IPF, the method comprising administering to a subject in need thereof a total daily dose of 1650 mg administered in three equal doses of 550 mg each of LYT-100, wherein the subject exhibits an improvement in treatment, relative to a subject which has been treated with 801 mg TID pirfenidone. In one aspect is provided a method for improving the treatment for IPF, the method comprising administering to a subject in need thereof a total daily dose of 2475 mg administered in three equal doses of 825 mg each of LYT-100, wherein the subject exhibits an improvement in treatment, relative to a subject which has been treated with 801 mg TID pirfenidone. In any of the described methods, the improvement in treatment relative to a subject which has been treated with 801 mg TID pirfenidone is a reduced number of one or more adverse event(s) (AEs) and/or a shorter duration of one or more adverse event(s) (AEs). In some embodiments, the one or more AEs is selected from nausea, vomiting, abdominal pain or distension, dyspepsia, diarrhea, decreased appetite, constipation, headache, dizziness, somnolence, fatigue, drug intolerance, increased AST, ALT, and/or GGT, and liver toxicity.

In any of the above-described methods, the improvement in treatment relative to a subject which has been treated with 801 mg TID pirfenidone is selected from a delayed progression of impaired respiratory function, a slower rate of progression of impaired respiratory function, and/or a longer length of time to impaired respiratory function. In any of the above-described methods, the improvement in treatment is selected from a delayed progression of IPF, a slower rate of progression of IPF, and/or a longer length of time to IPF progression. In some embodiments, IPF progression is determined by measuring a decline in FVC (mL). In some embodiments, the improvement is a lower rate of decline in FVC (mL). In some embodiments, IPF progression is measured over at least a 26-week treatment period. In some embodiments, the rate of decline in FVC (mL) over at least a 26-week treatment period is a value less than the rate of decline in FVC (mL) exhibited by a subject which has been treated with 801 mg TID pirfenidone. In some embodiments, IPF progression is determined by measuring a decline in FVCpp. In some embodiments, the improvement is a lower rate of decline in FVCpp. In some embodiments, IPF progression is measured over at least a 26-week treatment period. In some embodiments, the rate of decline in FVCpp over at least a 26-week treatment period is a value less than the rate of decline in FVCpp exhibited by a subject which has been treated with 801 mg TID pirfenidone. In some embodiments, IPF progression is determined by a decline in FVCpp of 5% or greater. In some embodiments, IPF progression is measured over at least a 52-week treatment period. In some embodiments, the rate of decline in FVCpp over at least a 52-week treatment period is a value less than the rate of decline in FVCpp exhibited by a subject which has been treated with 801 mg TID pirfenidone. In some embodiments, IPF progression is determined by a decline in FVCpp of 10% or greater.

In any of the above-described methods, the improvement in treatment relative to a subject which has been treated with 801 mg TID pirfenidone is selected from a longer period of time to hospitalization due to impaired respiratory function, less frequent (a lower number of) hospitalizations due to impaired respiratory function, and/or a shorter duration of hospitalization time(s) due to impaired respiratory function. In some embodiments, the length of time to hospitalization, the number of hospitalizations and/or the duration of hospitalization time(s) due to impaired respiratory function is measured over at least a 26-week treatment period, e.g., baseline to week 26 of treatment. In some embodiments, the length of time to hospitalization, the number of hospitalizations and/or the duration of hospitalization time(s) due to impaired respiratory function is measured over at least a 52-week treatment period, e.g., baseline to week 52 of treatment.

In any of the above-described methods, the improvement in treatment relative to a subject which has been treated with 801 mg TID pirfenidone is a longer period of time to mortality due to impaired respiratory function. In some embodiments, the subject exhibits a longer period of time to mortality due to IPF relative to a subject which has been treated with 801 mg TID pirfenidone. In some embodiments, the time to mortality due to impaired respiratory function or IPF is measured over at least a 26-week treatment period. In some embodiments, the time to mortality due to impaired respiratory function or IPF is measured over at least a 52-week treatment period.

In any of the above-described methods, the improvement in treatment relative to a subject which has been treated with 801 mg TID pirfenidone is an improved change in one or more serum biomarker(s) related to impaired respiratory function, e.g., collagen type 4. In some embodiments, the change in serum biomarker(s) related to impaired respiratory function is measured over at least a 26-week treatment period. In some embodiments, the change in serum biomarker(s) related to impaired respiratory function is measured over at least a 52-week treatment period.

In any of the above-described methods, the improvement in treatment relative to a subject which has been treated with 801 mg TID pirfenidone is an improvement in one or more of: King's Brief Interstitial Lung Disease Questionnaire (K-BILD) total score; Saint George Respiratory Questionnaire (SGRQ-I) domain score; EuroQol 5-Dimensional (EQ5D) Questionnaire score; and Cough visual analog scale (VAS), relative to a subject who has not received LYT-100. In some embodiments, the treatment is measured over at least a 26-week treatment period. In some embodiments, the treatment is measured over at least a 52-week treatment period.

In one aspect is provided a method of improving the treatment for IPF, relative to treatment with pirfenidone, the method comprising administering to a subject in need thereof a total daily dose from 825 mg to 2475 mg of a deuterium-enriched pirfenidone having the structure:

(LYT-100)

In some embodiments, the method comprises administering to a subject in need thereof a total daily dose of 825 mg administered in three equal doses of 275 mg each of LYT-100. In some embodiments, the method comprises administering to a subject in need thereof a total daily dose of 1650 mg administered in three equal doses of 550 mg each of LYT-100. In some embodiments, the method comprises administering to a subject in need thereof a total daily dose of 2475 mg administered in three equal doses of 825 mg each of LYT-100. In some embodiments, the treatment with pirfenidone is a total daily dose of 2403 mg pirfenidone, administered in three equal doses of 801 mg each. In some embodiments, the improvement in treatment, relative to treatment with pirfenidone, is an improved tolerability, as determined by a reduction in the incidence of one or more gastrointestinal AE(s) and/or a reduction in the duration of one or more gastrointestinal AE(s). In some embodiments, the one or more gastrointestinal AE(s) is selected from: nausea, vomiting, loss of appetite, and abdominal pain or distension. In some embodiments, the incidence of one or more gastrointestinal AE(s) is reduced by at least 30%. In some embodiments, the improvement in treatment, relative to treatment with pirfenidone, is an improved tolerability, as determined by a reduction in the incidence of one or more nervous system AE(s) and/or a reduction in the duration of one or more nervous system AE(s). In some embodiments, the one or more nervous system AE(s) is selected from: fatigue, headache, dizziness, and somnolence. In some embodiments, the incidence of one or more nervous system AE(s) is reduced by at least 30%. In some embodiments, the improvement in treatment, relative to treatment with pirfenidone, is a selected from: a lower incidence or frequency of dose reduction in the administered daily dose, a longer time to first dose reduction in the administered daily dose, a lower incidence of interrupted treatment or temporary stoppage of treatment, a longer time to first treatment interruption or temporary stoppage in treatment, and a reduction in the incidence of discontinuation of treatment. In some embodiments, the improvement in treatment is measured over at least 26 weeks of treatment. In some embodiments, the improvement in treatment is measured over at least 52 weeks of treatment. In any of the described methods, the improvement in treatment is relative to a subject who has been treated with 801 mg TID pirfenidone over the same treatment period.

In some embodiments, the improvement in treatment, relative to treatment with pirfenidone, is selected from: a slower or delayed progression of impaired respiratory function, a slower or delayed progression of IPF, a lower rate of decline in FVC (mL), a lower rate of decline in FVCpp, a longer period of time to hospitalization due to impaired respiratory function, a lower number of hospitalizations due to impaired respiratory function, a shorter duration of hospitalization time(s) due to impaired respiratory function, and a longer period of time to mortality due to impaired respiratory function. In some embodiments, the improvement in treatment is measured over at least 26 weeks of treatment. In some embodiments, the improvement in treatment is measured over at least 52 weeks of treatment. In any of the described methods, the improvement in treatment is relative to a subject who has been treated with 801 mg TID pirfenidone over the same treatment period.

In some embodiments, the improvement in treatment relative to treatment with pirfenidone, is determined in one or more of: King's Brief Interstitial Lung Disease Questionnaire (K-BILD) total score; Saint George Respiratory Questionnaire (SGRQ-I) domain score; EuroQol 5-Dimensional (EQ5D) Questionnaire score; and Cough visual analog scale (VAS)._In some embodiments, the improvement in treatment is measured over at least 26 weeks of treatment. In some embodiments, the improvement in treatment is measured over at least 52 weeks of treatment. In any of the described methods, the improvement in treatment is relative to a subject who has been treated with 801 mg TID pirfenidone over the same treatment period.

In one aspect is provided a method of treating IPF, the method comprising administering to a subject in need thereof a total daily dose of 1650 mg of a deuterium-enriched pirfenidone having the structure:

(LYT-100)

wherein the LYT-100 is administered in three equal doses of 550 mg each for a period of time and wherein the total daily dose may be reduced for one or more subsequent period(s) of time. In some embodiments, the total daily dose of 1650 mg is an initial dose. In some embodiments, the total daily dose of 1650 mg is not an initial daily dose. In some embodiments, the total daily dose of 1650 mg may be reduced in increments of 275 mg. In some embodiments, the total daily dose of 1650 mg may be reduced to a total daily dose of 825 mg, optionally administered in three equal doses of 275 mg each. In some embodiments, the total daily dose may be reduced to 825 mg for about 1 week to about one month. In some embodiments, the total daily dose may be reduced to 825 mg for longer than one month. In some embodiments, the total daily dose may be reduced to 825 mg as a daily maintenance dose.

In one aspect is provided a method of treating IPF, the method comprising administering to a subject in need thereof a total daily dose of 2475 mg of a deuterium-enriched pirfenidone having the structure:

(LYT-100)

26 wherein the LYT-100 is administered in three equal doses of 825 mg each for a period of time and wherein the total daily dose may be reduced for one or more subsequent period(s) of time. In some embodiments, the total daily dose of 2475 mg is an initial dose. In some embodiments, the total daily dose of 2475 mg is not an initial daily dose. In some embodiments, the total daily dose of 2475 mg may be reduced in increments of 275 mg. In some embodiments, the total daily dose of 2475 mg may be reduced to a total daily dose of 1650 mg, optionally administered in three equal doses of 550 mg each. In some embodiments, the total daily dose may be reduced to 1650 mg for about 1 week to about one month. In some embodiments, the total daily dose may be reduced to 1650 mg for longer than one month. In some embodiments, the total daily dose may be reduced to 1650 mg as a daily maintenance dose. In some embodiments, the total daily dose of 1650 mg may be further reduced in increments of 275 mg. In some embodiments, the total daily dose of 1650 mg may be further reduced to a total daily dose of 825 mg, optionally administered in three equal doses of 275 mg each. In some embodiments, the total daily dose may be further reduced to 825 mg for about 1 week to about one month. In some embodiments, the total daily dose may be further reduced to 825 mg for longer than one month. In some embodiments, the total daily dose may be further reduced to 825 mg as a daily maintenance dose. In some embodiments, the total daily dose of 2475 mg may be reduced to a total daily dose of 825 mg, optionally administered in three equal doses of 275 mg each. In some embodiments, the total daily dose of 2475 mg may be reduced to 825 mg for about 1 week to about one month. In some embodiments, the total daily dose of 2475 mg may be reduced to 825 mg for longer than one month. In some embodiments, the total daily dose of 2475 mg may be reduced to 825 mg as a daily maintenance dose.

In any of the above-described methods, the treatment with LYT-100 may be interrupted or temporarily stopped, for one or more periods of time, as needed.

In any of the method described herein, the subject has one or more of the following: Idiopathic Pulmonary Fibrosis as diagnosed by a physician based on ATS/ERS/JRS/ALAT 2018 guidelines or based on high resolution computed tomography (HRCT) performed within 12 months of initiating treatment, a clinically significant decline in DLCO corrected for hemoglobin $\geq30\%$ predicted of normal prior to initiating treatment, and an FVC$\geq45\%$ predicted prior to initiating treatment. In some embodiments, the subject has not received prior treatment for IPF. In some embodiments, the subject has received prior treatment for IPF. In some embodiments, the prior treatment for IPF is nintedanib. In some embodiments, the prior treatment for IPF is pirfenidone. In some embodiments, the subject has received less than 6 months prior exposure to nintedanib or pirfenidone.

BRIEF DESCRIPTION OF THE DRAWINGS

FIG. 2 is a graphical illustration of a crossover clinical trial study design according to a non-limiting embodiment of the disclosure.

FIG. 3 is a graphical illustration of another crossover clinical trial study design according to a non-limiting embodiment of the disclosure.

FIG. 4 is a table showing the extrapolated steady-state exposures ($AUC_{24ss}$) and steady-state $C_{max}$ values of LYT-100 for 450 mg-550 mg TID dosing based on PK data from two separate cohorts (12A and 12B) and a pooled dataset. The pharmacokinetic parameters were calculated using steady state $AUC_{0-24}$ after administration of LYT-100 dosed at 1000 mg BID or pirfenidone dosed at 801 mg TID. The data demonstrates that a dose of 550 mg TID LYT-100 has a steady-state exposure (AUC) that is calculated to be equivalent to 98.5% of the steady-state exposure (AUC) of pirfenidone dosed at 801 mg TID, and a $C_{max}$ that is calculated to be equivalent to 67.4% of the $C_{max}$ of pirfenidone dosed at 801 mg TID.

FIG. 5 is a table showing the extrapolated steady-state exposures ($AUC_{24ss}$) and steady-state $C_{max}$ values of LYT-100 for 700 mg-1000 mg BID dosing (1400 mg-2000 mg daily dose) versus 450 mg-850 mg TID dosing (1350 mg-2550 mg daily dose). The data demonstrates that a dose of 825 mg BID LYT-100 (1650 mg daily dose) has a steady-state exposure (AUC) that is calculated to be equivalent to 98.5% of the steady-state exposure (AUC) and 101.1% of the steady-state $C_{max}$ of pirfenidone dosed at 801 mg TID. In contrast, a dose of 550 mg TID LYT-100 (1650 mg daily dose) has a steady-state exposure (AUC) that is calculated to be equivalent to 98.5% of the steady-state exposure (AUC) and 67.4% of the steady-state $C_{max}$ of pirfenidone dosed at 801 mg TID.

FIG. 6A is a summary of the pharmacokinetic and tolerability results of a Phase 1 cross-over study conducted in healthy adults dosed with 850 mg BID LYT-100.

FIG. 6B is a table showing the incidence of treatment-emergent adverse events (TEAEs) in a cross-over study of healthy older adults comparing LYT-100 850 mg BID versus pirfenidone 801 mg TID. The data shows that the incidence of gastrointestinal AEs with LYT-100 was 37.1% with LYT-100 versus 29.7% with pirfenidone; the incidence of nervous system AEs was 45.7% with LYT-100 versus 35.1% with pirfenidone; and the incidence of nausea was increased with both LYT-100 and pirfenidone when dosed after fasting.

FIG. 9 is a table showing the pharmacokinetic parameters for LYT-100 and the major metabolite for doses of 550 mg TID and 824 mg TID.

FIG. 16A is a graphical summary of exposure versus dose in the crossover study of Example 1 and a prior dosing study demonstrating the achievement of bioequivalence to 801 mg TID pirfenidone for 550 mg TID LYT-100.

FIG. 16B is a graphical summary of exposure versus dose in the crossover study of Example 1 and a prior dosing study demonstrating the achievement of bioequivalence to 801 mg TID pirfenidone for 550 mg TID LYT-100.

FIG. 16C is a graphical summary of exposure versus dose in the crossover study of Example 1 and a prior dosing study demonstrating the achievement of bioequivalence to 801 mg TID pirfenidone for 550 mg TID LYT-100.

FIG. 16D is a graphical summary of exposure versus dose in the crossover study of Example 1 and pooled data from a prior dosing study demonstrating the achievement of bioequivalence to 801 mg TID pirfenidone for 550 mg TID LYT-100.

FIG. 17 is a graphical summary of exposure versus dose for pooled data from the crossover study of Example 1 and three prior dosing studies and demonstrating the achievement of bioequivalence to 801 mg TID pirfenidone for 550 mg TID and 687 mg TID LYT-100.

FIG. 18 is a table showing the predicted bioequivalence for various LYT-100 TID doses using data from the crossover study of Example 1 and three prior dosing studies.

FIG. 20 is a table showing a summary of baseline demographic characteristics with respect to age and sex for subjects in the COVID-19 clinical study of Example 3.

FIG. 21 is a table showing a summary of baseline demographic characteristics with respect to ethnicity, race, and time from COVID diagnosis for subjects in the COVID-19 clinical study of Example 3.

FIG. 22 is a table showing a summary of subject disposition for the enrolled population in the COVID-19 clinical study of Example 3.

FIG. 23 is a table showing a summary of treatment emergent adverse events judged to be at least possibly related to LYT-100 in the COVID-19 clinical study of Example 3.

FIG. 24A is a high-level graphical illustration of the IPF clinical trial study design of Example 4 according to a non-limiting embodiment of the disclosure.

FIG. 24D is a summary of recent protocol amendments to the IPF clinical trial study of Example 4 according to a non-limiting embodiment of the disclosure.

FIG. 25A is an example of a patient reported assessment of IPF symptoms survey according to a non-limiting embodiment of the disclosure.

FIG. 25B is an example of a patient reported assessment of side effect survey according to a non-limiting embodiment of the disclosure.

FIG. 26 is an example of a patient reported satisfaction survey according to a non-limiting embodiment of the disclosure.

FIG. 27 is a table showing the metabolism of pirfenidone and LYT-100 in the presence of individual CYP isozymes in the assay of Example 5.

FIG. 33A is a graphical depiction of lung weight to body weight percentage over time for rats in Phase II of the bleomycin induced lung fibrosis model of Example 7.

FIG. 33B is a graphical depiction of lung weight to body weight percentage over time for rats in Phase II of the bleomycin induced lung fibrosis model of Example 7.

FIG. 34A is a graphical depiction of hydroxyproline content in left lung tissue for rats in Phase II of the bleomycin induced lung fibrosis model of Example 7.

FIG. 34B is a graphical depiction of hydroxyproline content in left lung tissue for rats in Phase II of the bleomycin induced lung fibrosis model of Example 76.

FIG. 35 is a table showing the hydroxyproline content in left lung tissue across the various treatment groups in Phase II of the bleomycin induced lung fibrosis model of Example 7.

FIG. 37 is a table showing the hydroxyproline content in lung tissue across the various treatment groups in Phase II of the bleomycin induced lung fibrosis model of Example 7.

FIG. 40 is a graphical depiction of subject disposition in the IPF clinical trial study of Example 43.

FIG. 44B is a graphical depiction providing the summary of change from baseline in FVCpp over 26 weeks by Frequentist analysis for placebo, pirfenidone and 550 mg TID LYT-100 and 825 mg TID LYT-100 in the IPF clinical trial study of Example 4.

FIG. 45 is a graphical depiction illustrating the FVC decline over 26 weeks for placebo, average healthy adults over 60 years of age, and for 825 mg TID LYT-100 in the IPF clinical trial study of Example 4.

Figure 46:
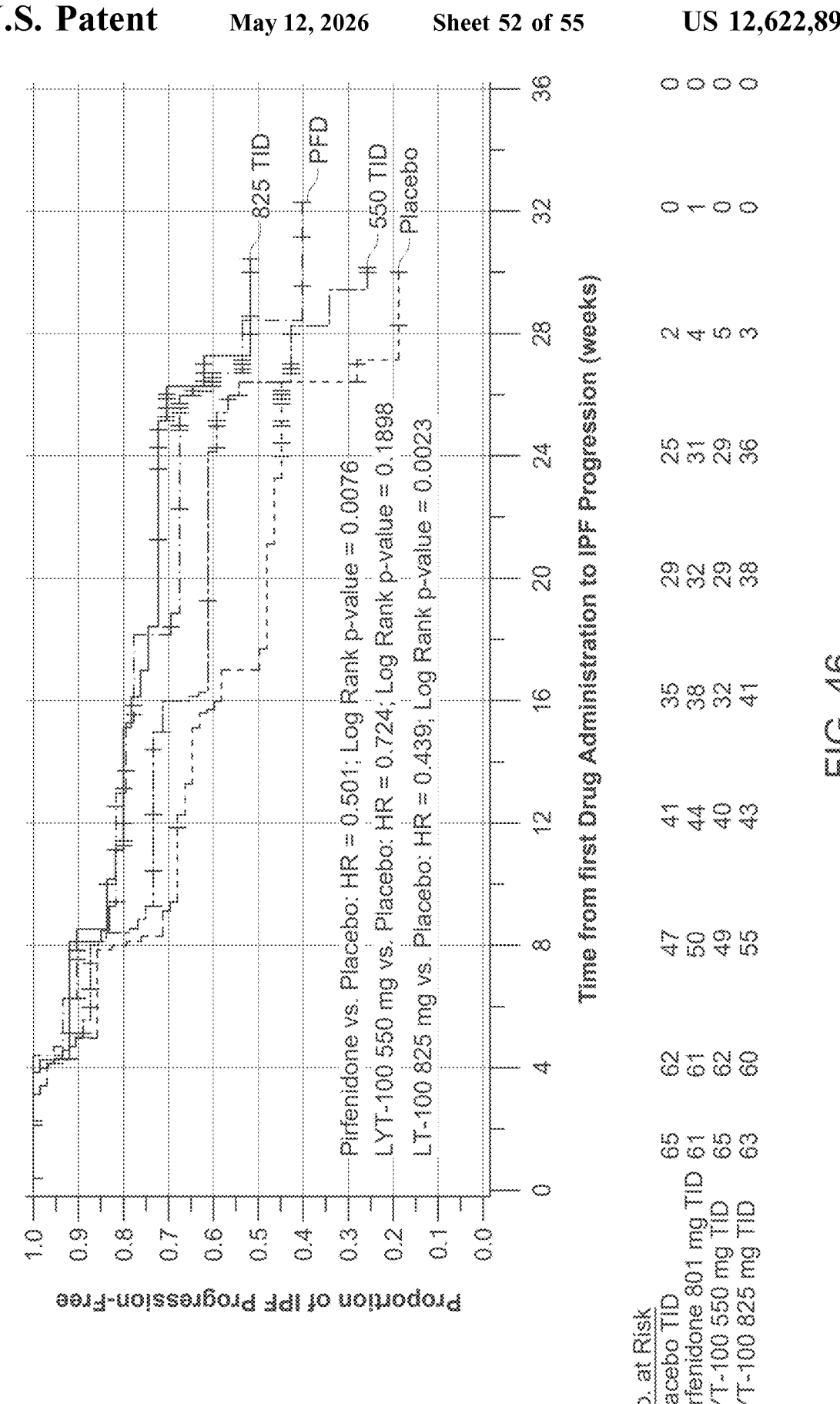

FIG. 46 is a graphical depiction showing the proportion of patients showing progression-free IPF over time for placebo, pirfenidone and 550 mg TID LYT-100 and 825 mg TID LYT-100 in the IPF clinical trial study of Example 4.

Figure 47:
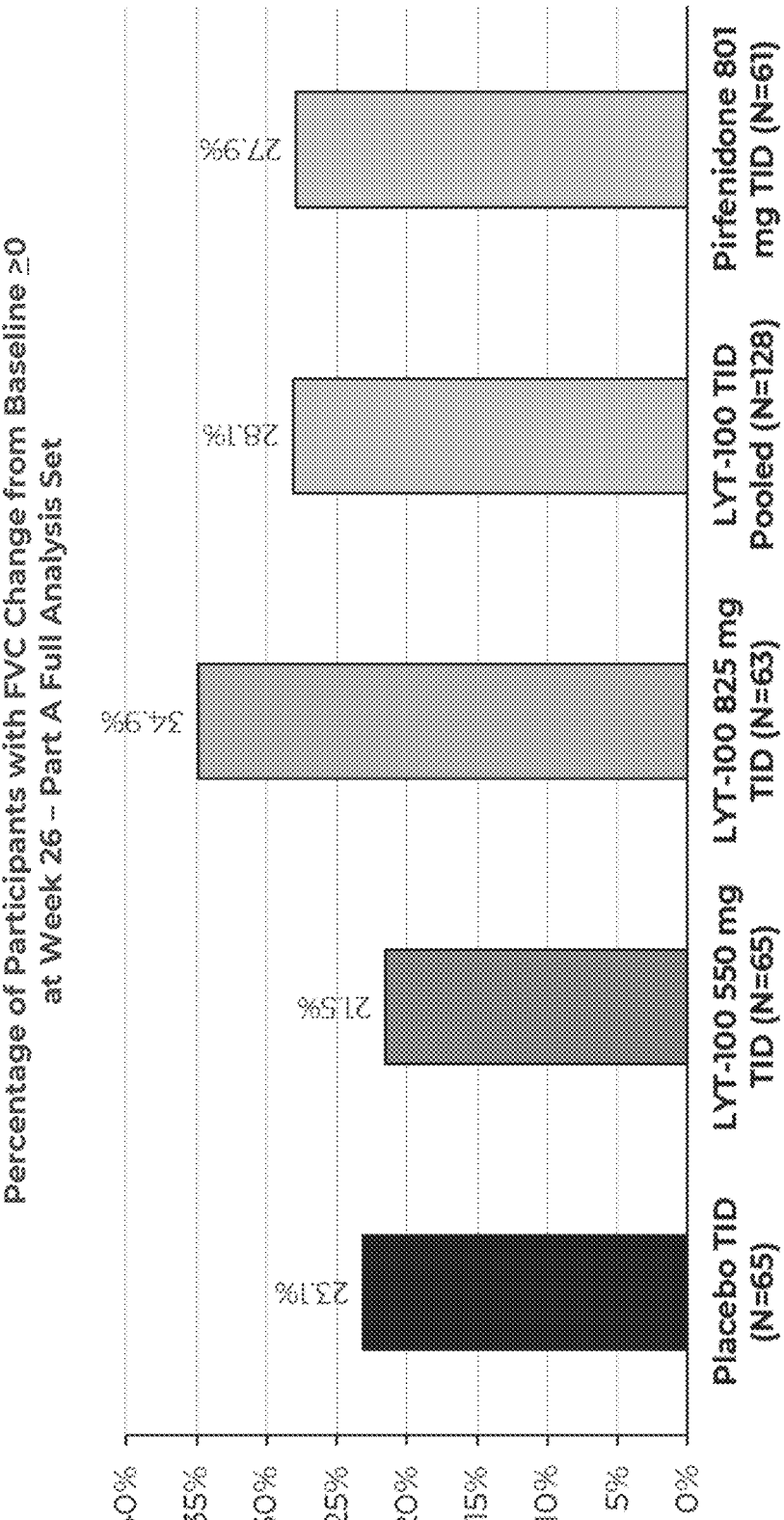

FIG. 47 is a graphical depiction showing the percentage of participants with a change from baseline greater than or equal to zero at week 26 for placebo, pirfenidone, 550 mg TID LYT-100, 825 mg TID LYT-100, and pooled LYT-100 doses in the IPF clinical trial study of Example 4.

Figure 48:
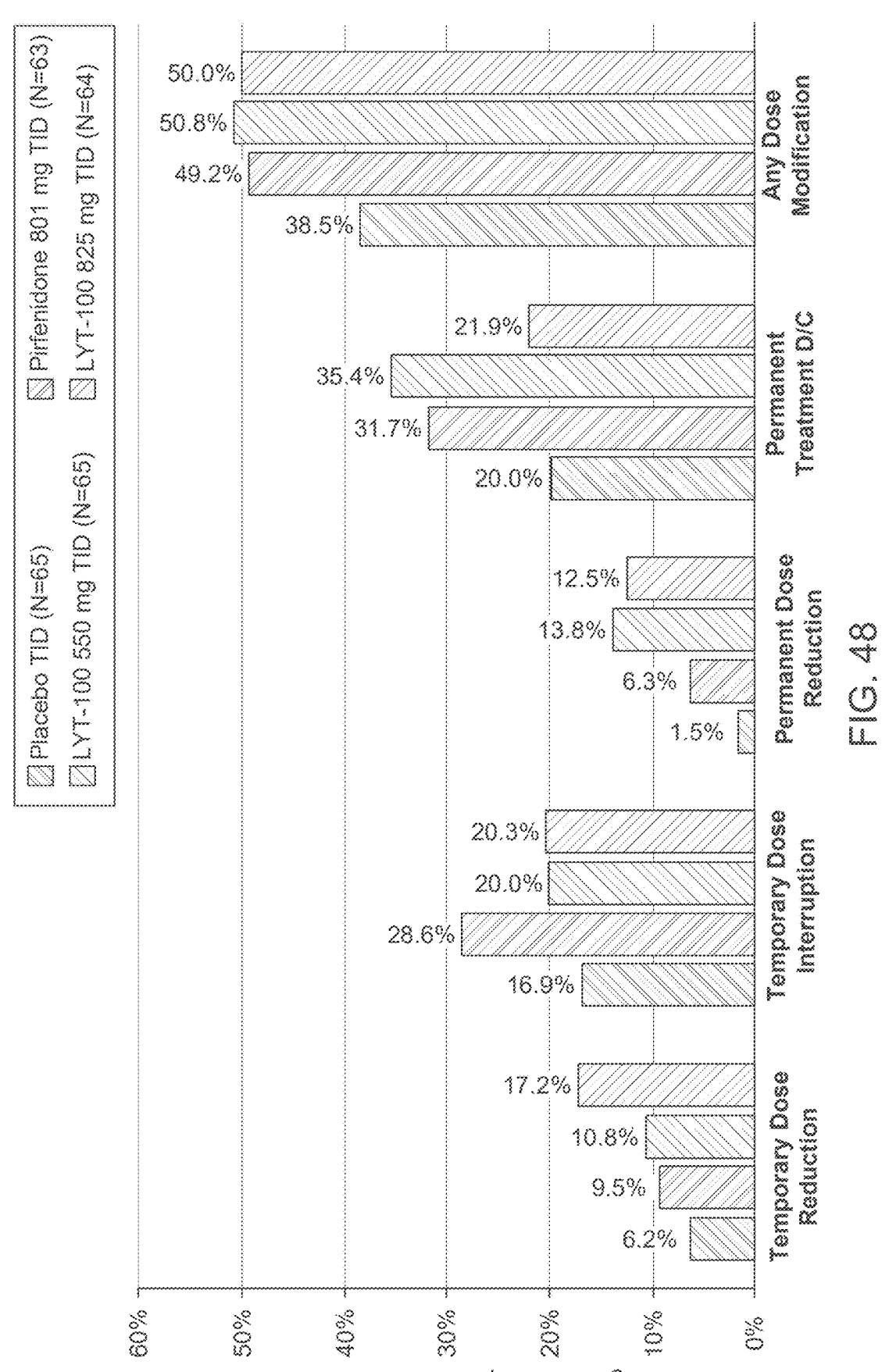

FIG. 48 is a graphical depiction showing percentage of participants with dose modification or discontinuation in the IPF clinical trial study of Example 4. For each category (temporary dose reduction, temporary interruption, permanent reduction, permanent discontinuation, and any modification), the bars from left to right show placebo, pirfenidone, 550 mg TID LYT-100, and 825 mg TID LYT-100.

Figure 49:
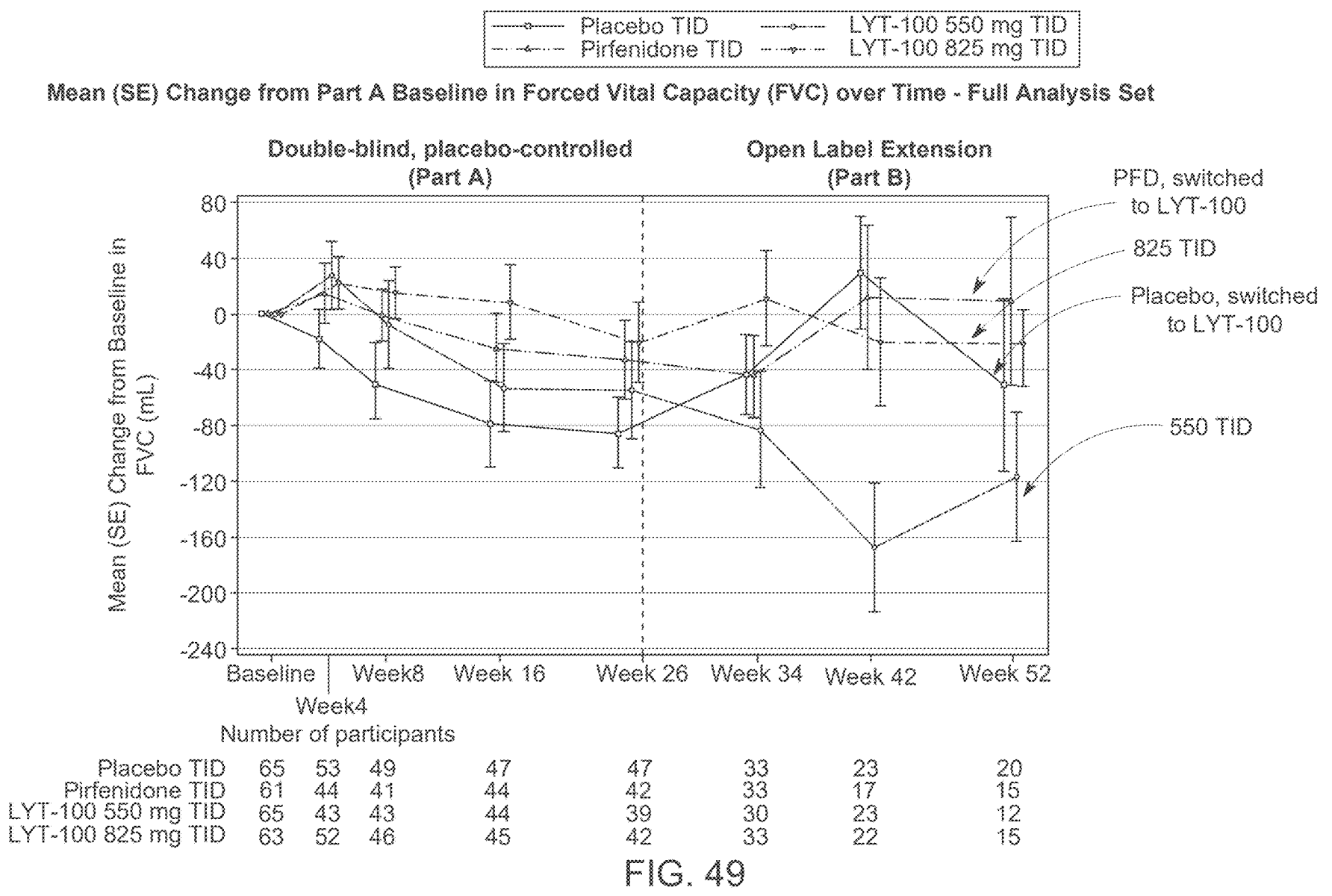

FIG. 49 is a graphical depiction of mean change in FVC over time for Part A and Part B in the IPF clinical trial study of Example 4. In Part B, participants on placebo and on pirfenidone were switched to 825 mg TID LYT-100.

DETAILED DESCRIPTION

Disclosed herein is a method of treating Idiopathic Pulmonary Fibrosis (IPF). The method generally comprises administering to a subject in need thereof the deuterated pirfenidone LYT-100. This method is expected to provide significantly increased efficacy, tolerability, and patient compliance in these subjects, as compared to treatment with pirfenidone. The features of the method are disclosed further herein below.

Definitions

While the terms used herein are believed to be well understood by one of ordinary skill in the art, definitions are set forth herein to facilitate explanation of the presently disclosed subject matter.

The articles "a" and "an" are used herein to refer to one or to more than one (i.e., to at least one) of the grammatical object of the article.

The term "about" used throughout this specification is used to describe and account for small fluctuations. For example, the term "about" can refer to greater than, less than or equal to +10%, such as greater than, less than or equal to +5%, greater than, less than or equal to +2%, greater than, less than or equal to +1%, greater than, less than or equal to +0.5%, greater than, less than or equal to +0.2%, greater than, less than or equal to +0.1% or greater than, ess than or equal to +0.05%. All numeric values herein are modified by the term "about," whether or not explicitly indicated. A value modified by the term "about" of course includes the specific value. For instance, "about 5.0" must include 5.0.

The term "Adverse Event" refers to any event, side-effect, or other untoward medical occurrence that occurs in conjunction with the use of a medicinal product in humans, whether or not considered to have a causal relationship to this treatment. An AE can, therefore, be any unfavourable and unintended sign (that could include a clinically significant abnormal laboratory finding), symptom, or disease temporally associated with the use of a medicinal product, whether or not considered related to the medicinal product. Events meeting the definition of an AE include: Exacerbation of a chronic or intermittent pre-existing condition including either an increase in frequency and/or intensity of the condition; New conditions detected or diagnosed after study drug administration that occur during the reporting periods, even though it may have been present prior to the start of the study; Signs, symptoms, or the clinical sequelae of a suspected interaction; Signs, symptoms, or the clinical sequelae of a suspected overdose of either study drug or concomitant medications (overdose per se will not be reported as an AE/SAE). AE's may have a causal relationship with the treatment, may be possibly related, or may be unrelated. Severity of AEs may be graded as one of: Mild (Grade 1): A type of AE that is usually transient and may require only minimal treatment or therapeutic intervention. The event does not generally interfere with usual activities of daily living; Moderate (Grade 2): A type of AE that is usually alleviated with additional specific therapeutic intervention. The event interferes with usual activities of daily living, causing discomfort but poses no significant or permanent risk of harm to the research participant; Severe (Grade 3): A type of AE that interrupts usual activities of daily living, or significantly affects clinical status, or may require intensive therapeutic intervention; Life-threatening (Grade 4): A type of AE that places the participant at immediate risk of death; Death (Grade 5): Events that result in death.

As used herein, the term "clinically effective amount," "clinically proven effective amount," and the like, refer to an effective amount of an API as shown through a clinical trial, e.g., a U.S. Food and Drug Administration (FDA) clinical trial.

The term "is/are deuterium," when used to describe a given variable position in a molecule or formula, or the symbol "D," when used to represent a given position in a drawing of a molecular structure, means that the specified position is enriched with deuterium above the naturally occurring distribution of deuterium. In some embodiments, deuterium enrichment is of no less than about 1%, no less than about 5%, no less than about 10%, no less than about 20%, no less than about 50%, no less than about 70%, no less than about 80%, no less than about 90%, no less than about 98%, or in some embodiments no less than about 99% of deuterium at the specified position. In some embodiments, the deuterium enrichment is above 90% at each specified position. In some embodiments, the deuterium enrichment is above 95% at each specified position. In some embodiments, the deuterium enrichment is about 99% at each specified position.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156%, deuterium enrichment at any position in a compound synthesized using non-enriched starting materials is about 0.0156%. The deuterium enrichment can be determined using conventional analytical methods, such as mass spectrometry and nuclear magnetic resonance spectroscopy.

The term "fibrosis" refers to the deposition of extracellular matrix components, excessive fibrous connective tissue, or scarring within an organ or tissue.

The term "idiopathic pulmonary fibrosis (IPF)" refers to a type of lung disease that results in scarring of the lungs (pulmonary fibrosis) for which the origin of the disease state may be unknown.

"Prevent" or "prevention" refers to prophylactic or preventative measures that obstruct, delay and/or slow the development of a targeted pathologic condition or disorder or one or more symptoms of a targeted pathologic condition or disorder. Thus, those in need of prevention include those at risk of or susceptible to developing the disorder.

The terms "subject" and "patient" refers to a mammalian subject, including a human subject. In some embodiments, the patient is human subject.

Terms such as "treating" or "treatment" or "to treat" refer to therapeutic measures that avoid, delay, and/or slow the occurrence of, avoid, delay, and/or slow the progression of, prevent, cure, ameliorate or lessen one or more symptoms of a pathologic condition or disorder; and/or that avoid occurrence of, prevent, cure, ameliorate, slow progression of, and/or halt progression of, a pathologic condition or disorder.

In some embodiments, treatment may be administered after one or more symptoms have developed. Thus, those in need of treatment include those already with the disorder (e.g., IPF). In some embodiments, treatment may be administered after one or more symptoms have developed. In some embodiments, a subject is successfully "treated" for a disease or disorder according to the methods provided herein if the patient shows, e.g., total, partial, or transient alleviation or elimination of one or more symptoms associated with the disease or disorder (e.g., IPF) or if the patient shows, e.g., partial or transient delay in the progression of one or more symptoms associated with the disease or disorder (e.g., IPF) and/or if the patient shows, e.g., partial, or transient decrease (reduction, lessening) in the rate of progression of one or more symptoms associated with the disease or disorder, e.g., IPF, including, for example, impaired respiratory function and pulmonary fibrosis, as well as other known symptoms of IPF.

The terms "subject" and "patient" refers to a mammalian subject, including a human subject. In some embodiments, the patient is human subject.

LYT-100

The methods disclosed herein comprise administering a deuterium-enriched pirfenidone which is LYT-100. LYT-100 is a selectively deuterated form of pirfenidone. Specifically, LYT-100 is the deuterium-enriched pirfenidone, 5-(methyl-$d_3$)-1-phenylpyridin-2-(1H)-one (CAS #1093951-85-9) which may alternatively be referred to as deupirfenidone or 2(1H)-Pyridinone, 5-(methyl-d3)-1-phenyl. LYT-100 has the following structure:

(LYT-100)

Reference to "LYT-100" herein further includes any hydrate, solvate, crystalline polymorph, amorphous form, or the like, of 5-(methyl-$d_3$)-1-phenylpyridin-2-(1H)-one.

The LYT-100 as disclosed herein can be prepared by methods known to one of skill in the art and routine modifications thereof, and/or procedures found in Esaki et al., Tetrahedron 2006, 62, 10954-10961, Smith et al., Organic Syntheses 2002, 78, 51-56, U.S. Pat. Nos. 3,974,281, 8,680,123, WO2003/014087, WO2008/157786, WO2009/035598, WO 2012/122165, or WO2015/112701; the entirety of each of which is hereby incorporated by reference; and references cited therein and routine modifications thereof.

Methods for Treating Idiopathic Pulmonary Fibrosis

Unmet Need for Improved Treatment of IPF

Pirfenidone is indicated for the treatment of idiopathic pulmonary fibrosis (IPF) and pirfenidone treatment is associated with clinical benefits. In a pooled analysis of phase 3 studies used for US registration (Noble 2016 et al. Pirfenidone for idiopathic pulmonary fibrosis: analysis of pooled data from three multinational phase 3 trials. *Eur Respir J.* 2016; 47(1):243-253):

1) The mean change from baseline to 1 year in FVC was −216 mL in the pirfenidone group and −363 mL in the placebo group (absolute difference 148 mL, relative difference 40.7%; p<0.001.

2) The proportion of patients with a ≥10% decline in FVC % predicted or death was reduced by 43.8% (95% CI 29.3-55.4) at one year in the pirfenidone group and the proportion of patients with no decline in FVC % predicted was increased by 59.3% (95% CI 29.0-96.8) compared with placebo (rank ANCOVA, p<0.001).

3) Pirfenidone reduced the risk of death or disease progression (defined as a confirmed ≥10% decline in FVC % predicted or a confirmed ≥50 m decline in 6MWD) at 1 year by 38% compared with placebo (hazard ratio 0.62, 95% CI 0.51-0.75; p<0.001).

The unmet medical needs for patients living with IPF include dose-limiting adverse events and toxicity associated with gastrointestinal intolerability (e.g., nausea, vomiting, diarrhea, dyspepsia, anorexia, and other GI events), dizziness, fatigue, rash and photosensitivity rash, as well as other adverse side-effects, which limits current treatment for IPF (Noble, 2016). Management of these adverse events includes dose reductions and discontinuations of pirfenidone, associated with a lost opportunity for the full clinical benefits when full dose pirfenidone is maintained.

The real-world use of pirfenidone is low. A study used the US OptumLabs Data Warehouse to identify 10,996 patients with IPF with medical and pharmacy claims between Oct. 1, 2014, to Jul. 31, 2019. The study showed that 73.6% of patients with IPF never received an antifibrotic (pirfenidone or nintedanib) during the observation period (Dempsey et al. Adoption of the Antifibrotic Medications Pirfenidone and Nintedanib for Patients with Idiopathic Pulmonary Fibrosis. *Ann Am Thorac Soc.* 2021; 18(7):1121-1128).

Pirfenidone is associated with poor tolerability in a population of patients with IPF that is older and typically has multiple comorbidities. In a pooled analysis of phase 3 studies used for US registration, patients receiving pirfenidone had a 31.5% rate of permanent dose reductions and a 15.2% rate of treatment discontinuation, compared to 20.8% and 12.7% for placebo, respectively (Nathan et al. Dose modification and dose intensity during treatment with pirfenidone: analysis of pooled data from three multinational phase III trials. BMJ Open Respir Res. 2018; 5(1):e000323). Patients on placebo also had dose reductions and discontinuations, but at a lower rate than with pirfenidone. In a multinational observational study of 1,009 patients with IPF who started pirfenidone 2,403 mg/day, by two years only 21.3% were still on full dose (2,403 mg/day) pirfenidone, 13.8% were on a lower dose, and 64.9% had discontinued treatment, with 27.9% of discontinuations due to adverse events associated with pirfenidone (Cottin et al. Long-term safety of pirfenidone: results of the prospective, observational PASSPORT study. ERJ Open Res. 2018; 4(4):00084-2018. Published 2018 Oct. 19). In the Optum database, Dempsey et al. found that 42.8% of patients discontinued treatment and the mean duration of antifibrotic treatment was 302 days (Dempsey 2021), Pirfenidone dose reductions are associated with lower efficacy than full dose pirfenidone. Nathan and colleagues compared patients who were able to maintain >90% of their pirfenidone dose (dose intensity) with those who had <90% dose intensity for the frequency of IPF progression, defined as a decline ≥10% in % FVC or death over 52 weeks. For patients with >90% dose intensity, 11.6% of patients treated with pirfenidone had IPF progression compared to 25.6% of patients receiving placebo (relative difference-54.8%, p<0.0001) while for patients with <90% dose intensity, 21.6% of patients treated with pirfenidone had IPF progression compared to 32.3% of patients receiving placebo (relative difference-33.1%, p<0.0805). This study showed that IPF progression was not statistically significantly different between those patients receiving <90% dose intensity of pirfenidone and those receiving placebo (Nathan 2018). Accordingly, improved tolerability—which enables the ability to stay on a clinically efficacious high dose of pirfenidone—is critical to patient outcome in IPF treatment.

Disclosed herein are methods of treating Idiopathic Pulmonary Fibrosis (IPF). The method generally comprises administering to a subject in need thereof a deuterium-enriched pirfenidone having the structure:

LYT-100 wherein the IPF is treated in the subject.

The dose and frequency of dosing may vary based on the severity of the IPF. In some embodiments, the total daily dose is from about 825 mg to about 2550 mg of LYT-100. In some embodiments, the total daily dose is about 1650 to about 2475 mg of LYT-100, such as about 1650, about 1700, about 1750, about 1800, about 1850, about 1900, about 1950, about 2000, about 2050, about 2100, about 2150, about 2200, about 2250, about 2300, about 2350, about 2400, about 2450, about 2475, about 2500, or about 2550 mg. In some embodiments, the total daily dose is 1650 mg. In some embodiments, the total daily dose is 2475 mg. In some embodiments, the total daily dose in 825 mg.

Doses and Dosing Schedule for LYT-100—Improved Tolerability

The poor tolerability of pirfenidone, commonly managed with dose reductions, treatment interruptions, and/or temporary or permanent discontinuations, is associated with reduced clinical efficacy of pirfenidone in the treatment of IPF. Therefore, currently there is a major unmet need in the treatment for IPF that may be addressed with LYT-100. The deuteration of pirfenidone to create LYT-100 slows its metabolism (Chen 2021). The altered metabolism of LYT-100 may be associated with the reduced adverse effects and improved tolerability observed with LYT-100. Improved tolerability of the current clinically efficacious dose of Pirfenidone (801 mg TID) can improve IPF patient outcomes due to increased compliance with a sustained clinically efficacious dose (e.g., by reducing the frequency of dose reductions, treatment interruptions, and/or temporary or permanent discontinuations currently experienced with the use of pirfenidone).

Numerous dose-ranging PK studies of LYT-100 were performed (e.g., several dose-ranging MAD studies ranging from total daily doses of 1000 mg to 4000 mg of LYT-100). PK modeling data incorporated the results of various MAD PK studies to reduce variability inherent in multiple studies of small sample size. The results of the pooled data from these various dose-ranging studies is shown below in Table 11 and indicated that a dose of 550 mg TID LYT-100 had a systemic exposure (AUC) of about 90-98% (average about 95%) of the AUC achieved with pirfenidone (2403 mg dose, 801 mg TID) and a Cmax of about 73-80% (average about 77%) of the Cmax achieved with pirfenidone (2403 mg dose, 801 mg TID). A dose of 825 mg TID had a systemic exposure (AUC) of about 139-148% (average about 143%) of the AUC achieved with pirfenidone (2403 mg dose, 801 mg TID) and a Cmax of about 109-121% (average about 115%) of the Cmax achieved with pirfenidone (2403 mg dose, 801 mg TID).

Pirfenidone has not been tested for clinical efficacy above doses of 801 mg TID due to poor tolerability. The dose of LYT-100 was optimized to achieve similar systemic exposure (AUC) to pirfenidone 801 mg TID. The dose of LYT-100 was also optimized to achieve similar Cmax to pirfenidone 801 mg TID while maximizing exposure (AUC). The Cmax and AUC values obtained using the pooled LYT-100 PK data in comparison with 801 mg TID pirfenidone were confirmed in subsequent individual studies of 550 mg TID LYT-100 and 824 mg TID LYT-100, thus confirming our confidence in the modeling data and the use of 550 mg TID and 825 mg TID LYT-100 doses.

Table A summarizes the pharmacokinetic results of a cross-over study administering a dose of LYT-100 550 mg TID versus pirfenidone 801 mg TID. The results are expressed as Mean (SD), and shows that at the 550 mg TID dose, the AUC of LYT-100 is similar to that of pirfenidone dosed at the 801 mg TID dose while the $C_{max}$ is lower. The $AUC_{0-24}$ of LYT-100 meets the criterion for bioequivalence (geometric mean ratio=0.875; 90% Confidence Interval=0.842 to 0.910) with pirfenidone 801 mg TID, while the $C_{max}$ does not). The major metabolite of both pirfenidone and LYT-100, 5-carboxypirfenidone, showed lower $C_{max}$ and $AUC_{0-24}$ after LYT-100 dosing at 550 mg TID compared to pirfenidone 801 mg TID. The reduced $C_{max}$ of the parent and the 5-carboxypirfenidone with LYT-100 may be responsible for lowering the gastric side effects of pirfenidone while the similar level of total exposure (AUC) is expected to maintain the efficacy in IPF. Similar results were also seen on Day 4 or 14 after a single 550 mg dose of LYT-100 or 801 mg of pirfenidone was administered in the fasted state (Table B). The $C_{max}$ of the parent and the 5-carboxy metabolite were increased to a smaller extent after LYT-100 dosing than after pirfenidone dosing.

TABLE A

Pharmacokinetic Parameters of LYT-100,
Pirfenidone, and 5-Carboxypirfenidone
after the 3 Days of Dosing in the Fed State

| Analyte | LYT-100 550 mg TID PK Parameters on Day 3/13 (Fed) Mean (SD) | | Pirfenidone 801 mg TID PK Parameters on Day 3/13 (Fed) Mean (SD) | |
|---|---|---|---|---|
| | $C_{max}$ (µg/mL) | $AUC_{0-24}$ (µg · hr/mL) | $C_{max}$ (µg/mL) | $AUC_{0-24}$ (µg · hr/mL) |
| Parent | 8.66 (3.0) | 131.4 (44.9) | 11.3 (4.8) | 155.2 (50.6) |
| 5-carboxy pirfenidone | 4.02 (1.0) | 67.19 (16.7) | 7.16 (2.5) | 108.2 (33.6) |

TABLE B

Pharmacokinetic Parameters of LYT-100, Pirfenidone, and
5-Carboxy-pirfenidone after the 3 Days of Dosing in the
Fed State Followed by a Single Dose in
the Fasted State on Day 4/14

| Analyte | LYT-100 550 mg TID PK Parameters on Day 4/14 (Fasted) Mean (SD) | | Pirfenidone 801 mg TID PK Parameters on Day 4/14 (Fasted) Mean (SD) | |
|---|---|---|---|---|
| | $C_{max}$ (µg/mL) | $AUC_{0-24}$ (µg · hr/mL) | $C_{max}$ (µg/mL) | $AUC_{0-24}$ (µg · hr/mL) |
| Parent | 9.78 (3.0) | 36.43 (11.5) | 13.1 (3.2) | 45.92 (12.1) |
| 5-carboxy pirfenidone | 4.14 (1.2) | 16.83 (4.68) | 7.88 (2.4) | 29.84 (9.29) |

In addition, further PK studies were performed to determine dosing frequency and dose amounts that were associated with improved tolerability (compared to the currently approved treatment of IPF, e.g., pirfenidone 801 mg TID).

The dose that minimized AEs with a similar overall exposure level (AUC) to pirfenidone 801 mg TID was LYT-100 550 mg TID.

As shown in Table C, LYT-100 550 mg TID and pirfenidone 801 mg TID PK and AE data were compared in the fed and fasted states (LYT-100-2021-103 Part 2). At the 550 mg TID (e.g., similar drug exposure level to approved 801 TID pirfenidone), lower AEs were observed with LYT-100 in both the fed and fasted states compared with pirfenidone. Specifically, administering a daily dose of 1650 mg LYT-100 demonstrated that LYT-100 550 mg TID was associated with improved tolerability compared to pirfenidone, including a 50% reduction in gastrointestinal-related AEs and a 45% reduction in CNS-related AEs (see Example 1 and Results for LYT-100-2021-103 Part 2 shown in Table C).

Although the AEs observed with the administration of 550 mg TID LYT-100 in the fasted state were higher than the AEs seen in the fed state, the AEs with LYT-100 550 mg TID in the fasted state were still much lower than those seen with pirfenidone 801 mg TID in the fasted state. These results demonstrate that, at the same/similar drug exposure level of 801 TID pirfenidone, LYT-100 administered 550 TID has improved tolerability (less AEs) and the option of being given in the fasted state if needed, such as with individual variation in timing of meals. These data provide the rationale for selecting the 550 mg TID dose of LYT-100 in the treatment of IPF.

When rates of AEs were ordered from lowest to highest, Cmax values for parent compound for each of these conditions similarly sorted from lowest to highest: Lowest AE rates and Cmax to highest AEs and Cmax=LYT-100 550 mg (fed) to LYT-100 550 mg (fasted) to pirfenidone 801 mg (fed) to pirfenidone 801 mg (fasted)-Table C (LYT-100-2021-103 Part 2). Levels of the 5-carboxy metabolite also sorted from lowest to highest in the above order (Table C) (LYT-100-2021-103 Part 2).

TABLE C

| Pharma-cokinetics | LYT-100 550 mg TID Fed N = 46 PK | | Pirfenidone 801 mg TID Fed N = 47 PK | | LYT-100 550 mg TID Fasted N = 44 PK | | Pirfenidone 801 mg TID Fasted N = 47 PK | |
|---|---|---|---|---|---|---|---|---|
| | $C_{max}$ (mcg/ mL) | $AUC_{0-24}$ mcg * hr/ mL | $C_{max}$ (mcg/ mL) | $AUC_{0-24}$ mcg * hr/ mL | $C_{max}$ (mcg/ mL) | $AUC_{0-6}$ mcg * hr/ mL | $C_{max}$ (mcg/ mL) | $AUC_{0-6}$ mcg * hr/ mL |
| | Mean (SD) | | Mean (SD) | | Mean (SD) | | Mean (SD) | |
| PK Parent | 8.66 (3.0) | 131.4 (44.9) | 11.3 (4.8) | 155.2 (50.6) | 9.78 (3.0) | 36.43 (11.5) | 13.1 (3.2) | 45.92 (12.1) |
| PK 5-carboxy metabolite | 4.02 (1.0) | 67.19 (16.7) | 7.16 (2.5) | 108.2 (33.6) | 4.14 (1.2) | 16.83 (4.68) | 7.88 (2.4) | 29.84 (9.29) |
| Adverse Events* | N = 46 n (%) | | N = 47 n (%) | | N = 45 n (%) | | N = 46 n (%) | |
| GI Disorders | 3 (6.5) | | 5 (10.6) | | 5 (11.1) | | 13 (28.3) | |
| Nausea | 2 (4.3) | | 4 (8.5) | | 5 (11.1) | | 12 (26.1) | |
| Vomiting | 2 (4.3) | | 2 (4.3) | | 0 | | 1 (2.2) | |
| Diarrhea | 0 | | 0 | | 0 | | 0 | |
| Dyspepsia | 0 | | 0 | | 0 | | 0 | |
| Abdominal Pain/ Discomfort/ Distension | 1 (2.2) | | 1 (2.2) | | 0 | | 2 (4.3) | |
| Nervous System Disorders | 4 (8.7) | | 7 (14.9) | | 4 (8.9) | | 10 (21.7) | |
| Headache | 4 (8.7) | | 5 (10.6) | | 2 (4.4) | | 5 (10.9) | |
| Dizziness | 0 | | 3 (6.4) | | 1 (2.2) | | 5 (10.9) | |

Table D summarizes the pharmacokinetic results and shows that at the 550 mg TID dose, the PK parameters of LYT-100 and the metabolite, 5-carboxypirfenidone were similar to those seen in Part 2 of the study at the 550 mg TID dose of LYT-100. At the higher dose of 824 mg TID, the $AUC_{0-24}$ and $C_{max}$ were higher than those seen with pirfenidone; however, the corresponding parameters of the metabolite 5-carboxypirfenidone were similar/slightly lower. The adverse event data (Table F) shows that even at the 824 mg TID dose, the frequency of the most common adverse events was very low. The higher exposures combined with low frequency of adverse events provide the rationale for using the 825 mg TID dose of LYT-100 in the treatment of IPF.

TABLE D

| | Pharmacokinetic Parameters of LYT-100, Pirfenidone, and 5-Carboxypirfenidone after the 3 Days of Dosing in the Fed State | | | |
| --- | --- | --- | --- | --- |
| | LYT-100 550 mg TID PK Parameters on Day 3 (Fed) N =1 3, Mean (SD) | | LYT-100 824 mg TID PK Parameters on Day 6 (Fed) N = 13, Mean (SD) | |
| Analyte | $C_{max}$ (µg/mL) | $AUC_{0-24}$ (µg · hr/mL) | $C_{max}$ (µg/mL) | $AUC_{0-24}$ (µg · hr/mL) |
| Parent | 9.34 (2.4) | 132.0 (31.2) | 13.7 (5.1) | 193.9 (60.6) |
| 5-carboxy pirfenidone | 4.74 (2.0) | 69.12 (22.9) | 6.75 (2.6) | 95.24 (32.3) |

Doses and Dosing Schedule for LYT-100-Higher Efficacious Dose

Pirfenidone has not been tested for clinical efficacy above doses of 801 mg TID due to poor tolerability, including gastrointestinal adverse effects, nausea, weight loss, and photosensitive skin rash (among other AEs). Although some studies have been performed using higher doses of pirfenidone, well-controlled efficacy studies have not yet been done with pirfenidone doses higher than 2403 mg daily dose. Thus, while high doses of pirfenidone-up to 801 mg TID pirfenidone—are associated with improved efficacy (compared with doses less than 2403 mg daily), an upper threshold to improved clinical efficacy has not been achieved to date because doses higher than 801 mg TID have not been tested in well-controlled clinical efficacy studies due to poor tolerability.

The dose of LYT-100 was optimized to achieve similar $C_{max}$ to pirfenidone 801 mg TID while maximizing drug exposure (AUC). Study LYT-100-2021-103 Part 3 was a randomized, double-blinded, parallel arm, placebo-controlled study conducted in healthy older adults to evaluate the safety and tolerability of titrated high dose LYT-100 compared to placebo under fed conditions. Based on the observations of improved tolerability (but comparable total exposure) for a lower TID dose of LYT-100 compared to pirfenidone in Part 2 (550 mg TID LYT-100), the decision was made to test the safety and tolerability of a higher TID dose of LYT-100, to achieve a higher overall predicted AUC or total exposure than the approved dose of pirfenidone (801 mg TID). Subjects between the ages of 60 and 80 were randomized to receive LYT-100 or placebo. Subjects were administered up to 550 mg LYT-100 TID for 3 days (to steady state [Day 1 to Day 3]) compared to placebo administered TID for 3 days to steady state. On Day 4 to Day 6, subjects were administered 824 mg LYT-100 TID for 3 days compared to placebo TID for 3 days to steady state. A summary of the dosing scheme is provided below in the Example section (Example 2).

Table E summarizes the pharmacokinetic results and shows that at the 550 mg TID dose, the PK parameters of LYT-100 and the metabolite, 5-carboxypirfenidone were similar to those seen in Part 2 of the study at the 550 mg TID dose of LYT-100. At the higher dose of 824 mg TID, the $AUC_{0-24}$ and $C_{max}$ were higher than those seen with pirfenidone 801 mg TID; however, the corresponding parameters of the metabolite 5-carboxypirfenidone were similar or slightly lower. The adverse event data (Table F) shows that even at the 824 mg TID dose, the frequency of the most common adverse events was very low. The higher exposures combined with low frequency of adverse events provide the rationale for using the 825 mg TID dose of LYT-100 in future trials of IPF.

TABLE E

| | Pharmacokinetic Parameters of LYT-100, Pirfenidone, and 5-Carboxypirfenidone after the 3 Days of Dosing in the Fed State | | | |
| --- | --- | --- | --- | --- |
| | LYT-100 550 mg TID PK Parameters on Day 3 (Fed) N = 13, Mean (SD) | | LYT-100 824 mg TID PK Parameters on Day 6 (Fed) N = 13, Mean (SD) | |
| Analyte | $C_{max}$ (µg/mL) | $AUC_{0-24}$ (µg · hr/mL) | $C_{max}$ (µg/mL) | $AUC_{0-24}$ (µg · hr/mL) |
| Parent | 9.34 (2.4) | 132.0 (31.2) | 13.7 (5.1) | 193.9 (60.6) |
| 5-carboxy pirfenidone | 4.74 (2.0) | 69.12 (22.9) | 6.75 (2.6) | 95.24 (32.3) |

LYT-100 824 mg TID achieved approximately 25% higher AUC with a modestly higher Cmax compared to historic pirfenidone PK values. Surprisingly, as shown in Table F, this high dose of LYT-100 (825 mg TID) was well-tolerated. Prior to completing the tolerability study shown in Table F, it was not known such high dose-825 mg TID LYT-100 which is the equivalent of about 120-150% exposure of 801 TID pirfenidone)-could be sufficiently tolerated to be included in a clinical efficacy study.

TABLE F

| | Healthy Older Part 3 | | | |
| --- | --- | --- | --- | --- |
| | LYT-100 550 mg TID Fed N = 13 | | LYT-100 824 mg TID Fed N = 13 | |
| Pharmacokinetics | $C_{max}$ (mcg/mL) Mean (SD) | $AUC_{0-24}$ mcg * hr/mL | $C_{max}$ (mcg/mL) Mean (SD) | $AUC_{0-24}$ mcg * hr/mL |
| PK Parent | 9.34 (2.4) | 132.0 (31.2) | 13.7 (5.1) | 193.9 (60.6) |
| PK 5-carboxy metabolite | 4.74 (2.0) | 69.12 (22.9) | 6.75 (2.6) | 95.24 (32.3) |
| Adverse Events* | N = 13 n (%) | | N = 13 n (%) | |
| GI Disorders | 2 (8.3) | | 0 | |
| Nausea | 0 | | 0 | |
| Vomiting | 0 | | 0 | |
| Diarrhea | 1 (4.2) | | 0 | |
| Dyspepsia | 1 (4.2) | | 0 | |
| Abdominal Pain/ Discomfort/ Distension | 0 | | 0 | |

41

TABLE F-continued

| Nervous System Disorders | 3 (12.5) | 0 |
|---|---|---|
| Headache | 3 (12.5) | 0 |
| Dizziness | 1 (4.2) | 0 |

*AEs reported are those that are most common for pirfenidone and seen across LYT-100 studies including GI and Nervous System Disorders Table G provides tolerability comparisons of LYT-100 with either 550 mg TID dosing or 824 mg TID dosing versus the 801 mg TID pirfenidone arm in the Part 2 study, along with Cmax and exposure data for parent drug and the major metabolite for each cohort. With reference to Table G, both doses of LYT-100 generally demonstrated improved tolerability relative to pirfenidone.

TABLE G

| Pharmacokinetics | Healthy Older Adult Part 3 | | | | Healthy Older Adult Part 2 (pirf. Arm-for comparison only) | |
|---|---|---|---|---|---|---|
| | LYT-100 550 mg TID Fed N = 13 | | LYT-100 824 mg TID Fed N = 13 | | Pirfenidone 801 mg TID Fed N = 47 PK | |
| | $C_{max}$ (mcg/mL) Mean (SD) | $AUC_{0-24}$ mcg * hr/mL Mean (SD) | $C_{max}$ (mcg/mL) Mean (SD) | $AUC_{0-24}$ mcg * hr/mL Mean (SD) | $C_{max}$ (mcg/mL) Mean (SD) | $AUC_{0-24}$ mcg * hr/mL Mean (SD) |
| PK Parent | 9.34 (2.4) | 132.0 (31.2) | 13.7 (5.1) | 193.9 (60.6) | 11.3 (4.8) | 155.2 (50.6) |
| PK 5-carboxy metabolite | 4.74 (2.0) | 69.12 (22.9) | 6.75 (2.6) | 95.24 (32.3) | 7.16 (2.5) | 108.2 (33.6) |
| Adverse Events* | N = 13 n (%) | | N = 13 n (%) | | N = 47 n (%) | |
| GI Disorders | 2 (8.3) | | 0 | | 5 (10.6) | |
| Nausea | 0 | | 0 | | 4 (8.5) | |
| Vomiting | 0 | | 0 | | 2 (4.3) | |
| Diarrhea | 1 (4.2) | | 0 | | 0 | |
| Dyspepsia | 1 (4.2) | | 0 | | 0 | |
| Abdominal Pain/ Discomfort/ Distension | 0 | | 0 | | 1 (2.2) | |
| Nervous System Disorders | 3 (12.5) | | 0 | | 7 (14.9) | |
| Headache | 3 (12.5) | | 0 | | 5 (10.6) | |
| Dizziness | 1 (4.2) | | 0 | | 3 (6.4) | |

*AEs reported are those that are most common for pirfenidone and seen across LYT-100 studies including GI and Nervous System Disorders The 550 mg TID and 825 mg TID doses of LYT-100 were optimized to key PK parameters and demonstrated to improve tolerability as compared with 2304 mg daily dose (801 mg TID) pirfenidone, surprisingly even at a higher systemic drug exposure. This improved tolerability of LYT-100 relative to pirfenidone was unexpected and may significantly improve clinical efficacy outcomes for IPF patients due to improved compliance with a sustained high efficacious dose (e.g., by reducing the frequency of dose reductions, treatment interruptions, and/or temporary or permanent discontinuations currently experienced with the use of pirfenidone).

Conclusions from the 550 mg TID and 824 mg TID PK studies (studies are fully described in Examples 1 and 2); Part 1 showed that 850 mg BID of LYT-100 closely matched the AUC with slightly higher Cmax with pirfenidone 801 mg TID. Part 2 of the Study showed that 550 mg TID LYT-100 dose matched the AUC (within BE) with lower Cmax compared to pirfenidone 801 mg TID. Part 3 of the Study had results that were unexpected given the predictions (based on Parts 1, 2):

(1) LYT-100 550 mg TID had much lower AUC but similar Cmax compared to Part 2.

(2) LYT-100 824 mg TID had lower AUC than predicted; Cmax was 17% higher than with pirfenidone.

(3) Although higher variability was seen in PK parameters of LYT-100 in Part 3, the 5-carboxy Metabolite/Parent Ratio was consistently lower with LYT-100 compared to pirfenidone (i.e., the 5-carboxy metabolite exposures are lower when comparing the same doses of LYT-100 and pirfenidone).

(4) The GI AE's and nausea are much lower with LYT-100 (550 mg TID) compared to pirfenidone 801 mg TID. Dosing in the Fed state lowered the GI-related AE's, especially for pirfenidone. Dosing in the fed state had less of an impact on AEs with LYT-100.

(5) The GI AE's appear early during treatment; better tolerability with LYT-100 at the 550 mg TID dose allows subjects to have better adherence with the full dose which may result in better clinical outcome.

In some embodiments, the total daily dose is administered in three equal administrations. In some embodiments, the LYT-100 is administered in three equal doses of 550 mg each (550 mg TID). In some embodiments, the LYT-100 is administered in three equal doses of 825 mg each (825 mg TID). In some embodiments, the LYT-100 is administered in three equal doses of 275 mg each (275 mg TID).

In some embodiments, the LYT-100 is administered without regard to food. In some embodiments, the LYT-100 is administered without food. In some embodiments, the LYT-100 is administered with food.

In some embodiments, the LYT-100 is administered orally without food in three daily doses of 550 mg each. In some embodiments, the LYT-100 is administered orally with food in three daily doses of 550 mg each.

In some embodiments, the LYT-100 is administered orally without food in three daily doses of 825 mg each. In some embodiments, the LYT-100 is administered orally with food in three daily doses of 825 mg each.

In some embodiments, the LYT-100 is administered orally without food in three daily doses of 275 mg each. In some embodiments, the LYT-100 is administered orally with food in three daily doses of 275 mg each.

In some embodiments, the LYT-100 is administered with dose escalation, as described previously above. In some embodiments, the LYT-100 is administered without dose escalation.

In some embodiments, LYT-100 administered in a total daily dose of 1650-2475, in three daily doses, results in increased tolerability as compared with pirfenidone administered at 801 mg TID. In some embodiments, the increased tolerability is due to a reduction in one or more adverse events or side effects. In some embodiments, the one or more adverse events are nervous system side effects. In some embodiments, the one or more adverse events are gastrointestinal events. In some embodiments, the LYT-100 is administered in three daily doses of 550 mg each.

In some embodiments, LYT-100 administered in a total daily dose of 1650-2475, in three daily doses, results in a lower steady-state $C_{max}$ as compared with pirfenidone administered at 801 mg TID. In some embodiments, the LYT-100 is administered in three daily doses of 550 mg each.

In some embodiments, LYT-100 administered in a total daily dose of 1650-2475, in three daily doses, results in a steady-state exposure (AUC) of LYT-100 which is the same or about the same as the steady-state exposure (AUC) of pirfenidone achieved when pirfenidone is administered at 801 mg TID. In some embodiments, LYT-100 administered in a total daily dose of 1650-2475, in three daily doses, results in a steady-state exposure (AUC) of LYT-100 which is bioequivalent to the steady-state exposure (AUC) of pirfenidone when pirfenidone is administered at 801 mg TID. In some embodiments, the LYT-100 is administered in three daily doses of 550 mg each.

In some embodiments, LYT-100 administered in a total daily dose of 1650-2475, in three daily doses, results in the same or about the same steady-state exposure (AUC) of LYT-100 achieved for pirfenidone when pirfenidone is administered at 801 mg TID, and results in a lower steady-state $C_{max}$ of LYT-100 achieved for pirfenidone when pirfenidone is administered at 801 mg TID. In some embodiments, the steady-state exposure of LYT-100 is about 90% of the AUC of pirfenidone achieved when pirfenidone is administered at a total daily dose of 2403 mg, and wherein the total daily dose of pirfenidone is administered in three doses of 801 mg each (801 mg TID). In some embodiments, the lower steady-state $C_{max}$ of LYT-100 is about 75-80% of the $C_{max}$ of pirfenidone achieved when pirfenidone is administered at a total daily dose of 2403 mg, and wherein the total daily dose of pirfenidone is administered in three doses of 801 mg each (801 mg TID). In some embodiments, at this dosing, the LYT-100 has an increased or improved tolerability that is due to a reduction in one or more adverse events or side effects as compared with pirfenidone administered at 801 mg TID. In some embodiments, the LYT-100 is administered in three daily doses of 550 mg each.

In some embodiments, LYT-100 administered in a total daily dose of 1650-2475, in three daily doses, results in the same or about the same steady-state exposure (AUC) as compared with pirfenidone administered at 801 mg TID and increased or improved tolerability as compared with pirfenidone administered at 801 mg TID. In some embodiments, the increased or improved tolerability is due to a reduction in one or more adverse events or side effects. In some embodiments, LYT-100 is administered in three daily doses of 550 mg each.

In some embodiments, LYT-100 administered in a total daily dose of 1650-2475, in three daily doses, results in a higher steady-state exposure (AUC) as compared with pirfenidone administered at 801 mg TID. In some embodiments, the LYT-100 is administered in three daily doses of 825 mg each.

In some embodiments, LYT-100 administered in a total daily dose of 1650-2475, in three daily doses, results in the same or about the same steady-state Cmax as compared with pirfenidone administered at 801 mg TID. In some embodiments, the LYT-100 is administered in three daily doses of 825 mg each.

In some embodiments, LYT-100 administered in a total daily dose of 1650-2475, in three daily doses, results in a higher steady-state exposure (AUC) as compared with pirfenidone administered at 801 mg TID and the same or about the same steady-state Cmax as compared with pirfenidone administered at 801 mg TID. In some embodiments, the LYT-100 is administered in three daily doses of 825 mg each.

In some embodiments, LYT-100 administered in a total daily dose of 1650-2475, in three daily doses, results in a higher steady-state exposure (AUC) as compared with pirfenidone administered at 801 mg TID and has the same or about the same tolerability (e.g., the incidence of adverse events is not significantly different) as compared with pirfenidone administered at 801 mg TID. In some embodiments, LYT-100 administered in a total daily dose of 1650-2475, in three daily doses, results in a higher steady-state exposure (AUC) as compared with pirfenidone administered at 801 mg TID and has an increased or improved tolerability that is due to a reduction in one or more adverse events or side effects. In some embodiments, the LYT-100 is administered in three daily doses of 825 mg each.

In some embodiments, LYT-100 administered in a total daily dose of 1650-2475, in three daily doses, results in the same or about the same steady-state Cmax as compared with pirfenidone administered at 801 mg TID and has the same or about the same tolerability (e.g., the incidence of adverse events is not significantly different) as compared with pirfenidone administered at 801 mg TID. In some embodiments, LYT-100 administered in a total daily dose of 1650-2475, in three daily doses, results in the same or about the same steady-state Cmax as compared with pirfenidone administered at 801 mg TID and has an increased or improved tolerability that is due to a reduction in one or more adverse events or side effects. In some embodiments, the LYT-100 is administered in three daily doses of 825 mg each.

In some embodiments, the LYT-100 is administered at a dose that achieves a systemic exposure of LYT-100 in the subject which is about 85-125% of the systemic exposure of pirfenidone achieved when pirfenidone is administered at a total daily dose of 2403 mg, and wherein the total daily dose of pirfenidone is administered in three doses of 801 mg each (801 mg TID).

In some embodiments, the dose of LYT-100 that achieves the systemic exposure of LYT-100 in the subject which is about 85-125% of the systemic exposure of pirfenidone is 825 mg TID.

In some embodiments, the dose of LYT-100 that achieves the systemic exposure of LYT-100 in the subject which is about 85-125% of the systemic exposure of pirfenidone also achieves a $C_{max}$ of LYT-100 in the subject which is about 115-125% of the $C_{max}$ of pirfenidone achieved when pirfenidone is administered at a total daily dose of 2403 mg, and wherein the total daily dose of pirfenidone is administered in three doses of 801 mg each (801 mg TID). In some embodiments, at this dosing, the LYT-100 has the same or about the same tolerability (e.g., the incidence of adverse events is not significantly different) as compared with pirfenidone administered at 801 mg TID. In some embodiments, at this dosing, the LYT-100 has an increased or improved tolerability that is due to a reduction in one or more adverse events or side effects as compared with pirfenidone administered at 801 mg TID. In some embodiments, the LYT-100 is administered in three daily doses of 825 mg each.

Referring to the crossover study described in Example 2, initial data for the occurrence of adverse events in healthy elderly subjects taking doses of 550 mg TID (1650 mg/day) followed by 824 TID (2472 mg/day) indicates that adverse events (particularly gastrointestinal (GI) disorders and nervous system disorders) do not increase and may decrease or even disappear with this dose titration scheme.

In comparison, as reported in regulatory summaries leading to approval of Esbriet (pirfenidone), escalating daily doses (801, 1602, 2403, 3204, and 4005 mg/day, provided in three equal doses) of pirfenidone were tested in a cohort of healthy older subjects (PIPF-005). The number of AEs (headache, dyspepsia, nausea, back pain) reported increased with increasing total daily dose. The higher $C_{max}$ values at higher dosages increased the odds of experiencing a gastrointestinal (GI) AE, and it was noted that this was consistent with previous studies for pirfenidone. As reported for study PIPF-005, for the three times daily dose of 801 mg (2403 mg/day), the $C_{max}$ was 11.85 µg/mL, which falls between the $C_{max}$ values reported for 550 mg TID and 824 mg TID in Example 2.

Accordingly, provided herein is a method of treating Idiopathic Pulmonary Fibrosis (IPF), comprising administering to a subject in need thereof a deuterium-enriched pirfenidone having the structure:

(LYT-100)

at a first total daily dose of 825 mg for a first period, a second total daily dose of 1650 mg for a second period, and a total daily dose of 2475 mg for a maintenance period, wherein IPF is treated in the subject.

In some embodiments the first period and the second period are 7 days each. In some embodiments, the LYT-100 is administered as 275 mg capsules or tablets. In one embodiment, upon initiation of treatment, the daily dosage is titrated to the maintenance dosage over a two-week period as follows:

| Period | Dosage |
| --- | --- |
| Days 1-7 | One capsule three times a day (825 mg/day) |
| Days 8-14 | Two capsules three times a day (1650 mg/day) |
| Days 15+ | Three capsules three times a day (2475 mg/day) |

In some embodiments, the first period, the second period, or both may be extended longer than 1 week. For example, in some embodiments, the first period and the second period are each 14 days.

In some embodiments, adverse events do not increase as the dose increases. In some embodiments, adverse events decrease as the dose increases. In some embodiments, there are no AEs at the maintenance dose. These AEs may be one or more GI AEs, e.g., selected from nausea, vomiting, diarrhea, dyspepsia, abdominal pain, abdominal discomfort, and abdominal distention. These AEs may be nervous system AEs, e.g., headache or dizziness, or both. In some embodiments, IPF is treated with mild or no AEs. In some embodiments, the subject is treated for IPF, and the treatment is not interrupted or discontinued due to adverse events.

In some embodiments, the method includes temporary dosage reduction, treatment interruption, or discontinuation for management of adverse reactions, drug interactions, or in response to altered liver function (e.g., as determined by a liver function test indicative of hepatic impairment). In some embodiments, the dose may be reduced from 2475 mg/day to 1650 mg/day or 825 mg/day. The reduction may be in the form of a titration down over a period of days, e.g., as described above for titration to the maintenance or full dose, but in a reverse order, or dosing may be interrupted entirely. In some embodiments, dosing may be interrupted temporarily. In some embodiments, dosing may be permanently discontinued. Following a dose reduction or temporary discontinuation, re-titration back up to 1650 mg/day or 2475 mg/day may be employed. In one embodiment, for a subject missing 14 or more days of LYT-100, the method includes re-initiating treatment by undergoing the above titration regimen over two weeks, up to the full maintenance dosage. In some embodiments, the method includes interrupting dosing, e.g., due to elevated liver enzymes, and thereafter resuming the dosage prior to treatment or re-titrating back up to the maintenance dosage. In one embodiment, due to a drug interaction, the method includes reducing the dosage to 825 mg/day or 1650 mg/day and maintaining this dose as a new maintenance dose.

In some embodiments, the method comprises obtaining the results of a liver function test for the subject prior to administration of LYT-100. In some embodiments, the method comprises obtaining the results of a liver function test after administering LYT-100 to the subject. In some embodiments, the method includes obtaining the results of liver function tests periodically for the subject.

In some embodiments, the method includes reducing or interrupting dosing of LYT-100 due to elevated liver enzymes. In some embodiments, a subject, after being administered LYT-100, exhibits >3 but≤5×the upper limit of normal (ULN) ALT and/or AST without exhibiting symptoms or hyperbilirubinemia, the method including discontinuing confounding medications, excluding other causes, and monitoring the patient closely; repeating liver chemistry tests; and maintaining, reducing, or interrupting dosing, with subsequent re-titration to the maintenance dose or a lower dose. In other embodiments, the subject exhibits >3 but ≤5×ULN ALT and/or AST accompanied by symptoms or hyperbilirubinemia, the method including permanently discontinuing LYT-100. In some embodiments, the subject exhibits >5×ULN ALT and/or AST, the method including permanently discontinuing LYT-100.

In IPF, a prominent feature of the disease is impaired respiratory function, resulting in reduced blood oxygen saturation. In some embodiments, the method disclosed herein prevents or reduces the progression of impaired respiratory function in a subject, including a human subject, having IPF. Impaired respiratory function may be determined by one or more of oximetry, reduced forced expiratory volume in one second (FEV1), reduced forced vital capacity (FVC), and reduced FEV1/FVC ratio. As used herein, the terms "reduced blood oxygen saturation", "reduced forced expiratory volume in one second (FEV1)", "reduced forced vital capacity (FVC)", or "reduced FEV1/FVC ratio" mean, respectively, a blood oxygen saturation, a forced expiratory volume in one second (FEV1), a forced vital capacity (FVC), or a FEV1/FVC ratio that is reduced or lower than that found in a subject with normal or healthy lungs.

In some embodiments, the method disclosed herein provides an improvement in the rate of decline in Forced Vital Capacity (FVC; in mL) over a period of treatment of 26 weeks, relative to the improvement in rate of decline in a subject treated with pirfenidone at 801 mg TID.

FVC is the maximum amount of air that can be exhaled after a deep breath. It's a measurement of lung function that is obtained during a spirometry test. The measurement requires the subject to make a maximal inspiration to total lung capacity (TLC; the maximal volume of gas in the lungs after a maximal inhalation), then make a maximal forced expiratory effort, leaving only the residual volume. Restrictive lung diseases such as pulmonary fibrosis prevent fulling filling the lungs on inspiration and result in reduced FVC. In pulmonary fibrosis, FVC decreases over time. Accordingly, rate of decline in FVC over time is a measure of lung function impairment indicative of disease progression. This impairment of lung function may adversely affect quality of life in a patient.

In some embodiments, the method disclosed herein prevents the progression of or reduces the progression of impaired respiratory function in the subject as determined by a minimal decline in Forced Vital Capacity % predicted (FVCpp) change over a 26-week treatment period.

FVCpp is the FVC predicted for an individual based on demographics (age, sex, and height). Generally, an FVC value which is greater than or equal to 80% of the predicted value is considered normal. A value of 70% for the FVCpp is average for patients with IPF, and a decline in FVCpp over time is considered a key marker for disease progression in IPF.

In some embodiments, the decline in FVCpp from baseline to week 26 is less than about 10%. In some embodiments, the decline in FVCpp predicted from baseline to week 26 is less than about 5%.

In some embodiments, the method disclosed herein increases a time to IPF progression as defined by a decline in FVCpp of 5% or greater over a 26-week treatment period. In some embodiments, the method disclosed herein increases a time to IPF progression as defined by a decline in FVCpp of 10% or greater over a 26-week treatment period.

In some embodiments, the method disclosed herein increases a time to hospitalization due to respiratory cause over a 26-week treatment period.

In some embodiments, the method disclosed herein lengthens a time to mortality due to respiratory cause relative to that in a subject who has not received treatment according to the disclosed method.

In some embodiments, the treatment efficacy may be evaluated through the King's Brief Interstitial Lung Disease Questionnaire (K-BILD) total score. In some embodiments, an improvement in the change from baseline to Week 26 in the K-BILD total score is observed, relative to a subject who has not received treatment according to the disclosed method.

In some embodiments, the treatment efficacy may be evaluated through the Saint George Respiratory Questionnaire-I (SGRQ-I). The SGRQ-I is an idiopathic pulmonary fibrosis disease-specific instrument designed to measure impact on overall health, daily life, and perceived well-being in patients with interstitial lung disease. There are 34 self-completed items with 3 domain component scores (Symptoms, Activities, and Impacts). Higher scores indicate more limitations. In some embodiments, an improvement in the change from baseline to Week 26 in the Saint George Respiratory Questionnaire-I (SGRQ-I) domain score is observed.

In some embodiments, the treatment efficacy may be evaluated through the EuroQol 5-Dimensional (EQ5D) Questionnaire score. The EQ-5D is an instrument developed in Europe and widely used for evaluation of the generic health-related quality of life. The EQ-5D is a preference-based HRQL measure with one question for each of five dimensions that include mobility, self-care, usual activities, pain/discomfort, and anxiety/depression. The responses can be converted into EQ-5D utility score anchored at 0 for death and 1 for perfect health. The EQ-5D questionnaire also includes a Visual Analog Scale (VAS), by which respondents can report their perceived health status with a grade ranging from 0 (the worst possible health status) to 100 (the best possible health status). In some embodiments, an improvement in the change from baseline to Week 26 in the EQ5D score is observed.

In some embodiments, an improvement in one or more of the following is observed, relative to a subject who has not received treatment according to the disclosed method:

the change from baseline to Week 26 in the cough visual analog scale (VAS);

the number and duration of respiratory hospitalizations;

the change in serum biomarkers (e.g., collagen type 4) from baseline through week 26.

In some embodiments, the patient experiences, relative to treatment with pirfenidone, one or more of: reduced frequency of dose modifications (reductions and interruptions), time to first dose modification (reduction or interruption), reduced duration of adverse events of special interest, increased time to treatment discontinuation due to an adverse event of special interest, and improvement in a patient reported assessment of symptoms and satisfaction.

In some embodiments, one or more of the following applies to the subject prior to treatment with LYT-100:

the subject has Idiopathic Pulmonary Fibrosis diagnosed by a physician based on ATS/ERS/JRS/ALAT 2018 guidelines;

the subject has Idiopathic Pulmonary Fibrosis based on high resolution computed tomography (HRCT), performed within 12 months of initiating treatment;

the subject has a clinically significant decline in DLCO corrected for hemoglobin ≥30% predicted of normal prior to initiating treatment.

the subject has FVC≥45% predicted prior to initiating treatment.

In some embodiments, the subject does not have any of the following, or none of the following apply, prior to initiating treatment: AST, ALT>1.5×ULN; bilirubin >1.5× ULN; creatinine clearance <30 mL/min calculated by Cockcroft-Gault formula; underlying chronic liver disease (Child Pugh B or C hepatic impairment); currently treated with nintedanib or pirfenidone; prior allergic reaction to pirfenidone; received other investigational therapy within 1 month; significant Pulmonary Arterial Hypertension (PAH) defined by any of the following: a) previous clinical or echocardiographic evidence of significant right heart failure, b) history of right heart catheterization showing a cardiac index≤2 l/min/m², c) PAH requiring parenteral therapy with epoprostenol/treprostinil; primary obstructive airway physiology (pre-bronchodilator FEV1/FVC<0.7); known explanation for interstitial lung disease, including but not limited to radiation, sarcoidosis, hypersensitivity pneumonitis, bronchiolitis obliterans organizing pneumonia, human immunodeficiency virus (HIV), viral hepatitis, and cancer; diagnosis of any connective tissue disease, including but not limited to scleroderma/systemic sclerosis, polymyositis/dermatomyositis, systemic lupus erythematosus, and rheumatoid arthritis; cardiovascular diseases, including any of the following: severe hypertension, uncontrolled under treatment (≥160/100 mm Hg), within 6 months of initiating treatment, myocardial infarction within 6 months of initiating treatment, unstable cardiac angina within 6 months of initiating treatment, a marked baseline prolongation of QT/QTc interval (e.g., repeated demonstration of a QTc interval >450 ms); a history of additional risk factors for TdP (e.g., heart failure, hypokalemia, family history of Long QT Syndrome, use of concomitant medications that prolong the QT/QTc interval; prior hospitalization for severe confirmed COVID-19; acute exacerbation of IPF within the 6-months prior to initiating treatment; lower respiratory tract infection within the 3-months prior to initiating treatment; known symptoms of dysphagia or known difficulty in swallowing tablets and/or total gastrectomy.

In some embodiments, the subject has not used any of the following drugs: strong and moderate CYP1A2 inhibitors (i.e. ciprofloxacin, fluvoxamine, verapamil, or enoxacin); strong and moderate inducers of CYP1A2 (e.g., St. John's Wort or phenytoin); drugs associated with substantial risk for prolongation of the QTc interval (including but not limited to moxifloxacin, quinidine, procainamide, amiodarone, sotalol); warfarin, imatinib, ambrisentan, azathioprine, cyclophosphamide, cyclosporin A, bosentan, methotrexate, sildenafil (except for occasional use), prednisone at steady dose >10 mg/day or equivalent; or tobacco products.

In some embodiments, the subject does not have a current immunosuppressive condition (e.g. human immunodeficient virus).

Embodiments of the present disclosure can be further defined by reference to the following non-limiting examples. It will be apparent to those skilled in the art that many modifications, both to materials and methods, can be practiced without departing from the scope of the present disclosure.

EXEMPLIFICATION

Examples 1 and 2 provide crossover studies comparing the safety, tolerability, and pharmacokinetics of deupirfenidone (LYT-100) and pirfenidone. Example 3 provides a study exploring tolerability of the deuterated pirfenidone LYT-100 in patients with COVID-19 Respiratory Illness. Example 4 provides a study exploring the efficacy, tolerability and safety of the deuterated pirfenidone LYT-100 in patients with Idiopathic Pulmonary Fibrosis. Example 5 provides the CYP isozyme profile of pirfenidone and LYT-100. Example 6 provides a BioMAP Fibrosis Panel screening study for LYT-100 and pirfenidone across a series of fibrosis biomarkers. Example 7 provides a study exploring the efficacy of LYT-100 in a bleomycin rat model of pulmonary fibrosis.

Example 1: Crossover Dosing Study

This study was a double-blind, randomized, two-period crossover study in older, healthy subjects to compare the safety, tolerability, and pharmacokinetics of deupirfenidone (LYT-100) and pirfenidone. The crossover study was performed at a single Study Center per Part in the United States.

Study Description

This study was conducted in two Parts: 1 and 2.

Part 1 was a randomized, double-blinded, two period crossover study conducted in healthy older adults to compare the safety, tolerability, and pharmacokinetics of deupirfenidone (LYT-100) with twice daily (BID) dosing of LYT-100 to pirfenidone.

Part 2 was a randomized, double-blinded, two period crossover study conducted in healthy older adults to compare the safety, tolerability, and pharmacokinetics of deupirfenidone (LYT-100) with three times daily (TID) dosing of LYT-100 to pirfenidone.

Study Endpoints

Safety:

Treatment-emergent adverse events (TEAEs), including severity, and relatedness to study drug)

Physical examination

Vital signs

Electrocardiograms (ECGs)

Clinical laboratory parameters, including hematology, serum chemistry, coagulation, and urinalysis New-onset concomitant medications Pharmacokinetics:

Comparison of the key PK parameters ($C_{max,ss}$, $C_{min,ss}$, and $AUC_{0-24,ss}$) between the parent compound (LYT-100 and pirfenidone) and primary metabolite (5-carboxypirfenidone). Other PK parameters were derived and compared.

Comparison of the key urine PK parameters ($Ae_{t1-t2}$, $CL_R$, $Fe_{t1-t2}$) between the parent compound (LYT-100 and pirfenidone) and primary metabolite (5-carboxypirfenidone). Other urine PK parameters were derived and compared.

Food effect evaluation of LYT-100 and pirfenidone ($C_{max,ss}$, and $AUC_{0-6,ss}$) for fed versus fasted.

Study Design

Part 1:

Part 1 was a double-blind, randomized, two-period crossover study conducted in older, healthy subjects to determine the safety, tolerability, and PK of LYT-100 administered twice daily (BID) for 3 days (to steady state [Day 1 to Day 3 and Day 11 to Day 13]) compared to pirfenidone administered 3 times daily (TID) for 3 days (to steady state) under fed conditions. A final single dose of study drug (LYT 100 or pirfenidone) was administered on the morning of the fourth day in each treatment period (Day 4/Day 14) following an overnight fast of at least 8 hours to determine the effect of food on steady state PK parameters.

Over encapsulation was utilized to match TID dosing for pirfenidone and to match the number of LYT-100 capsules administered for each dose. Thus, during LYT-100 treatment, the mid-day dose was placebo. Pirfenidone was administered at the current marketed dose of 801 mg TID (2403 mg daily dose).

Figure 2:
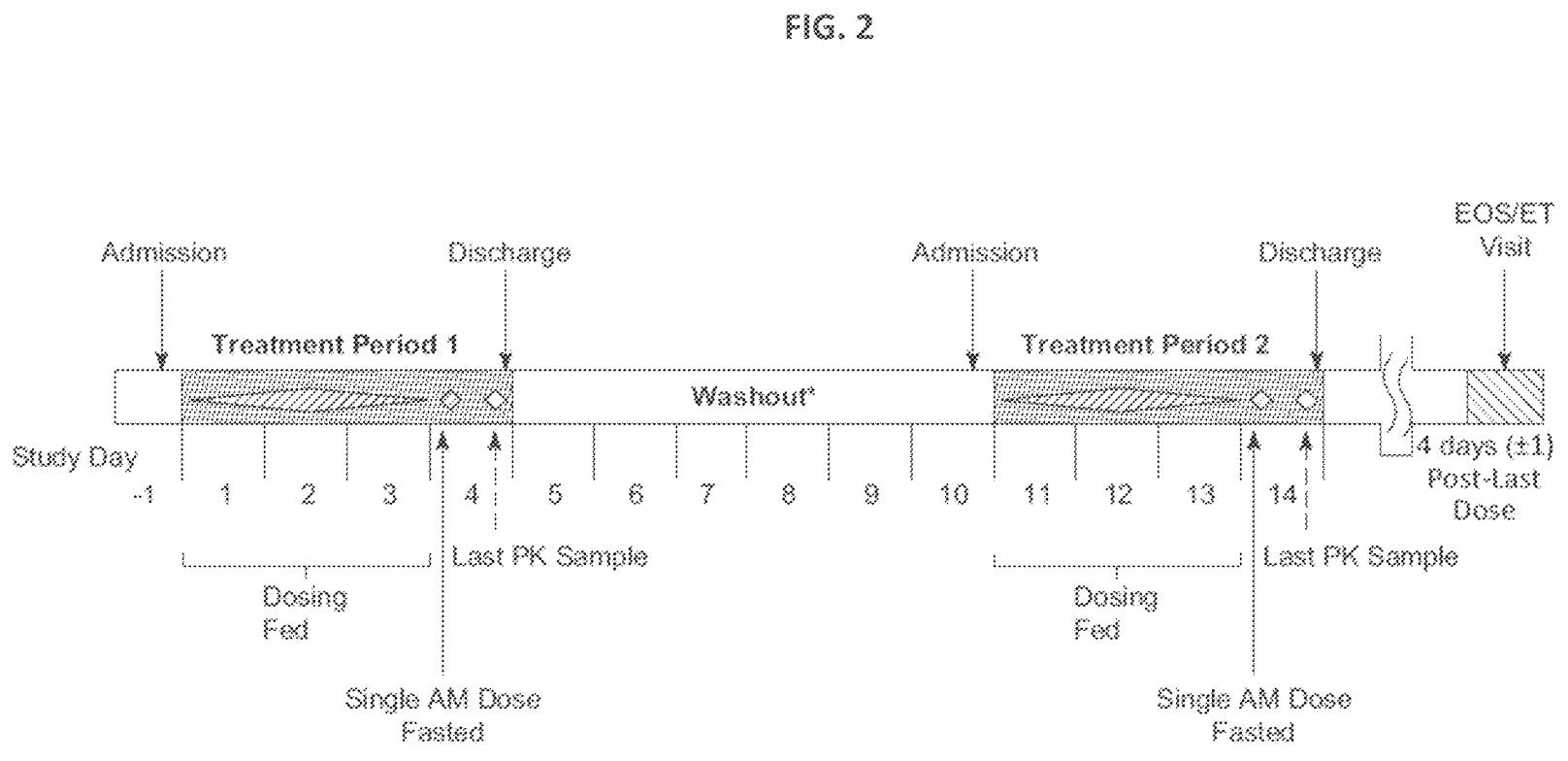

Approximately forty older healthy female and male adult subjects (1:1 target ratio) were randomized into 1 of 2 cohorts:Cohort 1 or Cohort 2, N=20 subjects per cohort; minimum of 8 per sex per cohort. Subjects in each cohort were randomized to treatment sequence as follows: Sequence A: Pirfenidone to LYT-100; Sequence B: LYT-100 to pirfenidone. Dosing is outlined in Table 1. A graphical illustration of the study design for Part 1 is provided as FIG. 2.

TABLE 1

| | | Treatment Period 1 | | Treatment Period 2 | |
|---|---|---|---|---|---|
| | Treatment | | | | |
| Cohort | Sequent | Days 1 to 3 | Day 4 | Days 11 to 13 | Day 14 |
| 1 | A (n = 10) | Pirfenidone 801 mg TID (every 6 hours) Fed | Pirfenidone 801 mg (AM only) Fasted | LYT-100 up to 1500 mg BID (every 12 hours) + placebo at mid-day[#] Fed | LYT-100 up to 1500 mg* (AM only) Fasted |
| | B (n = 10) | LYT-100 up to 1500 mg BID (every 12 hours) + placebo at mid-day[#] Fed | LYT-100 up to 1500 mg (AM only) Fasted | Pirfenidone 801 mg TID (every 6 hours)^ Fed | Pirfenidone 801 mg (AM only) Fasted |
| 2 | A (n = 10) | Pirfenidone 801 mg TID (every 6 hours) Fed | Pirfenidone 801 mg (AM only) Fasted | LYT-100 up to 1500 mg BID (every 12 hours) + placebo at mid-day[#] Fed | LYT-100 up to 1500 mg (AM only) Fasted |
| | B (n = 10) | LYT-100 up to 1500 mg BID (every 12 hours) + placebo at mid-day Fed | LYT-100 up to 1500 mg (AM only) Fasted | Pirfenidone 801 mg TID (every 6 hours) Fed | Pirfenidone 801 mg (AM only) Fasted |

The initial dose of LYT-100 for this crossover study directly comparing LYT-100 to pirfenidone in healthy adults was 850 mg BID LYT-100 (1700 mg daily dose) vs. 801 mg TID pirfenidone (2403 mg daily dose). The 850 mg BID LYT-100 (1700 mg daily dose) was selected based on the PK results from earlier studies. PK modelling work using data from the multiple ascending dose study and a single-dose crossover study of LYT-100 and pirfenidone indicated that a dose of LYT-100 of approximately 800-850 mg BID (1600-1700 mg daily dose) results in a similar systemic exposure to the marketed dose of pirfenidone (2403 mg daily dose). Based on these data, a randomized blinded cross-over study in older healthy adults was conducted (N=37) administering LYT-100 850 mg BID 3 days fed dosing versus pirfenidone 801 mg TID 3 days fed dosing. The study is blinded with a placebo mid-day dose for LYT-100 to match TID pirfenidone dosing. There was a single AM fasting dose on Day 4 for both drugs. There was a 6-day wash-out period between drug cross-over. The 850 mg BID dose was selected as a match to the exposure for pirfenidone based on the outcome of the earlier PK crossover study, which indicated that an 850 mg BID daily dose of LYT-100 has about 102% of the steady-state systemic exposure of pirfenidone dosed daily at 801 mg TID.

Part 2:

Part 2 was a double-blind, randomized, two-period cross-over study conducted in older healthy subjects to determine the safety, tolerability, and PK of LYT-100 administered three times daily (TID) for 3 days (to steady state [Day 1 to Day 3 and Day 11 to Day 13]) compared to pirfenidone administered TID for 3 days (to steady state) under fed conditions. A final single dose of study drug (LYT-100 or pirfenidone) was administered on the morning of the fourth day in each treatment period (Day 4/Day 14) following an overnight fast of at least 8 hours to determine the effect of food on steady state PK parameters. Over-encapsulation was utilized to maintain study blind. Screening was performed up to 28 days prior to administration of the first dose of LYT-100/pirfenidone. Only subjects who met all the applicable inclusion and none of the applicable exclusion criteria were randomized. Approximately 50 older healthy female and male adult subjects (1:1 ratio) were randomized into 1 of 2 cohorts:Cohort 1 or Cohort 2, N=~25 subjects per cohort. Subjects in each cohort were randomized to treatment sequence as follows:

Sequence A: Pirfenidone to LYT-100

Sequence B: LYT-100 to pirfenidone

Figure 3:
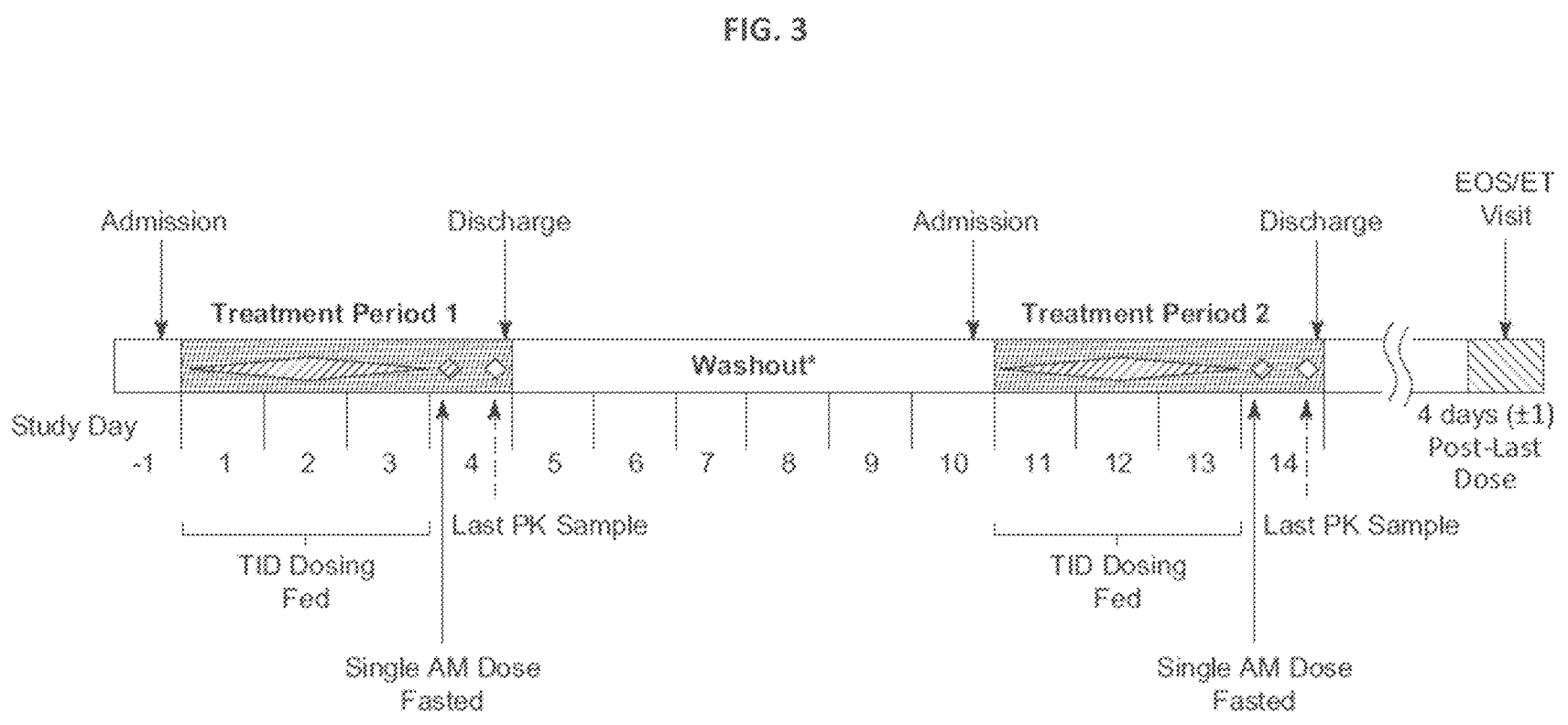

A graphical illustration of the study design for Part 2 is provided as FIG. 3. Dosing is outlined in Table 2.

TABLE 2

| | | Treatment Period 1 | | Treatment Period 2 | |
|---|---|---|---|---|---|
| | Treatment | | | | |
| Cohort | Sequent | Days 1 to 3 | Day 4 | Days 11 to 13 | Day 14 |
| 1 (n = 25) | A | Pirfenidone 801 mg TID | Pirfenidone 801 mg (AM | LYT-100, 550 mg TID (every 6 | LYT-100 550 mg single dose (AM |

TABLE 2-continued

| | | Dosing Regimens by Cohort and Treatment Sequence (Part 2) | | | |
|---|---|---|---|---|---|
| | Treatment | Treatment Period 1 | | Treatment Period 2 | |
| Cohort | Sequent | Days 1 to 3 | Day 4 | Days 11 to 13 | Day 14 |
| | | (every 6 hours) Fed | only) Fasted | hours), Fed | only), Fasted |
| | B | LYT-100, 550 mg TID (every 6 hours), Fed | LYT-100 550 mg single dose (AM only), Fasted | Pirfenidone 801 mg TID (every 6 hours)^ Fed | Pirfenidone 801 mg (AM only) Fasted |
| 2 (n = 25) | A | Pirfenidone 801 mg TID (every 6 hours) Fed | Pirfenidone 801 mg (AM only) Fasted | LYT-100, 550 mg TID (every 6 hours), Fed | LYT-100 550 mg single dose (AM only), Fasted |
| | B | LYT-100, 550 mg TID (every 6 hours), Fed | LYT-100 550 mg single dose (AM only), Fasted | Pirfenidone 801 mg TID (every 6 hours) Fed | Pirfenidone 801 mg (AM only) Fasted |

^Pirfenidone: AM dose: 3 × 267 mg, mid-day dose: 3 × 267 mg, PM dose: 3 × 267 mg. Each of the AM, mid-day, and PM doses are over-encapsulated to maintain study blind. Placebo capsules are administered as needed to match the number of LYT-100 capsules in order to maintain the blind. Each cohort starting concurrently or closely staggered.

The LYT-100 dose for this crossover study directly comparing LYT-100 to pirfenidone in healthy adults was 550 mg TID LYT-100 (1650 mg daily dose) vs. 801 mg TID pirfenidone (2403 mg daily dose). The 550 mg TID LYT-100 (1650 mg daily dose) was selected based on the PK results from earlier studies and the PK results obtained in Part 1 of this study. PK modelling work using data from the multiple ascending dose study, the single-dose crossover study of LYT-100 and pirfenidone and Part 1 of this study indicated that a dose of LYT-100 550 mg TID (1650 mg daily dose) results in a similar systemic exposure to the marketed dose of pirfenidone (2403 mg daily dose). Particularly, it was predicted that a dose of 550 TID LYT-100 (1650 mg total daily dose) would achieve a steady-state systemic exposure that is about 99% of the steady-state systemic exposure observed for pirfenidone dosed at 801 mg TID.

Based on these data, a randomized blinded cross-over study in older healthy adults was conducted (N=49) administering LYT-100 550 mg TID 3 days fed dosing versus pirfenidone 801 mg TID 3 days fed dosing. There was a single AM fasting dose on Day 4 for both drugs. There was a 6-day wash-out period between drug cross-over. The 550 mg TID dose was selected as a match to the exposure for pirfenidone based on the outcome of the earlier PK crossover studies. See FIG. 4 and FIG. 5, which show that the predicted steady-state systemic exposure (AUC24ss) for LYT-100 dosed at 550 TID is 98.5% of the steady-state systemic exposure ($AUC_{24ss}$) of pirfenidone dosed at 801 mg TID. Surprisingly, however, the $C_{max}$ for LYT-100 dosed at 550 mg TID is predicted to be lower than the pirfenidone $C_{max}$ resulting from pirfenidone administered at 801 mg TID. FIG. 5 shows that the predicted steady-state $C_{max}$ for LYT-100 dosed at 550 mg TID is 67.4% of the steady-state $C_{max}$ for pirfenidone dosed at 801 mg TID. Without wishing to be bound by any particular theory, it is believed that the lower $C_{max}$ of LYT-100 may contribute to the enhanced tolerability of LYT-100 relative to pirfenidone.

Treatment Period 1 (Day −1 to Day 4) Parts 1 and 2

Subjects were admitted to the Clinical Research Unit (CRU) on Day-1 of Treatment Period 1 and were administered their assigned study drug (pirfenidone or LYT-100, with or without matching placebo) every 6 hours for 3 days until steady state (Day 1 to Day 3) under fed conditions. Subjects were then administered a single dose of their randomized treatment (pirfenidone or LYT-100, with or without matching placebo) on the morning of Day 4 following an overnight fast of at least 8 hours. Subjects were discharged on Day 4 following successful completion of all assessments and at the Investigator's discretion.

Treatment Period 2 (Day 11 to Day 14) Parts 1 and 2

Following a minimum washout period of at least 7 days, subjects returned to the CRU and were admitted on the evening of Day 10 and were crossed over and administered the alternate study drug (pirfenidone or LYT-100, with or without matching placebo) every 6 hours for 3 days (Day 11 to Day 13) under fed conditions. Subjects were then administered a single dose of their randomized treatment on the morning of Day 14 following an overnight fast of at least 8 hours. Subjects were discharged on Day 14 following successful completion of all assessments and at the Investigator's discretion.

On Days 1 to 3 (Treatment Period 1) and Days 11 to 13 (Treatment Period 2) subjects were administered their assigned study drug TID, every 6 hours+0.25 hours (with approximately 240 mL of non-carbonated water), 30 minutes after the start of consumption of their standardized breakfast, lunch, or dinner (6 hours apart). An evening snack was served ≥3 hours following evening study medication administration. On Day 4 (Treatment Period 1) and Day 14 (Treatment Period 2), subjects were administered their assigned study drug once in the morning following an overnight fast of at least 8 hours (with approximately 240 mL of non-carbonated water). No additional fluids were allowed during the 1 hour pre- and post-dose.

On Fed Days, meals were provided as follows:
  Breakfast: meal served 30 mins prior to AM dosing. Breakfast was completed within 30 mins of start time.
  Lunch: meal served at least 4 h post-AM study drug dose, and 30 minutes prior to the mid-day dose in Part 5 (only).
  Dinner: meal served at least 11.5 h post-AM dose and served 30 minutes prior to PM study drug dose.
  Evening snack: Snack served at least 15 h post-AM dose (at least 3 h post-PM dose).
On Fasted Days, meals were provided as follows:
On Day 4 (Period 1) and Day 14 (Period 2), breakfast was provided ≥4 hours post-study drug administration.

Number of Subjects:

Part 1

The objective was to recruit approximately 40 healthy older female and male adult subjects (target ratio 1:1 of males: females with a minimum of 8 per sex per cohort), unless additional subjects were required to support the statistical analysis. Part 1 was conducted with N=37 subjects who completed the study.

Part 2

The objective was to recruit approximately 50 healthy older female and male adult subjects (target ratio 1:1 of males: females with a minimum of 15 per sex per cohort), unless additional subjects were required to support the statistical analysis. Part 1 was conducted with N=49 subjects who completed the study.

Main Criteria for Inclusion and Exclusion

Inclusion Criteria:

1. Male or female between 60 and 80 years old (inclusive) at the time of screening.
2. Subjects have a body mass index (BMI) between ≥18.0 and ≤35.0 kg/m2 at screening.
3. Willing and able to abstain from direct whole body sun exposure from 2 days prior to dosing and until final study procedures have been conducted. Subjects were instructed to avoid or minimize exposure to sunlight (including sunlamps), use an SPF 50 sun block, or higher, wear clothing that protects against sun exposure and avoid concomitant medications known to cause photosensitivity (including but not limited to tetracycline, doxycycline, nalidixic acid, voriconazole, amiodarone, hydrochlorothiazide, naproxen, piroxicam, chlorpromazine and thioridazine).

Exclusion Criteria:

1. Pregnant or lactating at screening or baseline or planning to become pregnant (self or partner) at any time during the study, including the specified follow-up period.
2. History or presence of malignancy at screening or baseline, with the exception of adequately treated localised skin cancer (basal cell or squamous cell carcinoma) or carcinoma in-situ of the cervix.
3. Clinically significant infection within 28 days of the start of dosing, or infections requiring parenteral antibiotics within the 3 months prior to screening. Known exposure to another person with COVID-19 within the last 14 days is also an exclusion criterion, or a positive COVID test within five days prior to dosing.
4. Had major surgery, (e.g., requiring general anesthesia) within 3 months before Screening, based on Investigator's discretion or has surgery planned during the time the participant is expected to participate in the study.
5. Suffering from clinically significant systemic allergic disease at screening or baseline or has a history of significant drug allergies including a history of anaphylactic reaction (particularly reactions to general anaesthetic agents); allergic reaction due to any drug which led to significant morbidity; prior allergic reaction to pirfenidone.
6. Chronic administration (defined as more than 14 consecutive days) of immunosuppressants or other immune-modifying drugs within 3 months prior to study drug administration. Corticosteroids are permitted at the discretion of the Investigator.
7. History or presence at screening or baseline of a condition associated with significant immunosuppression.

8. Positive test for hepatitis C antibody (HCV), hepatitis B surface antigen (HBsAg), or human immunodeficiency virus (HIV) antibody at screening.
9. Symptoms of dysphagia at screening or baseline or known difficulty in swallowing capsules.
10. Any condition at screening or baseline (e.g., chronic diarrhoea, inflammatory bowel disease or prior surgery of the gastrointestinal tract) that would interfere with drug absorption or any disease or condition that is likely to affect drug metabolism or excretion, at the discretion of the Investigator.
11. History or presence at screening or baseline of cardiac arrhythmia or congenital long QT syndrome.
12. QT interval corrected using Fridericia's formula (QTcF)>450 msec. ECG may be repeated 30 to 60 minutes apart from the first one collected at screening. If repeat ECG is ≤450 msec, the second ECG may be used to determine patient eligibility. However, if repeat ECG confirms QTcF remains >450 msec, the subject is not eligible.
13. Use of tobacco or nicotine containing products in the previous 3 months prior to dosing or a positive urine cotinine test at Screening or Baseline.
14. Lack of willingness to abstain from the consumption of tobacco or nicotine-containing products throughout the duration of the study and until completion of the final Follow-up visit.
15. Regular alcohol consumption defined as >21 alcohol units per week (where 1 unit=284 mL of beer, 25 mL of 40% spirit or a 125 mL glass of wine) or the Participant is unwilling to abstain from alcohol for 48 h prior to admission and 48 h prior to study visits.
16. Use of any of the following drugs within 30 days or 5 half-lives of that drug, whichever is longer, prior to study drug administration:
    a. Fluvoxamine, enoxacin, ciprofloxacin;
    b. Other inhibitors of CYP1A2 (including but not limited to methoxsalen or mexiletine);
    c. Contraceptives containing oestradiol, ethinyloestradiol or gestodene;
    d. Inducers of CYP1A2 (such as phenytoin), CYP2C9 or 2C19 (including but not limited to carbamazepine or rifampin);
    e. Any drug associated with prolongation of the QTc interval (including but not limited to moxifloxacin, quinidine, procainamide, amiodarone, sotalol).
17. Vaccination with a live vaccine within the 4 weeks prior to screening or that is planned within 4 weeks of dosing, and any non-live vaccination within the 2 weeks prior to screening or that is planned within 2 weeks of dosing (including those for COVID).
18. Use of any investigational drug or device within the longer of 30 days or five half-lives prior to screening.
19. Consumption of grapefruit, grapefruit juice, Seville oranges, Seville orange juice, or any foods containing these ingredients, within 7 days prior to dosing or unwilling to abstain from these throughout the duration of the study.

Dosage and Mode of Administration:

This was a crossover study in which subjects received both the test treatment (LYT-100) and the reference (pirfenidone). All subjects received LYT-100 (BID or TID) or pirfenidone (TID) for 3 days in each respective treatment period, with placebo over-encapsulation to maintain the blind. Part 1 subjects received LYT-100 850 mg BID. Part 2 subjects received LYT-100 550 mg TID. In Parts 1 and 2, all subjects also received a single dose of either LYT-100 or pirfenidone on the morning of the fourth day in each respective treatment period with placebo over-encapsulation to maintain the blind.

LYT-100 (Deupirfenidone) was provided as hard gelatin capsules. LYT-100 was stored at a controlled room temperature of 15° C. to 25° C.

Pirfenidone (Esbriet)_was provided as white to off-white hard gelatin capsules contain 267 mg of pirfenidone.

Both LYT-100 and pirfenidone were over-encapsulated to maintain study blind.

Duration of Treatment:

Parts 1 and 2

This study included a 28-day Screening period, two treatment periods (each 4 days in duration) with a minimum 7-day washout period between treatment periods, and a 3-day (±1 day) post-last-dose safety follow-up visit. Thus, total duration of study participation for each subject was approximately 50 days. Treatment with double-blind study medication was 4 days for each of the two treatment periods, 8 days in total.

Criteria for Evaluation

Safety:

Safety and tolerability was assessed by monitoring AEs, physical examination, vital signs, 12-lead ECGs, clinical laboratory values (hematology panel, multiphasic chemistry panel and urinalysis), and review of concomitant treatments/medication use.

Pharmacokinetics:

Parts 1 and 2

Subjects provided blood samples prior to treatment, i.e., Day-1 or Day 1 in Treatment Period 1, for the determination of CYP1A2, CYP2C9, CYP2C19, and CYP2D6 genotype to support exploratory PK analyses. Subjects were required to provide consent for genotyping.

Blood samples for PK were collected for Cohorts 1 and 2 at specified times during both periods, as follows:

Days 1 & 11:0 (pre-morning dose)

Days 2 & 12: no sampling.

Days 3 & 13:0 (pre-morning dose), and 1, 2, 3, 4, 6 (pre-mid-day dose), 7, 8, 9, 10, 12 (pre-evening dose), 13, 14, 15, 16, and 17 hours post-morning dose Days 4 & 14:0 (pre-morning dose), and 1, 2, 3, 4, 6 (post-dose), Plasma PK parameters for steady state dosing (Days 1 to 3 and Days 11 to 13) included, but are not limited to:

$AUC_{0-tau,ss}$ (area under the time concentration curve from time zero to tau at steady state).

$AUC_{0-24,ss}$ (area under the time concentration curve from time zero to 24 hours at steady state)

$\lambda z$ (terminal disposition rate constant/terminal rate constant)

$t^{1/2}$ (elimination half-life)

$C_{max,ss}$ (maximum concentration in a dosing interval)

$T_{max}$ (time to maximum concentration, as reported relative to the beginning of a dosing interval in which maximum concentration occurred)

$C_{min,ss}$ (lowest concentration in a dosing interval)

$C_{av,ss}$ (average concentration during a dosing interval).

$C_{max,ss}-C_{min,ss}/C_{av,ss}$ (degree of fluctuation).

$C_{max,ss}-C_{min,ss}/C_{min,ss}$ (swing)

PTF % (peak-trough fluctuation)

Plasma PK parameters for food effect analysis (Days 4 and 14) included, but are not limited to:

$AUC_{0-tau,ss}$ (area under the time concentration curve from time zero to tau at steady state).

$AUC_{0-6,ss}$ (area under the time concentration curve from time zero to 6 hours at steady state)

$AUC_{0-\infty}$ (area under the time concentration curve from time zero to infinity)+$AUC_{0-\infty/D}$ % $AUC_{ext}$ (area under the time concentration curve extrapolated from time t to infinity as a percentage of total AUC)

$\lambda z$ (terminal disposition rate constant/terminal rate constant)

CL/F (apparent total clearance)

Vz/F (apparent volume of distribution)

$T_{max}$ (time to maximum concentration)

$t_{lag}$ (lag time)

Part 1 Only

Urine samples for PK were collected for Cohorts 1 and 2 at specified intervals during both treatment periods, as follows:

Days 1 and 11: pre-dose (subjects instructed to empty their bladders approximately 30 minutes prior to dosing)

Days 2 and 12: no urine sampling

Days 3 and 13: pre-dose (subjects instructed to empty their bladders approximately 30 minutes prior to dosing), 0 to 4, 4 to 8, 8 to 12, 12 to 16, and 16 to 24 hours post-AM dose Days 4 and 14:0 to 3 and 3 to 6 hours post-AM dose Urine samples for analysis of excretion in urine were collected, separated by specified time interval, and analyzed. The total volume of urine collected in each interval (t1 to t2) was noted. The urine PK parameters included, but are not limited to:

$Ae_{t1/2}$ (Amount excreted in urine over time)

CLR (Renal clearance)

Fraction of systemic clearance (CL/F) represented by the renal clearance (CLR/[CL/F])

Fet1-t2 (Fraction of administered dose excreted in urine over the dosing intervals)

Study endpoints were defined as follows:

Safety

AEs (type, severity, and relatedness to study drug)

Physical examination

Vital signs

Electrocardiograms (ECGs)

Clinical laboratory parameters (hematology, serum chemistry, coagulation, and urinalysis)

New-onset concomitant medications

Pharmacokinetics:

Comparison of the key plasma PK parameters ($C_{max,ss}$, $C_{min,ss}$, and $AUC_{0-24,ss}$) between the parent compound (LYT-100 and pirfenidone) and primary metabolite (5-carboxypirfenidone). Other plasma PK parameters will also be derived and compared.

Comparison of the key urine PK parameters ($Ae_{t1-t2}$, $CL_R$, $Fe_{t1-t2}$) between the parent compound (LYT-100 and pirfenidone) and primary metabolite (5-carboxypirfenidone). Other urine PK parameters may be derived and compared.

Food effect evaluation of LYT-100 and pirfenidone ($C_{max,ss}$, and $AUC_{0-6,ss}$) for fed vs fasted.

Results

Part 1

It was determined that 1000 mg BID of LYT-100 provided an exposure (AUC) of LYT-100 which was greater than the exposure of pirfenidone resulting from administration of the approved dose of pirfenidone (801 mg TID). It was further determined based on dose projections that doses of LYT-100 in the range of 800 to 850 mg BID would provide exposure (AUC) and maximal concentration ($C_{max}$) values of LYT- 100 which are comparable to those of pirfenidone when administered at 801 mg TID (2403 mg daily).

The Part 1 study was conducted in healthy older adults as relevant age group for IPF. Overall, the head-to-head cross-over study of Part 1 was designed at least in part to evaluate the tolerability impact of reducing exposure to the major metabolite. To this end, thirty-seven subjects were randomized in the blinded crossover study to receive 850 mg BID LYT-100 or 801 mg TID pirfenidone with three days of fed dosing and a $4^{th}$ day morning fasted dose. With reference to FIG. 6A, the $C_{max}$ and AUC of parent drug for 850 mg BID LYT-100 were very similar to that of parent drug for 801 mg TID pirfenidone. Specifically, the steady-state AUC and with 850 mg BID dosing was 102% AUC compared with the steady-state AUC for pirfenidone dosed at 801 mg TID and the steady-state $C_{max}$ achieved was 104% of the $C_{max}$ of the steady-state $C_{max}$ for pirfenidone dosed at 801 mg TID. Fasting increased the $C_{max}$. The major metabolite (5-carboxypirfenidone) exposure was reduced for 850 mg BID LYT-100 relative to that when pirfenidone was dosed at 801 mg TID.

The adverse events encountered in each treatment group are provided in FIG. 6B, which shows that no serious adverse events occurred in either group, and similar types of AEs were observed across both groups. No clinically meaningful differences between LYT-100 and pirfenidone in overall AE rates.

With reference to FIG. 6B, the adverse events in both groups were primarily GI and nervous system, with nervous system AEs including headache and dizziness. As noted above, fasting increased $C_{max}$ and was hypothesized to increase overall GI AE rates. Consistent with this hypothesis, there was an increase in nausea in both groups when dosed after fasting, and the timing and duration of the AEs was consistent with a $C_{max}$-related effect. As illustrated in FIG. 6B, and with reference to FIG. 6A, the results of this study show that reducing exposure to the major metabolite did not improve tolerability.

Part 2

Part 2 was a double-blind, randomized, two-period cross-over study conducted in older healthy subjects to determine the safety, tolerability, and PK of 550 mg of LYT-100 administered three times daily (TID) for 3 days (to steady state [Day 1 to Day 3 and Day 11 to Day 13]) compared to pirfenidone administered 801 mg TID for 3 days (to steady state) under fed conditions. A final single dose of study drug (LYT-100 or pirfenidone) was administered on the morning of the fourth day in each treatment period (Day 4/Day 14) following an overnight fast of at least 8 hours to determine the effect of food on steady state PK parameters.

Overall, 49 subjects were enrolled and included in the Safety Population, 24 subjects to Sequence A and 25 subjects to Sequence B. Five subjects (10.2%) did not complete the study. Two subjects in Cohort 2 discontinued due to a TEAE (1 subject in Sequence A (LYT-100) and 1 subject in Sequence B (pirfenidone)). Two subjects in Cohort 2 discontinued due to physician decision (1 subject in Sequence A (LYT-100) and 1 subject in Sequence B (pirfenidone)). One subject in Cohort 1, randomized to Sequence A, withdrew consent while taking LYT-100.

The mean age of the overall population was 67.7; the mean age was similar in Cohorts 1 and 2 (68.5 and 66.9 years, respectively). The majority of subjects were female (53.1%; 52.2% in Cohort 1, 53.8% in Cohort 2), predominately white (81.6%), and the average BMI was 27.9 kg/m². The overall mean number of days of dosing with LYT-100 was 4.0 days (4.0 days in Cohort 1, 3.9 days in Cohort 2). The mean number of days of dosing with pirfenidone was 3.9 days (4.0 days in Cohort 1 and 3.9 days in Cohort 2).

Preliminary PK analyses have been conducted to assess the comparability of the exposure to parent (pirfenidone or deupirfenidone) and metabolite (5-carboxy pirfenidone, regardless of treatment) after administration of LYT-100 relative to after the administration of pirfenidone. Summary statistics of the key PK parameters, shown by analyte, fed status, and treatment, are shown in Table 3. Overall, exposure in terms of parent drug ($AUC_{0-24}$ and $C_{max}$) was slightly lower after administration of LYT-100 compared to pirfenidone and the time to $C_{max}$ was slightly longer (median of 3 hours for LYT-100 and 2 hours for pirfenidone). Specifically, the $C_{max}$ was about 20% lower for LYT-100 and did not meet criteria for bioequivalence. As expected, the major metabolite concentration was substantially lower after administration of LYT-100.

TABLE 3

Pharmacokinetic Parameters After Administration of Pirfenidone or LYT-100 in Subjects Enrolled in Part 2

| Fed Status | Analyte | Treatment | $C_{max}$ (µg/mL) | $T_{max}$ (hr) | $AUC_{0-24}$ (µg*hr/mL) |
|---|---|---|---|---|---|
| Fed (Day 3/13) | Parent | Pirfenidone 801 mg TID | 10.4 (37.5%) | 2.00 (0-12.0) | 150 (29.3%) |
| | | LYT-100 550 mg TID | 8.33 (31.7%) | 3.00 (1.00-12.0) | 130 (30.7%) |
| | Metabolite | Pirfenidone 801 mg TID | 6.82 (34.4%) | 2.00 (0-12.0) | 107 (28.1%) |
| | | LYT-100 550 mg TID | 3.88 (26.4%) | 3.00 (0-12.0) | 65.0 (24.0%) |
| Fasted (Day 4/14) | Parent | Pirfenidone 801 mg TID | 12.7 (23.5%) | 1.00 (0-2.00) | 44.1 (24.1%) |
| | | LYT-100 550 mg TID | 9.17 (47.5%) | 1.00 (0-3.00) | 34.1 (49.7%) |
| | Metabolite | Pirfenidone 801 mg TID | 7.52 (30.1%) | 1.00 (0-2.00) | 28.5 (29.7%) |
| | | LYT-100 550 mg TID | 3.80 (45.7%) | 1.00 (0-2.00) | 15.5 (48.0%) |

Summary statistics shown as geometric mean (CV %) or median (min-max) for $T_{max}$ Note:

only subjects with sufficient concentration data for all periods/analytes included

The results of the bioequivalence assessment when the treatments were administered in the fed state (Days 3 or 13) are provided in Table 4. Despite the slightly lower exposure seen after administration of LYT-100 in the fed state, LYT-100 at a dose of 550 mg TID met the criteria for bioequivalence based on $AUC_{0-24}$ as the lower and upper limits of the 90% confidence interval for the geometric mean ratio fall within the required interval of 0.8 to 1.25.

TABLE 4

Bioequivalence Assessment using Data from Subjects Enrolled in Part 2

| Parameter | Geometric Mean Ratio (Lower $5^{th}$, Upper $95^{th}$) |
|---|---|
| $AUC_{0-24}$ | 0.866 (0.831, 0.901) |
| $C_{max}$ | 0.800 (0.737, 0.868) |

Note:
only subjects with sufficient concentration data for all periods/analytes included. Bioequivalence assessment was done using the method of Chow et al. as implemented in the BE package for R Using the foregoing crossover data, a further simulation was performed. The simulation involved dose normalizing the observed $AUC_{0-24}$ after administration of LYT-100 in each subject to calculate the expected $AUC_{0-24}$ after administration of a hypothetical dose of 550 mg TID. The resultant $AUC_{0-24}$ was then compared to the observed $AUC_{0-24}$ after administration of pirfenidone 801 mg TID to calculate an individual ratio of LYT-100 to pirfenidone. These ratios were then assessed using the same process described in Chow (Design and Analysis of Bioavailability and Bioequivalence Studies; Chapman & Hall/CRC Biostatistics Series, Chapman; Hall/CRC 2008) and the CDER (Guidance for Industry Statistical Approaches to Establishing Bioequivalence Center for Drug Evaluation and Research [CDER], FDA, 2001). The results of the simulation are provided in Table 5. Based upon these assessments, an LYT-100 dose regimen of 550 mg TID is predicted to provide comparable parent drug exposure to pirfenidone dosed at 801 mg TID.

TABLE 5

Predicted Ratio of $AUC_{0-24}$ and $C_{max}$ (LYT-100: Pirfenidone 801 mg TID) after the Administration of Hypothetical LYT-100 Dose using Pooled Data.

| LYT-100 550 mg TID | 90% Confidence Interval | |
|---|---|---|
| | $AUC_{0-24}$ | $C_{max}$ |
| | 0.956 (0.926-0.986) | 0.764 (0.727-0.803) |

Adverse Event Summary

Overall, 28 subjects (57.1%) experienced at least one TEAE; 14 (30.4%) while taking LYT-100 and 23 (48.9%) while taking pirfenidone. The most common TEAEs (>5% overall) were nausea, headache, dizziness, vomiting, and somnolence. A summary of these TEAEs, overall and by study medication, is provided in Table 6.

TABLE 6

Summary of the Most Common (≥5% Overall) TEAEs (Safety Population)

| TEAE | LYT-100 N = 46 n (%); # | Pirfenidone N = 47 n (%); # |
|---|---|---|
| Overall AEs | 14 (30.4); 29 | 23 (48.9); 50 |
| GI Disorders | 8 (17.4); 13 | 16 (34.0); 22 |

62

TABLE 6-continued

Summary of the Most Common (≥5% Overall) TEAEs (Safety Population)

| TEAE | LYT-100 N = 46 n (%); # | Pirfenidone N = 47 n (%); # |
|---|---|---|
| Nausea | 7 (15.2); 8 | 14 (29.8); 16 |
| Vomiting | 2 (4.2); 4 | 3 (6.4); 3 |
| Nervous System Disorders | 8 (17.4); 9 | 15 (31.9); 22 |
| Headache | 6 (13.0); 7 | 9 (19.1); 12 |
| Dizziness | 1 (2.2); 1 | 7 (14.9); 8 |
| Somnolence | 1 (2.2); 1 | 2 (4.3); 2 |

Overall TEAEs during LYT-100 dosing were mild for 10 subjects (21.7%; 19 events) and moderate for 4 subjects (8.7%; 10 events). Overall TEAEs during pirfenidone dosing were mild in 17 subjects (36.2%; 42 events) and moderate in 6 subjects (12.8%; 8 events). Overall, TEAEs leading to study discontinuation were reported by 2 (4.1%) subjects in Cohort 2, one while receiving LYT-100 (nausea) and one while receiving pirfenidone (headache and dizziness). No deaths or serious AEs were reported.

In this group of older adults (mean age=68) across the two treatment groups (LYT-100 at 550 mg TID vs pirfenidone at 801 mg TID, fed and fasted), the incidence of TEAE's was notably reduced in the LYT-100 treatment arm compared to the pirfenidone arm for nausea and dizziness. Overall, in subjects experiencing at least one TEAE, the incidence was substantially lower in the LYT-100 group than in the pirfenidone group. Specifically, there was a 38% reduction in the overall incidence of TEAEs with LYT-100 vs. pirfenidone (30.4% versus 48.9%, respectively).

Figure 1A:
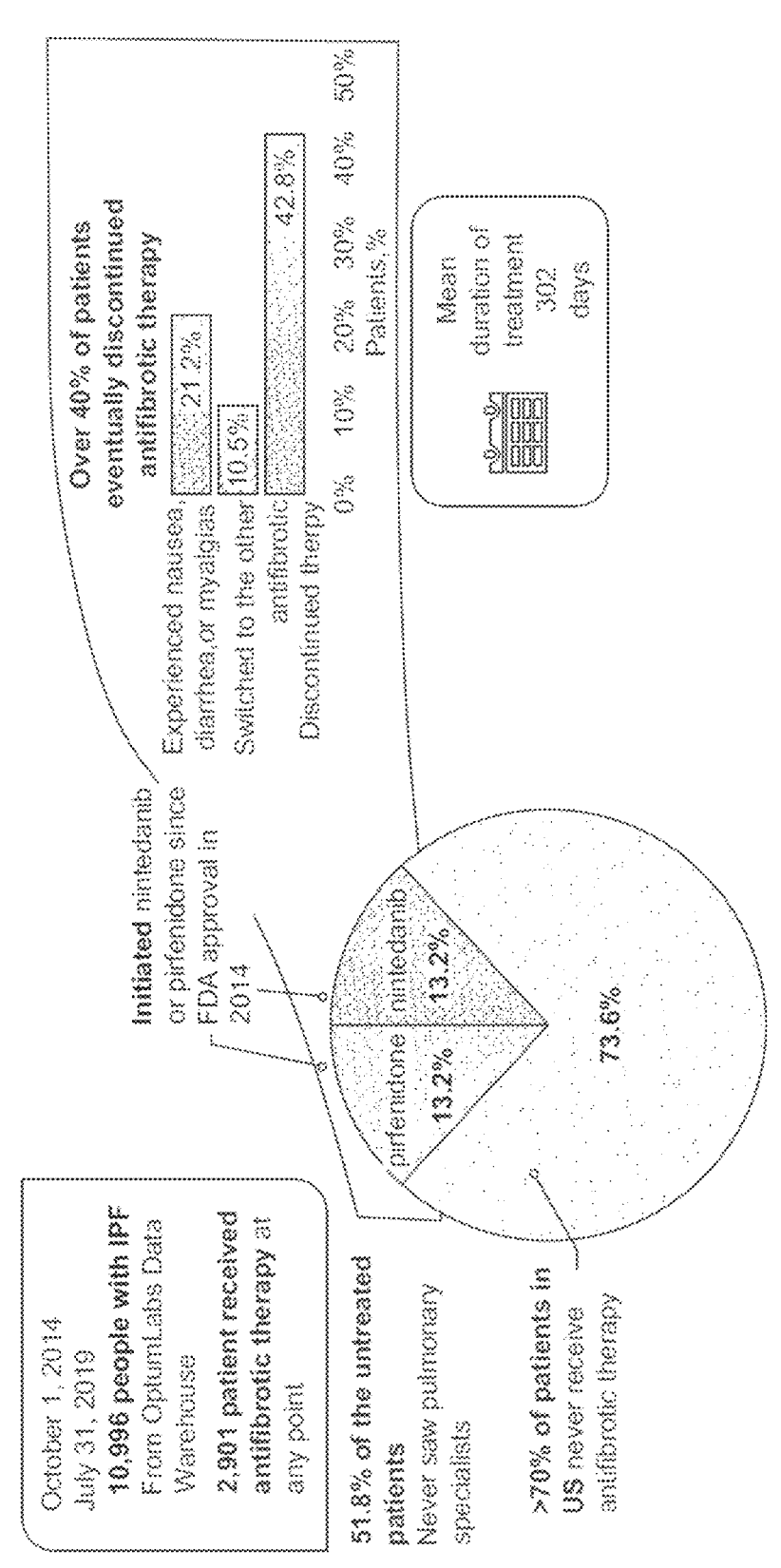
FIG. 1A is a graphical illustration of the low rates of treatment and poor tolerability with current antifibrotics (pirfenidone and nintedanib) for IPF.
Figure 1B:
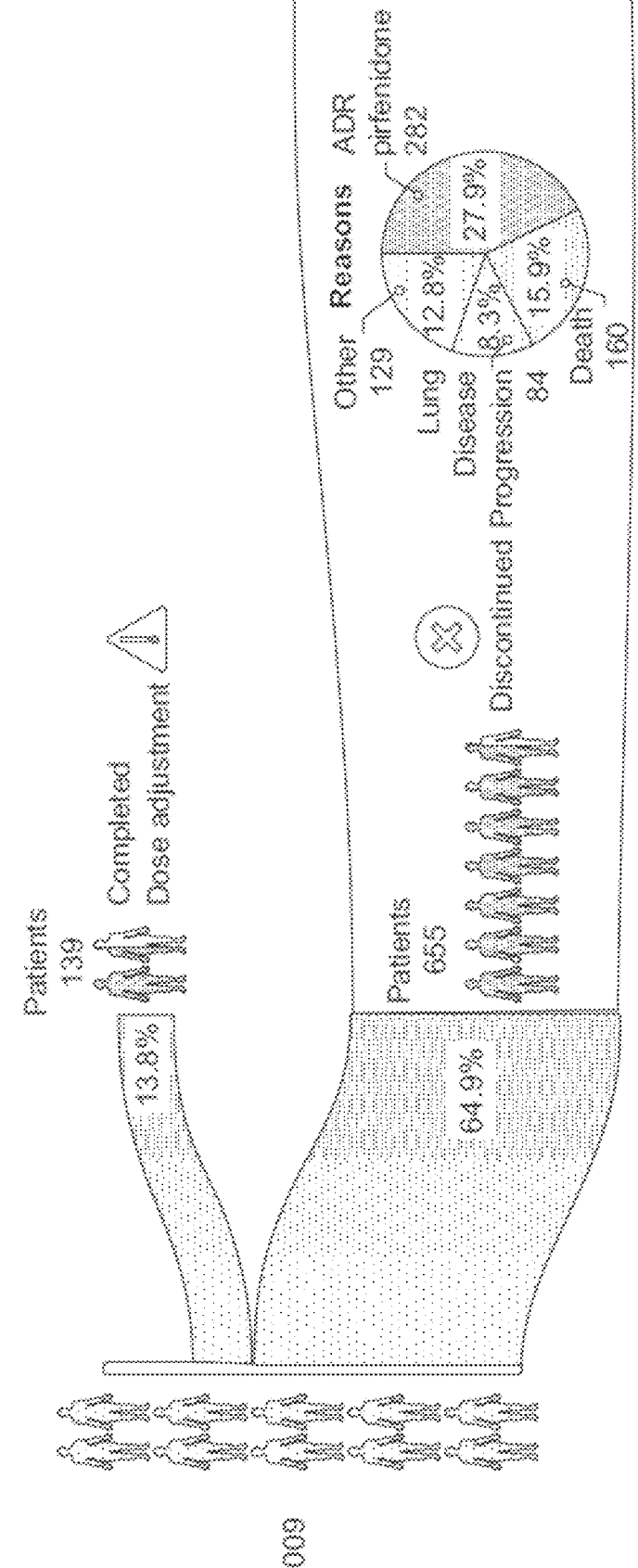
FIG. 1B is a graphical depiction of the high rate of discontinuation of pirfenidone therapy over time in the treatment of IPF.
Figure 7:
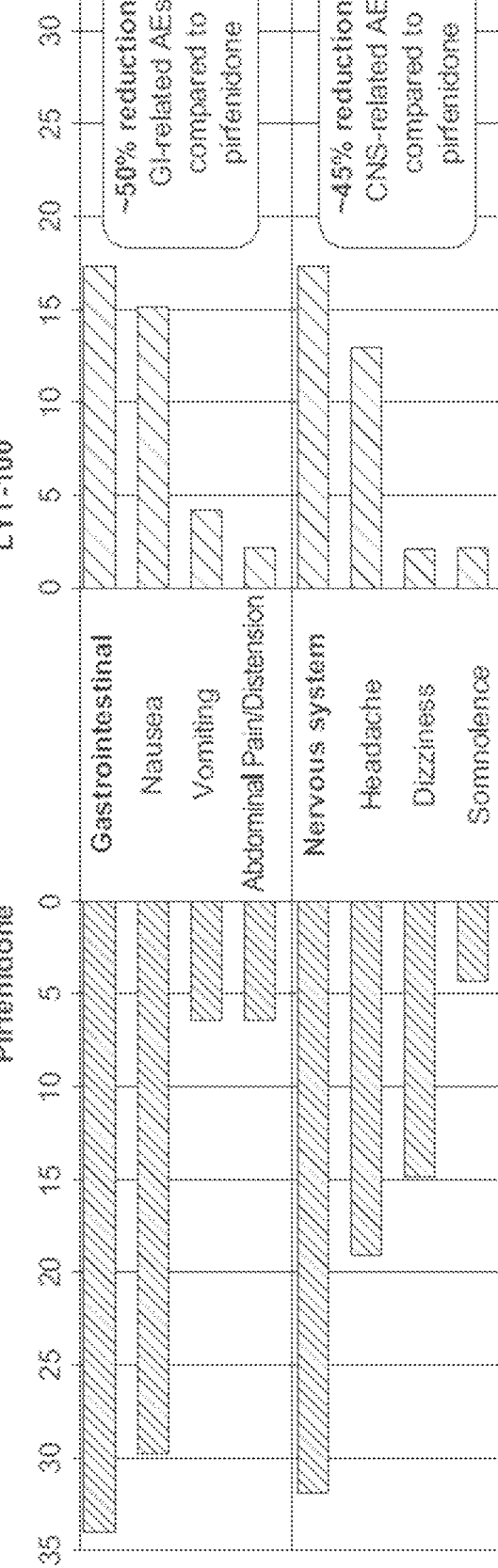
FIG. 7 is a graphical depiction of side effects encountered in a healthy older patient population for LYT-100 at 550 mg TID and pirfenidone at 801 mg TID.

FIG. 7 provides a graphical illustration of the reduction in GI and nervous system symptoms for LYT-100 at 550 mg TID versus pirfenidone at 801 mg TID in this patient population. With reference to FIG. 7, fifty percent fewer subjects experienced GI-related AEs with LYT-100 compared to pirfenidone (17.4% versus 34.0%, respectively), including 50% fewer with nausea (15.2% versus 29.8%). Fewer subjects experienced nervous system AEs with LYT-100 compared to pirfenidone (17.4% vs. 31.9%), notably dizziness (2.2% with LYT-100 versus 14.9% versus pirfenidone). These study results show that substantially fewer subjects taking LYT-100 experienced AEs compared with pirfenidone and approximately 50% fewer subjects experienced GI-related AEs with LYT-100 compared with pirfenidone. There were no differences in the incidence of study discontinuation between the treatment groups. The results suggest that LYT-100 may be better tolerated at 550 mg TID than pirfenidone 801 mg TID in this subject population.

With respect to fed versus fasted condition prevalence of TEAEs, there were 8 (17.4%) LYT-100-treated subjects who experienced at least 1 TEAE under fed conditions and 8 (17.8%) subjects under fasted conditions. There were 10 (21.3%) pirfenidone-treated subjects under fed conditions and 17 (37.0%) subjects under fasted conditions who experienced at least one TEAE. A summary of the most common TEAEs (≥10%) under fed and fasted conditions is provided in Table 7 for each study medication.

TABLE 7

Summary of the Most Common TEAEs (>5%) under Fed and Fasted
Conditions (Safety Population)

| TEAE | LYT-100 550 mg TID n (%) Fed (N = 46) | LYT-100 550 mg TID n (%) Fasted (N = 45) | Pirfenidone 801 mg TID n (%) Fed (N = 47) | Pirfenidone 801 mg TID n (%) Fasted (N = 46) |
|---|---|---|---|---|
| GI Disorders | 3 (6.5) | 5 (11.1) | 5 (10.6) | 13 (28.3) |
| Nausea | 2 (4.3) | 5 (11.1) | 4 (8.5) | 12 (26.1) |
| Vomiting | 2 (4.3) | 5 (11.1) | 2 (4.3) | 1 (2.2) |
| Nervous System Disorders | 4 (8.7) | 4 (8.9) | 7 (14.9) | 10 (21.7) |
| Headache | 4 (8.7) | 2 (4.4) | 5 (10.6) | 5 (10.9) |
| Dizziness | 0 | 1 (2.2) | 3 (6.4) | 5 (10.9) |

In this study, fed conditions reduced the incidence of TEAEs in both treatment arms. In addition, LYT-100 was better tolerated in both the fed and fasted conditions than pirfenidone within these two dose groups. This improved tolerability of LYT-100 also seems to be amplified in the fasted state. Without wishing to be bound by any particular theory, it is believed that the greater incidence of TEAEs experienced by fasting subjects in both treatment groups may be causally related to the higher peak plasma concentrations ($C_{max}$) of the parent molecules (pirfenidone or deupirfenidone) that result from their more rapid and extensive absorption during fasting than when taken with food. A causal role for higher $C_{max}$ in tolerability is suggested by the observations that on the days of fasting, $C_{max}$ was higher in both treatment groups, and the incidence of TEAEs was substantially greater for both treatment groups than on fed days. In addition, it is notable that the fasting increase in $C_{max}$ in the pirfenidone group was associated with the greatest incidence of TEAEs in the study. Overall, the head-to-head crossover study of Part 2 was designed at least in part to evaluate the tolerability impact of reducing the parent $C_{max}$. As described herein above, the results of this study show that reducing the parent drug $C_{max}$ improves tolerability.

Example 2: LYT-100 Crossover Study-550 and 824 mg TID

This study was a double-blind, randomized, two-period crossover study in older, healthy subjects to compare the safety, tolerability, and pharmacokinetics of deupirfenidone (LYT-100) and pirfenidone. The crossover study was performed at a single Study Center per Part in the United States.

Study Description

This study was a randomized, double-blinded, parallel arm, placebo-controlled study conducted in healthy older adults to evaluate the safety and tolerability compared to placebo of a dose of LYT-100 that provides an exposure of LYT-100 which is approximately 150% of the exposure of pirfenidone when dosed at 801 mg TID and did not exceed 850 mg TID LYT-100.

Study Endpoints

Safety:

Treatment-emergent adverse events (TEAEs), including severity, and relatedness to study drug)

Physical examination

Vital signs

Electrocardiograms (ECGs)

Clinical laboratory parameters, including hematology, serum chemistry, coagulation, and urinalysis New-onset concomitant medications Pharmacokinetics:

Comparison of the key PK parameters ($C_{max,ss}$, $C_{min,ss}$, and $AUC_{0\text{-}24,ss}$) between the parent compound (LYT-100 and pirfenidone) and primary metabolite (5-carboxypirfenidone). Other PK parameters will also be derived and compared.

Comparison of the key urine PK parameters ($Ae_{t1\text{-}t2}$, $CL_R$, $Fe_{t1\text{-}t2}$) between the parent compound (LYT-100 and pirfenidone) and primary metabolite (5-carboxypirfenidone). Other urine PK parameters may be derived and compared.

Food effect evaluation of LYT-100 and pirfenidone ($C_{max,ss}$, and $AUC_{0\text{-}6,ss}$) for fed versus fasted.

Study Design

This was a randomized, double-blinded, parallel arm, placebo-controlled study conducted in healthy older adults to evaluate the safety and tolerability of titrated high dose LYT-100 compared to placebo under fed conditions. Thirty older healthy adults between the ages of 60 and 80 were randomized to receive LYT-100 or placebo. Subjects were administered 550 mg LYT-100 three times daily (TID) for 3 days (to steady state [Day 1 to Day 3]) compared to 550 mg placebo administered TID for 3 days to steady state. Day 4 to Day 6, subjects were administered 824 mg LYT-100 TID for 3 days compared to 824 mg placebo TID for 3 days to steady state. Informed consent was obtained prior to the commencement of the study. Screening was performed up to 28 days prior to administration of the first dose of LYT-100/ placebo. Only subjects who met all the applicable inclusion and none of the applicable exclusion criteria were randomized. The dosing schedule is outlined in Table 8.

TABLE 8

Dosing Regimen and Treatment Sequence

| N | Dose, Days 1 to 3 | Daily total dose | Dose, Days 4 to 6 | Daily total dose |
|---|---|---|---|---|
| 24 | LYT-100, 550 mg TID | LYT-100, 1650 mg | LYT-100, 824 mg TID | LYT-100, 2427 mg |
| 6 | Placebo, 550 mg TID | Placebo, 1650 mg | Placebo, 824 mg TID | Placebo, 2427 mg |

Number of Subjects:

Thirty healthy older female and male adult subjects (target ratio 1:1 of males: females with a minimum of 10 per sex per cohort)

Main Criteria for Inclusion and Exclusion

Inclusion Criteria:

1. Male or female between 60 and 80 years old (inclusive) at the time of screening.

2. Subjects have a body mass index (BMI) between ≥18.0 and ≤35.0 kg/m² at screening.

3. Willing and able to abstain from direct whole body sun exposure from 2 days prior to dosing and until final study procedures have been conducted. Subjects should be instructed to avoid or minimize exposure to sunlight (including sunlamps), use an SPF 50 sun block, or higher, wear clothing that protects against sun exposure and avoid concomitant medications known to cause photosensitivity (including but not limited to tetracycline, doxycycline, nalidixic acid, voriconazole, amiodarone, hydrochlorothiazide, naproxen, piroxicam, chlorpromazine and thioridazine).

Exclusion Criteria:

1. Pregnant or lactating at screening or baseline or planning to become pregnant (self or partner) at any time during the study, including the specified follow-up period.

2. History or presence of malignancy at screening or baseline, with the exception of adequately treated localised skin cancer (basal cell or squamous cell carcinoma) or carcinoma in-situ of the cervix.

3. Clinically significant infection within 28 days of the start of dosing, or infections requiring parenteral antibiotics within the 3 months prior to screening. Known exposure to another person with COVID-19 within the last 14 days is also an exclusion criterion, or a positive COVID test within five days prior to dosing.

4. Had major surgery, (e.g., requiring general anesthesia) within 3 months before Screening, based on Investigator's discretion or has surgery planned during the time the participant is expected to participate in the study.

5. Currently suffering from clinically significant systemic allergic disease at screening or baseline or has a history of significant drug allergies including a history of anaphylactic reaction (particularly reactions to general anaesthetic agents); allergic reaction due to any drug which led to significant morbidity; prior allergic reaction to pirfenidone.

6. Chronic administration (defined as more than 14 consecutive days) of immunosuppressants or other immune-modifying drugs within 3 months prior to study drug administration. Corticosteroids are permitted at the discretion of the Investigator.

7. History or presence at screening or baseline of a condition associated with significant immunosuppression.

8. Positive test for hepatitis C antibody (HCV), hepatitis B surface antigen (HBsAg), or human immunodeficiency virus (HIV) antibody at screening.

9. Symptoms of dysphagia at screening or baseline or known difficulty in swallowing capsules.

10. Any condition at screening or baseline (e.g., chronic diarrhoea, inflammatory bowel disease or prior surgery of the gastrointestinal tract) that would interfere with drug absorption or any disease or condition that is likely to affect drug metabolism or excretion, at the discretion of the Investigator.

11. History or presence at screening or baseline of cardiac arrhythmia or congenital long QT syndrome.

12. QT interval corrected using Fridericia's formula (QTcF)>450 msec. ECG may be repeated 30 to 60 minutes apart from the first one collected at screening. If repeat ECG is ≤450 msec, the second ECG may be used to determine patient eligibility. However, if repeat ECG confirms QTcF remains >450 msec, the subject is not eligible.

13. Use of tobacco or nicotine containing products in the previous 3 months prior to dosing or a positive urine cotinine test at Screening or Baseline.

14. Lack of willingness to abstain from the consumption of tobacco or nicotine-containing products throughout the duration of the study and until completion of the final Follow-up visit.

15. Regular alcohol consumption defined as >21 alcohol units per week (where 1 unit=284 mL of beer, 25 mL of 40% spirit or a 125 mL glass of wine) or the Participant is unwilling to abstain from alcohol for 48 h prior to admission and 48 h prior to study visits.

16. Use of any of the following drugs within 30 days or 5 half-lives of that drug, whichever is longer, prior to study drug administration:
   a. Fluvoxamine, enoxacin, ciprofloxacin;
   b. Other inhibitors of CYP1A2 (including but not limited to methoxsalen or mexiletine);
   c. Contraceptives containing oestradiol, ethinyloestradiol or gestodene;
   d. Inducers of CYP1A2 (such as phenytoin), CYP2C9 or 2C19 (including but not limited to carbamazepine or rifampin);
   e. Any drug associated with prolongation of the QTc interval (including but not limited to moxifloxacin, quinidine, procainamide, amiodarone, sotalol).

17. Vaccination with a live vaccine within the 4 weeks prior to screening or that is planned within 4 weeks of dosing, and any non-live vaccination within the 2 weeks prior to screening or that is planned within 2 weeks of dosing (including those for COVID).

18. Use of any investigational drug or device within the longer of 30 days or five half-lives prior to screening.

19. Consumption of grapefruit, grapefruit juice, Seville oranges, Seville orange juice, or any foods containing these ingredients, within 7 days prior to dosing or unwilling to abstain from these throughout the duration of the study.

Dosage and Mode of Administration:

This was a crossover study in which subjects received both the test treatment (LYT-100) and the reference (pirfenidone).

LYT-100 (Deupirfenidone) was provided as hard gelatin capsules. LYT-100 should be stored at a controlled room temperature of 15° C. to 25° C.

Pirfenidone (Esbriet) was provided as white to off-white hard gelatin capsules contain 267 mg of pirfenidone. The cap of the capsule is printed with "PFD 267 mg" in brown ink. Pirfenidone should be stored at 15° C. to 25° C.

Both LYT-100 and pirfenidone were over-encapsulated to maintain study blind.

Duration of Treatment:

This study included a 28-day Screening period, a 6-day treatment period consisting of: 3 days of up to 550 mg TID LYT-100 followed directly by 3 days of 824 mg TID LYT-100, or placebo. A 3-day (±1 day) post-last-dose safety follow-up visit occurred. Thus, total duration of study participation for each subject was up to 40 days.

Criteria for Evaluation

Safety:

Safety and tolerability were assessed by monitoring AEs, physical examination, vital signs, 12-lead ECGs, clinical laboratory values (hematology panel, multiphasic chemistry panel and urinalysis), and review of concomitant treatments/medication use.

Pharmacokinetics:

Subjects provided blood samples prior to treatment, i.e., Day −1 or Day 1, for the determination of CYP1A2, CYP2C9, CYP2C19, and CYP2D6 genotype to support exploratory PK analyses. Subjects were required to provide consent for genotyping. Blood samples for PK were collected at specified times, as follows:

Day 1:0 (pre-AM dose)

Day 2: no sampling

Day 3:0 (pre-AM dose), and 1, 2, 3, 4, 6 (pre-mid-day dose), 7, 8, 9, 10, 12 (pre-PM dose), 13, 14, 15, 16, and 17 hours post-AM dose Day 4:0 (pre-AM dose)

Day 5: no sampling

Day 6:0 (pre-AM dose), and 1, 2, 3, 4, 6 (pre-mid-day dose), 7, 8, 9, 10, 12 (pre-PM dose), 13, 14, 15, 16, and 17 hours post-AM dose Day 7:0 (same time as Day 6 pre-AM dose, discharge)

Plasma concentration-time data for LYT-100, and its metabolite(s) were analyzed using noncompartmental methods. Plasma PK parameters for steady state dosing (Days 1 to 3 and Days 4 to 7) included, but were not limited to:

$AUC_{0\text{-}tau,ss}$ (area under the time concentration curve from time zero to tau at steady state)

$AUC_{0\text{-}24,ss}$ (area under the time concentration curve from time zero to 24 hours at steady state)

$\lambda_z$ (terminal disposition rate constant/terminal rate constant)

$t_{1/2}$ (elimination half-life)

$C_{max,ss}$ (maximum concentration in a dosing interval)

$T_{max}$ (time to maximum concentration, as reported relative to the beginning of a dosing interval in which maximum concentration occurred)

$C_{min,ss}$ (lowest concentration in a dosing interval)

$C_{av,ss}$ (average concentration during a dosing interval).

$C_{max, ss}\text{-}C_{min,ss}/C_{av,ss}$ (degree of fluctuation).

$C_{max,ss}\text{-}C_{min,ss}/C_{min,ss}$ (swing)

PTF % (peak-trough fluctuation)

Urine samples for PK were collected at specified intervals, as follows:

Days 1 and 4: pre-dose (subjects to be instructed to empty their bladders approximately 30 minutes prior to dosing)

Days 2 and 5: no urine sampling

Days 3 and 6: pre-dose (subjects to be instructed to empty their bladders approximately 30 minutes prior to dosing), 0 to 4, 4 to 8, 8 to 12, 12 to 16, and 16 to 24 hours post-AM dose Urine samples for analysis of excretion in urine will be collected, separated by specified time interval, and analyzed. The total volume of urine collected in each interval (t1 to t2) will be noted. The urine PK parameters included, but were not limited to:

$Ae_{t1\text{-}t2}$ (Amount excreted in urine over time)

$CL_R$ (Renal clearance)

Fraction of systemic clearance (CL/F) represented by the renal clearance (CLR/[CL/F])

$Fe_{t1\text{-}t2}$ (Fraction of administered dose excreted in urine over the dosing intervals)

Study endpoints are defined as follows:

Safety

AEs (type, severity, and relatedness to study drug)

Physical examination

Vital signs

Electrocardiograms (ECGs)

Clinical laboratory parameters (hematology, serum chemistry, coagulation, and urinalysis)

New-onset concomitant medications

Pharmacokinetics:

Comparison of the key plasma PK parameters ($C_{max,ss}$, $C_{min,ss}$, and $AUC_{0\text{-}24,ss}$) between the parent compound (LYT-100 and pirfenidone) and primary metabolite (5-carboxypirfenidone). Other plasma PK parameters were also derived and compared.

Comparison of the key urine PK parameters ($Ae_{t1\text{-}t2}$, $CL_R$, $Fe_{t1\text{-}t2}$) between the parent compound (LYT-100 and pirfenidone) and primary metabolite (5-carboxypirfenidone). Other urine PK parameters may have bene derived and compared.

Food effect evaluation of LYT-100 and pirfenidone ($C_{max,ss}$, and $AUC_{0\text{-}6,ss}$) for fed vs fasted.

Results—Pharmacokinetics

Based on the observations of improved tolerability (but comparable total exposure) for a lower TID dose of LYT-100 compared to pirfenidone in Example 1, the safety and tolerability of a higher TID dose of LYT-100 (to achieve a higher overall predicted AUC or total exposure than the approved dose of pirfenidone (801 mg TID), and to explore the possibility of evaluating that dose in future efficacy studies), was evaluated in this study.

Subjects between the ages of 60 and 80 were randomized to receive LYT-100 or placebo. Subjects were administered up to 550 mg LYT-100 TID for 3 days (to steady state [Day 1 to Day 3]) compared to placebo administered TID for 3 days to steady state. On Day 4 to Day 6, subjects were administered 824 mg LYT-100 TID for 3 days compared to placebo TID for 3 days to steady state. A summary of the dosing scheme is provided in Table 9.

TABLE 9

| | Dosing Scheme | | | |
| --- | --- | --- | --- | --- |
| Number of Subjects | Dose, Days 1 to 3 | Total Daily Dose | Dose, Days 4 to 6 | Total Daily Dose |
| 24 | LYT-100, 550 mg TID | 1650 mg | LYT-100, 824 mg TID | 2472 mg |
| 6 | Placebo TID | — | Placebo TID | — |

Overall, 30 subjects were enrolled and included in the Safety Population, 24 subjects to LYT-100 and 6 subjects to placebo. Seven subjects (23.3%) did not complete the study. The mean age of the overall population was 64.9; the mean age was similar in the LYT-100 and placebo groups, 65.0 and 64.5 years, respectively. The majority of subjects were male (56.7%; 66.7% in the LYT-100 group, 16.7% in the placebo group). The overall mean number of days of dosing with LYT-100 was 5.5 days. The mean number of days of dosing with placebo was 5.8 days.

Data was obtained for thirty subjects. Eight subjects had all values reported as below level of quantitation (BLQ; assumed to be 6 placebo subjects plus 2 active subjects with Day 1 pre-dose samples only). One additional subject was excluded due to a large number of BLQ samples on both Days 3-4 and 6-7. Accordingly, twenty-one subjects had sufficient PK data available to calculate PK parameters at the lower dose (550 mg TID on Days 3-4). Three subjects only had data for Days 3-4, and therefore had missing PK parameters for the higher dose (824 mg TID on Days 6-7).

Figures 8A, 8B:
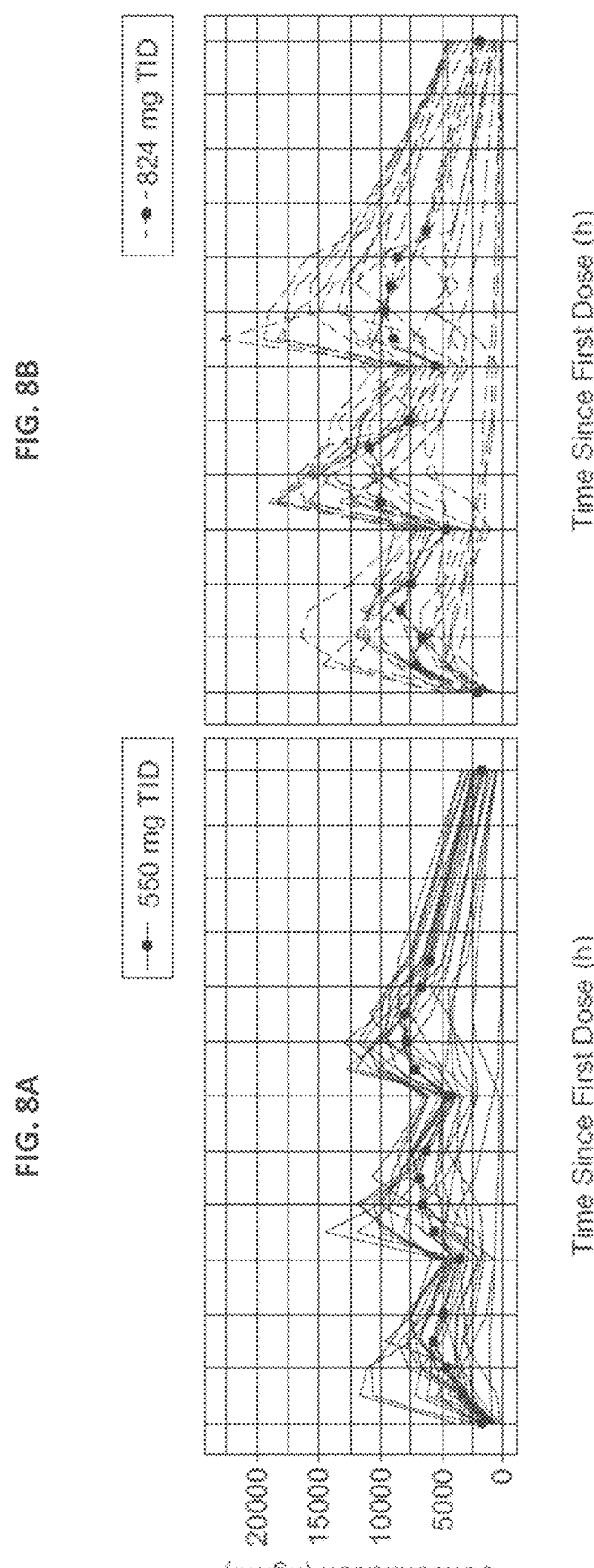
FIG. 8A is a graphical depiction of time versus exposure for LYT-100 for a dose of 550 mg TID.
FIG. 8B is a graphical depiction of time versus exposure for LYT-100 for a dose of 824 mg TID.
Figures 8C, 8D:
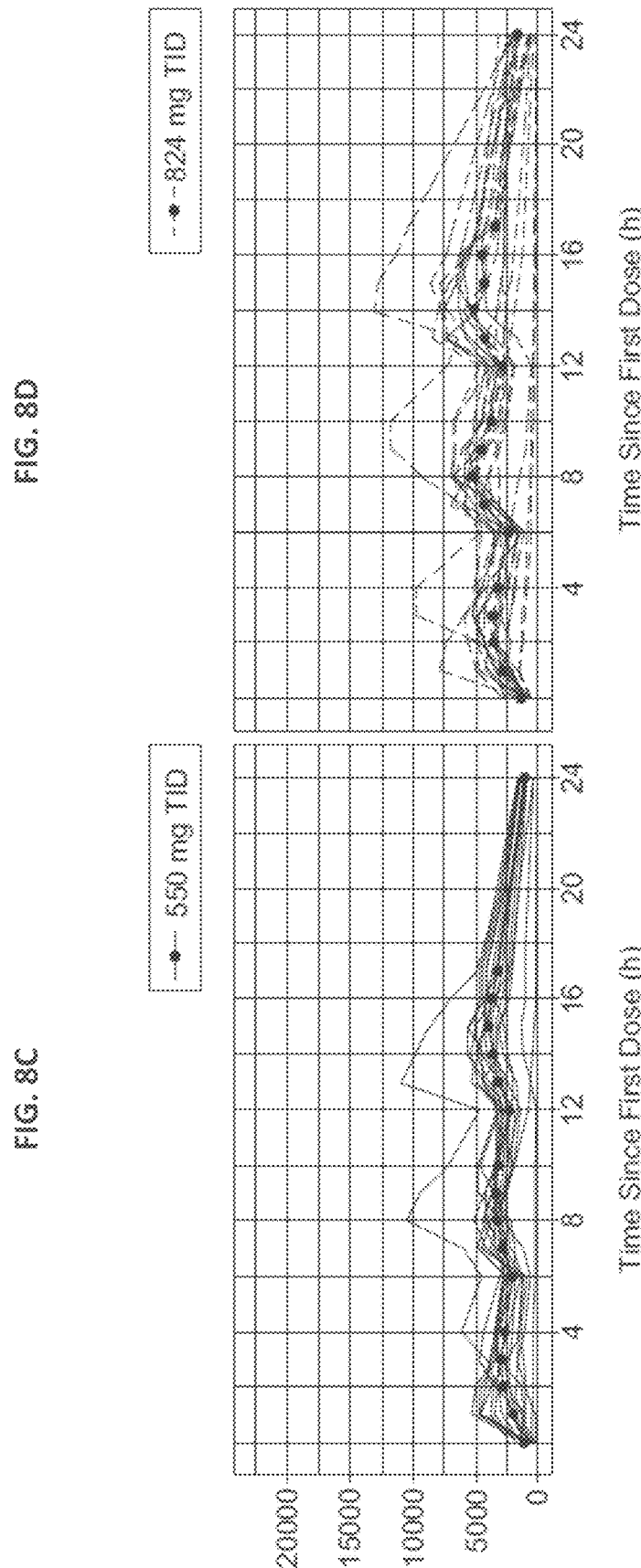
FIG. 8C is a graphical depiction of time versus exposure for the major metabolite for a dose of 550 mg TID.
FIG. 8D is a graphical depiction of time versus exposure for the major metabolite for a dose of 824 mg TID.

The results for the pharmacokinetic assessments are provide in FIG. 8A to FIG. 19B. With reference to FIGS. 8A-8D, the plasma concentrations for both the parent drug (LYT-100; SD-560) and major metabolite (5-carboxypirfenidone; SD-789) were higher for the 824 mg TID dose cohort (FIGS. 8B and 8D) relative to the 550 mg TID dose cohort (FIGS. 8A and 8C). The $C_{max}$, AUC, and $T_{max}$ values in the fed state for LYT-100 and the major metabolite at the 550 mg and 824 mg TID doses are provided in FIG. 9. With reference to FIG. 9, for LYT-100, the $C_{max}$ ratio for the 824 mg TID to the 550 mg TID dose was 1.45, and the AUC ratio was 1.44, demonstrating an approximately linear dose-exposure relationship. The $C_{max}$ and AUC ratios for the metabolite were slightly reduced at 1.32 and 1.42, respectively.

Figures 10A, 10B:
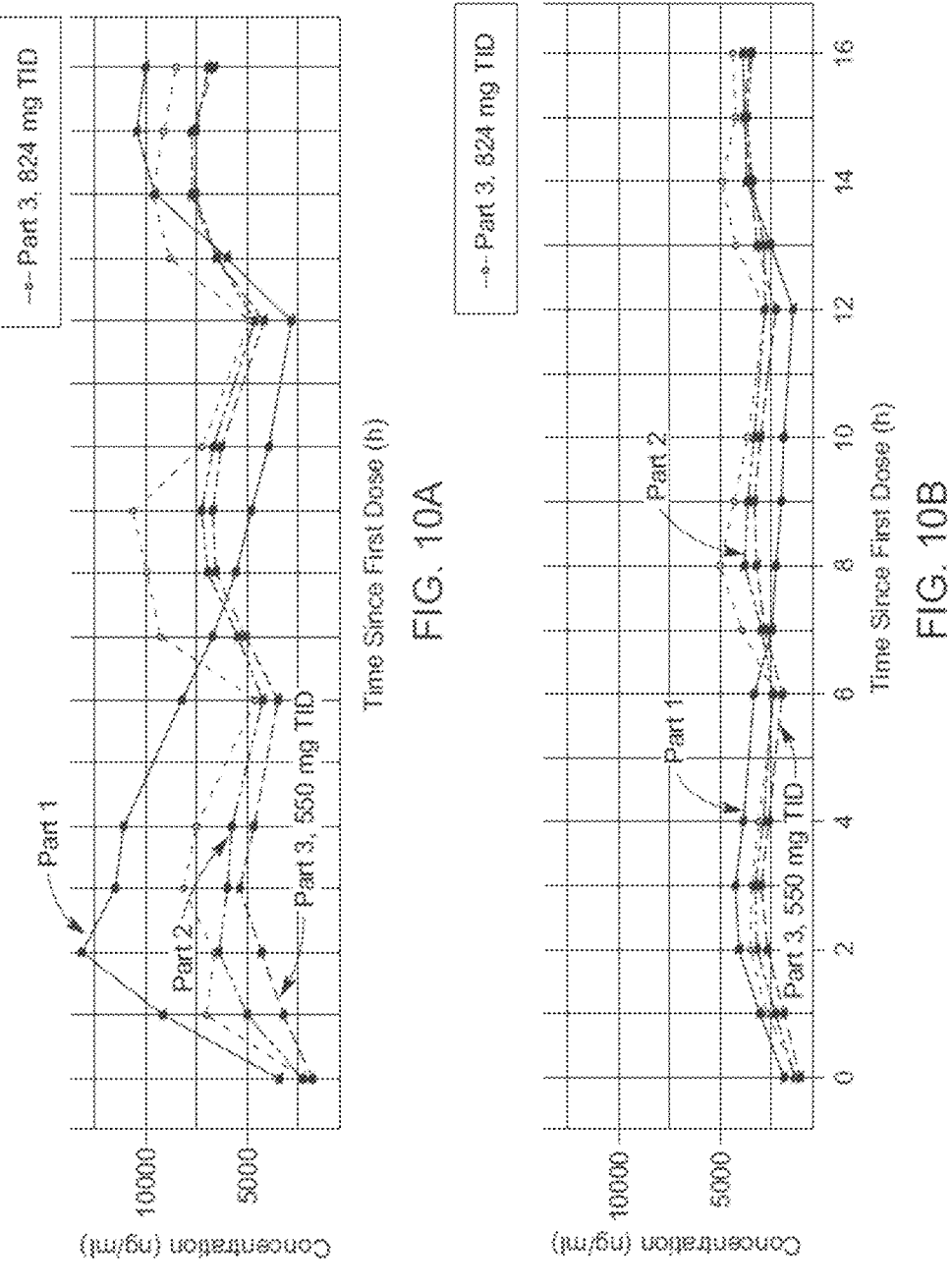
FIG. 10A is a graphical depiction of time versus exposure for LYT-100 for doses of 550 mg TID and 824 mg TID in the crossover study of Example 1 and two prior dosing studies.
FIG. 10B is a graphical depiction of time versus exposure for the major metabolite for doses of 550 mg TID and 824 mg TID in the crossover study of Example 1 and two prior dosing studies.

The results for this study were compared to the results obtained in a prior 850 mg BID study and a prior 550 mg TID study (described herein in Example 1). As shown in FIGS. 10A and 10B (LYT-100 and major metabolite, respectively), although slightly lower, the AUC for the present 550 mg TID (days 1-3) study roughly matches up with the AUC of 550 mg TID from the prior 550 mg TID study (part 2; solid blue and solid green lines respectively; see also Example 1, Table 6), and the AUC and $C_{max}$ for the 824 mg TID dose shows a pronounced/linear increase over that for the 550 mg TID dose.

Figure 11:
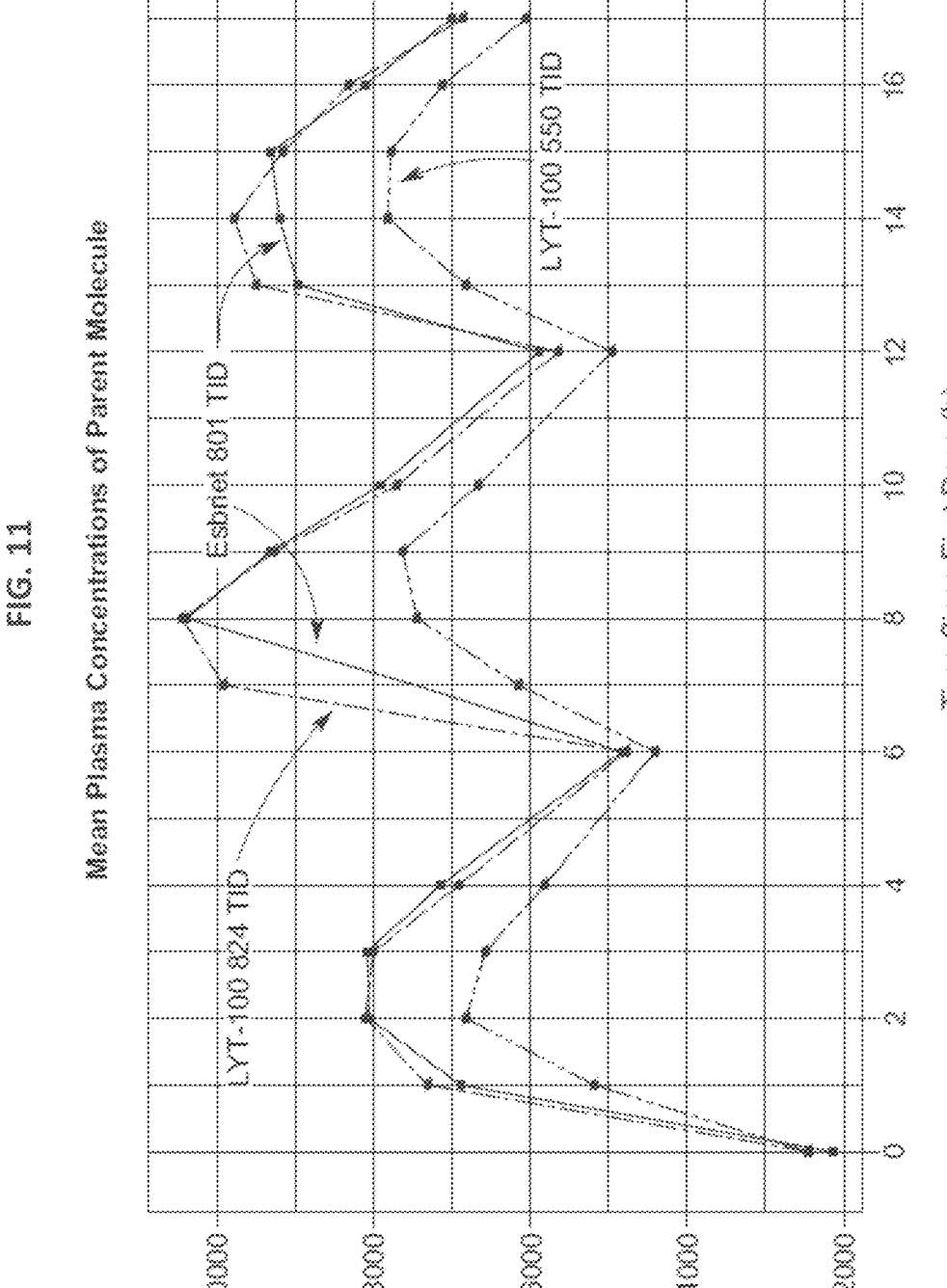
FIG. 11 is a graphical illustration of the mean plasma concentrations over time for pirfenidone dosed at 801 mg TID, and for LYT-100 dosed at 550 mg TID and 824 mg TID.
Figure 12:
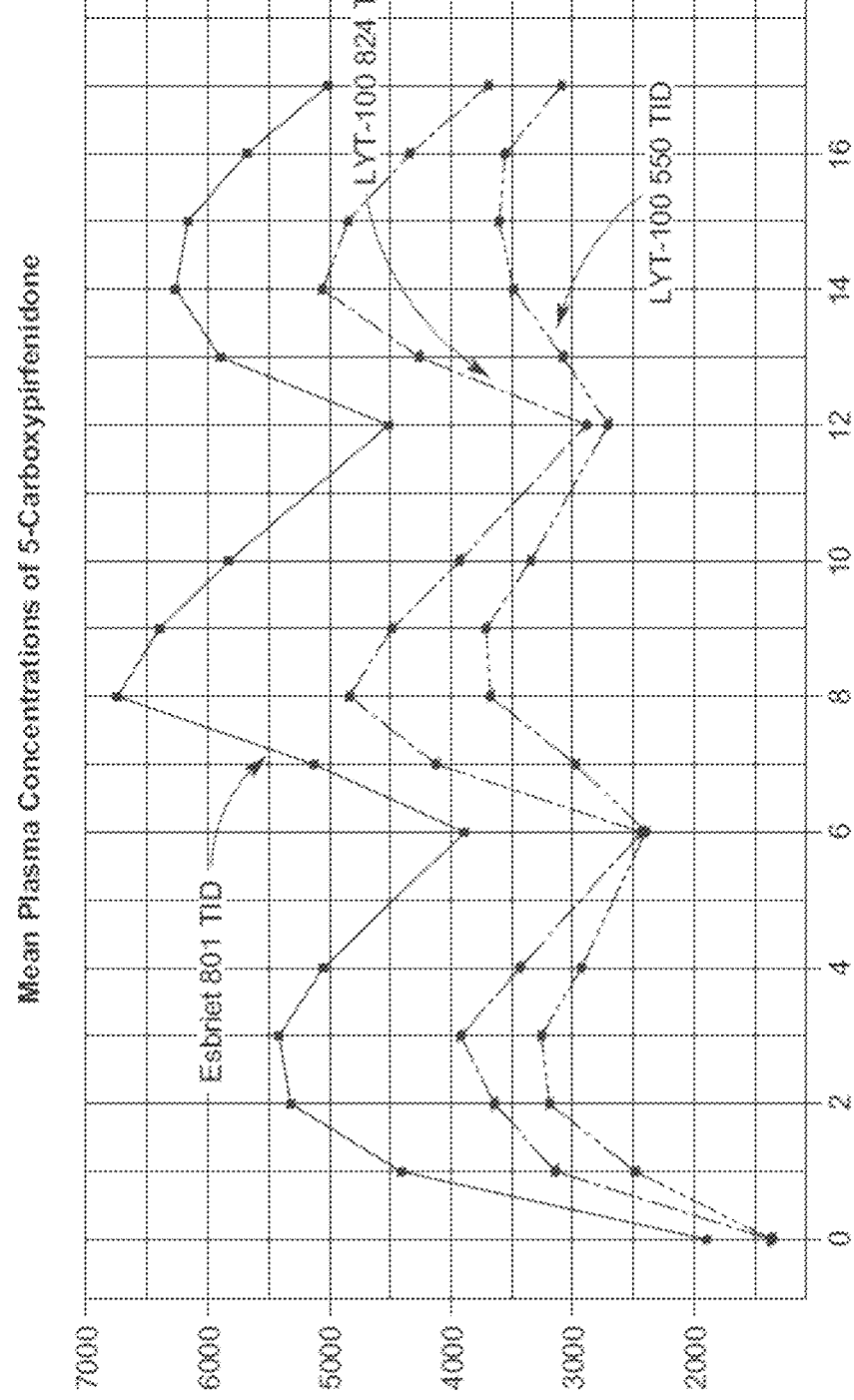
FIG. 12 is a graphical illustration of the mean plasma concentrations of the major metabolite over time for pirfenidone dosed at 801 mg TID, and for LYT-100 dosed at 550 mg TID and 824 mg TID.
Figure 13:
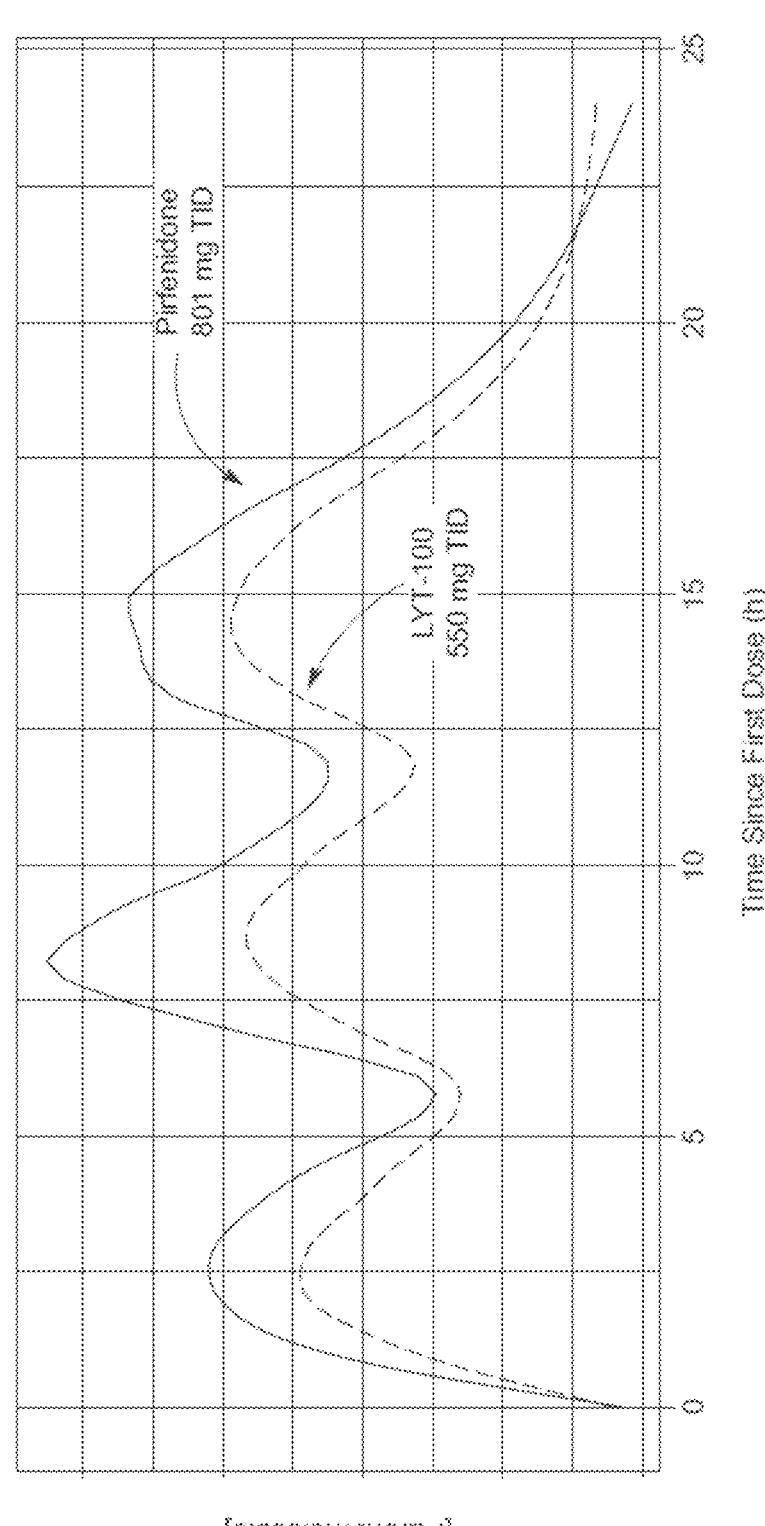
FIG. 13 is a graphical depiction of plasma concentration versus time for pirfenidone at 550 mg TID and LYT-100 at 824 mg TID following day 3 in the crossover study of Example 1.

FIG. 11 provides a comparison of plasma concentrations of LYT-100 (dosed at 550 mg and 824 mg TID) and pirfenidone (dosed at 801 mg TID) versus time following the day 3 doses. With reference to FIG. 11, the concentration peaks for pirfenidone are higher than those for 550 mg LYT-100. FIG. 12 provides a comparison of plasma concentrations of the major metabolite of LYT-100 (dosed at 550 mg and 824 mg TID) and pirfenidone (dosed at 801 mg TID) versus time following the day 3 doses. FIG. 13 provides a comparison of plasma concentrations versus time for pirfenidone at 801 mg TID and LYT-100 at 550 mg TID following the day 3 doses.

Figures 14A, 14B:
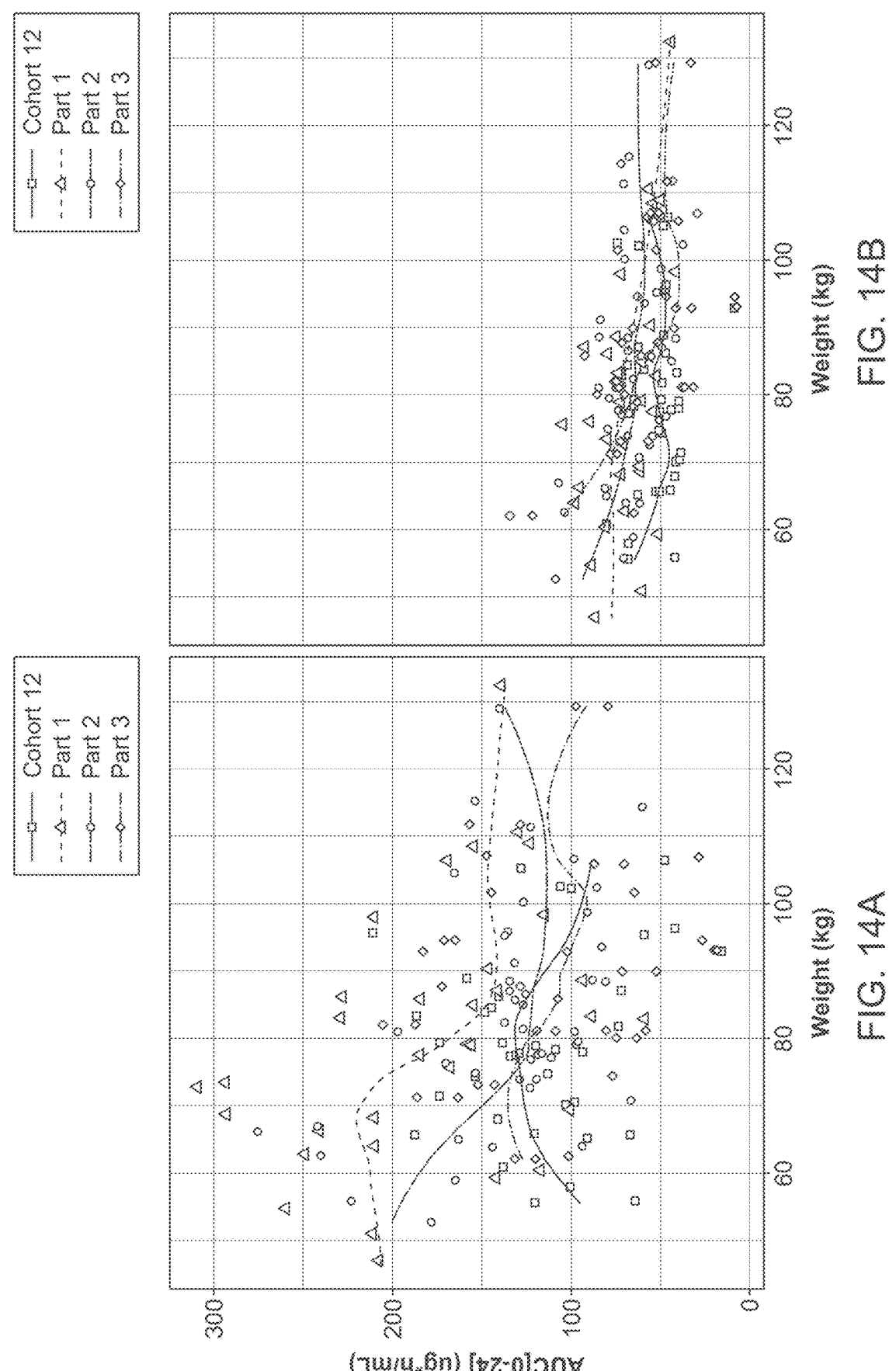
FIG. 14A is a graphical depiction of subject weight versus exposure for LYT-100 for 550 mg TID and 824 mg TID doses in the crossover study of Example 1 and in three prior dosing studies.
FIG. 14B is a graphical depiction of subject weight versus exposure for the major metabolite for 550 mg TID and 824 mg TID doses in the crossover study of Example 1 and in three prior dosing studies.

FIG. 14A provides a comparison of $AUC_{0-24}$ versus body weight for LYT-100 administration across this and previous studies. FIG. 14B provides a comparison of $AUC_{0-24}$ versus body weight for the major metabolite of LYT-100 across this and previous studies. With reference to FIGS. 14A and 14B, a similar trend for impact of body weight was observed across all three groups, with an apparent exposure difference above and below a threshold of 70-75 kg.

Figures 15A, 15B:
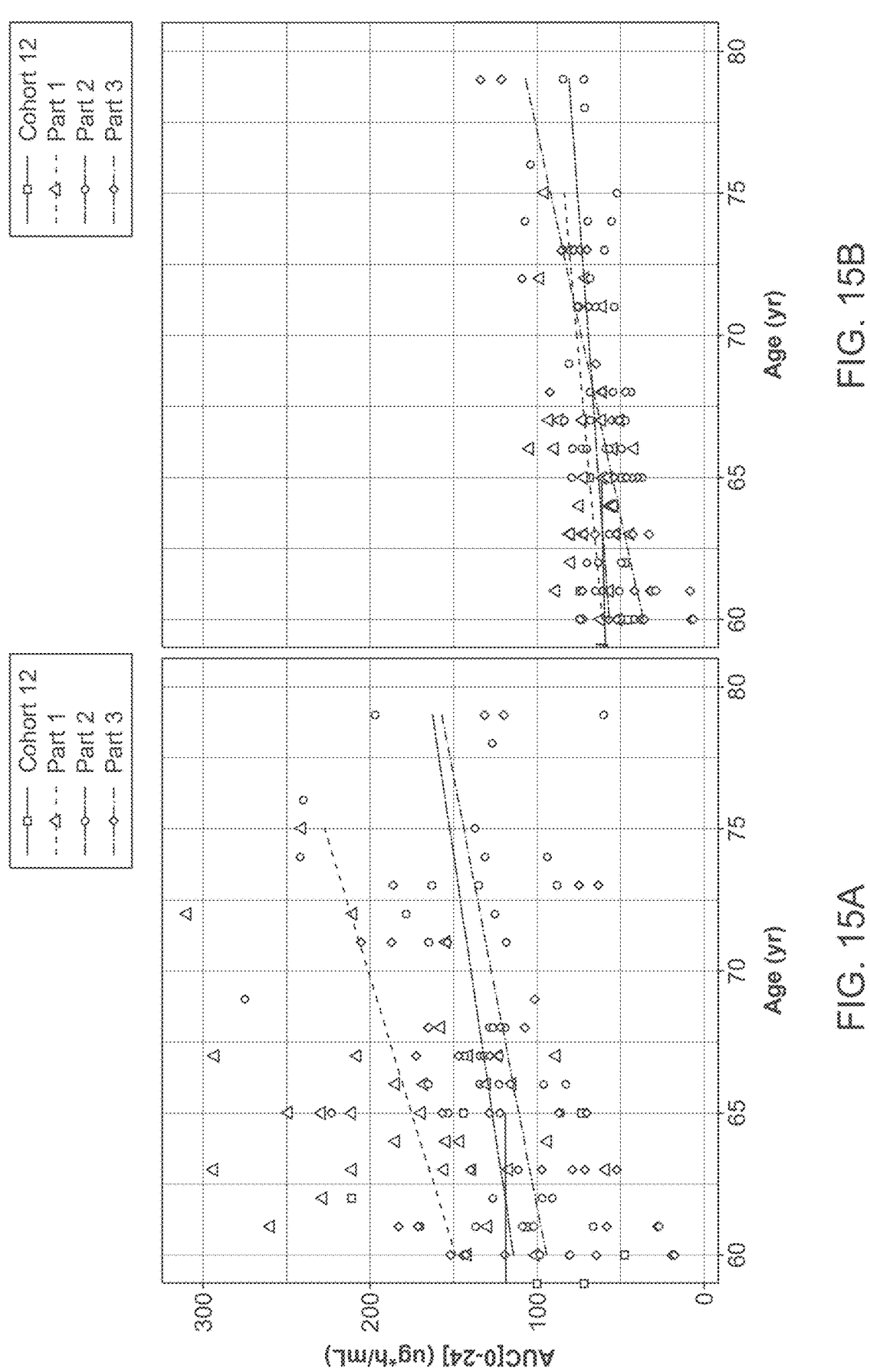
FIG. 15A is a graphical depiction of subject age versus exposure for LYT-100 normalized to 550 mg TID in the crossover study of Example 1 and in three prior dosing studies.
FIG. 15B is a graphical depiction of subject age versus exposure for the major metabolite of LYT-100 normalized to 550 mg TID in the crossover study of Example 1 and in three prior dosing studies.

FIGS. 15A and 15B provide a comparison of $AUC_{0-24}$ versus subject age for LYT-100 and the major metabolite, respectively, across this and previous studies. With reference to FIGS. 15A and 15B, age appears to impact AUC, with exposure increasing with age.

Figures 19A, 19B:
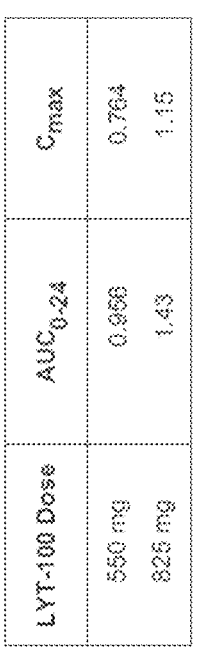
FIG. 19A is a graphical cartoon illustration of predicted plasma concentrations over time for pirfenidone at 801 mg TID, LYT-100 at 550 mg TID, and LYT-100 at 825 mg TID.
FIG. 19B is a table showing the ratio of predicted plasma concentrations for pirfenidone at 801 mg TID versus LYT-100 dosed at 550 mg TID and 825 mg TID.

Bioequivalence simulations were performed for $AUC_{24ss}$ across this dosing study and three prior dosing studies. Results are provided in FIGS. 16A-16D and FIG. 17, which show that bioequivalence to 801 mg TID pirfenidone was achieved for 550 mg TID LYT-100 when pooled data from the studies was used, and bioequivalence was observed for a theoretical 687 mg TID dose (FIG. 17). The results of the simulations across this study and three prior studies is provided in tabular form in FIG. 18. An illustrative prediction of plasma concentration over time for theoretical 550 mg TID and 825 mg TID dosing of LYT-100 and 801 mg TID dosing of pirfenidone is provided in FIG. 19A. With reference to FIG. 19A, it is predicted that for the 550 mg TID dosing, the maximal plasma concentration (Cmax) of LYT-100 achieved is less than the maximal plasma concentration of pirfenidone achieved with 801 mg TID dosing, but with a similar exposure (AUC). In contrast, it is predicted that with the 825 mg TID dosing, the Cmax of LYT-100 achieved is only slightly more than the maximal plasma concentration of pirfenidone achieved with 801 mg TID dosing, but with a higher AUC. The estimated Cmax and AUC ratios of LYT-100 to pirfenidone are provided in FIG. 19B.

Results—Tolerability

Four subjects discontinued due to an TEAE (3 (12.5%) subjects in the LYT-100 group and 1 (16.7%) subject in the placebo group). Three (12.5%) subjects withdrew consent; all were in the LYT-100 group. Overall, 9 subjects (30.0%) experienced at least one TEAE; 8 (33.3%) while taking LYT-100 and 1 (16.7%) while taking placebo. The most common TEAEs (>5% overall) were COVID-19 and headache. A summary of these TEAEs, overall and by study medication, is provided in Table 10.

TABLE 10

| Summary of the Most Common (>5% Overall) TEAEs (Safety Population) | | | |
|---|---|---|---|
| TEAE | LYT-100 N = 24 n (%) | Placebo N = 6 n (%) | Overall N = 30 n (%) |
| COVID-19 | 4 (16.7) | 1 (16.7) | 5 (16.7) |
| Headache | 3 (12.5) | 0 | 3 (10.0) |

A summary of TEAEs stratified by onset day 1 to 3 or day 4 to 6 showed that the onset of the COVID-19 events occurred within days 4 to 6; the onset of the headache events occurred within days 1 to 3. Overall, the majority of TEAEs were considered to be mild. There were 13 mild events reported by 8 (26.7%) subjects, 7 (29.2%) in the LYT-100 group and 1 (16.7%) in the placebo group. Two moderate TEAEs were reported by one (3.3%) subject; this subject was in the LYT-100 group. No TEAEs were severe. TEAEs were unrelated for 5 (16.7%) events and possibly related for 6 (13.3%) events. No events were probably related. Overall, TEAEs leading to study discontinuation were reported by 4 (13.3%) subjects; all were Covid-19. Of these 4 TEAEs, 3 (12.5%) occurred in the LYT-100 group and 1 (16.7%) occurred in the placebo group. No deaths or SAEs were reported during the study.

Based on prior PK modeling studies, the AUC of LYT-100 at 824 mg TID is expected to be approximately 150% of the AUC for the approved pirfenidone dose of 801 mg TID. Within the 824 mg TID LYT-100 group (mean age=65), the dose was well tolerated over the 3 treatment days. In this dosage group, the most common TEAE was headache, and the majority of the events were mild.

Using the foregoing crossover data, a further simulation was performed. The simulation involved dose normalizing the observed $AUC_{0-24}$ after administration of LYT-100 in each subject to calculate the expected $AUC_{0-24}$ after administration of various hypothetical TID doses. The resultant $AUC_{0-24}$ was then compared to the observed $AUC_{0-24}$ after administration of pirfenidone 801 mg TID to calculate an individual ratio of LYT-100 to pirfenidone. These ratios were then assessed using the same process described in Chow (Design and Analysis of Bioavailability and Bioequivalence Studies; Chapman & Hall/CRC Biostatistics Series, Chapman; Hall/CRC 2008) and the CDER (Guidance for Industry Statistical Approaches to Establishing Bioequivalence Center for Drug Evaluation and Research [CDER], FDA, 2001). The results of the simulation are provided in Table 11. Based upon these assessments, an LYT-100 dose regimen of 550 mg TID is predicted to provide comparable parent drug exposure to pirfenidone dosed at 801 mg TID. An LYT-100 dose regimen of 825 mg TID is predicted to provide parent drug exposure that is approximately 150% of that following administration of pirfenidone given 801 mg TID. Of note, the slower absorption of LYT-100 relative to pirfenidone results in a predicted $C_{max}$ for LYT-100 at a dose of 825 mg TID that is only 15% higher than the corresponding $C_{max}$ for pirfenidone at a dose of 801 mg TID.

The actual and extrapolated exposure and $C_{max}$ values for LYT-100 dosed at 550 and 824/825 mg TID, along with the tolerability data, support these two doses for studying the efficacy, safety, and dose response in idiopathic pulmonary fibrosis, as described below in Example 3.

TABLE 11

Predicted Ratio of $AUC_{0-24}$ and $C_{max\_X}$ (LYT-100: Pirfenidone 801 mg TID) after the Administration of Various Actual and Hypothetical LYT-100 Doses using pooled data

| LYT-100 Dose | 90% Confidence Interval | |
|---|---|---|
| (mg TID) | $AUC_{0-24}$ | $C_{max}$ |
| 550 | 0.956 (0.926-0.986) | 0.764 (0.727-0.803) |
| 687 | 1.19 (1.16-1.23) | 0.955 (0.908-1.00) |
| 825 | 1.43 (1.39-1.48) | 1.15 (1.09-1.21) |
| 962 | 1.67 (1.62-1.72) | 1.34 (1.27-1.41) |
| 1100 | 1.91 (1.85-1.97) | 1.53 (1.46-1.61) |

Example 3: LYT-100 Tolerability in Patients with COVID-19 Respiratory Illness A Phase 2 multi-center randomized, double-blind, parallel arm, placebo-controlled trial was performed to evaluate the safety and efficacy of deupirfenidone (LYT-100) compared to placebo in post-acute adult patients with COVID-19 respiratory disease who were treated with supplemental oxygen (including MV, ECMO or any other means of oxygen administration) in the hospital for at least 1 day and have required only low flow nasal oxygen or no oxygen supplementation for at least 72 hours prior to screening. Patients received LYT-100 (deupirfenidone) formulated as powder in 250 mg capsules or matching placebo. Dosing was as provided in Table 12. An initial dosage of 500 mg BID was given the first 3 days of dosing, followed by 750 mg BID thereafter. Patients took LYT-100 study medication, or placebo (in Part A), orally and preferably with food, (solid or nutritional supplements, whenever possible), with approximately 10 to 12 hours between the two daily doses.

TABLE 12

Dosing Regimens

| Day 1 to Day 3 | Day 4 through Day 91 |
|---|---|
| LYT-100 500 mg BID or matching Placebo × 3 days | LYT-100 750 mg BID or matching Placebo × 88 days |

The study enrolled 177 patients averaging 55 years of age who experienced continued respiratory complications following hospitalization for acute COVID-19 infection that required treatment with supplemental oxygen were randomized to receive LYT-100 or placebo in a ratio of 1:1, respectively. The baseline demographic characteristics of enrolled subjects and subject disposition are provided in FIG. 20 to FIG. 22.

Tolerability Results

LYT-100 was well-tolerated in this relatively sick patient population with multiple comorbidities and concomitant medications. There were no drug-related serious adverse events (SAEs) or deaths. The treatment emergent AE's occurring in the LYT-100 arm at a frequency greater than or equal to 5% are summarized in Table 13. With reference to Table 13, nausea was the only AE judged to be at least possibly related to LYT-100 with an incidence ≥5% (8.7% vs 2.4% with placebo). With further reference to Table 13, other AEs that have been commonly associated with pirfenidone and which were considered to be at least possibly related to LYT-100 treatment in this study included headache (4.3% vs. 1.2% with placebo), dizziness (3.3% vs. 1.2% with placebo), fatigue (2.2% vs. 0% with placebo), and rash (3.3% vs. 1.2% with placebo). Discontinuation rates due to AEs that were considered at least possibly related to LYT-100 were low in both arms (8.6% with LYT-100 vs. 2.4% with placebo) and the majority of discontinuations in the LYT-100 arm were due to idiosyncratic events and not AEs commonly associated with pirfenidone. A summary of all treatment emergent adverse events judged to at least possibly be related to LYT-100 are provided as FIG. 23.

TABLE 13

Treatment Emergent AEs occurring in LYT-100 (≥5%)

| Adverse Event | Placebo: N (%) Events | LYT-100 750 mg BID: N (%) Events |
|---|---|---|
| Nausea | 2 (2.4) 2 | 8 (8.7) 10 |
| Dyspepsia | 2 (2.4) 2 | 6 (6.5) 6 |
| Nasopharyngitis | 1 (1.2) 1 | 6 (6.5) 7 |
| Upper abdominal pain | 2 (2.4) 2 | 5 (5.4) 6 |
| Increase in Fibrin D Dimer | 2 (2.4) 2 | 5 (5.4) 6 |
| Headache | 3 (3.5) 3 | 5 (5.4) 5 |

Overall, the results of this study with respect to safety and tolerability reaffirm the profile of strong safety and tolerability profile of LYT-100 observed in previous studies, including those described in Examples 1 and 2 herein. The safety and tolerability of the 750 mg BID dosage in this relatively sick patient population suggest it may be equally well tolerated in other patient populations, such as those with Idiopathic Pulmonary Fibrosis.

Example 4: LYT-100 Efficacy, Safety, and Dose Response in Idiopathic Pulmonary Fibrosis (IPF)

This study was a randomized double-blind, four-arm active and placebo-controlled dose-finding trial to evaluate the efficacy, tolerability, safety, and dose response of LYT-100 in patients with Idiopathic Pulmonary Fibrosis (IPF). The study was conducted at approximately 100 study centers globally.

Study Description

Figure 24A:
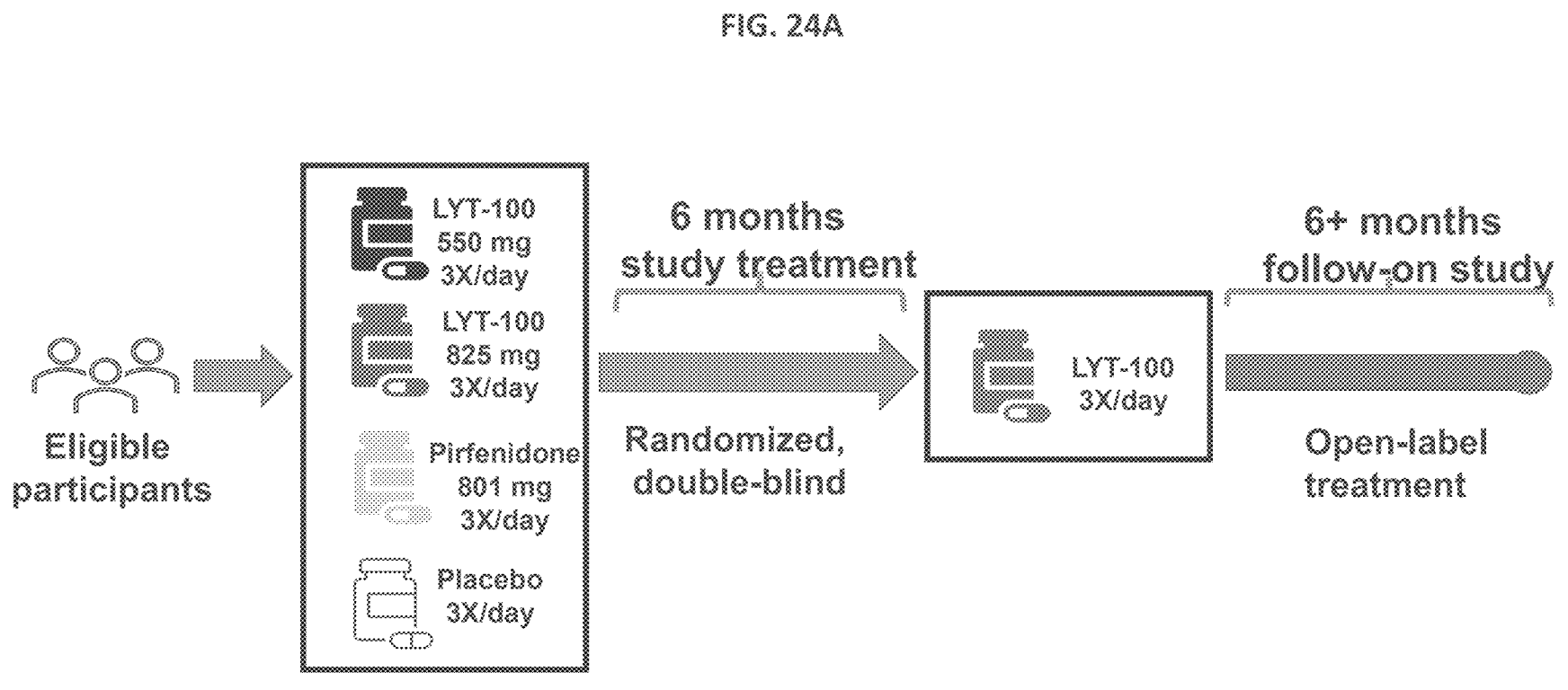
Figure 24B:
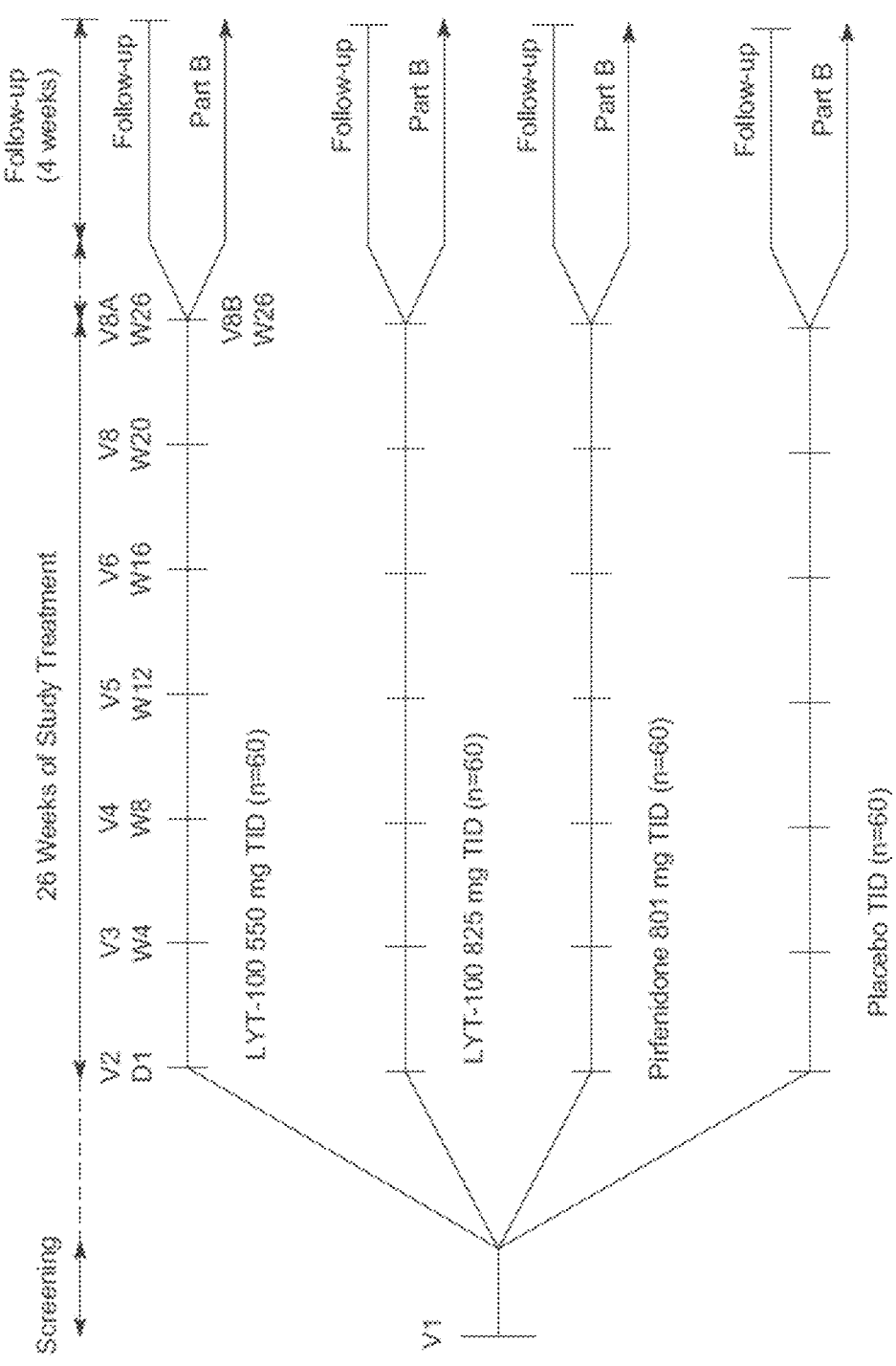
FIG. 24B is a graphical illustration of the double-blind portion of the IPF clinical trial study of Example 4 according to a non-limiting embodiment of the disclosure.

This study was conducted in two parts. A high-level graphical illustration is provided as FIG. 24A.

Double-Blind Treatment Period (Part A)

The Double-blind Treatment Period was a multi-center, four-arm, active and placebo-controlled, randomized, double-blind, trial comparing the efficacy, tolerability, and safety of LYT-100 550 mg oral capsules three times a day (TID), LYT-100 825 mg oral capsules TID, pirfenidone 801 mg oral capsules TID, and placebo oral capsules TID over a 26-week treatment period. The primary objective was to determine the dose(s) to carry into Phase 3. This determination was based on the overall benefit risk profile of LYT-100 via decline in forced vital capacity (FVC, mL), including both efficacy and tolerability outcomes over the 26-week treatment period. Patients were randomized to one of the four treatments in a 1:1:1:1 ratio and stratified based on prior exposure to nintedanib (<6 months) versus nintedanib-naïve patients. Patients who completed the Double-blind Treatment Period (Part A) were offered participation in the Long-term Extension (Part B). Patients who did not participate in the Part B had a follow-up visit 4 weeks after their last dose of study medication. For patients who participated in Part B, the follow-up was conducted at the end of Part B. A graphical illustration of an embodiment of the trial design is provided as FIG. 24B.

Long-Term Extension Period (Part B)

Figure 24C:
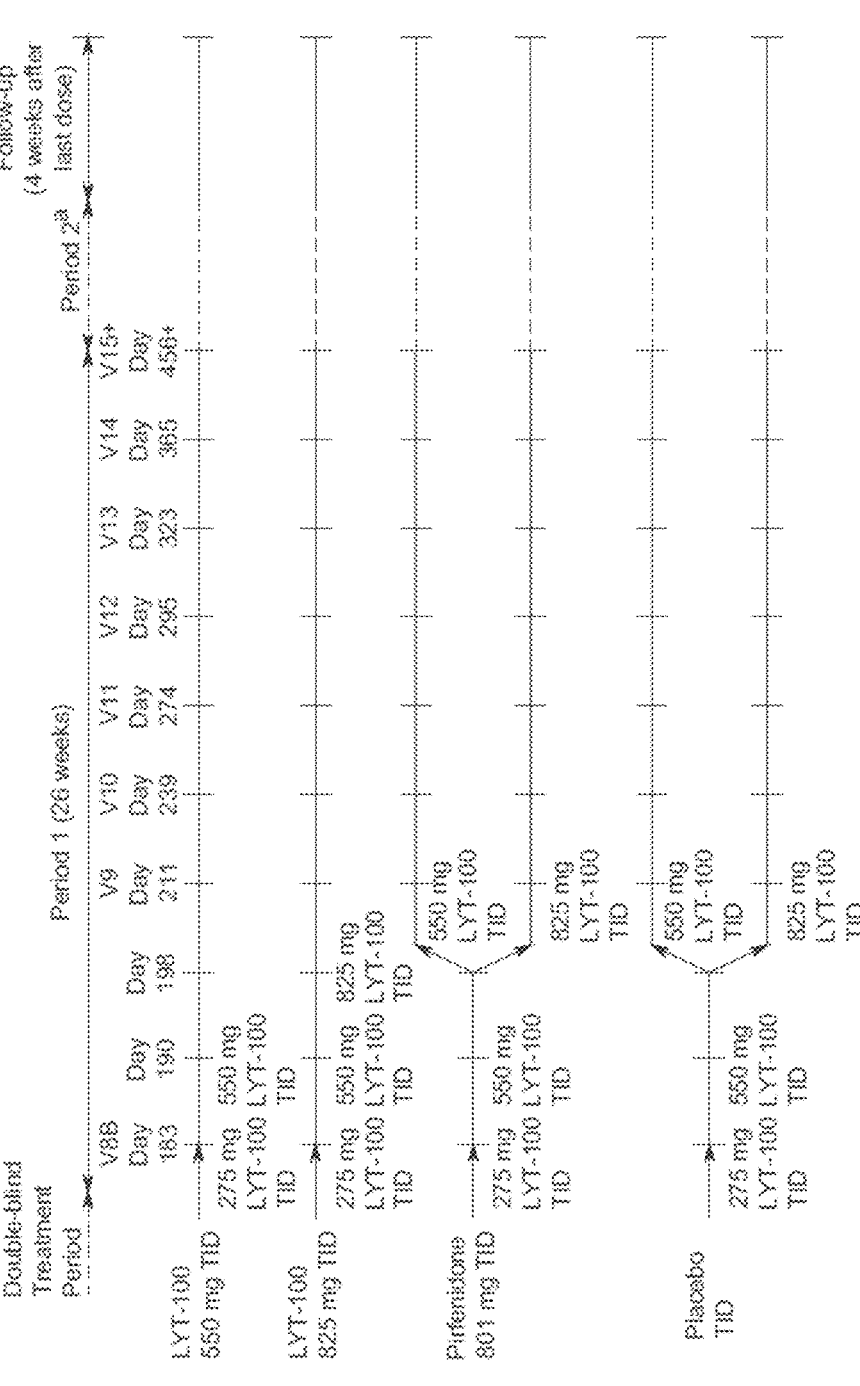
FIG. 24C is a graphical illustration of the open label portion of the IPF clinical trial study of Example 4 according to a non-limiting embodiment of the disclosure.

Part B (long-term extension) will evaluate the tolerability and long-term safety of LYT-100 in patients who complete the Double-blind Treatment Period. Part B has two periods. During Part 1 Period 1, patients are titrated over a period of 7 to 14 days to the target dose of either 550 or 825 mg LYT-100 TID, followed by maintenance treatment through Week 52. Patients completing Part B Period 1 will continue maintenance treatment in Part B Period 2 until the study ends. Part B Period 2 will continue at least until all patients who enter Part B Period 1 have the opportunity to complete Part B Period 1. Tolerability and safety during both Part B Period 1 and Part B Period 2 will be monitored by regularly scheduled review of adverse events (AEs), patient reported symptoms, concomitant medications, clinical laboratory findings, physical examinations, electrocardiograms (ECGs), and vital signs. Efficacy will be assessed by evaluation of pulmonary function and monitored by spirometry at regularly scheduled clinic visits. A graphical illustration of an embodiment of the trial design is provided as FIG. 24C. Recent amendments to the study protocol are summarized in FIG. 24D.

Study Objectives

The primary objective was to obtain clinical data establishing the efficacy, tolerability, safety, and dosing regimen of LYT-100 in patients with IPF in order to determine the dose to carry forward into Phase 3. A secondary objective was to obtain point estimates and measures of variability of efficacy endpoints in order to determine sample size for Phase 3 study. Another secondary objective was to assess the relative efficacy of LYT-100 as compared to pirfenidone. For Part B, the objectives were to assess the safety and tolerability of long-term treatment with LYT-100 in the IPF population to inform the optimal dosing regimen(s) to carry forward into Phase 3, and to compare the rate of change in FVC through the end of Part B Period 1 to that observed during Part A, by Part A treatment group assignment and by Part B LYT-100 target dose.

Study Drug Dosage and Mode of Administration

In Part A, patients received one of two doses of LYT-100 (550 mg or 825 mg) capsules, pirfenidone (801 mg) capsules, or placebo, each TID orally with meals, with approximately 6 hours between each of the three daily doses.

At the start of Part B, all patients received LYT-100 oral tablets. Patients were titrated onto their assigned doses. Dose titration was conducted as follows:

Patients who received 550 mg LYT-100 TID in the Double-blind Treatment Period:

Part B Treatment Days 183-189:1 tablet (275 mg) TID (825 mg/day)

Part B Treatment Day 190 to end of study: 2 tablets (550 mg) TID (1,650 mg/day)

Patients who received 825 mg LYT-100 TID in the Double-blind Treatment Period:

Part B Treatment Days 183-189:1 tablet (275 mg) TID (825 mg/day)

Part B Treatment Days 190-196:2 tablets (550 mg) TID (1,650 mg/day)

Part B Treatment Day 197 to end of study: 3 tablets (825 mg) TID (2,475 mg/day)

Patients who received 801 mg pirfenidone in the Double-blind Treatment Period:

Part B Treatment Days 183-189: One tablet (275 mg) TID (825 mg/day)

Part B Treatment Days 190-196: Two tablets (550 mg) TID (1,650 mg/day)

Part B Treatment Day 197 to end of study: Randomized to receive 2 tablets TID (1,650 mg/day) or three tablets (825 mg) TID (2,475 mg/day)

Patients who received placebo in the Double-blind Treatment Period:

Part B Treatment Days 183-189: One tablet (275 mg) TID (825 mg/day)

Part B Treatment Days 190-196: Two tablets (550 mg) TID (1,650 mg/day)

Part B Treatment Day 197 to end of study: Randomized to receive 2 tablets TID (1,650 mg/day) or three tablets (825 mg) TID (2,475 mg/day)

Number of Participants

Approximately 240 patients with physician diagnosis of IPF who were either treatment-naïve or were exposed to nintedanib for <6 months were intended to be randomized, in a 1:1:1:1 ratio, to receive one of four treatments:

550 mg LYT-100 (N=60)

825 mg LYT-100 (N=60)

801 mg Pirfenidone (N=60)

matching placebo (N=60)

The proportion of patients with prior exposure to nintedanib was limited to 50%. Patients assigned to receive pirfenidone or placebo in Part A were re-randomized in a 1:1 ratio to receive 550 mg LYT-100 TID or 825 mg LYT-100 TID. Following titration, all patients in Part B received 550 mg LYT-100 TID or 825 mg LYT-100 TID In each treatment group, dosing was three times a day (TID) of the indicated dosage (i.e., 550 mg of LYT-100 was administered three times daily for a total daily dose of 1650 mg; 825 mg of LYT-100 was administered three times daily for a total daily dose of 2475 mg). Patients took LYT-100, pirfenidone or placebo, orally and with food (solid or nutritional supplements, whenever possible), with approximately 6 hours between the three daily doses. Doses were adjusted according to safety and tolerability to avoid toxicity.

Table 14 below provides the dosing regimens used during the 6-month treatment period. Note that, for all treatment groups, the first 7 days of treatment, one capsule was taken TID., Day 8 through Day 14, two capsules TID., and Day 15 forward, 3 capsules TID. Each capsule was 275 mg LYT-100 (e.g., for the 550 mg TID dose at weeks 3-24, two 275 mg capsules of LYT-100 administered TID; for the 825 TID dose at weeks 3-24, three 275 mg capsules of LYT-100 administered TID).

TABLE 14

| Dosing Regimens | | | | | |
|---|---|---|---|---|---|
| Week # | Group | Dose | Morning Dose (mg) | Afternoon Dose (mg) | Evening Dose (mg) |
| 1 | LYT-100 E | Titration 275 | 275 | 275 | 275 |

TABLE 14-continued

Dosing Regimens

| Week # | Group | Dose | Morning Dose (mg) | | | Afternoon Dose (mg) | | | Evening Dose (mg) | | |
|---|---|---|---|---|---|---|---|---|---|---|---|
| 2 | LYT-100 E | Titration 275 | 275 | PTM* | | 275 | PTM | | 275 | PTM | |
| 3+ | LYT-100 E | Standard 550 | 275 | 275 | PTM | 275 | 275 | PTM | 275 | 275 | PTM |
| 1 | LYT-100 High | Titration 275 | 275 | | | 275 | | | 275 | | |
| 2 | LYT-100 High | Titration 550 | 275 | 275 | | 275 | 275 | | 275 | 275 | |
| 3+ | LYT-100 High | Standard 825 | 275 | 275 | 275 | 275 | 275 | 275 | 275 | 275 | 275 |
| 1 | Pirfenidone | Titration 267 | 267 | | | 267 | | | 267 | | |
| 2 | Pirfenidone | Titration 534 | 267 | 267 | | 267 | 267 | | 267 | 267 | |
| 3+ | Pirfenidone | Standard 801 | 267 | 267 | 267 | 267 | 267 | 267 | 267 | 267 | 267 |
| 1 | Placebo | N/A | PTM | | | PTM | | | PTM | | |
| 2 | Placebo | N/A | PTM | PTM | | PTM | PTM | | PTM | PTM | |
| 3+ | Placebo | N/A | PTM | PTM | PTM | PTM | PTM | PTM | PTM | PTM | PTM |

*PTM: placebo trial match

Dose Adjustment for Tolerability and Safety

The doses indicated (i.e., 550 mg TID and 825 mg TID) were adjusted based on any encountered adverse event or tolerability issues as follows.

Gastrointestinal Events

Patients who experienced intolerance to therapy due to gastrointestinal side effects were reminded again to take study drug with food. If gastrointestinal events did not improve, or worsened in severity, dose reduction was considered per Investigator judgment.

Photosensitivity Reaction or Rash

Patients were instructed to avoid or minimize exposure to sunlight (including sunlamps), to use a sunblock (SPF 50 or higher), and to wear clothing that protects against sun exposure. Additionally, patients were instructed to avoid concomitant medications known to cause photosensitivity. Dose reduction was considered per investigator judgement.

Dose Adjustment for Tolerability

If dose titration was well tolerated or the dose needed to be reduced due to tolerability or toxicity, adjustments to dosing were made as follows:

Part A:

Days 8-14: reduction from 2 capsules, TID, to 1 capsule, TID, ×2 days (longer if needed)

Days 15-182: reduction from 3 capsules, TID, to 2 capsules, TID×2 days (longer if needed); and if reduction from 3 capsules to 2 capsules of study drug TID was not sufficient to address difficulties with tolerability or toxicity, further reduction to one capsule TID was allowed Days 15-182: reevaluation for the ability to up titrate back to 3 capsules TID was performed Part B:

Days 183-189: reduction from 2 tablets, TID, to 1 tablet, TID, ×2 days (longer if needed)

Day 190-196: reduction from 2 tablets, TID, to 1 tablet, TID, ×2 days (longer if needed)

Day 197 onward:

For patients receiving 550 mg TID: reduction from 2 tablets, TID, to 1 tablet, TID, ×2 days (longer if needed)

For patients receiving 825 mg TID: reduction from 3 tablets, TID, to 2 tablets, TID×2 days (longer if needed); and if reduction from 3 tablets to 2 tablets of study drug TID is not sufficient to address difficulties with tolerability or toxicity, further reduction to 1 tablet TID is allowed Following dose reductions, patients were re-evaluated for the ability to up titrate back to 2 or 3 tablets TID at each scheduled study visit at a minimum or more frequently at the discretion of the investigator.

Patients who were unable to tolerate 275 mg (1 tablet) TID were discontinued from study medication but remained in the study.

In both Part A and Part B, patients who missed 14 consecutive days or more of treatment were to re-initiate therapy by undergoing the initial 2-week titration regimen up to the recommended daily dose. For treatment interruption of less than 14 consecutive days, the dose was resumed at the previous recommended daily dose without titration.

Dose Adjustment Due to Elevated Liver Enzymes

In the event of elevated liver function tests, clinical judgement was used to consider dose modifications to study medication as follows:

When ALT and/or AST are elevated >3 to ≤5× upper limit of normal (ULN) without elevation of bilirubin and in the absence of symptoms that may indicate liver injury:

Discontinued confounding medications, excluded other causes, and monitored the patient closely Repeated liver chemistry tests as clinically indicated The full daily dosage was maintained, if clinically appropriate, or reduced or interrupted (e.g., until liver chemistry tests were within normal limits). The patient was re-started on study drug at 1 capsule TID and following the up-titration schedule.

If ALT and/or AST>3 but ≤5×ULN was accompanied by symptoms that may indicate liver injury or hyperbilirubinemia, permanently discontinued study drug.

If ALT and/or AST>5×ULN, permanently discontinued study drug.

Eligibility Criteria

Inclusion Criteria

1. Male or female, aged ≥40 at the time of informed consent
2. Treatment naive patients or those with <6 months of exposure to nintedanib with physician diagnosed IPF based on ATS/ERS/JRS/ALAT 2018 guidelines
3. Idiopathic Pulmonary Fibrosis on HRCT, performed within 12 months of Visit 1 as confirmed by central readers
4. The extent of fibrotic changes was greater than the extent of emphysema on the most recent HRCT scan as determined by the investigator
5. Diffusing capacity of the lungs for carbon monoxide (DLCO) corrected for Hemoglobin (Hb) [visit 1] ≥30% and ≤90% of predicted of normal where available
6. FVC≥45% of predicted normal Exclusion Criteria 1. Significant clinical worsening of IPF between Screening and Baseline Visits.
2. AST, ALT>1.5×ULN at Visit 1
3. Bilirubin >1.5×ULN at Visit 1. Exceptions were made on a case-by-case basis for patients with Gilbert's syndrome
4. Creatinine clearance <30 mL/min calculated by Cockcroft-Gault formula at Visit 1. [Laboratory parameters from Visit I were used to satisfy the laboratory threshold values as shown above. Visit 2 laboratory results were available only after randomization. In case at Visit 2 the results no longer satisfy the entry criteria, the Investigator was to determine whether if it is justified that the patient remains on study drug. The justification for decision was to be documented]
5. Patients with underlying chronic liver disease (Child-Pugh B or C hepatic impairment)
6. Current or prior treatment with pirfenidone
7. Other investigational therapy received within 1 month prior to randomization visit (Visit 2)
8. Significant Pulmonary Arterial Hypertension (PAH) defined by any of the following:
   a. Previous clinical or echocardiographic evidence of significant right heart failure
   b. History of right heart catheterization showing a cardiac index≤2 l/min/m$^2$
   c. PAH requiring inhaled, subcutaneous or intravenous therapy with epoprostenol/Treprostinil.
9. Primary obstructive airway physiology (pre-bronchodilator FEV1/FVC<0.7 at Visit 1).
10. Known explanation for interstitial lung disease, including but not limited to radiation, sarcoidosis, hypersensitivity pneumonitis, bronchiolitis obliterans organizing pneumonia, human immunodeficiency virus (HIV), viral hepatitis, and cancer.
11. Diagnosis of any connective tissue disease, including but not limited to scleroderma/systemic sclerosis, polymyositis/dermatomyositis, systemic lupus erythematosus, and rheumatoid arthritis.
12. In the opinion of the Investigator, other clinically significant pulmonary abnormalities, including prior or current lung cancer (treated within the past 5 years).
13. Major extrapulmonary physiological restriction (e.g., chest wall abnormality, large pleural effusion),
14. Cardiovascular diseases, any of the following:
   a. Uncontrolled hypertension within 3 months of Visit 1
   b. Myocardial infarction within 6 months of Visit 1
   c. Unstable cardiac angina within 6 months of Visit 1

15. Prior hospitalization for severe confirmed COVID-19, acute exacerbation of IPF or any lower respiratory tract infection within 3-months of Visit 1.
16. Known symptoms of dysphagia or known difficulty in swallowing tablets and/or total gastrectomy.
17. Use of any of the following drugs within 2 weeks prior to Visit 2/baseline, during the screening period or planned during the duration of the study:
    a. Strong and moderate CYP1A2 inhibitors (i.e. ciprofloxacin, fluvoxamine, enoxacin, methoxsalen, mexiletine, vemurafenib) and phenytoin, rifampin, and terifluonmide (inducers of CYP1A2);
    b. Medications associated with substantial risk for prolongation of the QTc interval (including but not limited to moxifloxacin, quinidine, procainamide, amiodarone, sotalol). Note that QTc prolongation is not an all/nothing drug effect, and specifically the administration drugs such as hydroxychloroquine do not preclude participation in this trial but does mandate measurement of the QTc every 6 hours until deemed necessary in accordance with investigator judgement;
    c. Immunosuppressant medications such as azathioprine, cyclophosphamide, cyclosporin A, methotrexate, prednisone at steady dose >10 mg/day or equivalent
    d. Medications used to treat pulmonary hypertension such as ambrisentan, bosentan, and phosphodiesterase-5 inhibitors (sildenafil and tadalafil used to treat erectile dysfunction are allowed);
    e. Warfarin, as it may worsen IPF;
    f. Vaccination with a live vaccine is not permitted during the period from 4 weeks prior to screening to 4 weeks after the last dose; however, adenovirus and mRNA vaccines are allowed.
18. A current immunosuppressive condition (e.g., human immunodeficient virus).
19. Major surgical procedures during screening or study period, with the exception of pre-planned procedures that will not interfere with study participation.
20. Active alcohol or drug abuse.
21. Use of smoked (burnt) tobacco products.
22. Patients with a documented hypersensitivity to LYT-100.
23. Patients with a documented lactose or galactose intolerance.

Eligibility Criteria—Part B:

The following inclusion and exclusion criteria are to be met before the patient continues into the long-term extension (Part B)

Inclusion Criteria—Part B:

1. Patient must complete Part A of the study, through Day 183 of treatment.
2. In the opinion of the investigator, the patient is a good candidate for continued treatment.

Exclusion Criteria—Part B:

1. Patients must not meet any exclusion criteria listed for Part A.
2. Patients who discontinue study medication and start receiving commercially available antifibrotic medication during Part A are not eligible for Part B.
3. Patients whose treatment assignment is unblinded during Part A are not eligible for Part B.

Concomitant Medications and Other Therapy:

The following drugs were not permitted during the study, and they must have been discontinued at least 14 days prior to study drug administration (Visit 2):

Strong and moderate CYP1A2 inhibitors (i.e, ciprofloxacin, fluvoxamine, enoxacin, methoxsalen, mexiletine, vemurafenib) and phenytoin, rifampin, and teriflunomide (inducers of CYP1A2);

Any drug associated with prolongation of the QTc interval (including but not limited to moxifloxacin, quinidine, procainamide, amiodarone, sotalol). Warfarin, imatinib, ambrisentan, azathioprine, cyclophosphamide, cyclosporin A, bosentan, methotrexate, sildenafil (except for occasional use), prednisone at steady dose >10 mg/day or equivalent;

Immunosuppressant medications such as azathioprine, cyclophosphamide, cyclosporin A, methotrexate, and prednisone at steady dose >10 mg/day or equivalent;

Medications used to treat pulmonary hypertension such as ambrisentan, bosentan, and sildenafil (except for occasional use);

Warfarin, as it may worsen IPF;

Immunosuppressants or other immune-modifying drugs were to be discussed in consultation with the sponsor;

Use of concomitant pirfenidone and/or nintedanib while on study drug was prohibited. If a patient discontinued study medication and began receiving a commercially available antifibrotic medication during Part A, they were not eligible for Part B;

Some concomitant medications were to be administered with care in combination with pirfenidone and as such clinical judgement should be used to consider discontinuation of a concomitant medication such as in the event of LFT elevation. Investigators were to consult the local prescribing information for pirfenidone for their country for additional information on medications to be used with caution in combination with LYT-100 or pirfenidone.

Duration of Study and Study Treatment:

Screening: Participants were screened within 28 days of randomization. If the patient received prior nintedanib treatment, that patient must have discontinued nintedanib a minimum of 2 weeks prior to screening.

Randomization: Patients meeting all eligibility criteria were randomized at Visit 2/Study Day 1.

Double-blind Treatment Period (Part A): Patients were treated with double-blind study medication for 6 months (26 weeks).

Long-term Extension Period (Part B): Patients who participate in Part B are to be treated with 550 mg or 825 mg LYT-100 mg TID for at least an additional 6 months (26 weeks).

Post-treatment Period: A follow up post-treatment completion visit occurred within 28 days of last day of study treatment unless the patient elects to enter Part B, in which case this visit is performed at the end of Part B.

Assessments were performed according to the schedule of assessments provided in Tables 15 and 16 below.

Endpoints

Part A

Primary Efficacy Endpoint:

Rate of decline in Forced Vital Capacity (FVC; in mL) over Part A (26 weeks)

Key Secondary Efficacy Endpoints:

Change in FVC % predicted (FVCpp) from baseline to the end of the Double-blind Treatment Period (Week 26)

Secondary Efficacy Endpoints:

Time to hospitalization due to respiratory cause or all-cause mortality through 26 weeks.

Time to IPF progression through 26 weeks (the end of the Double-blind Treatment Period), as defined by a decline in FVC % predicted (FVCpp) of 5% or greater, or death Secondary Tolerability Endpoints:

Incidence of dose modifications (dose reductions and interruptions)

Time to first dose modification (reduction or interruption)

Duration of dose modifications (reductions and interruptions)

Number of days on full assigned dose

Incidence of patient-reported assessment of side effects (nausea, poor appetite, vomiting, belly discomfort, bloating, headache, tiredness [mental exhaustion], fatigue [physical exhaustion], no energy, and dizziness)

Incidence and duration of AEs of special interest

Time to treatment discontinuation due to an adverse event

Change from baseline to Week 26 in PGI-C cough

Exploratory Endpoints:

Time to hospitalization due to respiratory cause through 26 weeks

Time to all-cause mortality through 26 weeks

Change from baseline to Week 26 in King's Brief Interstitial Lung Disease Questionnaire (K BILD) total score Change from baseline to Week 26 in St. George's Respiratory Questionnaire-IPF Version (SGRQ-I)

Change from baseline to Week 26 in EuroQol 5-Dimensional Quality of Life Questionnaire (EQ-5D)

Change in serum biomarkers from baseline through Week 26

Number and duration of respiratory hospitalizations or pulmonary exacerbations through 26 weeks Changes from baseline to Week 26 in measures of fibrosis and lung structure, obtained by quantitative analysis of HRCT images Rate of hospitalization due to respiratory cause through 26 weeks Part B Key Secondary Efficacy Endpoints:

Change in FVCpp from the end of Part A (Week 26) to the end of Part B Period 1 (Week 52)

Rate of decline in FVC (in mL) from the end of Part A (Week 26) to the end of Part B Period 1 (Week 52) using the values obtained from the in-clinic spirometry assessments Secondary Efficacy Endpoints:

Time to IPF progression in Part B, as defined by a decline from the end of Part A (Week 26) to the end of Part B Period 1 (Week 52) in FVCpp of 5% or greater, or death Secondary Tolerability Endpoints:

Incidence of dose modifications (dose reductions and interruptions)

Time to first dose modification (reduction or interruption)

Duration of dose modifications (reductions and interruptions)

Number of days on full assigned dose

Incidence of patient-reported assessment of side effects (nausea, poor appetite, vomiting, belly discomfort, bloating, headache, tiredness [mental exhaustion], fatigue [physical exhaustion], no energy, and dizziness)

Incidence and duration of AESIs

Time to treatment discontinuation due to an AE

Exploratory Endpoints:

Time to hospitalization due to respiratory cause from the start of Part B (Week 26) through the end of Part B Period 1 (Week 52)

Time to all-cause mortality from the start of Part B (Week 26) through the end of Part B Period 1 (Week 52)

Time to hospitalization due to respiratory cause or all-cause mortality from the start of Part B (Week 26) through the end of Part B Period 1 (Week 52).

Total duration on assigned dose from the start of Part B through the end of Part B Period 1 (Week 52).

Change in EQ-5D from the end of Part A (Week 26) through the end of Part B Period 1 (Week 52)

Change in serum and plasma biomarkers from the end of Part A (Week 26) through the end of Part B Period 1 (Week 52)

Number and duration of respiratory hospitalizations or pulmonary exacerbations from the start of Part B (Week 26) through the end of Part B Period 1 (Week 52)

Rate of hospitalization due to respiratory cause from the start of Part B (Week 26) through the end of Part B Period 1 (Week 52)

Safety and Tolerability Endpoints

Safety endpoints included: Adverse events, concomitant medications, clinical laboratory findings (chemistry, hematology, urinalysis), physical examinations, ECGs, and vital signs. These will be summarized descriptively, where appropriate.

Tolerability endpoints included: Frequency of dose modifications (reductions and interruptions), time to first dose modification, (reduction or interruption), duration of adverse events of special interest, time to treatment discontinuation due to an adverse event of special interest and patient reported assessment of IPF symptoms, side-effects, severity, change and satisfaction.

Selected endpoints, including adverse events of special interest (AESIs) and all-cause mortality were considered efficacy outcomes in the context of the study objectives, the disease being studied, and the expected benefits of LYT-100. These endpoints were included in the overall discussion (as part of the clinical study report) of the safety and tolerability of LYT-100, where appropriate.

Pharmacokinetic Endpoint

A sparse PK sampling strategy was employed in which all patients provided pre-dose blood samples for determination of plasma concentrations of LYT-100/pirfenidone and its metabolite(s). In addition, an intensive PK sub-study was conducted in approximately 8 patients per treatment arm in which each patient provided up to 16 blood samples for PK over a 24-hour period at Study Visits 3, 5 and 8.

TABLE 15

| Study Schedule of Assessments-Part A | | | | | | | | | |
|---|---|---|---|---|---|---|---|---|---|
| Visit | 1 | 2 | 3 | 4 | 5 [a] | 6 | 7 [a] | 8A/ET [b] | FU [a] |
| Weeks of treatment | Screening | 0 | 4 | 8 | 12 | 16 | 20 | 26 | 30 |
| Day | ≤−28 to 0 | 1 | 29 | 57 | 85 | 113 | 141 | 183 | 211 |
| Time window | | | ±7 | ±7 | ±7 | ±7 | ±7 | ±7 | ±7 |
| Informed consent [c,u] | X | | | | | | | | |
| HRCT sent to central review [d] | X | | | | | | | | |
| Demographics | X | | | | | | | | |
| Questionnaires: K-BILD, EQ-5D, SGRQ-I [e] | | X | | | X | | | X [s] | |
| Medical history | X | X | | | | | | | |
| Adverse events, concomitant medications | X | | X | X | X | X | X | X | X |
| In/exclusion criteria | X | X | | | | | | | |
| Physical examination, (including height) [f] | X | | | | | | | X | |
| Vital signs (including weight) | X | X | X | X | | X | | X | |
| Resting 12-lead ECG [g] | X | | | | | | | X | |
| Safety Laboratory (blood and urine) | X | | X | X | X | X | X | X | |
| Pregnancy test [h] | X | X | | | | | | X | |
| Cotinine test (urine) [t] | X | X | | X | | | | X | |
| PK sample [i] | | | X | | | X | | X | |
| Genomic Analysis (DNA Sample) [j] | | X | | | | | | | |
| Serum and plasma biomarker samples [k] | | | | | | X | | X | |
| HCRU assessments (including non-elective hospitalization) | | X | X | | X | X | X | X | X |
| In-Clinic Spirometry (including FVC & DLCO) [l] | X | X | X | | | | | X | |
| Weekly Home Spirometry [m] | X | | | | | | | | |
| Patient-reported assessment [n] | X | | | | | | | | |
| PGI-S Cough/IPF Severity; PGI-C Cough/IPF Severity [n] | X | | | | | | | | |
| Patient Satisfaction [o] | | X | X | X | X | X | X | X | |
| Patient Interviews [p] | | | | | | | | | X |
| Randomization | | X | | | | | | | |
| Administer 1st dose of study drug in the clinic | | X | | | | | | | |
| Compliance/drug accountability and dispensation [q] | | X | X | X | X | X | X | X | |
| Vital status assessment [r] | | | | | | | | X | |

TABLE 15-continued

Study Schedule of Assessments-Part A

DLCO = diffusing capacity of the lungs for carbon monoxide;

ECG = electrocardiogram;

eCRF = electronic case report form;

EQ-5D = EuroQol 5-Dimensional Quality of Life Questionnaire;

FVC = forced vital capacity;

FU = follow-up;

HCRU = healthcare resource utilization;

HRCT = high-resolution computed tomography;

IPF = idiopathic pulmonary fibrosis;

K-BILD = King's Brief Interstitial Lung Disease;

PGI-C = Patient Global Impression-Change;

PGI-S = Patient Global Impression-Severity;

PK = pharmacokinetic;

SGRQ-I = St. George's Respiratory Questionnaire-IPF Version

Note:

In case of dose modification (reduction or re-escalation) additional visits may be included. In case of premature discontinuation of study drug, the patient will be expected to attend all visits as originally planned until the end of the trial.

[a] Visits 5 and 7 may be conducted in-clinic, remote or hybrid. Follow-up visit can be conducted via telephone or televisit.

[b] Early termination (ET) should be done in cases of premature trial medication discontinuation during the study when the patient will not continue all study visits along with a FU Visit 4 weeks later.

[c] Informed consent via written, electronic, or oral must be documented before any study-specific Screening procedures are performed. When it is signed before visit 1, eg to allow shipment of images for central review, all AEs and concomitant treatments occurring after the informed consent have to be recorded. The Screening Period (informed consent to Visit 2) must not be longer than 28 days. Upon obtaining informed consent, the patient will be instructed on the medication washout and other restrictions needed.

[d] Central review HRCT not older than 12 months should be sent. If the patient does not have a HRCT within 12 months of Visit 1 or the available HRCT scan fails to meet the required image acquisition specification, a new HRCT can be performed for the purposes of participation in the trial, provided the patient meets all other inclusion and no exclusion criteria.

[e] Self-reported outcomes/Questionnaires must always be done by the patients in a quiet place prior to any other visit procedure. Order of questionnaires: 1. K-BILD, 2. EQ-5D, 3. SGRQ-I.

[f] Height collected at Visit 1 only.

[g] Resting ECGs will be performed at Screening (Visit 1), Visit 2 prior to randomization, and Visit 8A/ET.

[h] To be performed in all women of childbearing potential. Where required by local regulations, a serum pregnancy test should be conducted in addition to the urine pregnancy test. (ie, in certain countries, a serum pregnancy test is required at Screening). If a urine pregnancy test is positive, a serum pregnancy test must also be performed as confirmation. Documentation will be done in patient's notes. Where required by local regulations, an appropriate pregnancy test may be performed more frequently than this schedule.

[i] In all patients, PK samples will be obtained immediately prior to drug administration at Visits 3, 5 and 8. Date and exact clock time of drug administration and blood sampling must be recorded on the eCRF. Patients will be provided (Visits 2 and 4) with a PK-card to support the record of the exact clock time of medication intake 3 days preceding PK sampling. Approximately 8 patients per treatment group will participate in the intensive PK substudy at Visits 3, 5 and 8. PK samples will be obtained from these patients immediately prior to dosing and 0.5, 1, 1.5, 2, 2.5, 3, 3.5, 4, 6, 8, 10, 12, 15, 18 and 24 hours postdose. Pre-dose sample to be collected within 30 minutes prior to dosing. Acceptable windows for PK sampling are as follows: +/− 2 minutes during 0.5 to 4-hour postdose period, +/− 5 minutes 6-16 h postdose and +/− 10 minutes 24 h postdose. Exact time of each sample collection to be recorded.

[j] Deoxyribonucleic Acid (DNA) and serum banking samples will be taken from eligible patients at Visit 2 who consent. Participation is voluntary and is not a prerequisite for participation in the trial. Note, the DNA sample may not be taken prior to Visit 2.

[k] Biomarker samples will be taken just before drug administration at Visits 2, 5 and 8.

[l] Order of lung function measurements: 1. FVC followed by patients rest at Screening (Visit 1), baseline (Visit 2) and weeks 4 (Visit 3), 8 (Visit 4), 16 (Visit 6) and 26 (Visit 8A/ET); 2. DLCO. Measurements at approximately the same time each visit. DLCO will be done at Screening (Visit 1) and Week 26 (Visit 8A/ET) where available at the study site. If a patient's in-clinic spirometry (and DLCO where applicable) assessments are being conducted in a pulmonary function lab not in close proximity to the research clinic where other study assessments are performed, the sequence of assessments may be modified to reduce burden on study patients as long as spirometry continues to be performed in the morning.

[m] Weekly spirometry is to be performed by patients at home weekly in the am. Site staff will schedule televisits with patients to coach the weekly FVC maneuvers, as needed. On the weeks where in-clinic spirometry is performed, home spirometry should not be performed on that same day. Patients may do their weekly home spirometry assessment the following day. The final home spirometry assessment should be performed no later than the day prior to Visit 8A (Week 26).

[n] Patients will be asked weekly to complete ePROs to assess their symptoms, cough and IPF severity starting during Screening (Visits 1-2) and will continue to assess symptoms and side effects, cough and IPF severity weekly through the 26-week treatment period (Visits 2-8). Patients will also be asked to assess PGI-C Cough and PGI-C IPF Severity at Visit 8A/ET.

[o] Patients will be asked at baseline (Visit 2) to assess satisfaction expectations with their study treatment and then access overall satisfaction with study medication weekly beginning on Day 7 through Visit 8A/ET.

[p] Up to 30 (English speaking) patients will be asked to participate in interviews to discuss their symptoms at the end of the treatment period (either on/after the ET visit for those who discontinue treatment early or on/after Day 183 for those who complete study treatment).

[q] Dispensation at Visits 2, 3, 4, and 7; Compliance/Accountability at Visits 2, 3, 4, 6, and 8A. All unused capsules will be collected at Visit 8A.

[r] Vital status check will be done at Week 26 for randomized patients who discontinued study drug early and do not complete all study visits.

[s] HRCT of the lungs will be performed prior to Visit 8A/ET. The CT scan should be performed between Visit 7 and Visit 8A/ET per the vendor imaging guidelines. The HRCT should be performed within 28 days of Visit 8A/ET whenever possible. If the Week 26 HRCT at Visit 8A/ET is less than 12 months since the baseline CT, the Visit 8A/ET HRCT may be waived as required by local or national health authorities, ethics committees and/or imaging guidelines for this patient population.

[t] Cotinine testing to be performed for sensitivity analysis.

[u] Patients must provide a signed genetic sample informed consent form prior to blood collection at Visit 2.

TABLE 16

| Study Period | | Period 1 | | | | | | Period 2 Every 13 weeks | | FU |
|---|---|---|---|---|---|---|---|---|---|---|
| Visit | 8B | 9ᵃ | 10 | 11ᵃ | 12 | 13ᵃ | 14 | 15+ | ETᵇ | FU |
| Weeks of treatment | 26 | 30 | 34 | 39 | 42 | 46 | 52 | 65+ | | |
| Day | 183 | 211 | 239 | 274 | 295 | 323 | 365 | 456+ | | 28 |
| Visit window | | ±7 days | ±7 days | ±7 days | ±7 days | ±7 days | ±7 days | ±2 weeks | ±2 weeks | ±7 days |
| Informed consentᶜ | X | | | | | | | | | |
| In/exclusion criteriaᵈ | X | | | | | | | | | |
| Adverse events, concomitant medication | | X | X | X | X | X | X | X | X | X |
| Patient satisfaction | | X | X | | X | | X | X | X | |
| HCRU assessments (including non-elective hospitalization) | | X | X | X | X | X | X | X | X | X |
| Resting 12-lead ECGᵉ | | | | | | | X | | X | |
| Vital signs (including weight) | | X | X | X | X | X | X | X | X | |
| Physical examination | | | | | | | | | X | |
| Spirometry (including FVC ± DLCO)ᶠ | | | X | | X | | X | X | X | |
| Pregnancy test | | | X | | X | | X | X | X | |
| Cotinine test (urine) | | | | X | | | X | X | X | |
| Safety laboratory (blood and urine) | | X | X | X | X | X | X | X | X | |
| EQ-5D | | | | X | | | X | X | X | |
| Serum and plasma biomarker samplesʰ | | | | X | | | X | X | X | |
| Collection of all unused capsules and dispensation of tablets for Long-term extension Period | X | | | | | | | | | |
| Tablet compliance/medication accountability and dispensation of tabletsⁱ | | | X | | X | | X | X | X | |
| Vital status (living/dead) assessmentʲ | | | | | | | X | | | X |

ALT = alanine aminotransferase;
AST = aspartate aminotransferase;
DLCO = diffusing capacity of the lungs for carbon monoxide;
ECG = electrocardiogram;
eCRF = electronic case report form;
ET = end of treatment;
FVC = forced vital capacity;
FU = follow-up;
HCRU = healthcare resource utilization;
IPF = idiopathic pulmonary fibrosis
Note:
In case of dose modification (reduction or re-escalation) additional visits may be included. In case of discontinuation of study medication, the patient will be expected to attend all visits as originally planned until the end of the study.
ᵃVisits 9, 11, and 13 may be conducted in clinic, remote, or hybrid. FU Visit can be conducted via telephone or televisit.
ᵇEarly termination should be done in cases of study medication discontinuation during the study when the patient will not continue all study visits along with a FU Visit 4 weeks later.
ᶜInformed consent via written, electronic, or oral must be documented before any study-specific procedures are performed.
ᵈTo be reviewed at each visit to confirm the patient's continued eligibility for the study. Note that samples will be collected for ALT, AST, bilirubin and creatine as part of safety laboratory testing, but values need not be confirmed to proceed.
ᵉResting ECGs will be performed at Visit 8B, Visit 14 and ET (if applicable).
ᶠOrder of lung function measurements: 1. FVC followed by patients rest at Weeks 34 (Visit 10), 42 (Visit 12), and 52 (Visit 14) during Period 1, and every 13 weeks during Period 2. DLCO. Measurements at approximately the same time each visit. Where available at the study site, DLCO will be done at Week 52 (Visit 14) during Period 1 and every 13 weeks during Period 2.
ᵍTo be performed in all WOCBPs. Where required by local regulations, a serum pregnancy test should be conducted in addition to the urine pregnancy test. (ie, in certain countries, a serum pregnancy test is required at enrollment.) If a urine pregnancy test js positive, a serum pregnancy must also be performed as confirmation.
ʰBiomarker samples will be taken just before drug administration at Visit 11 in Period 1, and every 13 weeks during Period 2.
ⁱDispensation at Visits 8B, 10, 12, and 14 in Period 1, and at all visits in Period 2; compliance/accountability at Visits 11, 13, and 15 in Period 1, and through the end of treatment in Period 2.
ʲVital status check (living/dead) will be done for all patients at Week 26 and at the end of the study for patients who discontinue study medication early and do not complete all study visits.

Efficacy Assessments

Spirometry

Assessment of FVC

Weekly home FVC was assessed with an individual spirometer, which was supplied to each patient. The site used its own equipment for in-clinic FVC assessments. Spirometry measurements were performed according to the American Thoracic Society/European Respiratory Society ("An Official American Thoracic Society and European Respiratory Society Technical Statement Technical Statement" Am J Respir Crit Care Med. 2019; 200(8):e71-e83) and the study specific Pulmonary Function Manual, at timepoints specified in the Schedule of Assessments. Spirometry was conducted while the patient was in a seated position. The test was done in order to achieve three acceptable FVC measurements (three curves to be provided), and the best result selected according to the guidelines. The best of three efforts was defined as the highest FVC, obtained on any of the three blows meeting the ATS/ERS/JRS/ALAT 2019 criteria (Graham et al, 2019) with preferably a maximum of eight attempts.

For the in-clinic assessments effort was be made to schedule the spirometric measurements at approximately the same time of the day with reference to the baseline measurement (Visit 2). On days of clinic visits, patients were to refrain from strenuous activity at least 12 hours prior to pulmonary function testing. Patients were to avoid cold temperatures, environmental smoke, dust, or areas with strong odors (e.g., perfumes).

If treated with bronchodilators, patients were instructed to withhold medications as follows prior to the in-clinic spirometry assessments:

| Bronchodilator Medication | Withholding Time |
|---|---|
| SABA (e.g., albuterol or salbutamol) | 4-6 h |
| SAMA (e.g., ipratropium bromide) | 12 h |
| LABA (e.g., formoterol or salmeterol) | 24 h |
| Ultra-LABA (e.g., indacaterol, vilanterol, or olodaterol) | 36 h |
| LAMA (e.g., tiotropium, umeclidinium, aclidinium, or glycopyrronium) | 36-48 h |

Definition of abbreviations: LABA = long-acting β₂-agonist; LAMA = long-acting muscarinic antagonist; SABA = short-acting β₂-agonist; SAMA = short-acting muscarinic antagonist.

Prior to weekly home FVC, patients were advised to hold all bronchodilators on the day of the weekly FVC assessment. If rescue bronchodilator use was required during the weekly home FVC assessment, the patient was to abandon the FVC assessment for that week and then perform the weekly home FVC as planned the following week.

Pulmonary function was measured in a standardized manner and results transmitted electronically during the visit immediately after performing the spirometry and evaluated by a central reader. In case the acceptability and repeatability criteria as specified by ATS/ERS/JRS/ALAT guidelines were not met, a repeat spirometry was performed during the same visit.

In-clinic spirometry was performed at the following visits: Visit 1 (Screening), Visit 2 (baseline), Visits 4, 6, and 8/ET (premature study medication discontinuation).

The primary efficacy endpoint was the rate of decline in FVC mL over 26 weeks. In addition, decline in FVC % predicted from baseline to Week 26 and by >10% and >5% was assessed.

The secondary endpoint was comparison of FVC % predicted change from baseline to Week 26.
Assessment of DLCO The site used DLCO equipment available onsite. All measurements at a site were conducted with the same DLCO device (i.e., if multiple devices were available, selected only one for the entire study). Single-breath DLCO measurement was carried out according to local practice at the time points specified in the Schedule of Assessments. Before beginning the test, the technique was demonstrated, and the patient carefully instructed. The DLCO assessment was always to be performed after the FVC measurement and following a few minutes of rest.
Other Secondary and Exploratory Endpoints
Clinical Endpoints The following parameters were measured or calculated as part of the spirometry assessment:

FVC (mL) and FVC % predicted (FVCpp)
FEV1 (mL) and percent predicted forced expiratory volume in 1 second (FEV1% p)
FEV1/FVC ratio
Forced expiratory flow between 25% and 75% of exhaled volume (FEF25-75)
The '2012 Global Lung Function Initiative Equations' was used to calculate the predicted values (Quanjer et al, "Multi-ethnic reference values for spirometry for the 3-95 year age range: the global lung function 2012 equations: Report of the Global Lung Function Initiative (GLI), ERS Task Force to establish improved Lung Function Reference Values.," Eur Respir J, vol. 40(6), pp. 1324-1343, 2012).
Exploratory parameters included:
Duration on assigned dose from the end of Part A (Week 26) through the end of Part B Period 1 (Week 52)
Number and duration of respiratory hospitalizations or pulmonary exacerbations through 26 weeks
Number and duration of respiratory hospitalizations or pulmonary exacerbations from the end of Part A (Week 26) through the end of Part B Period 1 (Week 52)
Measures of fibrosis and lung structure, obtained by quantitative analysis of HRCT images
Rate of hospitalization due to respiratory cause through 26 weeks
Rate of hospitalization due to respiratory cause from the end of Part A (Week 26) through the end of Part B Period 1 (Week 52)
A time to (first) event analysis was conducted for each of the following endpoints:
Hospitalization due to respiratory cause or all-cause mortality through 26 weeks
IPF progression through 26 weeks (the end of Part A), as defined by a decline in FVC % predicted (FVCpp) of 5% or greater, or death
IPF progression through 52 weeks (the end of Part B Period 1)
Hospitalization due to respiratory cause through 26 weeks
Hospitalization due to respiratory cause from the end of Part A (Week 26) through the end of Part B Period 1 (Week 52)
All-cause mortality through 26 weeks.
All-cause mortality from the end of Part A (Week 26) through the end of Part B Period 1 (Week 52)
Hospitalization due to respiratory cause or all-cause mortality from the end of Part A (Week 26) through the end of Part B Period 1 (Week 52)
Quality of Life Assessment/PRO Questionnaires
Change from baseline to week 26 was analyzed for the QOL assessments listed below.
1. King's Brief Interstitial Lung Disease Questionnaire (K-BILD)
2. EuroQol 5-Dimensional quality of life Questionnaire (EQ-5D)
3. St. George Respiratory Questionnaire-I (SGRQ-I)
4. Baseline Satisfaction (Visit 2 only)
5. Patient reported assessment of IPF symptoms (Visit 8/ET only)
6. PGI-S Cough (Visit 8/ET Only)
7. PGI-C Cough (Visit 8/ET Only)
8. PGI-S IPF Severity (Visit 8/ET Only)
9. PGI-C IPF Severity (Visit 8/ET Only)
10. Patient reported assessment of side effects (Visit 8/ET Only)
11. PGI-S Side Effects (Visit 8/ET Only)
12. Overall Satisfaction (Visit 8/ET Only)

King's Brief Interstitial Lung Disease Questionnaire (K-BILD)

The K-BILD is a self-administered health status questionnaire that was developed and validated specifically for patients with ILD. Questionnaire development and validation included a range of ILDs, including the ILD disease types in this study population. The questionnaire consists of 15 items and 3 domains: breathlessness and activities, psychological, and chest symptoms. Possible score ranges from 0-100, with a score of 100 representing the best health status. The efficacy endpoint is the change from baseline to Week 26 in the total score.

EuroQol 5-Dimensional Quality of Life Questionnaire (EQ-5D)

The EQ-5D was developed by the European Quality of Life Group (EuroQol Group) and is a standardized instrument for use as a measure of health outcome. The version used in this trial was the new five-level version (EQ-5D-5L). The questionnaire consists of 2 sections. The first section is the descriptive system with 5 questions regarding the patient's health state on the day of the assessment. Each question captures one dimension of health (e.g., mobility, self-care, usual activities, pain/discomfort, and anxiety/depression). Each dimension has three levels, which results in a 1-digit number that expresses the level selected for that dimension. The digits for the five dimensions can be combined into a 5-digit number that describes the patient's health state) and has five levels to answer. The second section records the patient's self-rated health status on the day of the assessment on a vertical graduated (0 to 100) visual analogue scale. The EQ VAS records the patient's self-rated health on a vertical VAS and can be used as a quantitative measure of health outcome that reflects the patient's own judgment.

St. Georges Respiratory Questionnaire (SGRQ-I)

The SGRQ-I is an idiopathic pulmonary fibrosis disease-specific instrument designed to measure the impact of the disease on overall health, daily life, and perceived well-being in patients with interstitial lung disease. There are 34 self-completed items with 3 domain component scores (Symptoms, Activities, and Impacts). Higher scores indicate more limitations and provides a sample of the scale. Changes from baseline in the component scores of the SGRQ-I will be assessed as secondary efficacy endpoint. Further, a responder analysis will be performed in which the proportion of patients experiencing an increase of ≥4 units (vs <4 units) will be assessed.

Patient Reported Assessment of IPF Symptoms

From screening to the end of treatment, patients were asked weekly to describe specific symptoms (shortness of breath, fatigue, tiredness, discomfort in the chest, loss of appetite) "In the past 7 days" how often these symptoms occurred on a scale from 0 (never) to 4 (always) and "at its worst, how bad" was the symptom from 0 (not all) to 4 (very bad). An example survey is provided as FIG. 25A.

Patient Reported Assessment of Side Effects and PGI-S Side Effects

From Baseline to the end of treatment, patients were asked weekly to describe specific side effects (nausea, poor appetite, vomiting, abdominal discomfort, bloating, headache, dizziness, and fatigue) "In the past 7 days" how often these side effects occurred on a scale from 0 (never) to 4 (always) and "at its worst, how bad" was the side effect from 0 (not all) to 4 (very bad). An example survey is provided as FIG. 25B. In addition, PGI—S-Side Effects asks, "Over the past 7 days, how bad were the study treatment side effects?" from 0 (not all) to 4 (very bad).

PGI-S Cough Assessment and PGI-C Cough

From screening to the end of treatment, patients were asked weekly "Over the past 7 days, how bad was your cough?" on a scale from 0 (not bad at all) to 4 (very bad). In addition, at the end of the study, the PGI-C Cough asked patients to "Compare your cough over the past 7 days to your cough at the beginning of the study?" on a scale from 0 (much better) to 6 (much worse).

PGI-S IPF Severity and PGI-C IPF Severity

From screening to the end of treatment, patients were asked weekly "Over the past 7 days, how bad was your IPF severity?" on a scale from 0 (not bad at all) to 4 (very bad). In addition, at the end of the study, the PGI-C IPF Severity asked patients to "Compare your cough over the past 7 days to your cough at the beginning of the study? on a scale from 0 (much better) to 6 (much worse)."

Patient Satisfaction

Patients were asked questions regarding expected satisfaction with IPF treatment and how bad side effects could be to remain satisfied. In addition, beginning on Day 7, patients were asked weekly through Visit 8/ET about Overall Satisfaction "Considering your overall experience over the past 7 days, how satisfied are you with the study medication on a scale from 0 (very satisfied) to 6 (very dissatisfied). An example survey is provided as FIG. 26.

Patient Interviews

Up to thirty (30) patients were targeted to participate in the qualitative interviews. The interviews were to occur after completion of blinded treatment for patients who discontinued treatment early or who completed study treatment. The sample size was elected to be in line with evidence-based recommendations for the estimate of sample sizes for qualitative interviews. This research has demonstrated that, across a wide range of diseases, 84% of all relevant symptom concepts will emerge by the tenth interview and 97% of relevant symptom concepts will emerge by the twentieth interview. Every effort was made to address demographic representativeness in the sample, including recruiting patients across education, race/ethnicity, gender, and age range.

All interviews were conducted based on the International Society for Pharmacoeconomics and Outcomes Research (ISPOR) task force recommendations. The interviews were based on an interview guide with open-ended questions that were used to encourage spontaneous responses and good qualitative data. For example, the interview guide included non-leading questions such as "What is a bad day like with IPF?" The interview guide included topics, questions, and probes designed to understand IPF from the patient's perspective. The interview guide was to begin with an overall introduction about the interview and then move into a general discussion about the patient's experience. During this concept elicitation phase of the interview, the interviewer listened for terms and wording that were spontaneously voiced by the patient when describing any problems they may have experienced (with particular reference to respiratory problems). A mix of open-ended and probing questions was to be used.

Laboratory Assessments

Safety laboratory tests (hematology, biochemistry, coagulation, urinalysis, and urine cotinine) were performed at the time points specified in the Schedule of Assessments (Tables 16 and 17). Additional clinical laboratory tests may have been performed at other times if deemed necessary based on the patient's clinical condition. Each patient had blood samples taken for hematology, coagulation, biochemistry and as necessary for serum pregnancy and FSH analyses at the time points delineated in the study schedules. In addition, urine sample were taken for urinalysis at the time points delineated in the study schedules.

Safety Biomarkers:

C-reactive protein (CRP-collected with biomarkers and at screening)

Troponin 1 (TROP1-collected with biomarkers

Ferritin (collected with biomarkers and at screening)

Lymphocytes (LYM-collected with hematology biomarkers and at screening)

D-dimer (collected with biomarkers)

Inflammatory and Fibrotic Biomarkers:

Transforming Growth Factor Beta 1 (TGF-β1)

Tumor necrosis factor alpha (TNF-α)

Interleukin 6 (IL-6)

Interleukin 1 beta (IL-1β)

Platelet-derived growth factor-β (PDGF-β)

Granulocyte colony-stimulating factor (GCSF)

Vascular endothelial growth factor (VEGF)

Coagulation

Coagulation parameters to be tested were:

INR

Prothrombin time

APTT

D-dimer (collected with biomarkers)

Disease-Specific Biomarker Evaluations

Disease and/or drug-related biomarkers including, but not limited to, extracellular matrix synthesis and turnover (i.e., neo-epitopes), inflammatory cells, alveolar epithelial and oxidative stress markers, were to be assessed in plasma and/or serum, if deemed appropriate. In addition, other analytes such as metabolites or endogenous biomarkers might have been assessed in plasma and/or serum, if deemed appropriate. Blood samples for potential serum disease-specific biomarker analysis and for potential plasma disease-specific biomarker analysis were collected before study medication administration at Visits 2, 5 and 8/ET. The details on blood sample collection, handling, storage, and shipment instructions were to be provided in a separate laboratory manual.

Adverse Events and Serious Adverse Events

Safety and tolerability were assessed throughout the study by monitoring AEs, physical examination, vital signs, 12-lead ECGs, clinical laboratory values (hematology panel, multiphasic chemistry panel and urinalysis), and concomitant treatments. In this study, AEs are reported for all patients from the time of consent until the completion of the Follow-up visit. AEs reported prior to the first dose are denoted as pre-treatment. SAEs are reported for all patients (randomized or not) from the time of consent. AEs reported from the time of consent to confinement on Day 0 were recorded as pre-treatment AEs.

Treatment emergent adverse events (TEAEs) are defined as an AE that occurs following first dose of study medication and were evaluated from the first administration of study drug on Day 1 until the Follow-up visit.

Adverse Events of Special Interest (AESIs) relate to any specific AE identified at the project level as being of particular concern for prospective safety monitoring and safety assessment within this trial, (e.g., the potential for AEs based on knowledge from other compounds in the same class). AESI were to be reported to the Sponsor's Pharmacovigilance Department within the same timeframe that applies to SAEs, Adverse Events of Special Interest (AESI)

For this study, the following were considered AESIs for LYT-100:

1) General disorders: anorexia, decreased appetite, fatigue

2) GI disorders: diarrhea, nausea, vomiting

3) Investigations, e.g., hepatic laboratory abnormalities: increase in transaminases 4) Skin and subcutaneous tissue disorders, e.g., photosensitivity reaction and rash Elevations in liver enzymes as well as post-marketing reports of drug-induced liver injury have been associated with the parent compound, pirfenidone. Therefore, these were monitored as AESIs and have dose modification instructions were provided.

Serious Adverse Event

An SAE is an AE occurring during any study phase (i.e., baseline, treatment, washout, or follow-up), and at any dose of the study drug (active or placebo), that fulfils one or more of the following:

Results in death

It is immediately life-threatening

Figure 40:
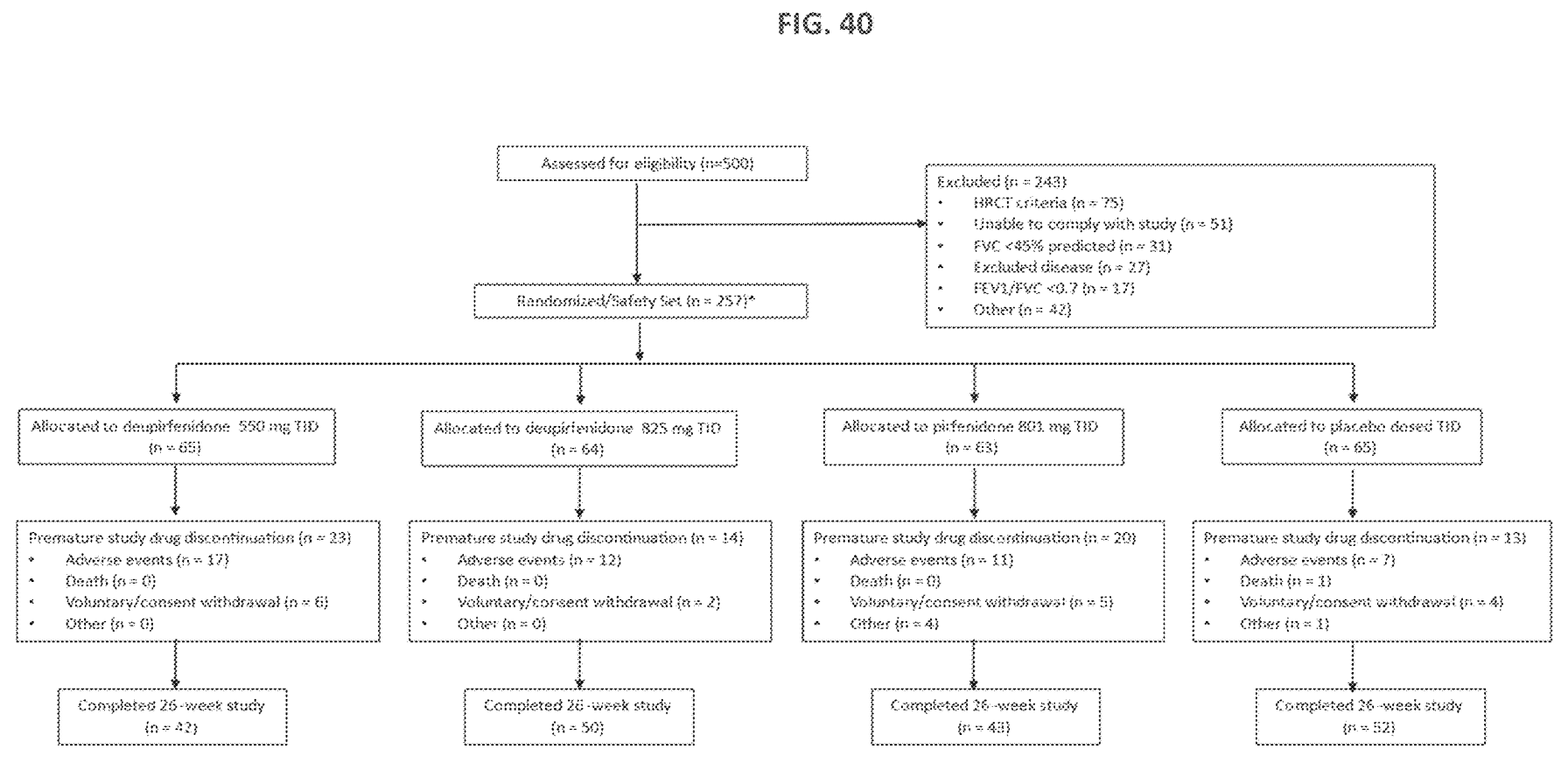

It requires in-patient hospitalization or prolongation of existing hospitalization It results in persistent or significant disability or incapacity Results in a congenital abnormality or birth defect It is an important medical event that may jeopardize the patient or may require medical intervention to prevent one of the outcomes listed above Results—Part A Subject Disposition and Demographics Subject disposition is summarized in FIG. 40. With reference to FIG. 40, 500 potential subjects were assessed for eligibility, resulting in randomization of 257 patients. Allocation to each study arm was nearly equal. Overall, 42 patients in the 550 mg TID LYT-100 group, 50 patients in the 825 mg TID LYT-100 group, 43 patients in the 801 mg TID pirfenidone group, and 52 patients in the placebo group completed the 26-week study treatment.

Patient demographics for Part A of the study are summarized in Table 17. The population included in this study was consistent with other IPF trials. Patients were predominantly male (71.2%) and older (mean age was 70.9 years) population. There were several differences from other IPF studies, such as regional differences (relatively higher enrollment from Latin America and Asia, and relatively less enrollment from Europe in this study) and background antifibrotic therapy was not allowed.

TABLE 17

| | | | | |
|---|---|---|---|---|
| Patient Demographics- Part A | | | | |
| Characteristic | Placebo TID N = 65) | Pirfenidone 801 mg TID N = 63) | Deupirfenidone 550 mg TID (N = 65) | Deupirfenidone 825 mg TID (N = 64) |
| Age (mean, SD) | 71.7 (7.27) | 71.0 (8.50) | 70.9 (7.89) | 70.0 (8.31) |
| Age group, | | | | |

TABLE 17-continued

| | Placebo TID N = 65) | Pirfenidone 801 mg TID N = 63) | Deupirfenidone 550 mg TID (N = 65) | Deupirfenidone 825 mg TID (N = 64) |
|---|---|---|---|---|
| Characteristic | | | | |

Patient Demographics- Part A

| Characteristic | Placebo TID N = 65) | Pirfenidone 801 mg TID N = 63) | Deupirfenidone 550 mg TID (N = 65) | Deupirfenidone 825 mg TID (N = 64) |
|---|---|---|---|---|
| n (%) | | | | |
| <65 years | 8 (12.3) | 14 (22.2) | 13 (20.0) | 17 (26.6) |
| ≥65 and <75 | 36 (55.4) | 22 (34.9) | 31 (47.7) | 25 (39.1) |
| ≥75 | 21 (32.3) | 27 (42.9) | 21 (32.3) | 22 (34.4) |
| Male | 47 (72.3) | 47 (74.6) | 46 (70.8) | 43 (67.2) |
| Female | 18 (27.7) | 16 (25.4) | 19 (29.2) | 21 (32.8) |
| Race, n (%) | | | | |
| White or Caucasian | 38 (58.5) | 42 (66.7) | 40 (61.5) | 42 (65.6) |
| Asian | 22 (33.8) | 21 (33.3) | 22 (33.8) | 21 (32.8) |
| Black or African American | 3 (4.6) | 0 | 1 (1.5) | 0 |
| Other | 2 (3.1) | 0 | 2 (3.1) | 1 (1.6) |
| Ethnicity, n (%) | | | | |
| Hispanic or Latino | 23 (35.4) | 14 (22.2) | 16 (24.6) | 14 (21.9) |
| Region, n (%) | | | | |
| United States | 10 (15.4) | 20 (31.7) | 13 (20.0) | 11 (17.2) |
| Central/South America | 23 (35.4) | 16 (25.4) | 17 (26.2) | 14 (21.9) |
| Europe and South Africa | 10 (15.4) | 8 (12.7) | 14 (21.5) | 19 (29.7) |
| Asia | 22 (33.8) | 19 (30.2) | 21 (32.3) | 20 (31.3) |
| BMI (kg/m2; mean, SD) | 27.39 (5.079) | 27.60 (4.018) | 26.96 (4.788) | 27.12 (4.942) |
| Comorbidities (>20% frequency overall) | | | | |
| Prior nintedanib use <6 months, n (%) | 1 (1.5) | 2 (3.2) | 3 (4.6) | 3 (4.7) |
| Years of IPF diagnosis (mean, SD) | 1.4 (1.75) | 1.8 (2.50) | 1.8 (2.42) | 2.1 (2.30) |
| IPF diagnosis <2 years, n (%) | 51 (78.5) | 45 (71.4) | 46 (70.8) | 39 (60.9) |
| HRCT pattern, n (%) | | | | |
| Probably UIP | 31 (47.7) | 32 (50.8) | 31 (47.7) | 32 (50.0) |
| UIP | 34 (52.3) | 31 (49.2) | 34 (52.3) | 32 (50.0) |
| Baseline FVC (mL) mean, SD | 2550.5 (974.01) | 2682.6 (729.79) (n = 61) | 2672.9 (845.35) | 2659.2 (871.70) (n = 63) |
| Baseline FVC (percent predicted) mean, SD | 76.74 (19.822) | 79.52 (17.203) (n = 61) | 80.11 (20.438) | 79.45 (20.951) (n = 63) |
| Baseline FVC pp <50%, n (%) | 3 (4.6) | 3 (4.9) | 1 (1.5) | 5 (7.9) |

Efficacy

The primary efficacy endpoint was rate of decline in FVC (in mL) over 26 weeks. The primary analysis was performed based on the full analysis set (FAS). The FAS was defined as all randomized study participants who received at least one dose of study drug and had at least one valid efficacy assessment.

The primary efficacy analysis was performed using the Bayesian linear mixed effects model, in which the two LYT-100 groups (550 mg TID and 825 mg TID) were pooled together and compared to placebo. Bayesian methods include prior elicitation utilizing historical data and the ability to update over time and test inferences as new data becomes available. Bayesian analysis provides posterior probability distributions of parameters of interest (e.g., treatment effects), allowing for direct interpretation of the probability that a treatment is effective (i.e., the analysis allows calculation of the probability of an outcome). Bayesian methods have been implemented in two previous phase 2 clinical trials in IPF. See Richeldi et al, "Trial of a Preferential Phosphodiesterase 4B Inhibitor for Idiopathic Pulmonary Fibrosis", NEJM, 2022; 386:2178-87) and "Bristol Myers Squibb's Investigational LPA1 Antagonist Reduces the rate of Lung Function Decline in Patients with Idiopathic Pulmonary Fibrosis", May 22, 2023. The FDA has issued several guidance documents relating to the use of Bayesian statistical methods in drug development. See "Adaptive Designs for Clinical Trials of Drugs and Biologics", FDA guidance, November 2019, and "Guidance for the Use of Bayesian Statistics in Medical Device Clinical Trials", February 2010.

Specifically, in the present study, a prespecified Bayesian analysis was utilized to assess the primary endpoint and provided the probability of a positive treatment difference for deupirfenidone compared to placebo. This also allowed for augmentation of the placebo arm with placebo data from historical IPF trials. This approach enabled a more patient-centric clinical trial design by minimizing the number of trial participants exposed to placebo—a key consideration since IPF is progressive and fatal—while delivering a robust, placebo-controlled dataset.

The primary efficacy analysis of the study assessed the superiority of LYT-100 to placebo as measured by the difference in rate of decline ($\theta$) in FVC between the combined LYT-100 and placebo arms. The primary analysis was to be declared successful if the posterior probability Pr ($\theta$>0|Data)>0.90. The response variable was the absolute FVC over time, including baseline. The model included fixed effects for treatment, time in weeks (as a continuous covariate), and treatment by time interaction, as well as subject-level random effects for the intercept and slope.

In addition to the Bayesian analysis, the FVC data (both pooled and individual dose) was also compared to placebo using the frequentist approach, applying a random coefficient regression model with absolute FVC as a response, including baseline. The model included fixed effects of week, treatment, and interaction between week and treatment. The random effects were subject-specific intercept and slope. The effect of interest was change from baseline in FVC at Week 26 between the combined LYT-100 and placebo arms.

The key secondary efficacy endpoint of this study was change from baseline in forced vital capacity % predicted (FVCpp). The secondary endpoint analysis was performed using a Bayesian linear mixed effects model. The response variable was the absolute FVCpp over time, including baseline. The fixed effects included treatment, time in weeks (as a continuous covariate), and treatment by time interaction, as well as the random effects for the intercept and slope for each subject. The posterior probability threshold 0.90 was chosen to be consistent with the hypothesis testing of the primary endpoint. Posterior probability that the difference exceeds 0 is provided. Pooled and individual dose data for FVCpp was also compared to placebo using the frequentist approach as described above.

Figure 41:
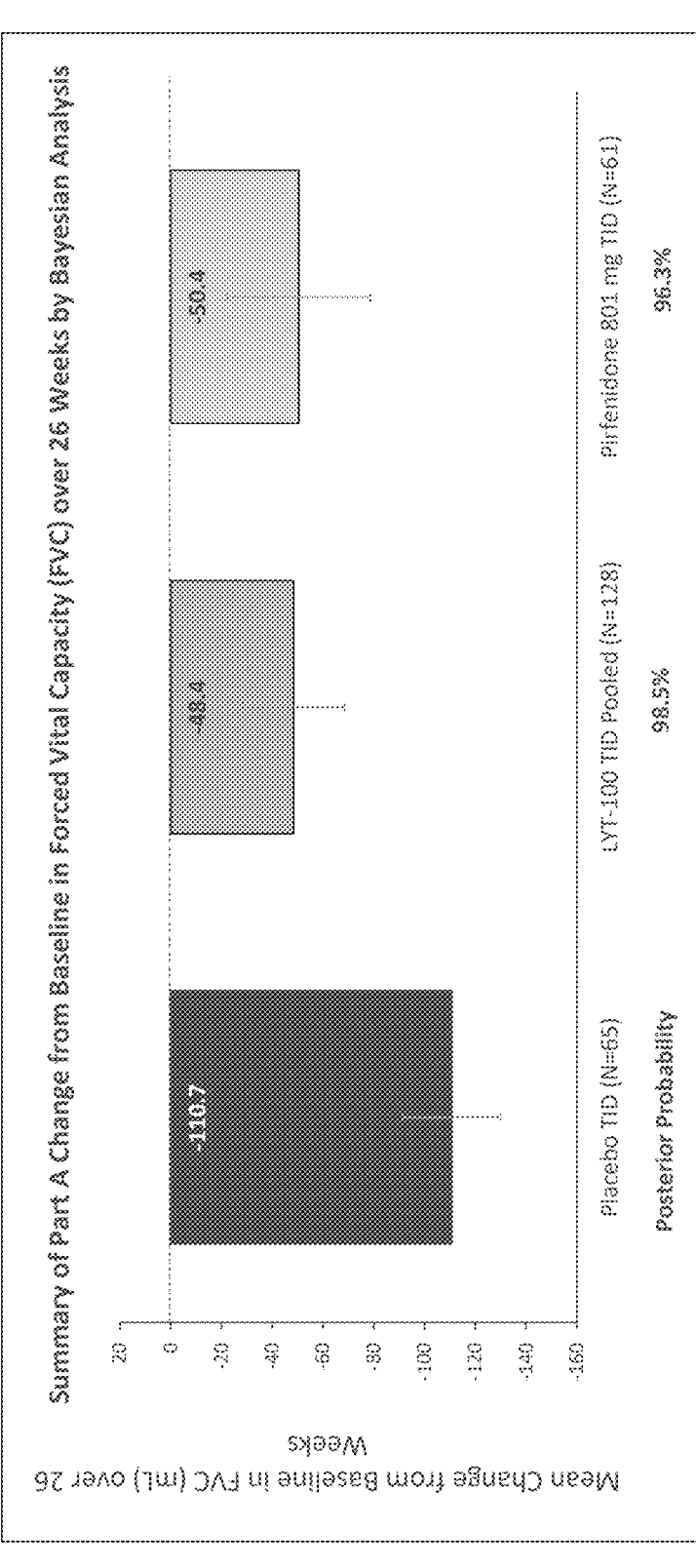
FIG. 41 is a graphical depiction providing the summary of change from baseline in Forced Vital Capacity (FVC) over 26 weeks by Bayesian analysis for placebo, pirfenidone and pooled doses of LYT-100 in the IPF clinical trial study of Example 4.

Efficacy results according to the primary and secondary endpoints are summarized in FIGS. 41 to 47 and Tables 18 to 21, noting that the primary endpoint was for pooled 550 mg TID and 825 mg TID arms, while Table 18 presents efficacy analyses for the individual dose arms. With reference to FIG. 41, the study achieved the primary endpoint for LYT-100 with the 550 mg and 825 mg pooled arms, demonstrating reduced lung function decline compared to placebo as measured by Forced Vital Capacity with a posterior probability value vs. placebo of 98.5%. With reference to FIG. 42A, 825 mg TID LYT-100 outperformed pirfenidone in change from baseline FVC by Bayesian analysis (99.7% posterior probability).

Based on historical development in IPF with single agents, a statistically significant effect was not anticipated between any individual arm vs placebo given the size of this Phase 2b trial; however, the magnitude of the efficacy demonstrated with deupirfenidone 825 mg TID was large enough to achieve a statistically significant p value in both the primary endpoint (efficacy, FVC) and the secondary endpoint (efficacy, FVCpp) as discussed below.

Figures 42A, 42B:
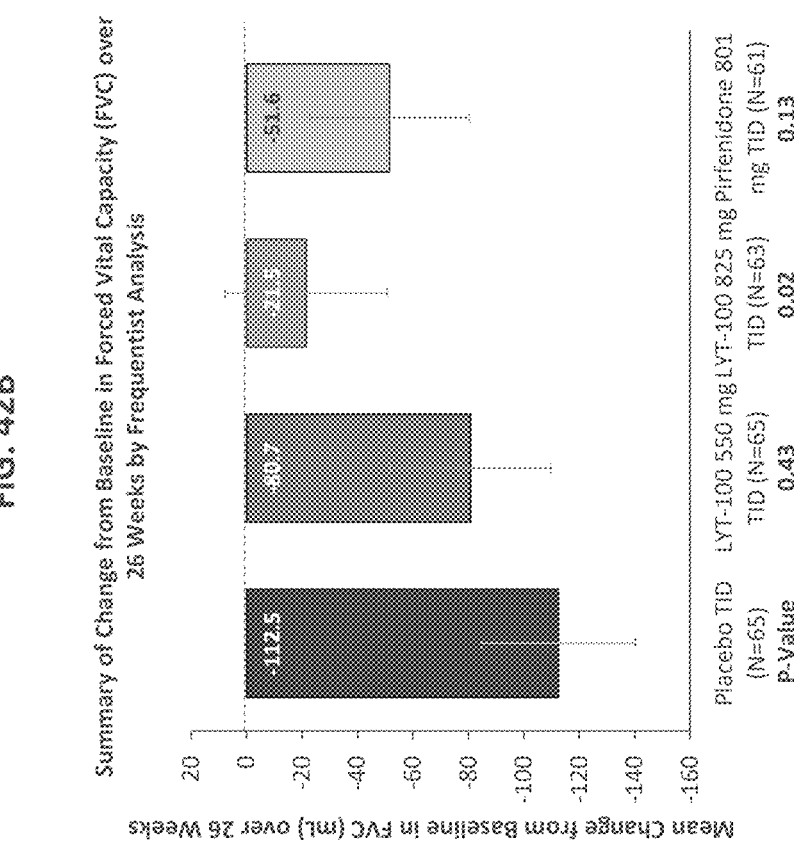
FIG. 42A is a graphical depiction providing the summary of change from baseline in FVC over 26 weeks by Bayesian analysis for placebo, pirfenidone and 550 mg TID LYT-100 and 825 mg TID LYT-100 in the IPF clinical trial study of Example 4.
FIG. 42B is a graphical depiction providing the summary of change from baseline in FVC over 26 weeks by Frequentist analysis for placebo, pirfenidone and 550 mg TID LYT-100 and 825 mg TID LYT-100 in the IPF clinical trial study of Example 4.

With reference to FIG. 42B and Table 18, the 825 mg dose of LYT-100 demonstrated a p-value vs. placebo (p-value of 0.02). With reference to Tables 19 and 20, LYT-100 at 825 mg TID had an approximately 50% greater effect size compared to pirfenidone. Specifically, LYT-100 825 mg TID demonstrated strong, consistent and durable efficacy with a treatment effect of 80.9% compared to 54.1% with pirfenidone 801 mg TID (91.0 mL vs. 60.9 mL improvement in FVC, respectively), versus placebo (Table 20).

Figures 43A, 43B:
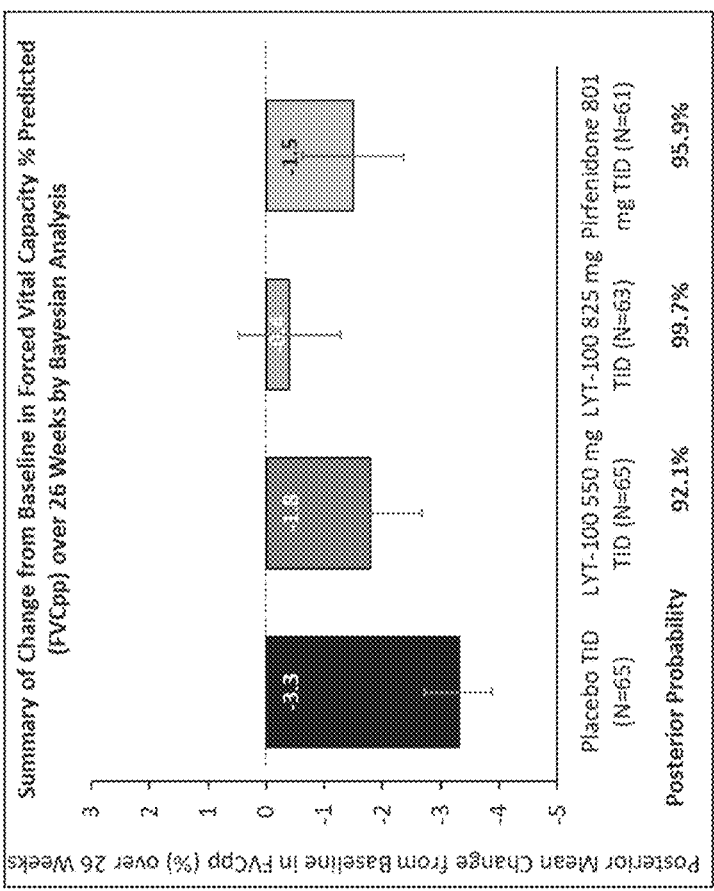
FIG. 43A is a graphical depiction providing the summary of change from baseline in Forced Vital Capacity percent predicted (FVCpp) over 26 weeks by Bayesian analysis for placebo, pirfenidone and 550 mg TID LYT-100 and 825 mg TID LYT-100 in the IPF clinical trial study of Example 4.
FIG. 43B is a graphical depiction providing the summary of change from baseline in FVCpp over 26 weeks by Frequentist analysis for placebo, pirfenidone and 550 mg TID LYT-100 and 825 mg TID LYT-100 in the IPF clinical trial study of Example 4.

The study also achieved its key secondary endpoint, with the pooled deupirfenidone arms demonstrating a 99.7% posterior probability on the change in FVCpp based on a prespecified Bayesian analysis of forced vital capacity percent predicted (FVCpp) from baseline to week 26. While FVC (the primary endpoint) and FVCpp and are both measures of lung capacity, FVCpp accounts for key patient characteristics and therefore standardizes the results. Notably, this key secondary endpoint accounts for patient characteristics of height, age, and sex. With reference to FIGS. 43A and 43B, LYT-100 825 mg also outperformed pirfenidone on FVCpp. Although a statistically significant difference was not anticipated between any individual arms given the size of this Phase 2b trial, deupirfenidone 825 mg TID demonstrated a statistically significant benefit on this secondary endpoint compared to placebo (−0.43 vs. −3.43, respectively; p=0.01), reinforcing the robustness of the treatment's impact. With reference to Table 21, notably, the 825 mg TID LYT-100 arm had the greatest number of patients with advanced lung disease (FVCpp of 45-50%).

Figure 44B:
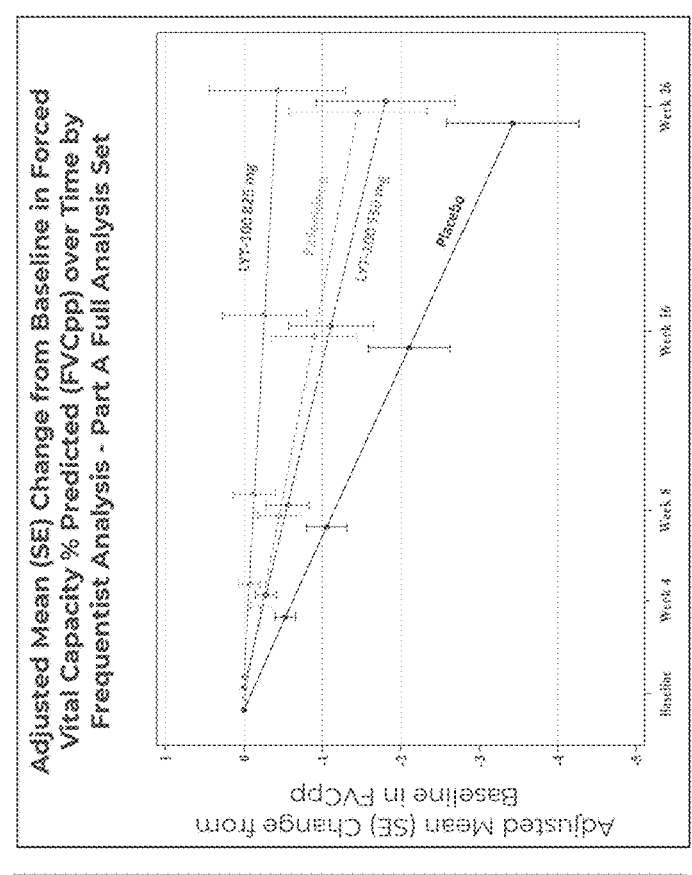
Figure 44A:
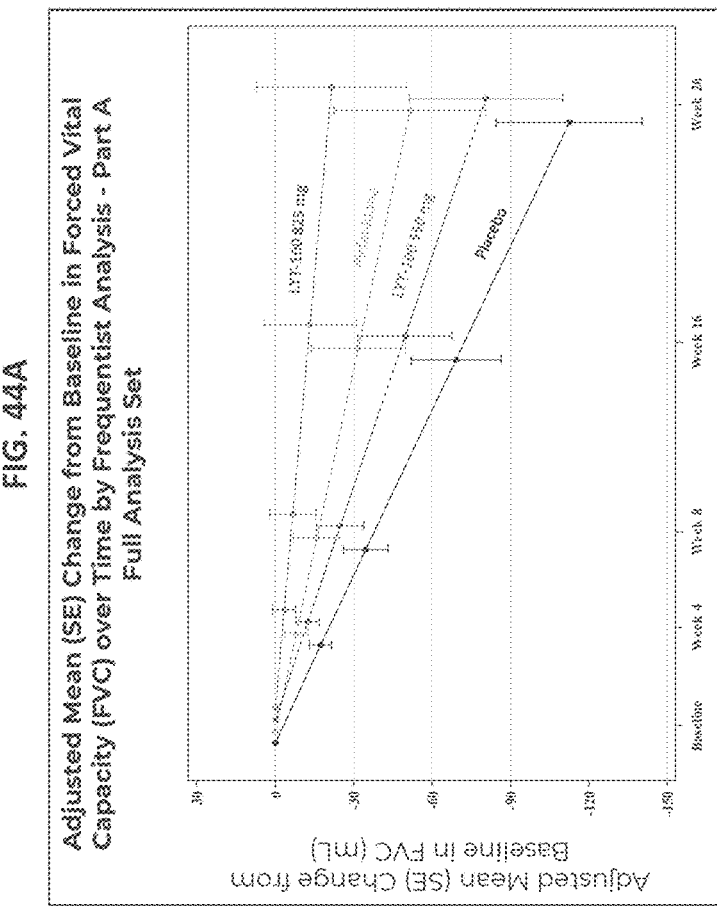
FIG. 44A is a graphical depiction providing the summary of change from baseline in FVC over 26 weeks by Bayesian analysis for placebo, pirfenidone and 550 mg TID LYT-100 and 825 mg TID LYT-100 in the IPF clinical trial study of Example 4.

With reference to FIGS. 44A and 44B, LYT-100 demonstrated a clear dose-dependent effect with respect to change from baseline in FVC and FVCpp (Mixed Model Repeated Measure). With reference to FIG. 45, the 825 mg TID dose stabilized lung function. Specifically, the IPF patients in the LYT-100 825 mg TID arm had a 6-month FVC decline in line with that seen for healthy adults >60 years. See, e.g., [1]Valenzuela, C. Poster 673, ERS Congress 2024) and [2]Luoto et al., Eur Respir J. 53(3):1701812 March 2019; 6-month decline in general population aged 60-102 years, estimated by taking reported 1-year decline and dividing by 2. Accordingly, FVC values for patients receiving the 825 mg TID LYT-100 dose for 26 weeks approached those expected for normal physiological decline in healthy older adults over the same time frame, suggesting the potential for this dose to stabilize lung function in IPF patients.

With reference to FIG. 46, a secondary endpoint of ELEVATE was time to IPF progression, as defined by time to an FVC decline of 5% or more or death. Deupirfenidone 825 mg TID was statistically significantly different from placebo with a hazards ratio (HR) of 0.439, with a log rank p value=0.002. Pirfenidone 801 mg TID was statistically significantly different from placebo with a hazards ratio (HR) of 0.501, with a log rank p value=0.008. With reference to FIG. 47, the 825 mg TID dose demonstrated an increase in the percentage of subjects with a positive change in FVC from baseline at week 26 relative to pirfenidone and placebo.

With reference to Tables 18 and 20 and FIG. 42B, the difference in the rate of FVC decline with deupirfenidone 825 mg TID compared to placebo was large enough to be statistically significant (−21.5 mL vs. −112.5 mL, respectively; p=0.02), which represents a robust treatment effect of 80.9%. In contrast, the pirfenidone 801 mg TID arm in this study showed a treatment effect of 54.1% compared to placebo (−51.6 mL vs. −112.5 mL). While the 550 mg TID dose did not demonstrate statistical significance in change from baseline for FVC or FVCpp versus placebo, efficacy comparable to that of 801 mg pirfenidone, the current standard of care, was shown (FIGS. 42A, 42B, 43A, and 43B) and as described below, exhibited improved tolerability relative to pirfenidone. Accordingly, by various measures, LYT-100 distinguished over the current standard of care (801 mg TID pirfenidone). As described herein above, the 825 mg TID dose of LYT-100 provides an AUC of LYT-100 which is 143% that of the AUC of pirfenidone dosed at 801 mg TID. However, the efficacy of pirfenidone has not been explored above 2403 mg total daily dose in view of tolerability issues, and the dose-response effect has not been previously explored.

TABLE 18

| | | | Efficacy Endpoints: Bayesian and Frequentist Analyses | | |
| --- | --- | --- | --- | --- | --- |
| | Endpoint | Placebo TID (N = 65) | Deupirfenidone 550 mg TID (N = 65) | Deupirfenidone 825 mg TID (N = 63) | Pirfenidone 801 mg TID (N = 61) |
| | | Change from Baseline in FVC (mL) over 26 Weeks | | | |
| Bayesian Analysis | Posterior Mean (SE) Comparison vs. Placebo | −110.8 (19.63) | −76.7 (28.60) | −19.9 (28.29) | −50.4 (28.33) |
| | Posterior Mean Difference (95% Credible Interval) | | 34.1 (−33.5, 100.0) | 90.9 (24.2, 159.1) | 60.4 (−8.6, 127.0) |
| | Posterior Probability (%) of Difference Over Placebo >0 | | 84.1 | 99.7 | 95.7 |
| | | Change from Baseline in FVCpp over 26 Weeks | | | |
| | Posterior Mean (SE) Comparison vs. Placebo | −3.27 (0.57) | −1.80 (0.88) | −0.42 (0.88) | −1.45 (0.89) |
| | Posterior Mean (95% Credible Interval) | | 1.47 (−0.58, 3.51) | 2.85 (0.82, 4.93) | 1.81 (−0.22, 3.91) |
| | Posterior Probability (%) of Difference Over Placebo >0 | | 92.1 | 99.7 | 95.9 |
| Frequentist Analysis | | Change from Baseline in FVC (mL) over 26 Weeks | | | |
| | Adjusted Mean (SE) Comparison vs. Placebo | −112.5 (27.84) | −80.7 (29.32) | −21.5 (28.86) | −51.6 (29.13) |
| | Adjusted Mean Difference (95% Confidence Interval) | | 31.8 (−47.6, 111.2) | 91.0 (12.2, 169.7) | 60.9 (−18.3, 140.0) |
| | P-Value | | 0.43 | 0.02 | 0.13 |

TABLE 18-continued

| | | Efficacy Endpoints: Bayesian and Frequentist Analyses | | |
|---|---|---|---|---|
| Endpoint | Placebo TID (N = 65) | Deupirfenidone 550 mg TID (N = 65) | Deupirfenidone 825 mg TID (N = 63) | Pirfenidone 801 mg TID (N = 61) |
| | | Change from Baseline in FVCpp over 26 Weeks | | |
| Adjusted Mean (SE) Comparison vs. Placebo | −3.43 (0.842) | −1.81 (0.886) | −0.43 (0.872) | −1.46 (0.881) |
| Adjusted Mean (95% Confidence Interval) | | 1.62 (−0.78, 4.02) | 3.00 (0.62, 5.38) | 1.97 (−0.42, 4.37) |
| P-Value | | 0.18 | 0.01 | 0.11 |

Efficacy analyses used a random coefficient regression model with absolute FVC or FVCpp including baseline as response variable and week, treatment and interaction between week and treatment as fixed effect. The analyses were performed based on the predefined Full Analysis Set. N = number of participants in the specified analysis set under each treatment group; SE = standard error; TID = 3 times per day. Baseline is defined as the last available measurement performed before the first study drug administration in Part A. Adjusted mean is estimated based on a random coefficient regression model with absolute FVC over time, including baseline, as a response, and fixed effects for treatment, visit (week), and treatment by visit interaction, as well as participant-level random effects for the intercept and slope.

TABLE 19

| | | Cohen's D | |
|---|---|---|---|
| | Pirfenidone 801 mg TID (N = 63) n (%) | Deupirfenidone 550 mg TID (N = 65) n (%) | Deupirfenidone 825 mg TID (N = 64) n (%) |
| FVC | 0.27 | 0.14 | 0.40 |
| FVCpp | 0.29 | 0.23 | 0.44 |

TABLE 20

| | | Treatment effect | |
|---|---|---|---|
| | Pirfenidone 801 mg TID (N = 63) n (%) | Deupirfenidone 550 mg TID (N = 65) n (%) | Deupirfenidone 825 mg TID (N = 64) n (%) |
| FVC | 54.1% | 28.3% | 80.9% |
| FVCpp | 57.4% | 47.2% | 87.5% |

TABLE 21

| | | Patients with advanced lung disease by arm | | |
|---|---|---|---|---|
| Baseline FVCpp | Placebo TID (N = 65) | Pirfenidone 801 mg TID (N = 61) | LYT-100 550 mg TID (N = 65) | LYT-100 825 mg TID (N = 63) |
| <50% | 3 (4.6) | 3 (4.9) | 1 (1.5) | 5 (7.9) |
| ≥50% | 62 (95.4) | 58 (95.1) | 64 (98.5) | 58 (92.1) |

Safety and Tolerability

Tolerability (secondary) endpoints included incidence and duration of dose modifications (dose reductions or interruptions), time to first dose modification, number of days on full assigned dose, time to treatment discontinuation due to an adverse event, and incidence and duration of adverse events of special interest (AESI; i.e., anorexia, decreased appetite, fatigue, diarrhea, nausea, vomiting, increase in aspartate aminotransferase (AST) and/or alanine aminotransferase (ALT) levels, photosensitivity reaction, rash of grade 3 severity or higher).

Both doses of LYT-100 were generally well-tolerated in the trial. The tolerability of study drug for each of the treatment arms for Part A is summarized in Tables 22 to 24 and FIG. 48. This study evaluated in particular the tolerability based on prioritized gastrointestinal adverse events (GI AEs). Prioritized GI AEs reflect those with rates ≥5% overall in comparative drug arm, e.g., nausea/abdominal pain/decreased appetite/dyspepsia/diarrhea). Success was defined as meeting criteria for nausea (i.e., ≥25% improvement) with other prioritized AEs trending towards placebo rates. The desired endpoints were met for both LYT-100 doses (550 mg and 825 mg). Table 22 provides a summary of all treatment emergent adverse events in the study, while Table 7 summarizes AEs of special interest in specific patients. The 550 mg TID dose of LYT-100 also met the success criteria of ≥25% reduction in AEs vs. pirfenidone (combined GI SOC, nausea, dyspepsia, constipation).

The 825 mg TID dose of LYT-100 met the success criteria of less than 25% difference in AEs vs. pirfenidone (i.e., a similar tolerability profile). Specifically, this dose met the defined GI tolerability criteria, including improvement vs. PFD on nausea, dyspepsia, and diarrhea.

Table 24 provides a summary of treatment discontinuations, while FIG. 48 provides a graphical depiction of all dose modifications and discontinuations across treatment arms. As shown in Table 24, discontinuation rates in the LYT-100 825 mg TID arm were similar to placebo (21.9% vs. 20.0%, respectively). Both doses of deupirfenidone were generally well-tolerated in the trial. The overall number of patients experiencing any gastrointestinal (GI)-related adverse events (AEs) was similar across the deupirfenidone 825 mg TID and pirfenidone 801 mg TID arms (53.1% vs. 52.4%, respectively) compared to 24.6% in the placebo arm. With reference to Table 24 and FIG. 48, 26% of patients on LYT-100 550 mg and 19% of patients on 825 mg TID discontinued treatment due to AEs. LYT-100 825 mg TID demonstrated a favorable tolerability profile compared to pirfenidone 801 mg TID, with a lower percentage of patients reporting key GI AEs. The clinically meaningful GI AEs occurring in ≥5% of participants in at least one arm were: nausea (20.3% vs. 27.0%), dyspepsia (14.1% vs. 22.2%), diarrhea (7.8% vs. 11.1%), constipation (4.7% vs. 6.3%) and vomiting (1.6% vs. 3.2%). The only increase was observed in abdominal pain (14.1% vs. 7.9%).

TABLE 22

| | Placebo TID (N = 65) n (%) | Pirfenidone 801 mg TID (N = 63) n (%) | Deupirfenidone 550 mg TID (N = 65) n (%) | Deupirfenidone 825 mg TID (N = 64) n (%) |
|---|---|---|---|---|
| | | Summary of Treatment-Emergent Adverse Events | | |
| >=1 TEAE | 48 (73.8%) | 53 (84.1%) | 47 (72.3%) | 55 (85.9%) |
| All TE SAE | 10 (15.4%) | 6 (9.5%) | 12 (18.5%) | 7 (10.9%) |
| Study drug-related TE SAE | 2 (3.1%) | 1 (1.6%) | 0 (0%) | 1 (1.6%) |
| AESI | 1 (1.5%) | 5 (7.9%) | 2 (3.1%) | 4 (6.3%) |
| TEAE leading to study treatment discontinuation | 8 (12.3%) | 11 (17.5%) | 16 (24.6%) | 12 (18.8%) |
| TEAE leading to dose modifications | 20 (30.8%) | 24 (38.1%) | 27 (41.5%) | 30 (46.9%) |
| TEAE leading to death | 2 (3.1%) | 5 (7.9%) | 1 (1.5%) | 1 (1.6%) |
| All-cause mortality | 3 (4.6%) | 5 (7.9%) | 2 (3.1%) | 1 (1.6%) |
| SOC/PT | | | | |
| Gastrointestinal disorders | 16 (24.6%) | 33 (52.4%) | 23 (35.4%) | 34 (53.1%) |
| Nausea | 5 (7.7%) | 17 (27.0%) | 11 (16.9%) | 13 (20.3%) |
| Dyspepsia | 2 (3.1%) | 14 (22.2%) | 8 (12.3%) | 9 (14.1%) |
| Diarrhea | 6 (9.2%) | 7 (11.1%) | 7 (10.8%) | 5 (7.8%) |
| Abdominal pain | 3 (4.6% | 5 (7.9%) | 4 (6.2%) | 9 (14.1%) |
| Constipation | 1 (1.5%) | 4 (6.3%) | 1 (1.5%) | 3 (4.7) |
| Vomiting | 0 (0%) | 2 (3.2%) | 5 (7.7%) | 1 (1.6%) |
| Nervous system disorders | 7 (10.8%) | 11 (17.5%) | 12 (18.5%) | 13 (20.3%) |
| Dizziness | 2 (3.1%) | 5 (7.9%) | 6 (9.2%) | 8 (12.5%) |
| Headache | 3 (4.6%) | 8 (12.7%) | 5 (7.7%) | 2 (3.1%) |
| Skin disorders | 3 (4.6%) | 18 (28.6%) | 12 (18.5%) | 20 (31.3%) |
| Photosensitivity reaction | 0 (0%) | 5 (7.9%) | 4 (6.2%) | 5 (7.8%) |
| Rash | 1 (1.5%) | 6 (9.5%) | 3 (4.6%) | 6 (9.4%) |
| Pruritus | 0 (0%) | 3 (4.8%) | 5 (7.7%) | 5 (7.8%) |
| Metabolism and nutrition disorders | 9 (13.8%) | 12 (19.0%) | 14 (21.5%) | 17 (26.6%) |
| Decreased appetite | 5 (7.7%) | 9 (14.3%) | 12 (18.5%) | 13 (20.3%) |
| General disorders | 7 (10.8%) | 11 (17.5%) | 10 (15.4%) | 11 (17.2%) |
| Fatigue | 1 (1.5%) | 7 (11.1%) | 5 (7.7%) | 6 (9.4%) |
| Respiratory disorders | 23 (35.4%) | 12 (19.0%) | 13 (20.0%) | 15 (23.4%) |
| Cough | 7 (10.8%) | 3 (4.8%) | 1 (1.5%) | 8 (12.5%) |
| IPF | 10 (15.4%) | 2 (3.2%) | 3 (4.6%) | 4 (6.3%) |
| Dyspnea | 4 (6.2%) | 3 (4.8%) | 2 (3.1%) | 1 (1.6%) |
| Infections | 20 (30.8%) | 17 (27.0%) | 17 (26.2%) | 14 (21.9%) |

TABLE 22-continued

| Summary of Treatment-Emergent Adverse Events | | | |
| --- | --- | --- | --- |
| | Placebo TID (N = 65) n (%) | Pirfenidone 801 mg TID (N = 63) n (%) | Deupirfenidone 550 mg TID (N = 65) n (%) | Deupirfenidone 825 mg TID (N = 64) n (%) |
| Upper respiratory infections | 6 (9.2%) | 9 (14.3%) | 8 (12.3%) | 6 (9.4%) |
| Urinary tract infections | 2 (3.1%) | 5 (7.9%) | 4 (6.2%) | 3 (4.7%) |
| Pneumonia | 3 (4.6%) | 2 (3.2%) | 4 (6.2%) | 1 (1.6%) |
| Psychiatric disorders | 1 (1.5%) | 5 (7.9%) | 3 (4.6%) | 7 (10.9%) |
| Insomnia | 0 (0%) | 3 (4.8%) | 1 (1.5%) | 4 (6.3%) |

TABLE 23

| Adverse Events of Special Interest | | | | | | | |
| --- | --- | --- | --- | --- | --- | --- | --- |
| Years from IPF diagnosis | Treatment arm | Start day from random | Description AESI | Grade of severity | Action Taken for Study drug | Outcome | Related to study drug per PI |
| 1.1 | Deupirfenidone 550 mg TID | 64 | Photosensitivity reaction | 3 | Interrupted | Resolved | Probably |
| 0.5 | Deupirfenidone 825 mg TID | 123 | Fatigue | 3 | w/d | Resolved | Probably |
| 4.0 | Pirfenidone 801 mg TID | 26 | Fatigue | 3 | w/d | Resolved | Not related |
| 1.5 | Pirfenidone 801 mg TID | 37 | Diarrhea | 3 | w/d | Resolved | Probably |
| 0.5 | Deupirfenidone 825 mg TID | 42 | Elevated liver enzymes | 3 | w/d | Resolved | Possibly |
| 2.4 | Deupirfenidone 825 mg TID | 86 | Nausea | 3 | w/d | Resolved | Possibly |
| 2.1 | Pirfenidone 801 mg TID | 34 | Decreased appetite, nausea | 3 | Interrupted | Resolved | Probably |
| 0.6 | Pirfenidone 801 mg TID | 117 | Fatigue, anorexia | 3 | Dose not changed | Resolved | Possibly |
| 0.4 | Placebo | 66 | Liver function test increased | 3 | Dose not changed | Resolved | Not related |
| 0.1 | Pirfenidone 801 mg TID | 22 | Vomiting | 3 | Dose not changed | Resolved | Probably |
| 0.1 | Deupirfenidone 550 mg TID | 44 | ALT elevation | 3 | w/d | Resolved | Possibly |
| 3.5 | Deupirfenidone 825 mg TID | 57 | Liver transaminase elevation | 3 | w/d | Resolved | Possibly |

TABLE 24

| Summary of Treatment Discontinuations | | | | |
| --- | --- | --- | --- | --- |
| Participants Who Discontinued 26-Week Double-Blind Study Treatment | Placebo TID (N = 65) n (%) | Pirfenidone 801 mg TID (N = 63) n (%) | Deupir- fenidone 550 mg TID (N = 65) n (%) | Deupir- fenidone 825 mg TID (N = 64) n (%) |
| Total Primary Reason for Discontinuation | 13 (20.0) | 20 (31.7) | 23 (35.4) | 14 (21.9) |
| Withdrew Consent | 4 (6.2) | 5 (7.9) | 5 (7.7) | 2 (3.1) |
| Patient Discontinued Treatment | 0 | 0 | 1 (1.5) | 0 |

TABLE 24-continued

| Summary of Treatment Discontinuations | | | | |
| --- | --- | --- | --- | --- |
| Participants Who Discontinued 26-Week Double-Blind Study Treatment | Placebo TID (N = 65) n (%) | Pirfenidone 801 mg TID (N = 63) n (%) | Deupir- fenidone 550 mg TID (N = 65) n (%) | Deupir- fenidone 825 mg TID (N = 64) n (%) |
| Adverse Event | 7 (10.8) | 11 (17.5) | 17 (26.2) | 12 (18.8) |
| Significant Protocol Deviation | 1 (1.5) | 0 | 0 | 0 |
| Investigator Decision | 0 | 2 (3.2) | 0 | 0 |
| Lack of Efficacy | 0 | 0 | 0 | 0 |
| Lost to Follow-up | 0 | 0 | 0 | 0 |
| Death | 1 (1.5) | 0 | 0 | 0 |

TABLE 24-continued

Summary of Treatment Discontinuations

| Participants Who Discontinued 26-Week Double-Blind Study Treatment | Placebo TID (N = 65) n (%) | Pirfenidone 801 mg TID (N = 63) n (%) | Deupir-fenidone 550 mg TID (N = 65) n (%) | Deupir-fenidone 825 mg TID (N = 64) n (%) |
|---|---|---|---|---|
| Pregnancy | 0 | 0 | 0 | 0 |
| Study Termination | 0 | 0 | 0 | 0 |
| Other | 0 | 2 (3.2) | 0 | 0 |

Toxicity

LYT-100 showed a small number of elevated liver enzymes as expected (Table 25). All liver enzyme elevation cases were transitory, with no instances of drug-induced liver injury or Hy's Law.

TABLE 25

Clinical Laboratory Parameters-Liver

| Parameter (unit) Category | Placebo TID (N = 63) n (%) | Pirfenidone 801 mg TID (N = 63) n (%) | LYT-550 mg TID (N = 63) n (%) | LYT-825 mg TID (N = 63) n (%) | LYT-100 TID Pooled (N = 129) n (%) | Overall (N = 257) n (%) |
|---|---|---|---|---|---|---|
| Alanine Aminotransferase (U/L) at Worst Post-Baseline, N1 | 62 | 62 | 59 | 61 | 120 | 244 |
| Total (>3 ULN) | 1 (1.6) | 1 (1.6) | 2 (3.4) | 3 (4.9) | 5 (4.2) | 7 (2.9) |
| 3-5 ULN | 1 (1.6) | 1 (1.6) | 1 (1.7) | 1 (1.6) | 2 (1.7) | 4 (1.6) |
| 5-8 ULN | 0 | 0 | 1 | 0 | 1 | 1 |
| >8 ULN | 0 | 0 | 0 | 2 | 2 | 2 |
| Aspartate Aminotransferase (U/L) at Worst Post-Baseline, N1 | 62 | 62 | 59 | 61 | 120 | 244 |
| Total (>3 ULN) | 0 | 0 | 1 (1.7) | 3 (4.9) | 4 (3.3) | 4 (1.6) |
| 3-5 ULN | 0 | 0 | 1 (1.7) | 1 (1.6) | 2 (1.7) | 2 |
| 5-8 ULN | 0 | 0 | 0 | 0 | 0 | 0 |
| >8 ULN | 0 | 0 | 0 | 2 | 2 | 2 |
| Alanine Aminotransferase or Aspartate Aminotransferase (U/L) at Worst Post-Baseline, N1 | 62 | 62 | 59 | 61 | 120 | 244 |
| Total (>3 ULN) | 1 (1.6) | 1 (1.6) | 2 (3.4) | 3 (4.9) | 5 (4.2) | 7 (2.9) |
| 3-5 ULN | 1 (1.6) | 1 (1.6) | 1 (1.7) | 1 (1.6) | 2 (1.7) | 4 (1.6) |
| 5-8 ULN | 0 | 0 | 1 | 0 | 1 | 1 |
| >8 ULN | 0 | 0 | 0 | 2 | 2 | 2 |

In summary:

LYT-100 550 mg TID (1650 mg total daily dose) provided efficacy (FVC) within one standard error of that of 801 mg TID pirfenidone (2403 total daily dose), while demonstrating a significant, i.e., a ≥25%, reduction in adverse events (Tables 18 and 22).

LYT-100 825 mg TID (2475 mg total daily dose) provided a significantly great efficacy (FVC) than that of pirfenidone at 801 mg TID (2403 total daily dose) (FIGS. 42A and 42B), while meeting the GI tolerability criteria defined for 550 mg TID (Table 22), and an improvement compared to pirfenidone on nausea, dyspepsia, and diarrhea (Table 22). Notably, the LYT-100 825 mg TID patients included patients who were titrated down to a 1650 mg total daily dose of LYT-100 during the study, either temporarily or permanently.

LYT-100 825 mg TID provided an approximately 50% greater effect size as compared to 801 mg TID pirfenidone for both FVC and FVCpp (Tables 19 and 20).

LYT-100 825 mg TID had a consistent benefit across age groups, gender, region, and diagnosis group (Table 18)

LYT-100 825 mg TID improved time to progression as compared to placebo (FIG. 46) and had the greatest percentage of patients with no decline (FIG. 44A).

LYT-100 825 mg TID (2475 mg total daily dose) stabilized lung function for IPF patients in-line with that seen for healthy older adults (FIG. 45).

The pooled LYT-100 doses (1650 mg total daily and 2475 total daily) provided significantly better efficacy (FVC) than placebo using Bayesian statistical analysis (posterior probability >98.5%) (FIG. 41).

The LYT-100 825 mg TID dose provided significantly better change from baseline FVC than placebo (99.7% posterior probability and a p-value of 0.02) (FIG. 42B) and FVCpp (99.7% posterior probability and a p-value of 0.01) (FIGS. 43A and 43B).

LYT-100 demonstrated a favorable tolerability profile at both doses evaluated and—most importantly—has the potential to offer patients enhanced efficacy that approaches the stabilization of lung function at the higher dose.

Preliminary data support a durable treatment effect, and a consistently well-tolerated profile with deupirfenidone 825 mg.

Results—Part B

Subject Disposition and Demographics

One hundred and seventy (170) patients (greater than 90%) enrolled in the Open Label Extension (Part B) of the study. Eighty-nine (89) received 550 mg TID LYT-100, and eighty-one (81) received 825 mg TID LYT-100.

Efficacy, Safety and Tolerability

Results of the ongoing Open Label Extension Study this far suggest a durable response for 825 mg TID and improvement for pirfenidone and placebo patients switched to LYT-100 (FIG. 49). Further, the AE data obtained this far (Table 26) support the safety and tolerability conclusions from Part A. Currently, the longest treatment duration with LYT-100 is 79 weeks for 825 mg TID and 81 weeks for 550 mg TID. Together, the data support progression into a Phase 3 trial and highlight the potential for LYT-100 to serve as a new standard-of-care treatment for IPF.

TABLE 26

| Summary of Treatment-Emergent Adverse Events | | | | |
|---|---|---|---|---|
| SOC/PT | Part A Placebo → Part B LYT-100 (N = 50) n (%) | Part A Pirfenidone → Part B LYT-100 (N = 39) n (%) | Part A LYT-100 → Part B LYT-100 (N = 81) n (%) | Subtotal (N = 170) n (%) |
| Gastrointestinal disorders | 18 (36.0) | 5 (12.8) | 17 (21.0) | 40 (23.5) |
| Dyspepsia | 7 (14.0) | 0 | 7 (8.6) | 14 (8.2) |
| Nausea | 7 (14.0) | 2 (5.1) | 5 (6.2) | 14 (8.2) |
| Abdominal Pain | 2 (4.0) | 1 (2.6) | 2 (2.5) | 5 (2.9) |
| Diarrhea | 2 (4.0) | 1 (2.6) | 2 (2.5) | 5 (2.9) |
| Vomiting | 3 (6.0) | 0 | 2 (2.5) | 5 (2.9) |

Example 5: In Vitro Stability of Pirfenidone and LYT-100 in the Presence of Recombinant Human CYP Isozymes The metabolism of LYT-100 by isolated CYP isozyme preparations was evaluated and compared with the metabolism of pirfenidone (FIG. 27). Pirfenidone and LYT 100 were each incubated with recombinant human CYP1A2, CYP2C8, CYP2C9, CYP2C19, CYP2D6, CYP3A4, and CYP3A5 expressed in heterologous cell systems. The half-life (t½) of each test article was determined.

With reference to FIG. 27, pirfenidone and LYT-100 concentrations decreased by at least 15% during incubation with recombinantly expressed human CYP1A2, CYP2D6 and CYP2C19 isozymes. The $t_{1/2}$ of pirfenidone following incubation with CYP1A2, CYP2C19 and CYP2D6 was 3.18, 2.13 and 2.30 hours, respectively. The $t_{1/2}$ of LYT-100 following incubation with CYP1A2, CYP2C19 and CYP2D6 was 9.08, 3.67 and 2.72 hours, respectively. There was no significant metabolism by CYP2C8, CYP2C9, CYP3A4 or CYP3A5 isozymes, with more than 92% of the compounds remaining at the end of incubation. Therefore, no $t_{1/2}$ was calculated for those isozymes. These results confirm the stabilization against metabolism of LYT-100 vs. pirfenidone. Metabolism by CYP1A2 was the most affected by deuteration (~3-fold longer $t_{1/2}$ compared to pirfenidone). This result demonstrates the effect of deuteration of LYT- 100 on the overall metabolism of pirfenidone as the CYP1A2 isozyme plays a key role in the metabolism of pirfenidone.

Example 6: Activity Screen

Figure 28:
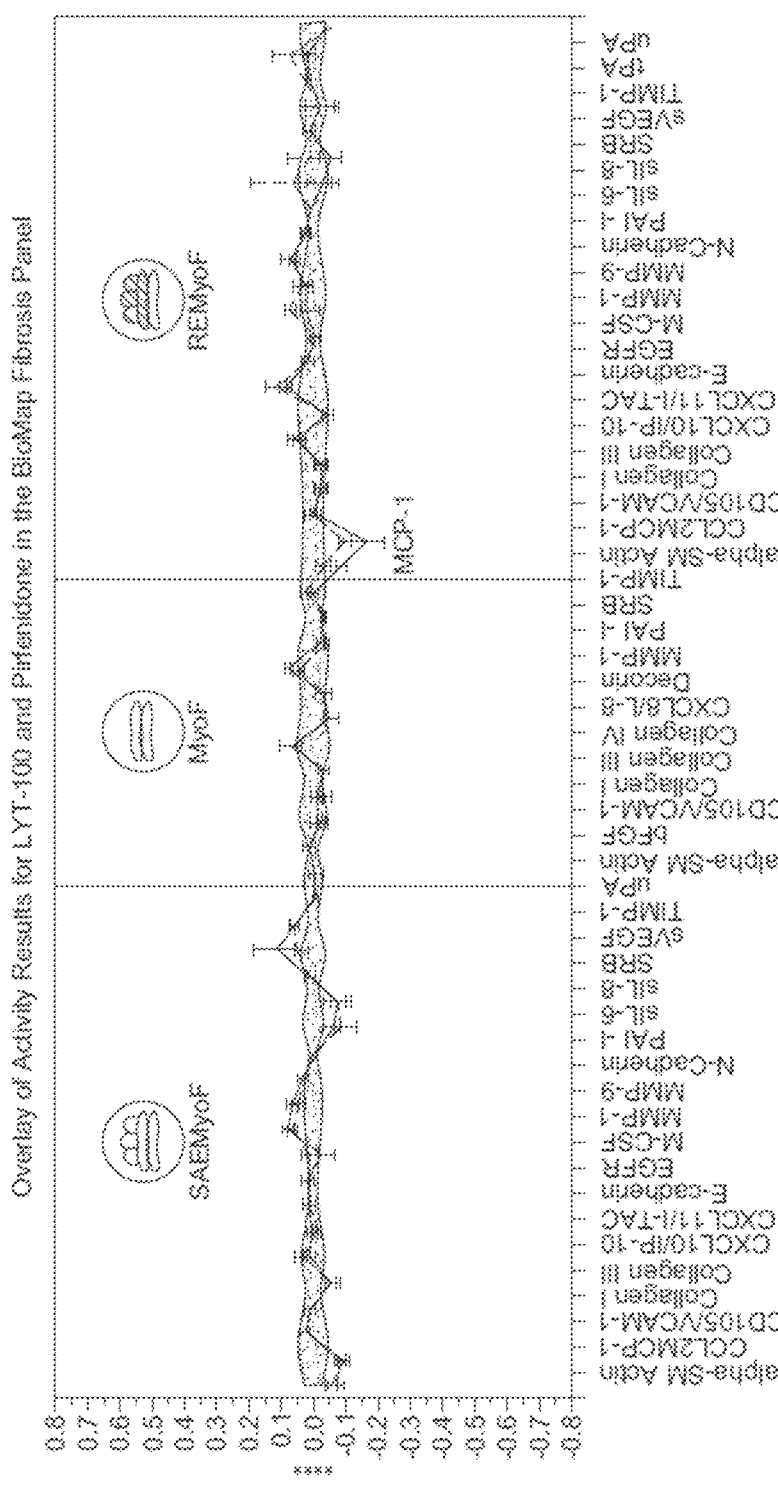
FIG. 28 is a graphical depiction of activity results for LYT-100 and pirfenidone in the BioMap Fibrosis Panel of Example 6.

The DiscoverX BioMAP Fibrosis Panel was used to evaluate LYT-100 and pirfenidone. The panel contains 54 biomarker (cell surface receptors, cytokines, chemokines, matrix molecules and enzymes) readouts that capture biological changes that occur within the physiological context of the particular BioMAP system. LYT-100 and pirfenidone were tested in the BioMAP Fibrosis Panel at various dilutions starting at highest dose of 1700 μM in three cell/stimulus systems (myofibroblast [MyoF] composed of lung fibroblasts treated with TNF-a, and TGF-β, renal proximal tubule epithelial cell (RE) MyoF including renal tubule epithelial cells and lung fibroblasts treated with TNF-a, and TGF-β, and small airway epithelial cell (SAE) MyoF comprising small airway epithelial cells and lung fibroblasts treated with TNF-a, and TGF-β). Similar results were observed with both compounds in the three systems (FIG. 28).

Example 7: Evaluation of LYT-100 Efficacy in a Rodent Bleomycin-Induced Fibrosis Model The rodent bleomycin-induced fibrosis model (BLM) is commonly utilized in the preclinical setting as it appears to have clinical relevance as an animal model of human fibrosis (e.g., idiopathic pulmonary fibrosis) based on the observed pulmonary pathophysiology following the bleomycin challenge in rats. See, e.g., Corboz et al., Pumonary Pharm. & Ther. 49(2018), 95-103). Bleomycin is a metabolite of the bacterium *Streptomyces verticillus* first identified in 1962. Specifically, bleomycin is a non-ribosomal hybrid peptide-polyketide natural product having the structure:

While bleomycin possesses antibacterial activity, its toxicity precludes use as an antibiotic. Bleomycin is used as a chemotherapeutic agent in the treatment of various cancers, including Hodgkin's lymphoma, non-Hodgkin's lymphoma, testicular cancer, ovarian cancer, and cervical cancer among others. Bleomycin acts by induction of DNA strand breaks and may also inhibit incorporation of thymidine into DNA strands. DNA cleavage by bleomycin depends on oxygen and metal ions, at least in vitro, though the exact mechanism of DNA strand scission is unresolved.

Common side effects associated with bleomycin chemotherapy include fever, weight loss, vomiting, rash, and a severe type of anaphylaxis. The most serious complication of bleomycin therapy, occurring with increasing dosage, is pulmonary fibrosis and impaired lung function. In high concentrations, bleomycin induces DNA strand rupture, generates free radicals, and causes oxidative stress tresulting in cell necrosis and/or apoptosis. Recent studies support the role of the proinflammatory cytokines IL-18 and IL-1beta in the mechanism of bleomycin-induced lung injury. Bleomycin is normally metabolized by the enzyme bleomycin hydrolase, but the lung is particularly susceptible to bleomycin toxicity by virtue of the scarcity of this enzyme in the lung. Lung inflammation, fibrosis, reductions in lung compliance, and impaired gas exchange are the consequences of a bleomycin challenge.

In assessing anti-fibrotic potential of compounds of interest, evaluation is generally performed in the phase of established fibrosis, i.e., 10-15 days after the initiation, rather than in the early period of bleomycin-induced inflammation. Conversion of proline into hydroxyproline and incorporation into lung collagen occurs as early as 4 days after bleomycin administration. The switch between inflammation and fibrosis occurs in rats around day 9 after bleomycin administration. It was deemed desirable to evaluate activity of LYT-100 during both the inflammatory and fibrotic stages of the model. Accordingly, LYT-100 was administered starting at day 8 following bleomycin administration.

Phase I Study

Initially, a Phase I study was conducted to evaluate the effect of bleomycin and LYT-100 on body weight and lung weight in the rat BLM induced lung fibrosis model. The Phase I study design is provided in Table 27.

TABLE 27

| | | | BLM Study Design- Phase I | | |
|---|---|---|---|---|---|
| Group | Intervention (days 1-7) | Test Article and Dose | Test Article Dosing (Day 8-13) | Number of Animals | Day 14 Necropsy and analysis |
| 1 | Saline; Days 1, 2, 3, 6, and 7 | LYT-100 (400 mg/kg) | PO; oral gavage as solution in 1% aq. CMC; | N = 3 | Lung weights, Lungs inflation (fixed with |
| 2 | Bleomycin 0.45 mg/kg; Days 1, 2, 3, 6, and 7 | LYT-100 (250 mg/kg) | QD | N = 4 | 10% NBF overnight, then kept in 70% ethanol) |
| 3 | Bleomycin 0.45 mg/kg; Days 1, 2, 3, 6, and 7 | LYT-100 (400 mg/kg) | | N = 4 | |

For Groups 1, 2 and 3, bleomycin and vehicle dosing were conducted as indicated in Table 27 (0.45 mg/kg, at 1696 IU/mg of Bleomycin or saline on Day 1, 2, 3, 6 and 7). On days 8 to 13, LYT-100 was dosed via oral gavage once daily.

Observations

Animals were observed for a variety of clinical signs and symptoms following bleomycin and LYT-100 dosing. All animals dosed with bleomycin or saline had 100% incidence of abnormal sounds on Days 1, 2, 3, 6 and 7 which was alleviated by the next study day, confirming dosing to the lung. All animals dosed with bleomycin (Group 2 and 3) were observed with respiratory signs from Day 3, with 100% incidence of increased respiratory rate by Day 5. There was no observed increased respiratory rate for Group 1. Respiratory signs are an indication of acute inflammation secondary to bleomycin challenge. Some animals were observed with abnormal gait following initiation of LYT-100 administration on Day 8. The sign disappeared from the animals that showed it ~5 h after it was observed and it did not appear in the subsequent dosing occasions. Almost all the animals were noted to be subdued and with decreased activity following LYT-100 dosing on Days 8, 9 and 10, after which point the sign appeared only in Group 3 (Bleomycin/400 mg/kg LYT-100) on Day 13. When this signa appeared, it disappeared ~5 h after it was recorded. All animals were observed with eyelids closed following initiation of LYT-100 administration on Day 8. The sign disappeared from the animals that showed it ~5 h after it was observed and it did not appear in the subsequent dosing occasions. Some animals in Groups 1 and 2 were observed with erected fur following initiation of LYT-100 administration on Day 8 and again on Day 11. The sign disappeared from the animals that weight gain was impeded in Groups 2 and 3 that received Bleomycin between Days 1 to 9. From Day 10 and until the end of Phase 1 on Day 14, body weight gain in Groups 2 and 3 resumed at a rate similar to Group 1 that received saline.

Figures 30A, 30B:
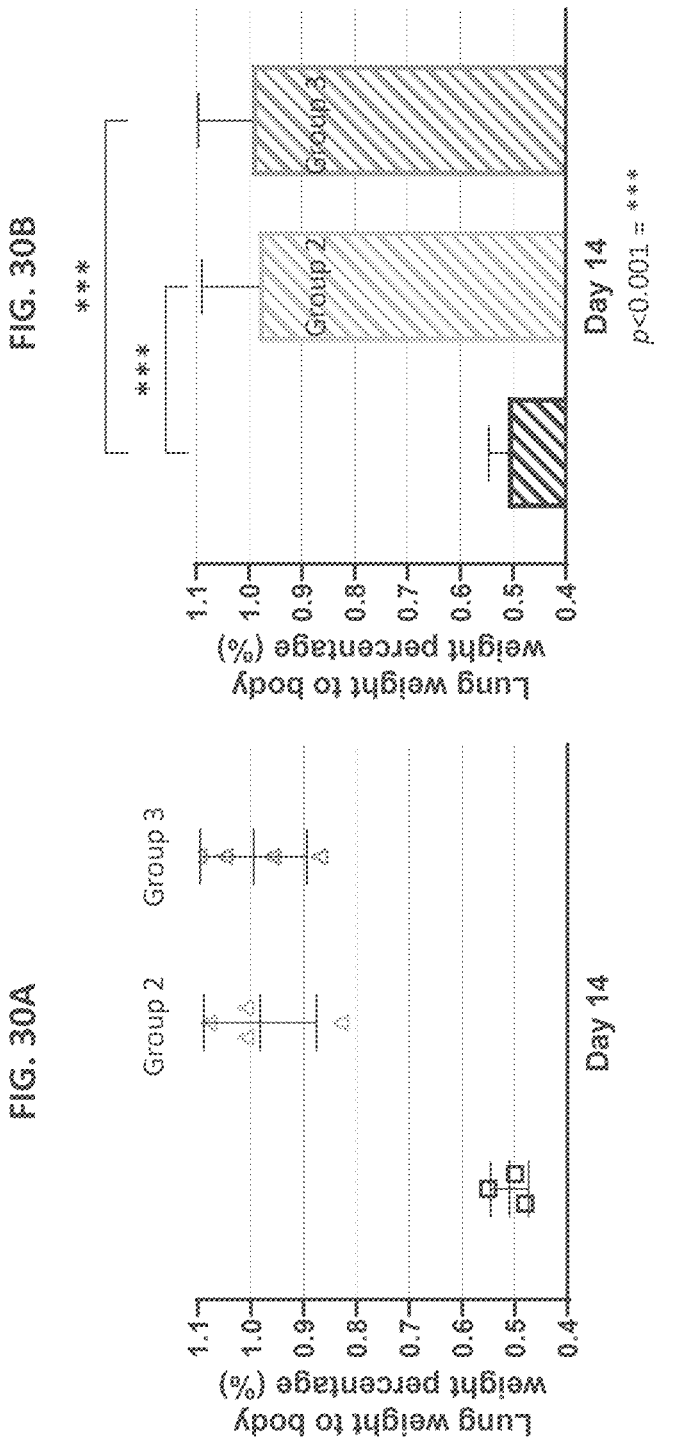
FIG. 30A is a graphical depiction of lung weight to body weight percentage over time for rats in Phase I of the bleomycin induced lung fibrosis model of Example 7.
FIG. 30B is a graphical depiction of lung weight to body weight percentage over time for rats in Phase I of the bleomycin induced lung fibrosis model of Example 7.

Lung weights were heavier in the bleomycin-treated animals (Group 1 vs Group 2 and Group 3 comparisons) as expected from this model. Lung weight ratios (expressed as % of body weight; FIGS. 30A and 30B) were heavier in the bleomycin-treated animals (Group 1 vs Group 2 and Group 3 comparisons) as expected from this model.

Overall, Phase 1 was performed as per protocol and no deviations were considered to affect the integrity of the Phase's outcome. During Phase 1 (Tolerability), LYT-100 was administered at high (400 mg/kg) and low (250 mg/kg) dose levels once daily (QD) from Day 8 until (including) Day 13 in healthy (high dose) and bleomycin-challenged (low and high dose) rats. LYT-100 was well tolerated by all animals and there was not an obvious correlation between dose level and presence of side effects. Any side effects observed were resolved within ~5 hours after they were first observed and they did not reappear before the following dosing occasions. Based on the animals' body weight developments, clinical signs, lung weights and lung weight to body weight ratios, the tolerability phase determined that LYT-100 administered QD at 400 mg/kg was well-tolerated by both healthy and bleomycin-challenged rats and that this dose levels will be used to examine LYT-100's therapeutic potential during Phase 2 (Efficacy).

Phase II Study

Subsequently, a Phase II study was conducted to evaluate the efficacy of LYT-100 in the rat BLM induced lung fibrosis model. The Phase II study design is provided in Table 28.

TABLE 28

| | | | Test Article | | |
|---|---|---|---|---|---|
| Group | Intervention (days 1-7) | Test Article and Dose | Test Article Dosing (Day 8-27) | Number of Animals | Day 28 Necropsy and analysis |
|---|---|---|---|---|---|
| 4 | Saline; Days 1, 2, 3, 6, and 7 | Vehicle control | PO; oral gavage as solution in 1% aq. CMC; | N = 10 | Preterminal blood for plasma Lungs removed and |
| 5 | Bleomycin 0.45 mg/kg; | Vehicle control | QD | N = 12 | weighed Left Lung Lobe |
| 6 | Days 1, 2, 3, 6, and 7 | LYT-100 (400 mg/kg) | | N = 12 | snap frozen for HP Right lung lobe |
| 7 | | Nintedanib 60 mg/kg | PO; oral gavage as solution in 1% aq. CMC; BID | N= 10 | inflation fixed | showed it ~5 h after it was observed and it did not appear in the subsequent dosing occasions. Almost all of the animals were observed salivating following initiation of LYT-100 administration on Day. The sign disappeared from the animals that showed it ~5 h after it was observed and it did not appear in the subsequent dosing occasions.

Results

Figure 29:
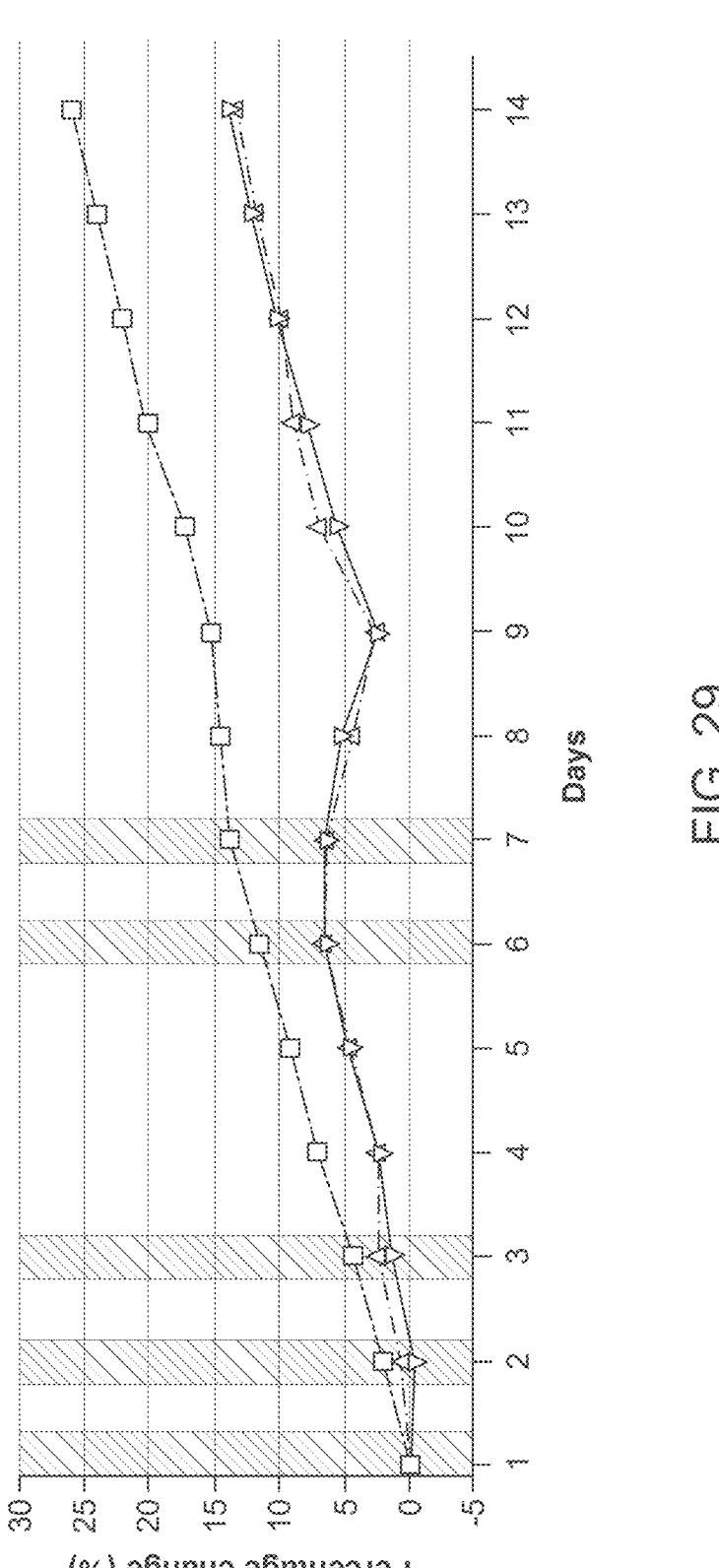
FIG. 29 is a graphical depiction of percent change in body weight over time for rats in Phase I of the bleomycin induced lung fibrosis model of Example 7.

Body weight and lung weight were evaluated over the duration of the study to determine the effects of bleomycin and LYT-100 in the model. Body weight gain was impeded in Groups 2 and 3 that received Bleomycin between Days 1 to 9 (FIG. 29). With continued reference to FIG. 29, from Day 10 and until the end of Phase 1 on Day 14, body weight gain in Groups 2 and 3 resumed at a rate similar to Group 1 that received saline. Body weight gain (expressed as % of body weight compared with Day Minus 1 body weights)

For Groups 4, 5, 6, and 7, bleomycin and vehicle dosing were conducted as indicated in Table 28 (0.45 mg/kg, at 1696 IU/mg of Bleomycin or saline on Day 1, 2, 3, 6 and 7). On days 8 to 27, LYT-100 was dosed via oral gavage once daily, and nintedanib was dosed twice daily via oral gavage.

Observations

Animals were observed for a variety of clinical signs and symptoms following bleomycin, saline, and LYT-100 dosing. All animals dosed with bleomycin or saline had 100% incidence of abnormal sounds on Days 1, 2, 3, 6 and 7 which was alleviated by the next study day, confirming dosing to the lung. All animals dosed with bleomycin (Groups 5 to 7) were observed with respiratory signs from Day 2, with 100% incidence of increased respiratory rate from Day 4 and until the end of the Study on Day 28. There was no observed increased respiratory rate for Group 4 that received saline.

Respiratory signs are an indication of acute inflammation secondary to bleomycin challenge.

Results

Figure 31A:
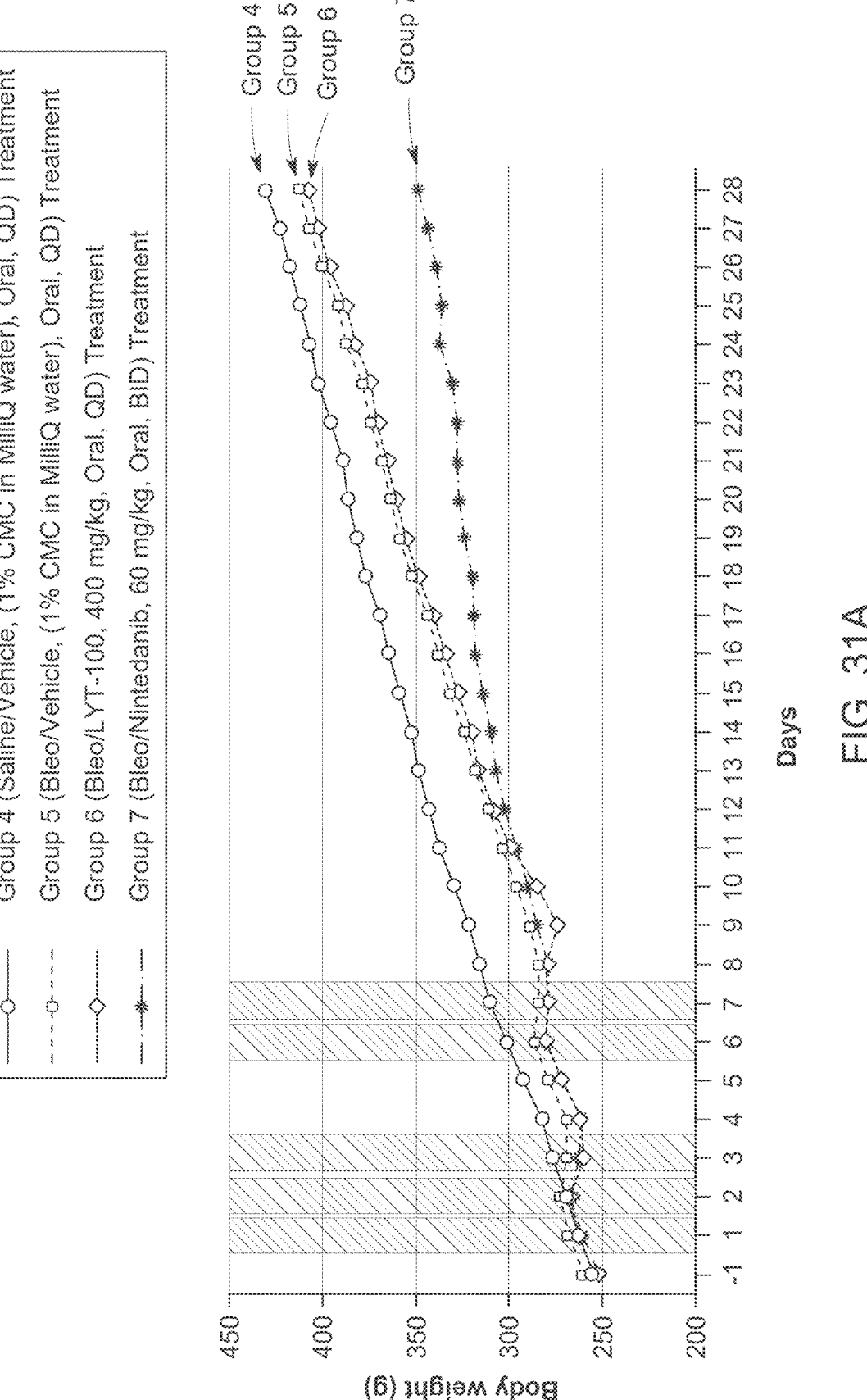
FIG. 31A is a graphical depiction of body weight over time for rats in Phase II of the bleomycin induced lung fibrosis model of Example 7.
Figure 31B:
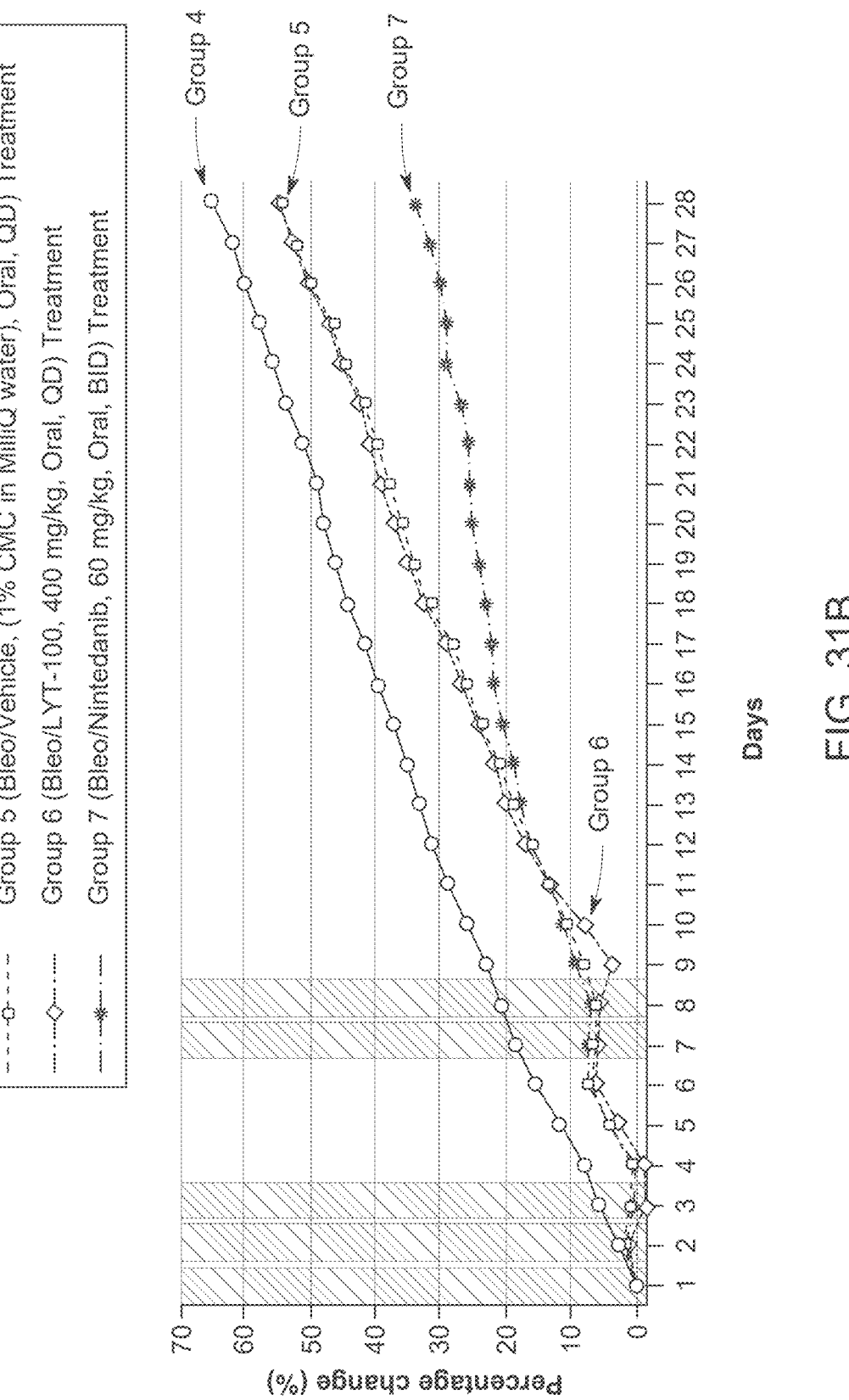
FIG. 31B is a graphical depiction of percent change in body weight over time for rats in Phase II of the bleomycin induced lung fibrosis model of Example 7.

Body weight and lung weight were evaluated over the duration of the study to determine the effects of bleomycin and LYT-100 in the model. Body weight gain was impeded between Days 1 to 9 in Groups 5, 6, and 7 that received Bleomycin (FIG. 31A). With continued reference to FIG. 31A, from Day 10 and until the end of the efficacy Phase on Day 28, body weight gain in Groups 5 (Bleomycin/Vehicle) and 6 (Bleomycin/LYT-100) resumed and at a rate similar to Group 4 that received Saline/Vehicle. Body weight gain in Group 7 (Blemoycin/Nintedanib) showed modest improvement after Day 8 and the rate of body weight gain remained slower compared with the other groups. Body weight gain (expressed as % of body weight compared with Day 1 body weights) was impeded between Days 1 to 9 in Groups 5, 6, and 7 that received bleomycin (FIG. 31B). With continued reference to FIG. 31B, from Day 10 and until the end of the Efficacy Phase on Day 28, % of body weight gain in Groups 5 (Bleomycin/Vehicle) and 6 (Bleomycin/LYT-100) resumed and at a rate similar to Group 4 that received Saline/Vehicle. Percent of body weight gain in Group 7 (Bleomycin/Nintedanib) showed modest improvement after Day 8 and the rate of body weight gain remained slower compared with the other groups.

Figures 32A, 32B:
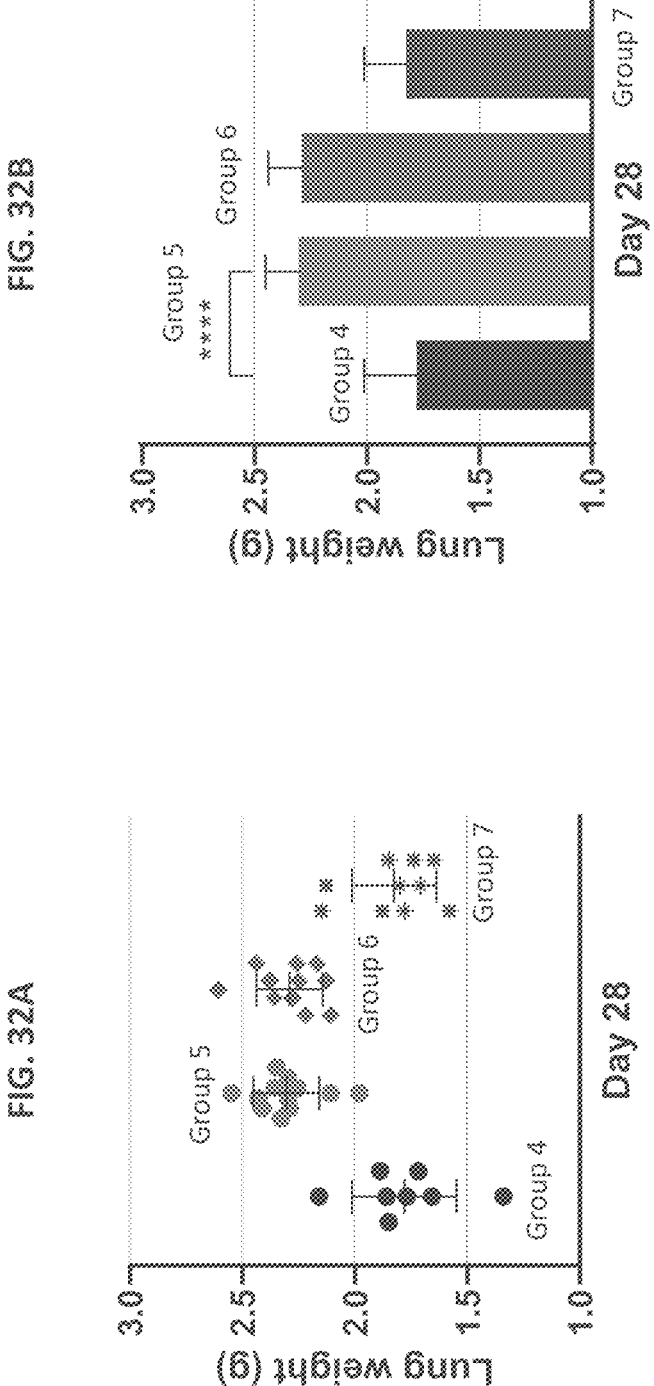
FIG. 32A is a graphical depiction of lung weight over time for rats in Phase II of the bleomycin induced lung fibrosis model of Example 7.
FIG. 32B is a graphical depiction of lung weight over time for rats in Phase II of the bleomycin induced lung fibrosis model of Example 7.
Figure 36:
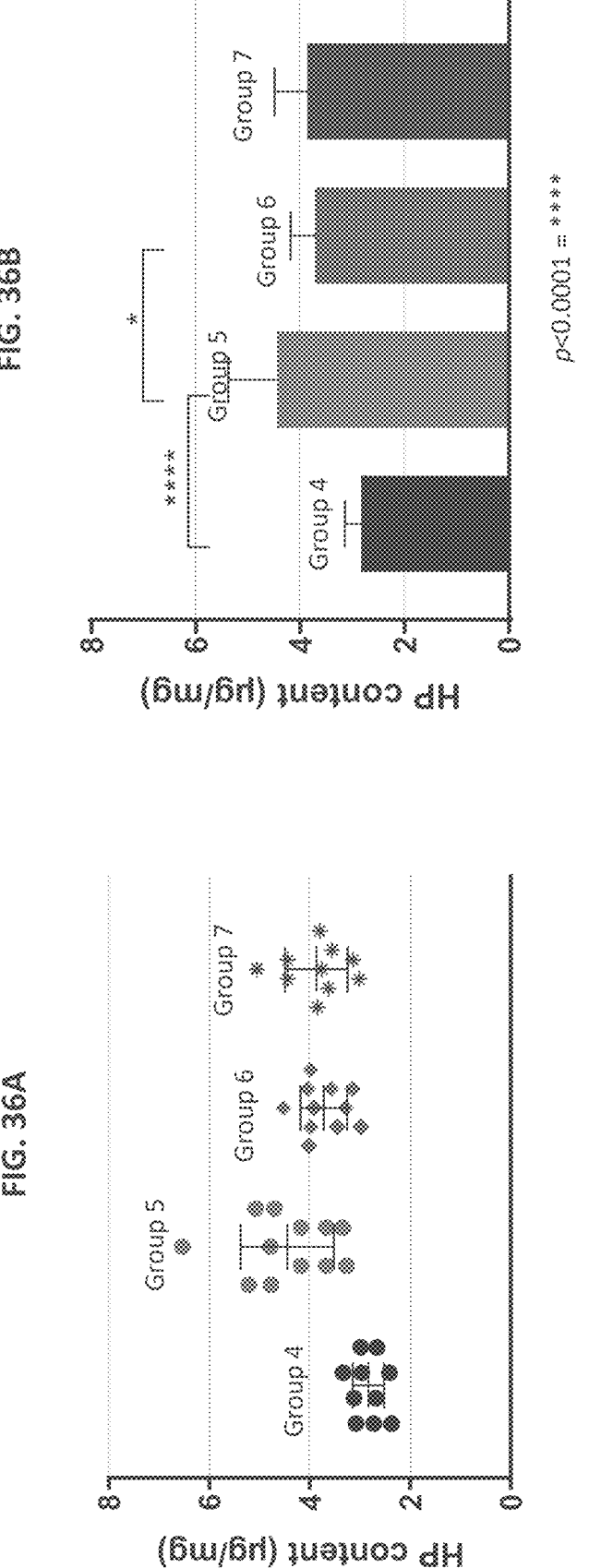
FIG. 36A is a graphical depiction of hydroxyproline content in lung tissue across the various treatment groups in Phase II of the bleomycin induced lung fibrosis model of Example 7.
FIG. 36B is a graphical depiction of hydroxyproline content in lung tissue across the various treatment groups in Phase II of the bleomycin induced lung fibrosis model of Example 7.
Figures 38A, 38B:
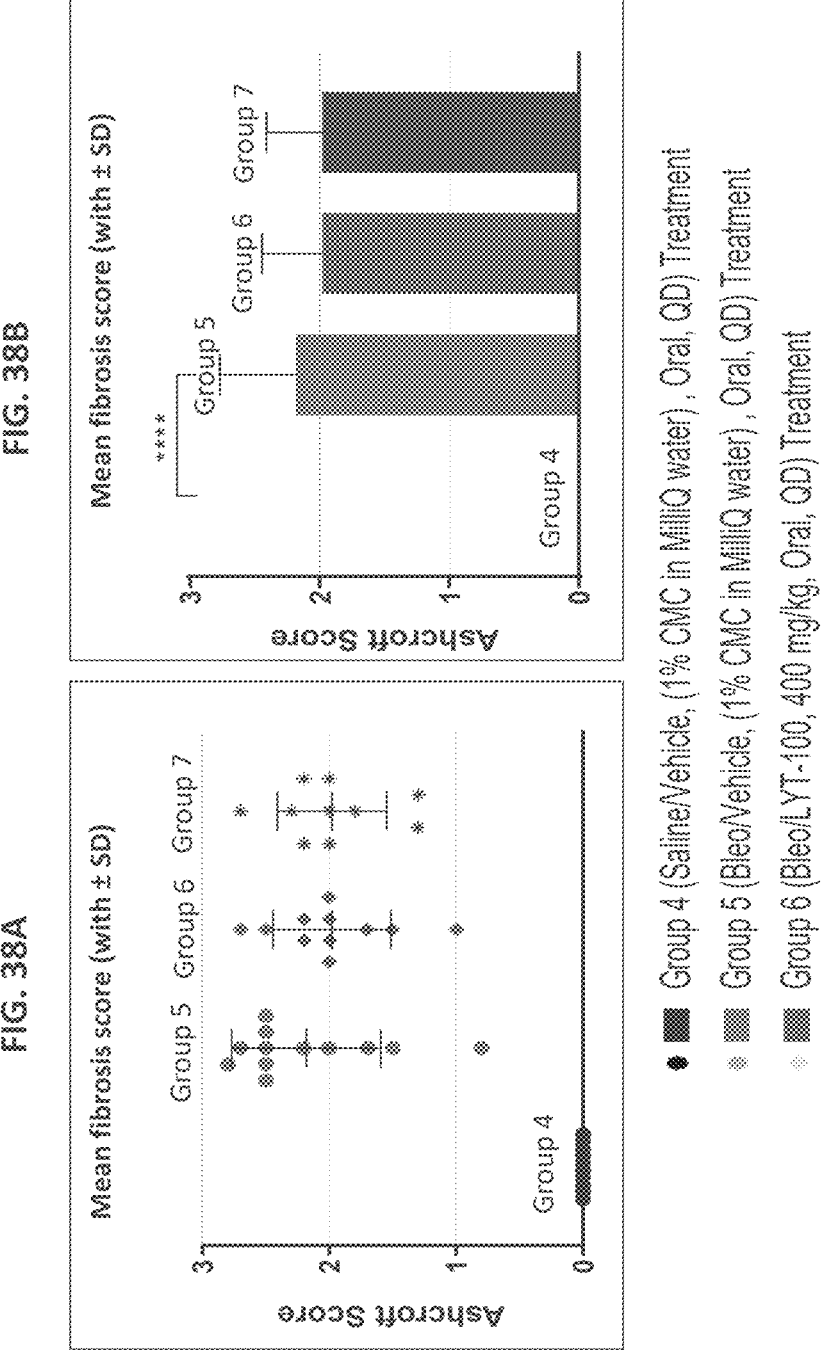
FIG. 38A is a graphical depiction of mean lung fibrosis score across the various treatment groups in Phase II of the bleomycin induced lung fibrosis model of Example 7.
FIG. 38B is a graphical depiction of mean lung fibrosis score across the various treatment groups in Phase II of the bleomycin induced lung fibrosis model of Example 7.
Figures 38C, 38D:
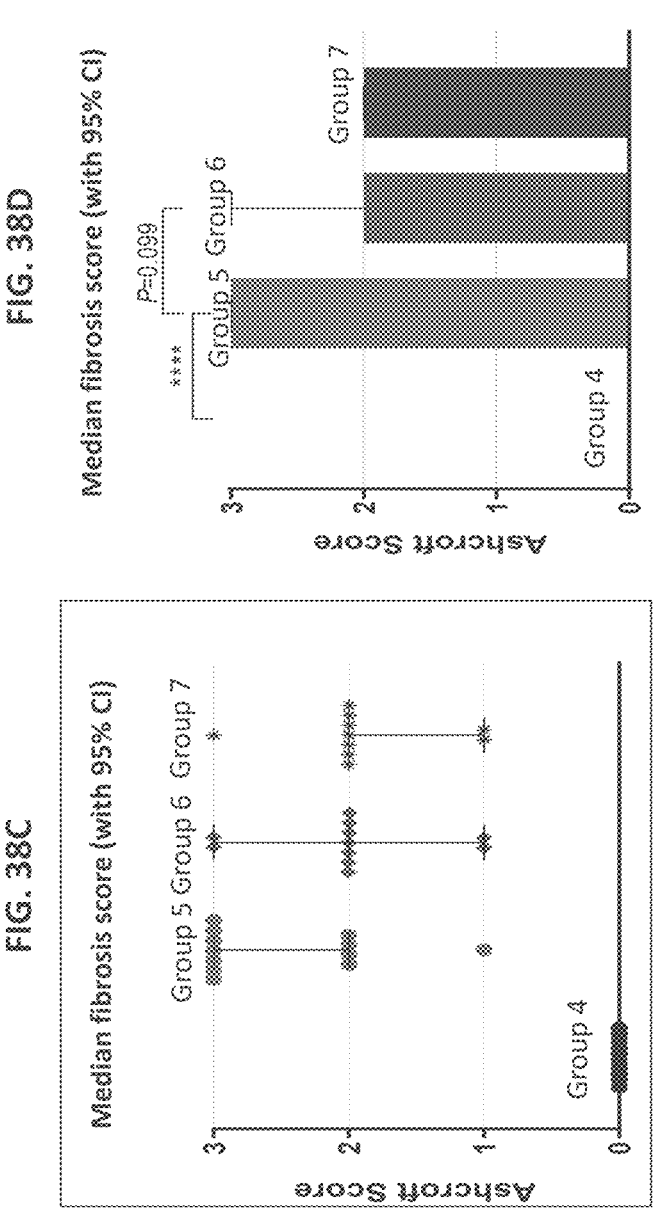
FIG. 38C is a graphical depiction of median lung fibrosis score across the various treatment groups in Phase II of the bleomycin induced lung fibrosis model of Example 7.
FIG. 38D is a graphical depiction of median lung fibrosis score across the various treatment groups in Phase II of the bleomycin induced lung fibrosis model of Example 7.
Figure 39:
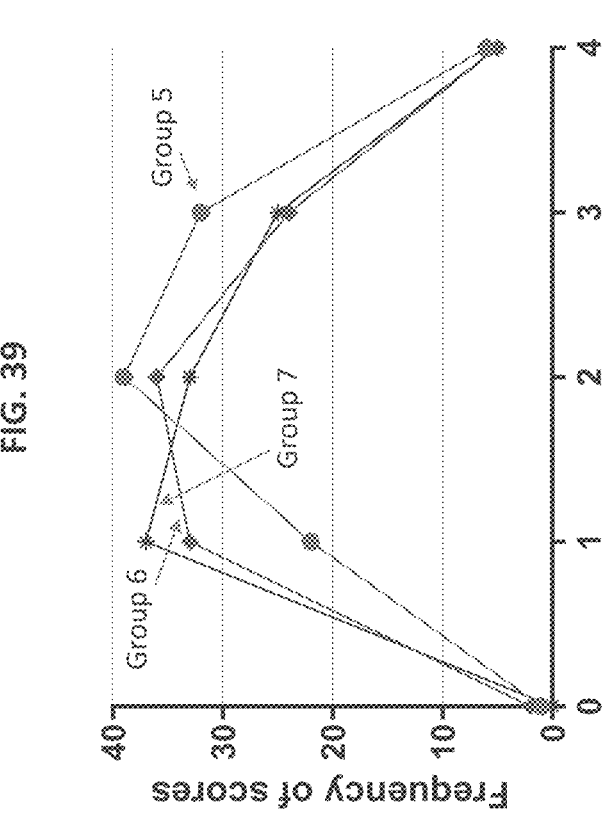
FIG. 39 is a graphical depiction of frequency of lung fibrosis scores across the various treatment groups in Phase II of the bleomycin induced lung fibrosis model of Example 7.

Mean lung weight increased in the bleomycin-treated rats (Group 4, saline vs Group 5, Bleomycin; FIGS. 32A and 32B). With continued reference to FIGS. 32A and 32B, LYT-100 treatment did not affect mean lung weight in the bleomycin-treated rats (Group 5, Bleomycin/vehicle vs Group 6, Bleomycin LYT-100). Nintedanib-treated rats had reduced lung weight (Group 7 vs Group 5) similar to non-challenged rats (Group 7 vs Group 4). Lung weight ratios (expressed as % percentage of body weight; FIGS. 33A and 33B) increased in the bleomycin-treated rats (Group 4, saline vs Group 5, Bleomycin). LYT-100 treatment did not affect lung weight ratios in the bleomycin-treated rats (Group 5, Bleomycin/vehicle vs Group 6, Bleomycin/LYT-100). There was a trend for lower lung weight ratios in the Nintedanib-treated rats (Group 5 vs Group 7), however this lung ratio remained higher compared with non-challenged rats (Group 7 vs Group 4).

Lung hydroxyproline content was measured for all groups (FIGS. 34A, 34B, 35, 36A, 36B, 37). With reference to FIGS. 34A, 34B, 35, 36A, 36B, and 37, total left lung hydroxyproline (μg per left lung) was higher in the bleomycin-treated rats (Group 4, saline vs Group 5, Bleomycin). LYT-100 treatment did not affect total hydroxyproline levels in the bleomycin-treated rats (Group 5, Bleomycin/vehicle vs Group 6, Bleomycin/LYT-100). Lungs from animals treated with Nintedanib had lower levels of total hydroxyproline (Group 7 vs Group 5) but higher than non-challenged rats (Group 7 vs Group 4). Hydroxyproline content (μg per mg of wet lung) was higher in the bleomycin-treated rats (Group 4, saline vs Group 5, Bleomycin). LYT-100 treatment reduced the hydroxyproline content in the bleomycin-treated rats (Group 5, Bleomycin/vehicle vs Group 6, Bleomycin/LYT-100). Nintedanib treatment also reduced hydroxyproline content (Group 7 vs Group 5).

Histopathology studies were performed to evaluate the extent of fibrosis in lung (FIGS. 38A-38D and FIG. 39). Mean and median fibrosis scores increased in the Bleomy-cin-treated rats (Group 4, saline vs Group 5, Bleomycin). LYT-100 or nintedanib treatment did not affect the fibrosis scores (Group 5, Bleomycin/vehicle vs Group 6, Bleomycin/LYT-100 or Group 7, Bleomycin/Nintedanib). LYT-100 and Nintedanib treatments reduced median fibrosis scores (Groups 6 and 7 compared with Group 5). The majority of the fibrosis scores in Group 5 (Bleomycin/vehicle) distributed around Score 2 (39% of the lung sections and 3 (32% of the lung sections). In the LYT-100 and Nintedanib treatments (Groups 6 and 7, respectively) the distribution of lung section fibrosis scores shifted towards Scores 1 (33% and 37% respectively) and 2 (36% and 33% respectively).

Overall, Phase 2 was performed as per protocol and no deviations were considered to affect the integrity of the Phase's outcome. Mirroring Phase 1, LYT-100 administered QD at 400 mg/kg from Day 8 until (including) Day 27 was well tolerated by all animals and any side-effects observed were resolved within ~5 hours after they were noticed and did not reappear before the following dosing occasions. Nintedanib administered twice daily (BID) at 60 mg/kg was used as a reference. LYT-100 did not negatively affect body weight developments, in contrast to nintedanib. LYT-100 reduced lung hydroxyproline content, suggesting reduced presence of connective tissue in the lungs. Consistent with the latter, lungs from LYT-100-treated rats also had reduced median fibrosis scores compared with vehicle controls.

The invention claimed is:

1. A method of treating Idiopathic Pulmonary Fibrosis (IPF), the method comprising orally administering to a subject in need thereof a total daily dose of 1600 mg to 2500 mg in three equal administrations of a deuterium-enriched pirfenidone having the structure:

(deupirfenidone)

wherein deupirfenidone provides improved efficacy compared to pirfenidone without a loss of tolerability.

2. The method of claim 1, wherein the subject is orally administered a total daily dose of 2400 mg to 2500 mg of deupirfenidone.

3. The method of claim 2, wherein the subject is orally administered a 2475 mg total daily dose of deupirfenidone.

4. The method of claim 1, wherein the deupirfenidone is orally administered in an oral dose form selected from a capsule or a tablet.

5. The method of claim 1, wherein orally administering a total daily dose of 1650 mg deupirfenidone provides comparable efficacy and improved tolerability relative to treating with a total daily dose 2403 mg pirfenidone.

6. The method of claim 1, wherein orally administering a total daily dose of 2475 mg deupirfenidone provides an approximately 50% greater effect size compared to a total daily dose 2403 mg pirfenidone without a loss of tolerability.

* * * * *